United States Patent
Lim et al.

(10) Patent No.: US 12,186,426 B2
(45) Date of Patent: *Jan. 7, 2025

(54) SOLID DOSAGE FORM

(71) Applicant: IX BIOPHARMA LTD, Singapore (SG)

(72) Inventors: Chin Beng Stephen Lim, Willeton (AU); Vivian Bruce Sunderland, Claremont (AU); Yip Hang Eddy Lee, Singapore (SG)

(73) Assignee: IX Biopharma Ltd., Singapore (SG)

( * ) Notice: Subject to any disclaimer, the term of this patent is extended or adjusted under 35 U.S.C. 154(b) by 707 days.

This patent is subject to a terminal disclaimer.

(21) Appl. No.: 16/990,739

(22) Filed: Aug. 11, 2020

(65) Prior Publication Data

US 2022/0347095 A1 Nov. 3, 2022

Related U.S. Application Data

(60) Division of application No. 16/020,880, filed on Jun. 27, 2018, now Pat. No. 10,857,097, which is a continuation of application No. 14/052,331, filed on Oct. 11, 2013, now abandoned, which is a continuation-in-part of application No. 13/504,309, filed as application No. PCT/SG2010/000409 on Oct. 26, 2010, now Pat. No. 10,744,086.

(30) Foreign Application Priority Data

Oct. 30, 2009 (SG) ............................. 200907221-6
Oct. 11, 2012 (AU) ............................. 2012238330
Feb. 8, 2013 (AU) ............................. 2013200684
Aug. 8, 2013 (AU) ............................. 2013200682

(51) Int. Cl.
| | | |
|---|---|---|
| *A61K 9/20* | (2006.01) | |
| *A61K 9/00* | (2006.01) | |
| *A61K 9/19* | (2006.01) | |
| *A61K 31/00* | (2006.01) | |
| *A61K 31/135* | (2006.01) | |
| *A61K 31/137* | (2006.01) | |
| *A61K 31/439* | (2006.01) | |
| *A61K 31/4468* | (2006.01) | |
| *A61K 31/519* | (2006.01) | |
| *A61K 31/5517* | (2006.01) | |
| *A61K 31/724* | (2006.01) | |
| *A61K 47/26* | (2006.01) | |

(52) U.S. Cl.
CPC .......... *A61K 9/0056* (2013.01); *A61K 9/2018* (2013.01); *A61K 9/2095* (2013.01); *A61K 31/00* (2013.01); *A61K 31/135* (2013.01); *A61K 31/137* (2013.01); *A61K 31/439* (2013.01); *A61K 31/4468* (2013.01); *A61K 31/519* (2013.01); *A61K 31/5517* (2013.01)

(58) Field of Classification Search
CPC .. A61K 9/0056; A61K 9/2095; A61K 9/2018; A61K 9/2054; A61K 9/20; A61K 9/19; A61K 9/00; A61K 8/02; A61K 9/0218; A61K 31/70; A61K 9/006

See application file for complete search history.

(56) References Cited

U.S. PATENT DOCUMENTS

| | | | |
|---|---|---|---|
| 3,767,807 A | 10/1973 | Blonde et al. | |
| 4,946,684 A | 8/1990 | Blank et al. | |
| 5,558,880 A * | 9/1996 | Gole ...................... | A61K 8/34 424/484 |
| 6,200,604 B1 | 3/2001 | Pather et al. | |
| 6,221,392 B1 | 4/2001 | Khankari et al. | |
| 6,316,027 B1 | 11/2001 | Johnson et al. | |
| 6,509,040 B1 | 1/2003 | Murray et al. | |
| 6,974,590 B2 | 12/2005 | Pather et al. | |
| 7,118,498 B2 | 10/2006 | Meadows et al. | |
| 7,357,891 B2 | 4/2008 | Yang et al. | |
| 7,407,669 B2 | 8/2008 | Leung et al. | |
| 7,425,292 B2 | 9/2008 | Yang et al. | |
| 8,221,269 B2 | 7/2012 | Meadows et al. | |
| 10,744,086 B2 | 8/2020 | Lim et al. | |
| 10,857,097 B2 | 12/2020 | Lim et al. | |
| 2002/0082775 A1 | 6/2002 | Meadows et al. | |
| 2003/0129226 A1 | 7/2003 | Liu et al. | |
| 2003/0224090 A1 | 12/2003 | Pearce et al. | |
| 2003/0236183 A1 | 12/2003 | De Bruijn et al. | |

(Continued)

FOREIGN PATENT DOCUMENTS

| | | |
|---|---|---|
| AU | 764346 | 8/2003 |
| AU | 764473 | 8/2003 |

(Continued)

OTHER PUBLICATIONS

Ahmed, et al., "Formulation of a Fast-Dissolving Ketoprofen Tablet Using Freeze-Drying in Blisters Technique," Drug Development and Industrial Pharmacy, 32:437-442, 2006.

Definition of Dissolve. Merriam-Webster (Online Webpage). Date retrieved: Aug. 12, 2015. <http://www.merriamwebster.com/dictionary/dissolve>.

Erickson, Megan. Starch. Central Washington University. Slides 3 and 6., 2013.

International Search Report and Written Opinion for International Application No. PCT/SG2010/000409, dated Jan. 21, 2011.

Jacob, S., et al., "Novel Co-Processed Excipients of Mannitol and Microcrystalline Cellulose for Preparing Fast Dissolving Tablets of Glipizide," Indian Journal of Pharmaceutical Sciences, Sep.-Oct. 2007, pp. 633-639.

Teknova. Common Biological Buffers. p. 1., 2012.

(Continued)

*Primary Examiner* — Tracy Liu
(74) *Attorney, Agent, or Firm* — Fish & Richardson P.C.

(57) ABSTRACT

There is provided a solid dosage form adapted for the release of a biologically active material in the oral cavity wherein the dosage form includes at least one biologically active material, and at least one matrix forming agent, wherein the dosage form substantially dissolves in the oral cavity. A method of producing the same and a kit including the same are also provided.

11 Claims, 85 Drawing Sheets

(56) References Cited

U.S. PATENT DOCUMENTS

| | | | |
|---|---|---|---|
| 2004/0033205 A1* | 2/2004 | Date | A61K 8/22 |
| | | | 424/53 |
| 2004/0033258 A1 | 3/2004 | Koike et al. | |
| 2004/0156895 A1 | 8/2004 | Pruitt et al. | |
| 2004/0228919 A1* | 11/2004 | Houghton | A61K 39/36 |
| | | | 424/484 |
| 2004/0247649 A1 | 12/2004 | Pearce et al. | |
| 2005/0118217 A1 | 6/2005 | Barnhart et al. | |
| 2005/0163830 A1* | 7/2005 | Rademacher | A61K 47/02 |
| | | | 424/449 |
| 2005/0196438 A1 | 9/2005 | Wang et al. | |
| 2005/0208110 A1* | 9/2005 | Singh | A61K 9/006 |
| | | | 424/443 |
| 2006/0207911 A1 | 9/2006 | Bullock | |
| 2006/0251716 A1 | 11/2006 | Norman et al. | |
| 2007/0092553 A1 | 4/2007 | Tengler et al. | |
| 2007/0265207 A1 | 11/2007 | Fein | |
| 2007/0293582 A1 | 12/2007 | Hill | |
| 2008/0050422 A1 | 2/2008 | Myers et al. | |
| 2008/0152712 A1 | 6/2008 | Monteith et al. | |
| 2008/0220029 A1 | 9/2008 | Ng et al. | |
| 2009/0047350 A1 | 2/2009 | Bangalore | |
| 2009/0170955 A1 | 7/2009 | Alur | |
| 2009/0246257 A1 | 10/2009 | Modi | |
| 2010/0240724 A1 | 9/2010 | Chang et al. | |
| 2011/0009834 A1 | 1/2011 | Asmussen et al. | |
| 2011/0021643 A1 | 1/2011 | Endo et al. | |
| 2012/0219628 A1 | 8/2012 | Lim et al. | |
| 2014/0178473 A1 | 6/2014 | Lim et al. | |

FOREIGN PATENT DOCUMENTS

| | | | |
|---|---|---|---|
| AU | 2004242477 | 1/2005 | |
| AU | 2002348432 | 8/2007 | |
| AU | 2007203233 | 8/2007 | |
| AU | 2002362772 | 9/2007 | |
| AU | 2002332118 | 6/2008 | |
| AU | 2004208644 | 7/2009 | |
| AU | 2010219449 | 9/2011 | |
| AU | 2010244194 | 11/2011 | |
| CN | 1085081 | 4/1994 | |
| CN | 101084891 | 12/2007 | |
| CN | 101332197 | 12/2008 | |
| CN | 102438596 | 5/2012 | |
| EP | 1621186 | 2/2006 | |
| EP | 1923074 | 5/2008 | |
| FR | 2967066 | 5/2012 | |
| JP | S48-68726 | 9/1973 | |
| JP | H04-230212 | 8/1992 | |
| JP | H07-508019 | 9/1995 | |
| JP | H08-325141 | 12/1996 | |
| JP | 2001278812 | 10/2001 | |
| JP | 2002179558 | 6/2002 | |
| JP | 2003506480 | 2/2003 | |
| JP | 2003516356 | 5/2003 | |
| JP | 2006519187 | 8/2006 | |
| JP | 2008273989 | 11/2008 | |
| JP | 2008546786 | 12/2008 | |
| JP | 2009517468 | 4/2009 | |
| JP | 2012051875 | 3/2012 | |
| JP | 2013142076 | 7/2013 | |
| JP | 2015529243 | 10/2015 | |
| KR | 20090034729 | 4/2009 | |
| WO | WO 1991009591 | 7/1991 | |
| WO | WO 1993023017 | 11/1993 | |
| WO | WO 1994014422 | 7/1994 | |
| WO | WO 1995020377 | 8/1995 | |
| WO | WO 1997006786 | 2/1997 | |
| WO | WO 1998031368 | 7/1998 | |
| WO | WO 1998036738 | 8/1998 | |
| WO | WO 1999002140 | 1/1999 | |
| WO | WO 1999009989 | 3/1999 | |
| WO | WO 1999038496 | 8/1999 | |
| WO | WO 2000016750 | 3/2000 | |
| WO | WO 2000016751 | 3/2000 | |
| WO | WO 2000042992 | 7/2000 | |
| WO | WO 2000044351 | 8/2000 | |
| WO | WO 2000051539 | 9/2000 | |
| WO | WO 2000061117 | 10/2000 | |
| WO | WO 2001012161 | 2/2001 | |
| WO | WO-0137814 A1 * | 5/2001 | A61K 31/465 |
| WO | WO 2001037814 | 5/2001 | |
| WO | WO 2002005820 | 1/2002 | |
| WO | WO 2003030882 | 4/2003 | |
| WO | WO 2004043439 | 5/2004 | |
| WO | WO 2004066986 | 8/2004 | |
| WO | WO 2004067004 | 8/2004 | |
| WO | WO 2004075875 | 9/2004 | |
| WO | WO 2005105048 | 11/2005 | |
| WO | WO 2006031209 | 3/2006 | |
| WO | WO 2006039264 | 4/2006 | |
| WO | WO 2006085101 | 8/2006 | |
| WO | WO 2006102990 | 10/2006 | |
| WO | WO 2006103418 | 10/2006 | |
| WO | WO 2006114868 | 11/2006 | |
| WO | WO 2007028247 | 3/2007 | |
| WO | WO 2007030754 | 3/2007 | |
| WO | WO 2007034287 | 3/2007 | |
| WO | WO-2007034287 A2 * | 3/2007 | A61K 47/38 |
| WO | WO 2007067494 | 6/2007 | |
| WO | WO 2007075422 | 7/2007 | |
| WO | WO 2007143676 | 12/2007 | |
| WO | WO 2008039737 | 4/2008 | |
| WO | WO 2008068471 | 6/2008 | |
| WO | WO 2008100375 | 8/2008 | |
| WO | WO 2009045022 | 4/2009 | |
| WO | WO 2009123102 | 10/2009 | |
| WO | WO 2010005400 | 1/2010 | |
| WO | WO 2010062688 | 6/2010 | |
| WO | WO-2010139987 A2 * | 12/2010 | A23L 1/0305 |
| WO | WO 2011053251 | 5/2011 | |
| WO | WO 2011076621 | 6/2011 | |
| WO | WO 2011117313 | 9/2011 | |
| WO | WO 2011120903 | 10/2011 | |
| WO | WO 2012012417 | 1/2012 | |
| WO | WO 2013037708 | 3/2013 | |
| WO | WO 2013128562 | 9/2013 | |
| WO | WO 2014145068 | 9/2014 | |

OTHER PUBLICATIONS

Thesaurus.com. Comprise. Date retrieved: Jun. 23, 2014.
"Definition of Dissolution and Theoretical Concepts for the Release of the Drug from Dosage Forms," Remington: The Science and Practice of Pharmacy, 22nd Edition, Philadelphia College of Pharmacy, © 2006, 434.
"Modified Starch," The Scientific World Journal, 2013, 2232.
"Oral Solid Dosage Forms: Uniformity of Dosage Units," Pharmaceutical Dosage Forms: Manufacturing and Compounding, 968-969, 1110.
"Remeron SolTab: Mirtazapine 15mg, 30mg and 45mg Orally Disintegrating Tablets," Merck Sharp & Dohm (Australia), Jul. 2015, 5 pages.
AUS-e-TUTE.com.au, "Chemistry Tutorial: Carbohydrates (sugars)," Aug. 2, 2014, [retrieved on Jul. 7, 2016] retrieved from URL <http://www.ausetute.com.au/sugars.html>, 3 pages.
Boateng et al., "Characterisation of freeze-dried wafers and solvent evaporated films as potential drug delivery systems to mucosal surfaces," Int. J of Pharmaceutics, Apr. 2010, 389(1-2): 24-31.
C27524 Analytical Report, Chemical Analysis, Feb. 1, 2016, 14 pages.
C27751 Analytical Report, Chemical Analysis, March, 2, 2016, 10 pages.
Cable, "Starch," Feb. 20, 2009, 685-690.
Chem4Kids [online], "Sweet, Sweet Carbs," Chem4Kids.com, available on or before Oct. 2001, [retrieved on Apr. 18, 2018] retrieved from URL <http://www.chem4kids.com/files/bio_carbos.html>, 4 pages.
Chong et al., "Development of a Sublingual/Oral Formulation of Ketamine for Use in Neuropathic Pain: Preliminary Findings from a Three-Way Randomized, Crossover Study", Clin. Drug Invest., 2009, 29(5): 317-324.

(56) References Cited

OTHER PUBLICATIONS

Cook, "Analytical Report: C27751/1 Ketamine Wafers 35 mg Batch: 160105," Chemical Analysis Pty Ltd, Mar. 2, 2016, 2 pages.
Deveci et al., "Sublingual sildenafil in the treatment of erectile dysfunction: Faster onset of action with less dose," Int. J of Urology, 2004, 11: 989-992.
Dixit et al., "Oral strip technology: Overview and future potential", Journal of Controlled Release, Oct. 2009, 139(2): 94-107.
Drugs.com [online], "Hetastarch," Drug Information Online, [retrieved on Sep. 12, 2013] retreived from URL <http://www.drugs.com/pro/hetastarch.html?printable=1>, 11 pages.
Engin, et al., "Anxiolytic- and antidepressant-like properties of ketamine in behavioral and neurophysiological animal models," Neuroscience, 2009, 161:359-369.
European Search Report (Extended) in European Application No. 13845400, date Sep. 16, 2016, 18 pages.
European Search Report (Supplemental) in European Application No. 10827255, filed Jun. 5, 2013, 6 pages.
European Search Report (Supplemental) in European Application No. 13845400, dated May 10, 2016, 9 pages.
European Search Report in European Application No. 17179150, dated Nov. 14, 2017, 8 pages.
Gitto, et al., "Melatonin versus midazolam premedication in childrenundergoing surgery: a pilot study," J. Paediatrics and Child Health, 2015, 52:291-295.
International Preliminary Report on Patentability for International Application No. PCT/IB2013/002594, dated Apr. 14, 2015, 5 pages.
International Preliminary Report on Patentability for International Application No. PCT/SG2010/000409, dated Sep. 2, 2011, 10 pages.
International Search Report and Written Opinion for International Application No. PCT/IB2013/002594, dated Feb. 27, 2014, 8 pages.
Johnson, et al., "The use of melatonin as an alternative to sedation in uncooperative children undergoing an MRI examination," Clin. Radiol, 2002, 57:502-506.
Kidd, et al., "Paediatric procedural sedation using ketamine in a UK emergency department: a 7 year review of practice," Br. J. Anaesthesia, 2016, 116(4):518-523.
Kumar et al., "Overview of Fast Dissolving Films," Int. J. Pharmacy and Pharmaceutical Sciences, May 2010, 29-33, available at <URL:http://www.ijppsjournal.com/Vol2Suppl3/665.pdf>.
Kurdi, et al., "KetaminE: current applications in anesthesia, pain, and critical care," Anesth. Essays Res., 2014, 8(3):283-290.
Lim et al., "A phase I pharmacokinetics and bioavailability study of a sublingual fentanyl wafer in healthy volunteers," Anesth. Analg., May 14, 2012, 115(3):554-559.
Lim et al., "Pharmacokinetics and bioavailability study of sublingual fentanyl wafer in adult postoperative female patients," Anesth. Analg., Jul. 2011, 39(4):746.
List and Muazzam, "Quellung—die treibende Kraft beim Tablettenzerfall," Pharm. Ind., 1981, 43(5):480-484, English abstract only.
Lomaestro and Malone, "Glutathione in health and disease: pharmacotherapeutic issues," The Annals of Pharmacotherapy, 1995, 29:1263-73.
Lutfy and Cowan, "Buprenorphine: a unique drug with complex pharmacology," Curr. Neuropharmacol., 2004, 2(4):395-402.
Ma, "Analytical Report: iX Biopharma WaferiX," Chemical Analysis Pty Ltd, Feb. 1, 2016, 14 pages.
Mannelli, "Agonist-antagonist combinations in opioid dependence: a translational approach," Dipendenze Patalogiche, 2010, 5(1):17-24.
PubChem [online], "Amylopectin," PubChem: Open Chemistry Database, created date Jun. 24, 2005, retrieved on Apr. 18, 2018, https://pubchem.ncbi.nlm.nih.gov/compound/amylopectin#section=Top, 20 pages.
Remington: The Science and Practice of Pharmacy, 22nd Edition, Philadelphia College of Pharmacy, © 2006, 1839; 1843; 1851.
Remington: The Science and Practice of Pharmacy, 22nd Edition, Philadelphia College of Pharmacy, 2006, pp. 434, 735-736, 968-969, 1110.
Sanford, "Vardenafil Orodispersible Tablet," Drugs, Jan. 2012, 72(1): 87-98.
Schmitt, et al., "Effects of N-acetylcysteine, oral glutathione (GSH) and a novel sublingual form of GSH on oxidative stress markers: a comparative crossover study," Redox Biology, 2015, 6:198-205.
Swarbrick et al., "Chapter 36: Coarse Dispersions," Pharmaceutics, 735-736.
Tourdot et al., "The use of a mucoadhesive microparticulate delivery system enables allergen dose reduction with equivalent efficacy in sublingual immunotherapy: 296," Allergy: European Journal of Allergy and Clinical Immunology, Jun. 2011, 66: 135.
Vitamin.sg, "Holistic Way Melatonin 5mg, 30 Tablets," https://www.vitamin.sg/holistic-way-melatonin-sleep-aid-5-mg-30-tablets?search=melatonin&sort=p.price&order=ASC, available on or before Apr. 18, 2016,.
Winger et al., "On the Conformational Properties of Amylose and Cellulose Oligomers in Solution," Int. J. Carbohydrate Chem, 2009, 8 pages.
Yousaf, et al., "Efficacy and safety of melatonin as an anxiolytic and analgesic in the perioperative period," Anesthesiology, 2010, 113:968-76.

\* cited by examiner

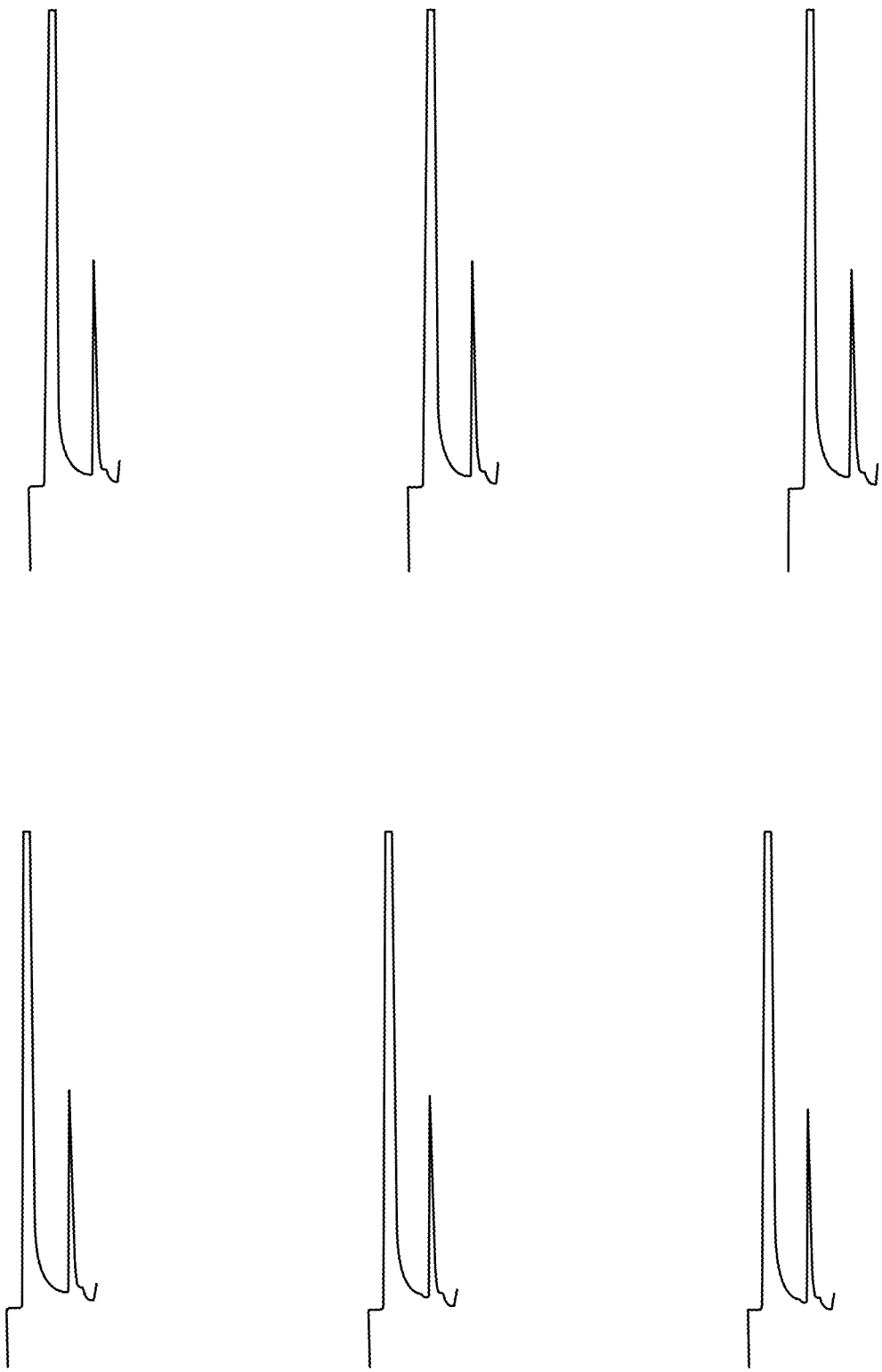

| DEMOGRAPHIC CHARACTERISTICS OF THE STUDY VOLUNTEERS | |
|---|---|
| Number | 24 |
| Mean age years (range) | 23.2 (19-32) |
| Sex | 14 female; 10 male |
| Mean weight in kg (range) | 67.1 (51.4-100.7) |
| Study dose of fentanyl (µg) | 100 |

MEAN VALUES (±1 SD) OF FENTANYL PLASMA PHARMACOKINETIC PARAMETERS[a]

| Treatment | $T_{max}$ (hours) | $C_{max}$ (pg/mL) | $AUC_{0-t}$ (h·pg/mL) | $AUC_{0-\tau}$ (h·pg/mL) | $AUC_{0-\infty}$ (h·pg/mL) |
|---|---|---|---|---|---|
| IV fentanyl[b] (100 μg)(n = 22) | 0.12 (±0.05) | 3451.0 (±970.1) | 1504.5 (±265.5) | 1702.7 (±375.3) | 1802.9 (±378.6) |
| Sublingual fentanyl water (100 μg)(n = 22) | 0.91 (±0.73) | 219.3 (±70.5) | 1046.1 (±398.4) | 1356.8 (±617.1) | 1759.0 (±815.2) |

AUC = area under curve.
[a] Two volunteers were excluded. They did not complete IV randomization.
[b] Given as a 5-minute infusion.

FIGURE 82

COMPARATIVE LITERATURE PHARMACOKINETIC DATA (MEAN ±1 SD) FOR BUCCAL AND SUBLINGUAL (SL) FENTANYL DOSAGE FORMS[a]

| Data | Buccal soluble film[b] | Buccal tablet[c] | SL tablet[d] | SL water (this study) |
|---|---|---|---|---|
| Dose (μg) | 800 | 400 | 100 | 100 |
| Study period (hours) | 48 | 72 | 30 | 24 |
| $AUC_{0-\infty}$, h·ng/mL | 13.03 ± 3.45 | 8.96 ± 2.98 | 1.24 ± 0.52 | 1.76 ± 0.82 |
| $t_{1/2}$, hours | 18.05 ± 6.61 | 11.6 ± 7.8 | 6.1 ± 2.9 | 12.5 ± 6.2 |
| $C_{max}$, ng/mL | 1.35 ± 0.33 | 1.02 ± 0.42 | 0.24 ± 0.14 | 0.22 ± 0.07 |
| $t_{max}$, hours (range) | 1.5 (0.75-4.00) | 0.75 (0.33-4.0) | 0.66 ± 0.26 | 0.91 ± 0.73 |
| Bioavailability (%) | 71 | 65 | Not available | 78.0 |

AUC = area under curve; $C_{max}$ = peak plasma concentration; $t_{max}$ = time to peak plasma concentration.
[a] The $t_{1/2}$ describes elimination profile.

FIGURE 83

SOLID DOSAGE FORM

CROSS REFERENCE TO RELATED APPLICATIONS

The present application is a continuation-in-part application and claims priority benefit under 35 USC § 120 to U.S. patent application Ser. No. 13/504,309 filed on Apr. 26, 2012, which is a national stage application of PCT Patent Application No. PCT/SG2010/000409 filed on Oct. 26, 2010, claiming priority benefit to Singapore Patent Application No. 200907221-6 filed on Oct. 30, 2009, the entireties of which are incorporated by reference herein. The present application also claims priority benefit under 35 USC § 119(a) to Australian Patent Application No. 2012238330, filed Oct. 11, 2012, Australian Patent Application No. 2013200682, filed Aug. 8, 2013 and Australian Patent Application No. 2013200684, filed Feb. 8, 2013, the entireties of which are incorporated by reference herein.

FIELD OF THE INVENTION

This invention relates to dosage forms adapted for administration to a subject. Preferably, the solid dosage forms have fast dissolution rates.

BACKGROUND

Tablets are a common dosage form to deliver an agent to human beings via oral administration. Drug delivery via the oral cavity mucosa, for example the sublingual mucosa, allows a rapidly dissolving drug to be absorbed by simple diffusion, directly into the systemic circulation via the jugular vein, bypassing the gastrointestinal tract and the hepatic first-pass effect. The sublingual route usually produces a fast and reliable onset of action, and is more suitable for fast dissolving dosage forms.

There is an unmet need in the medical field for dosage forms, which have a rapid dissolution rate in the oral cavity. The previous attempts to overcome the problems associated with solid dosages forms include effervescent tablets, films, chewable tablets, disintegrants and wicking agents. These dosage forms are particularly useful for patients who have difficulty in swallowing e.g. children and elderly people. There are several technologies used for preparing such dosage forms, including freeze-drying, spray-drying, tablet moulding and tablet compression.

Freeze drying processes have been used to prepare fast dissolving solid dosage forms. Depending on the manufacturing process, the product obtained is characterised by a highly porous microstructure of the supporting matrix (i.e. mannitol, glycine, lactose, gelatines etc.) in which the active agent is homogeneously dispersed. This technology produces a product which rapidly dissolves in water or in the oral cavity; however, the poor physical integrity of its physical structure severely limits further manufacturing operations such as forming blister packs. Moreover, the freeze drying technology in manufacturing such dosage forms is the high production costs because of the lengthy duration of each freeze drying cycle (normally from 24 to 48 hours). The complexity of the industrial plants is another important factor which prejudices the large scale use of this technology for the development of rapidly dissolving tablets. In addition, the thermal shocks, as a direct consequence of each freeze drying cycle, might physically modify the physical-chemical properties of the outer membrane of microencapsulated particles.

In the freeze-drying processes, gelatine and other gelatine-related materials have been used to formulate agents in fast dissolving dosage forms. Gelatine is carrier or structure-forming agent, and it is commonly used in preparing fast dissolving forms for a wide range of drugs. Gelatine provides strength to the dosage form, thus preventing cracking and break-up of the dosage form. This is especially a problem when the dosage form is being removed from the blister package. Gelatine is advantageous in fast dissolving drug from the dosage form because once the dosage form is placed in the oral cavity it provides rapid dissolution of the dosage form.

Gelatine is a protein which is obtained by the partial hydrolysis of animal collagenous tissue, such as skins, tendons, ligaments and bone. However, one significant problem with mammalian-derived gelatine is that it has a bland taste. This results in the fast dissolving dosage form requiring the use of sweeteners and flavours to hide and mask the taste of the gelatine component. A further problem with conventional mammalian derived gelatine is that it requires the use of heat to affect the gelatine solution. This additional step adds time and cost to the process of manufacture.

An additional problem with the use of gelatine-based material as fast dissolving dosage form matrices is that the gelatine can increase in viscosity of the solution with time. This can lead to processing difficulties. Moreover, the gelatine can lead to homogeneity and sedimentation problems associated with the gelatine solution during the holding period. Other disadvantages of gelatine formulations include being prone to bacterial growth and some individuals dislike the fact it is from animal origin.

Other agents which have been used to replace gelatine in fast dissolving dosage forms are starch and modified starches. One problem with starch is that it has a particulate feel for the patient when in the mouth and can lead to dissatisfaction for the patient. Many modified starches also result in this problem. Furthermore, they are expensive.

Ketamine is a rapid-acting, general anaesthetic approved only for intravenous injection. In recent years there has been increasing interest in its use at non-anaesthetic doses as an adjunct in acute and chronic pain management. Its pain modifying properties are attributed to its antagonism at the N-methyl-D-aspartate (NMDA) receptor, binding non-competitively to the phencyclidine binding site. When administered at sub-anaesthesia levels, ketamine is effective at producing analgesia and also demonstrates opioid sparing activity, although the mechanisms behind this remain poorly understood. Ketamine's analgesic efficacy correlates well with its inhibiting action on N-methyl-D-aspartate receptor-mediated pain facilitation and a decrease in activity of brain structures that respond to noxious stimuli. Therefore its utility in the management of acute pain is of interest. Although parenteral administration of ketamine might provide almost instant pain relief, this route may not be suitable or convenient for the patient.

Cyclic guanosine monophosphate (cGMP) phosphodiesterase type 5 (PDE5) inhibitors are a class of compounds that reduce the level of cGMP degradation in smooth muscles, leading to smooth muscle relaxation and increased blood flow. The most well-known cyclic guanosine monophosphate (cGMP) phosphodiesterase type 5 (PDE5) inhibitor is sildenafil, specifically sildenafil citrate or Viagra®. Sildenafil is usually taken in the form of a tablet about 30 minutes to four hours before sexual intercourse. However, faster acting delivery of sildenafil or other cyclic guanosine monophosphate (cGMP) phosphodiesterase type 5 (PDE5) inhibitors may be advantageous, particularly in their other use as a treatment for pulmonary hypertension.

Adrenaline is a hormone and a neurotransmitter used to treat a number of conditions including: cardiac arrest and other cardiac dysrhythmias resulting in diminished or absent cardiac output; anaphylaxis; superficial bleeding; and asthma, bronchospasm and croup. Adrenaline is often delivered via an autoinjector delivery system; however, alternative delivery systems for rapid delivery may be advantageous for those who cannot safely administer an autoinjector (such as children and those in care of children who are unfamiliar with an autoinjector device), and those who do not wish to use such a device.

Therefore, there is a need in the art for a fast dissolving dosage form which delivers a biologically active material such as an N-methyl-D-aspartate receptor antagonist, adrenaline or a cyclic guanosine monophosphate (cGMP) phosphodiesterase type 5 (PDE5) inhibitor to a patient via oral administration, wherein the dosage form rapidly dissolves in the oral cavity of the patient, and wherein the dosage form does not use substantial amounts of mammalian gelatine.

SUMMARY OF THE INVENTION

According to one aspect of the present invention there is provided a solid dosage form adapted for the release of a biologically active material in the oral cavity wherein the dosage form comprises:
  (a) at least one biologically active material, and
  (b) at least one matrix forming agent, wherein the dosage form substantially dissolves in the oral cavity.

Preferably, the solid dosage form is a fast dissolving solid dosage form.

Preferably, the biologically active material is chosen from the list comprising: at least one cyclic guanosine monophosphate (cGMP) phosphodiesterase type 5 (PDE5) inhibitor, an active material that binds to one or more adrenergic receptors, and an N-methyl-D-aspartate receptor antagonist. Preferably, the N-methyl-D-aspartate receptor antagonist is chosen from the list comprising: dextromethorphan, dextrorphan or ketamine. Preferably, the active material that binds to one or more adrenergic receptors is adrenaline (epinephrine), or an adrenaline salt. Preferably, the cyclic guanosine monophosphate (cGMP) phosphodiesterase type 5 (PDE5) inhibitor is sildenafil or a pharmaceutically acceptable salt thereof. Preferably, the sildenafil salt is sildenafil citrate.

Preferably, the dosage form is adapted to not leave a residue of said dosage form in the oral cavity that is detectable by the patient.

Preferably, the dosage form quickly disintegrates in the oral cavity, and allows the rapidly dissolving biologically active material to be absorbed by diffusion through the oral mucosa and directly into the systemic blood circulation system. By this method, the hepatic first-pass effect is avoided. Preferably, the dosage form is adapted to be delivered directly into the systemic circulation via the jugular vein, bypassing the gastrointestinal tract and the hepatic first-pass effect.

According to another aspect of the present invention there is provided a method to produce the solid dosage form of the present invention comprising the steps of:
  (a) combining at least one matrix forming agent with a biologically active material to form a homogeneous mixture; and
  (b) freeze drying the mixture to prepare the solid dosage form of the present invention.

Preferably, the method is a method to produce a fast dissolving solid dosage form.

Preferably, the biologically active material is chosen from the list comprising: at least one cyclic guanosine monophosphate (cGMP) phosphodiesterase type 5 (PDE5) inhibitor, an active material that binds to one or more adrenergic receptors, and an N-methyl-D-aspartate receptor antagonist. Preferably, the N-methyl-D-aspartate receptor antagonist is chosen from the list comprising: dextromethorphan, dextrorphan or ketamine. Preferably, the active material that binds to one or more adrenergic receptors is adrenaline, or an adrenaline salt. Preferably, the cyclic guanosine monophosphate (cGMP) phosphodiesterase type 5 (PDE5) inhibitor is sildenafil or a pharmaceutically acceptable salt thereof. Preferably, the sildenafil salt is sildenafil citrate.

According to another aspect of the present invention there is provided a kit comprising:
  (a) the solid dosage form, wherein the dosage form comprises:
    (i) at least one biologically active material, and
    (ii) at least one matrix forming agent, and
  (b) instructions for its use
wherein the dosage form substantially dissolves in the oral cavity. Preferably, the solid dosage form is a fast dissolving solid dosage form. Preferably, the biologically active material is chosen from the list comprising: at least one cyclic guanosine monophosphate (cGMP) phosphodiesterase type 5 (PDE5) inhibitor, an active material that binds to one or more adrenergic receptors, and an N-methyl-D-aspartate receptor antagonist. Preferably, the N-methyl-D-aspartate receptor antagonist is chosen from the list comprising: dextromethorphan, dextrorphan or ketamine. Preferably, the active material that binds to one or more adrenergic receptors is adrenaline, or an adrenaline salt. Preferably, the cyclic guanosine monophosphate (cGMP) phosphodiesterase type 5 (PDE5) inhibitor is sildenafil or a pharmaceutically acceptable salt thereof. Preferably, the sildenafil salt is sildenafil citrate.

According to another aspect of the present invention there is provided solid dosage form adapted for the release of at least one cyclic guanosine monophosphate (cGMP) phosphodiesterase type 5 (PDE5) inhibitor in an oral cavity wherein said dosage form comprises:
  (a) at least one cyclic guanosine monophosphate (cGMP) phosphodiesterase type 5 (PDE5) inhibitor; and
  (b) at least one matrix forming agent;
wherein said dosage form substantially dissolves in the oral cavity. Preferably, the solid dosage form is a fast dissolving solid dosage form. Preferably, the cyclic guanosine monophosphate (cGMP) phosphodiesterase type 5 (PDE5) inhibitor is sildenafil or a pharmaceutically acceptable salt thereof. Preferably, the sildenafil salt is sildenafil citrate.

According to another aspect of the present invention there is provided a solid dosage form adapted for the release of an active material that binds to one or more adrenergic receptors in an oral cavity wherein said dosage form comprises:
  (a) an active material that binds to one or more adrenergic receptors; and
  (b) at least one matrix forming agent;
wherein said dosage form substantially dissolves in the oral cavity. Preferably, the solid dosage form is a fast dissolving solid dosage form. Preferably, the active material that binds to one or more adrenergic receptors is adrenaline, or an adrenaline salt.

According to another aspect of the present invention there is provided a solid dosage form adapted for the release of N-methyl-D-aspartate receptor antagonist in an oral cavity wherein said dosage form comprises:

(a) an N-methyl-D-aspartate receptor antagonist; and
(b) at least one matrix forming agent;

wherein said dosage form substantially dissolves in the oral cavity. Preferably, the solid dosage form is a fast dissolving solid dosage form. Preferably, the N-methyl-D-aspartate receptor antagonist is chosen from the list comprising: dextromethorphan, dextrorphan or ketamine.

According to another aspect of the present invention there is provided a wafer comprising a solid dosage form adapted for the release of a biologically active material in an oral cavity. Preferably, the solid dosage form is a fast dissolving solid dosage form. Preferably, the biologically active material is chosen from the list comprising: at least one cyclic guanosine monophosphate (cGMP) phosphodiesterase type 5 (PDE5) inhibitor, an active material that binds to one or more adrenergic receptors, and an N-methyl-D-aspartate receptor antagonist. Preferably, the N-methyl-D-aspartate receptor antagonist is chosen from the list comprising: dextromethorphan, dextrorphan or ketamine. Preferably, the active material that binds to one or more adrenergic receptors is adrenaline, or an adrenaline salt. Preferably, the cyclic guanosine monophosphate (cGMP) phosphodiesterase type 5 (PDE5) inhibitor is sildenafil or a pharmaceutically acceptable salt thereof. Preferably, the sildenafil salt is sildenafil citrate. The wafer may be accompanied by instructions for its use.

According to another aspect of the present invention, there is provided a pharmaceutical composition comprising the solid dosage form of the invention. Preferably, the solid dosage form is a fast dissolving solid dosage form.

BRIEF DESCRIPTION OF THE DRAWINGS

FIG. 82 shows a table showing the mean values (±1 SD) of fentanyl plasma pharmacokinetic parameters.

FIG. 83 shows is table showing the comparative literature pharmacokinetic data (mean±1 SD) for buccal and sublingual (SL) fentanyl dosage forms.

DETAILED DESCRIPTION

Solid Dosage Form

Figure 1:
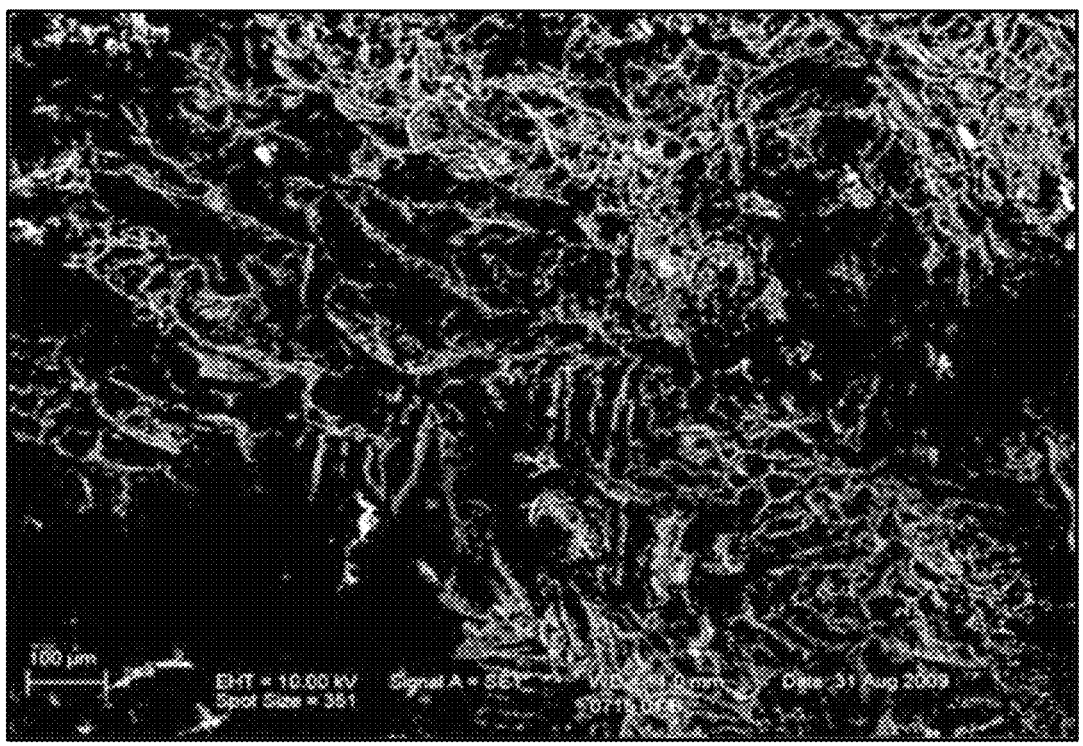
FIG. 1 shows scanning electron micrographs of the surface of wafers from batch numbers 071501 B and 071502B.
Figure 1:
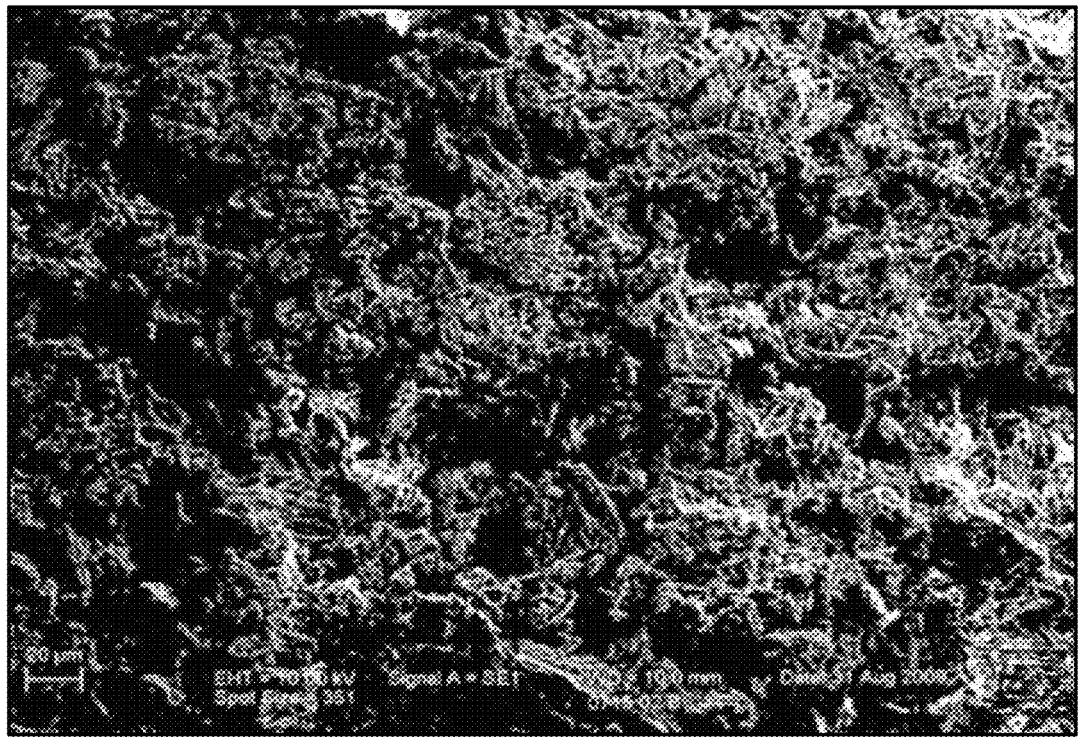
Figure 2:
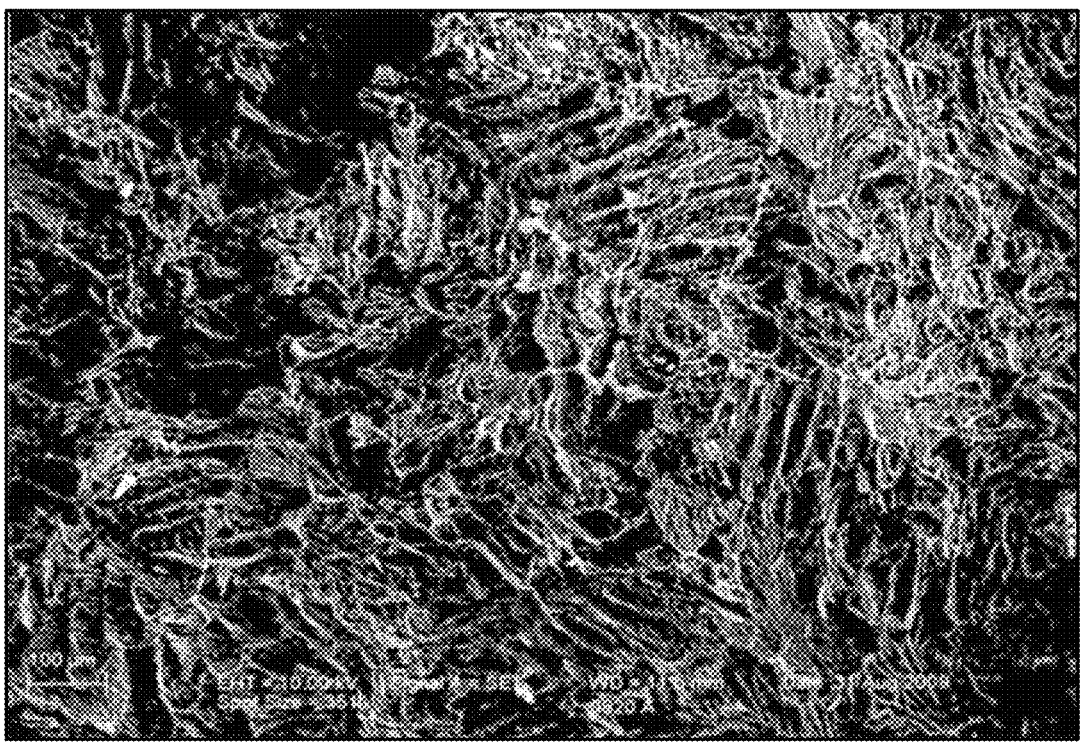
FIG. 2 shows scanning electron micrographs of the surface of wafers from batch numbers 0820A and 0820B.
Figure 2:
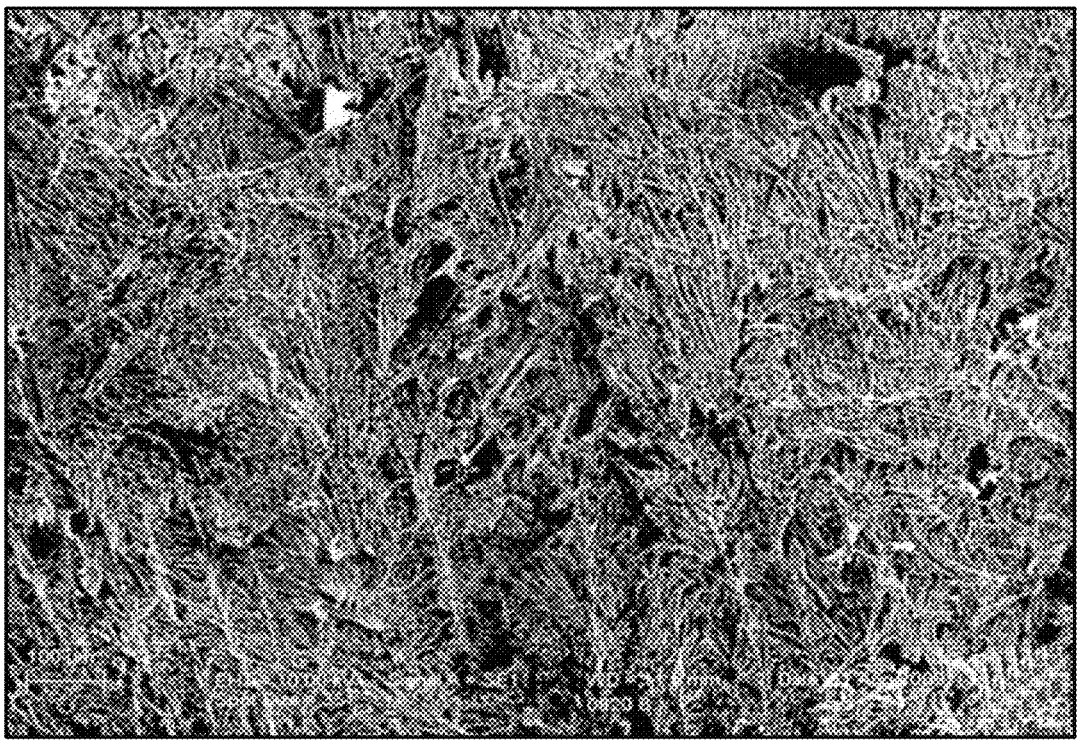
Figure 3:
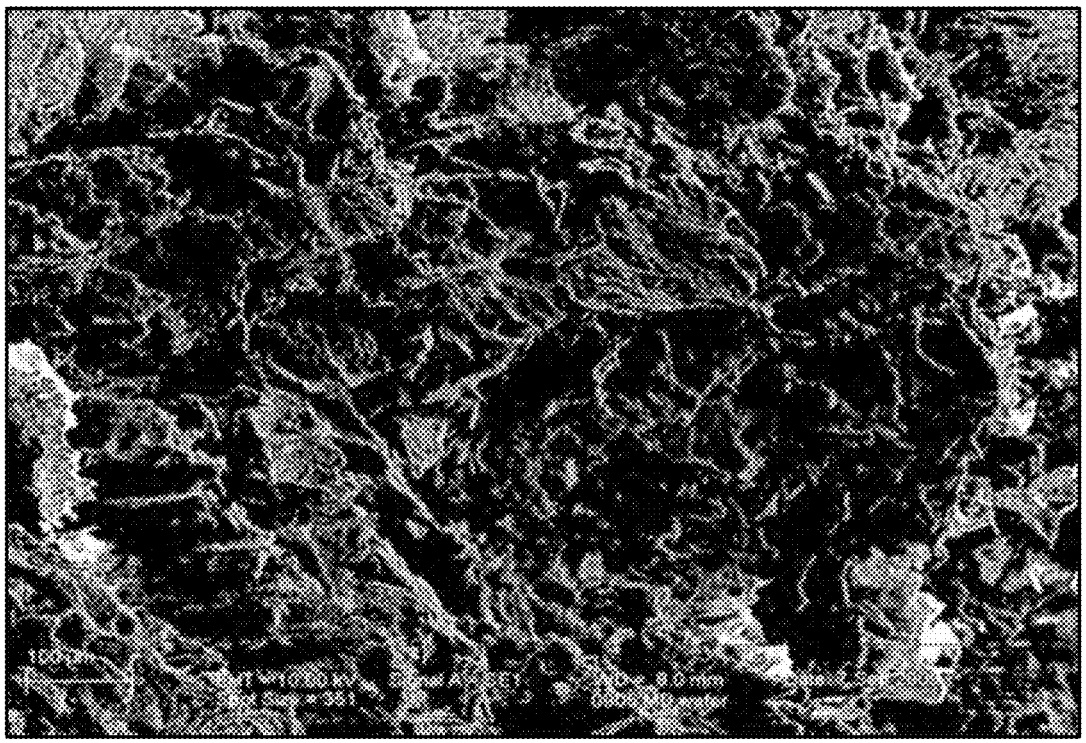
FIG. 3 shows a scanning electron micrograph of the surface of wafer from batch number 0905MD.
Figure 4:
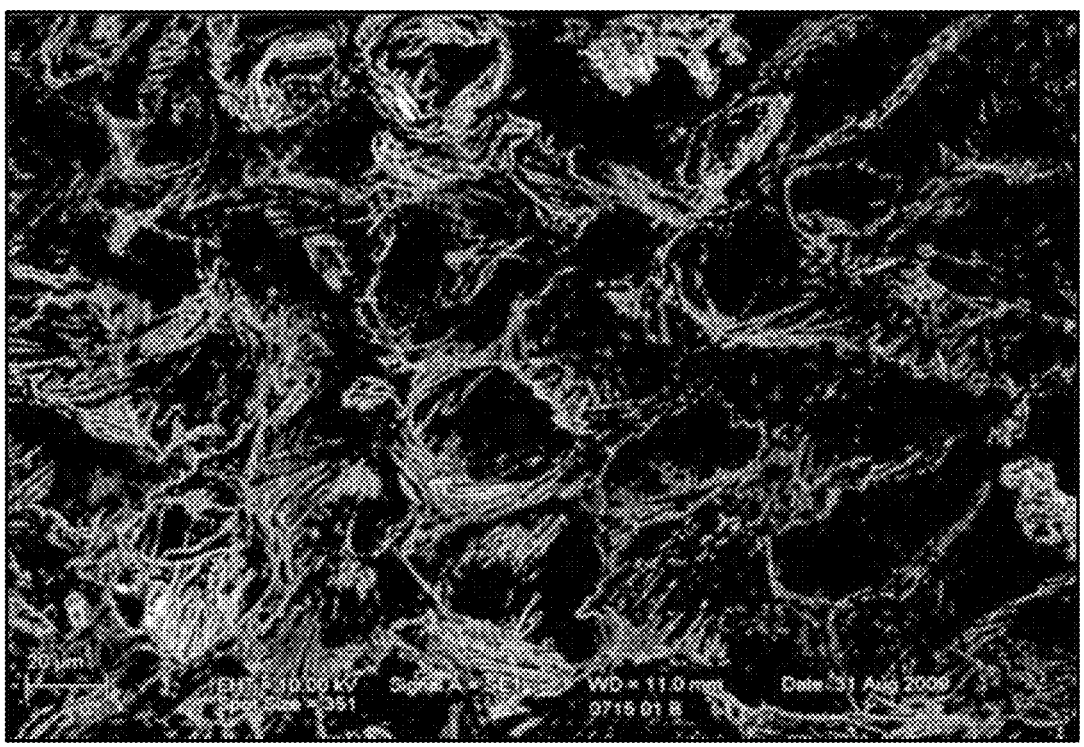
FIG. 4 shows scanning electron micrographs of the cross section of wafers from batch numbers 071501B and 071502B.
Figure 4:
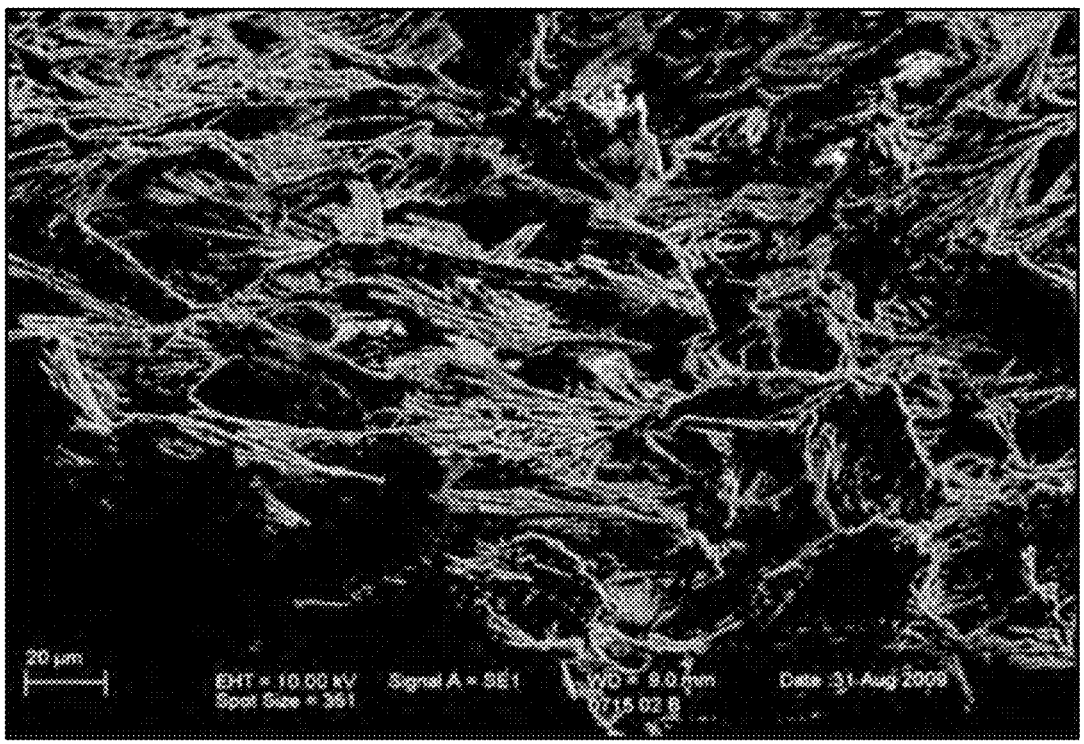
Figure 5:
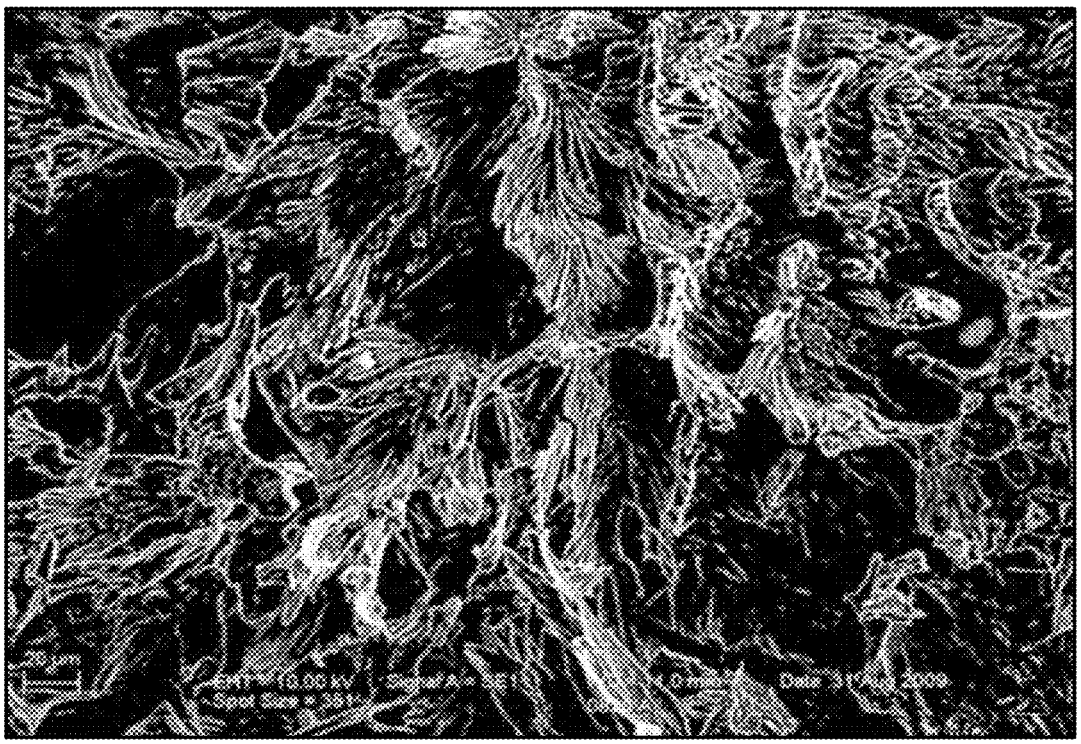
FIG. 5 shows scanning electron micrographs of the cross section of wafers from batch numbers 0820A and 0820B.
Figure 5:
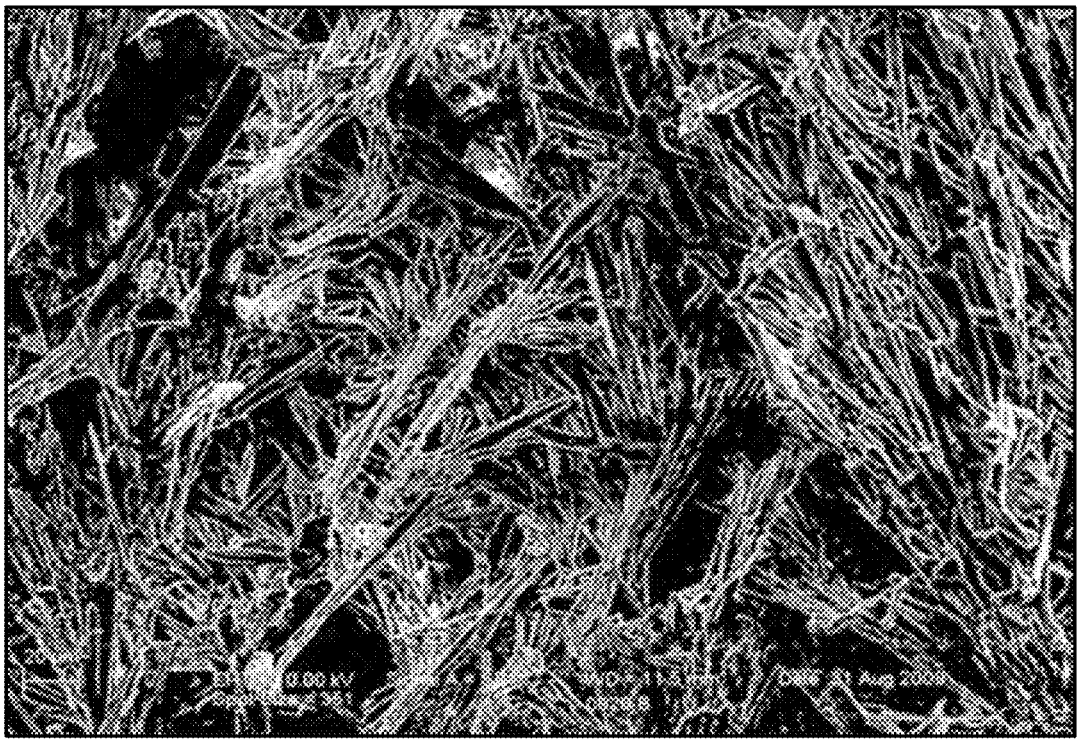
Figure 6:
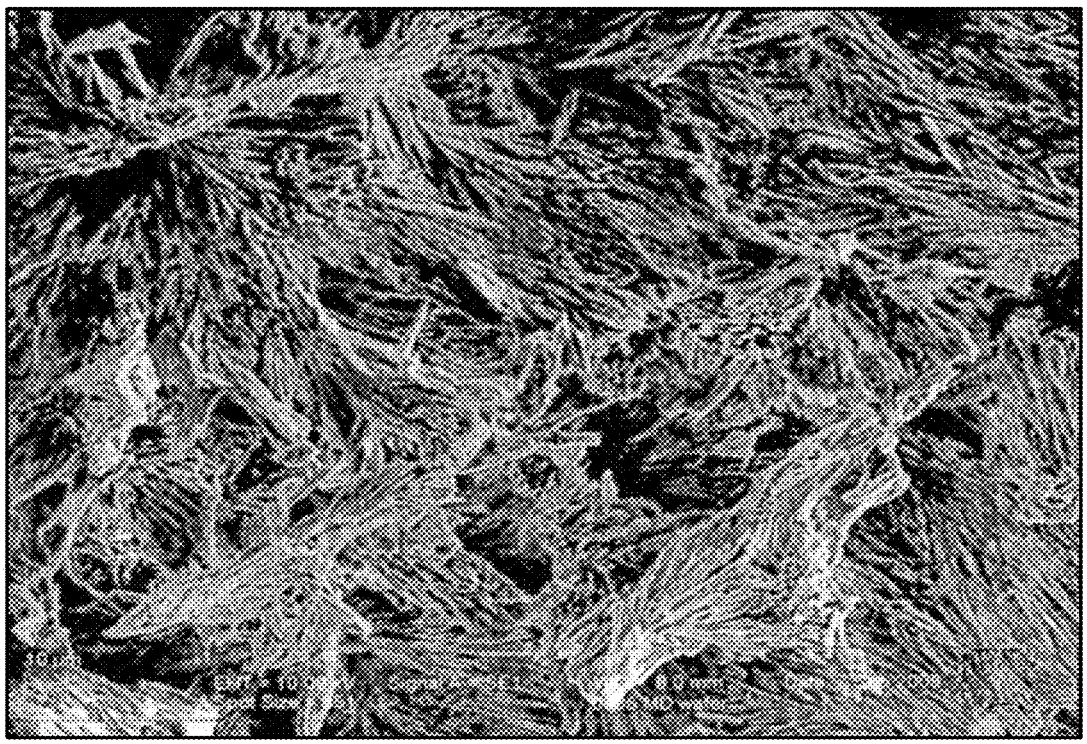
FIG. 6 shows a scanning electron micrograph of the cross section of wafer from batch number 0905MD.

According to one aspect of the present invention, there is provided a solid dosage form adapted for the release of a biologically active material in the oral cavity wherein the dosage form comprises:

(a) at least one biologically active material, and (b) at least one matrix forming agent, wherein the dosage form substantially dissolves in the oral cavity.

Preferably, the solid dosage form is a fast dissolving solid dosage form. Preferably, the biologically active material is chosen from the list comprising: at least one cyclic guanosine monophosphate (cGMP) phosphodiesterase type 5 (PDE5) inhibitor, an active material that binds to one or more adrenergic receptors, and an N-methyl-D-aspartate receptor antagonist.

Preferably, the N-methyl-D-aspartate receptor antagonist is chosen from the list comprising: dextromethorphan, dextrorphan or ketamine. If the antagonist is ketamine, preferably the ketamine is a ketamine salt, such as ketamine hydrochloride. In one embodiment, the ketamine is in the form of a racemic mixture of the R and S enantiomers. Preferably, the ketamine is a mixture of two enantiomers R-(−) and S-(+).

Preferably, the biologically active material that binds to one or more adrenergic receptors is adrenaline, or an adrenaline salt.

Preferably, the cyclic guanosine monophosphate (cGMP) phosphodiesterase type 5 (PDE5) inhibitor is sildenafil or a pharmaceutically acceptable salt thereof. Preferably, the sildenafil salt is sildenafil citrate.

In one embodiment, the biologically active material is present in an amount by dry weight of the solid dosage form selected from the group consisting of: 0.01 to 95%; 0.1 to 75% and 1 to 45% weight by dry weight of the dosage form.

Preferably, the dosage form quickly disintegrates in the oral cavity, and allows the rapidly dissolving biologically active material to be absorbed by diffusion through the oral mucosa and directly into the systemic blood circulation system. By this method, the hepatic first-pass effect is avoided. Preferably, the dosage form is adapted to be delivered directly into the systemic circulation via the jugular vein, bypassing the gastrointestinal tract and the hepatic first-pass effect.

By "fast dissolving", it is preferably meant that the dosage form substantially dissolves once placed in the oral cavity in a time period selected from the group consisting of: less than 2 minutes; less than 1 minute; less than 50 seconds; less than 40 seconds; less than 30 seconds; less than 20 seconds; less than 15 seconds; less than 10 seconds; less than 7.5 seconds; less than 5 seconds; less than 4 seconds; less than 3 seconds; and less than 2 seconds after administration of the dosage form. Preferably, the fast dissolving dosage form's dissolution rate is higher than the dissolution rates of conventional dosage forms.

More preferably, the "fast dissolving" solid dosage form completely dissolves once placed in the oral cavity in a time period selected from the group consisting of: less than 2 minutes; less than 1 minute; less than 50 seconds; less than 40 seconds; less than 30 seconds; less than 20 seconds; less than 15 seconds; less than 10 seconds; less than 7.5 seconds; less than 5 seconds; less than 4 seconds; less than 3 seconds; and less than 2 seconds after administration of the dosage form.

By "substantially", it is meant that at least 60% of the fast dissolving dosage form has been dissolved in the oral cavity in the time period selected. Preferably, at least 65%, 70%, 75%, 80%, 85%, 90%, 95%, 96%, 97% or 98% of the fast dissolving dosage form has been dissolved in the oral cavity in the time period selected. Most preferably, at least 99% of the fast dissolving dosage form has been dissolved in the oral cavity in the time period selected.

In a highly preferred embodiment of the present invention, there is no residue remaining that is detectable by the patient of the dosage form of the present invention after administration. Preferably, the dosage form completely dissolves after oral, preferably sublingual, administration to the patient. As such, the subject has no urge to swallow the dosage form. In particular, the pharmaceutical composition may be, for example, designed for buccal or sublingual delivery.

Active Agents

The biologically active material includes active compounds, and compounds for veterinary and human use, such as but not limited to: pharmaceutical actives, neutraceuticals, cosmeceuticals, cosmetics, complementary medicines, natural products, foods, vitamins, nutrients, biologics, amino acids, proteins, peptides, nucleotides, and nucleic acids. In a preferred form the biologically active material is adapted for oral administration.

In a preferred embodiment of the invention, the biologically active material is an organic compound. In a highly preferred embodiment of the invention, the biologically active material is an organic, therapeutically active compound for human use. In another embodiment of the present invention, the biologically active material is an inorganic compound. When the biological active material is a drug, it can be of a neutral species, basic or acidic as well as salts of an acid or base. This invention is not limited to any drug specific class, application type, chemical type or function grouping.

The biologically active material is ordinarily an agent for which one of skill in the art desires improved fast dissolution for oral administration. The biologically active material may be a conventional active agent or drug.

Examples of biologically active materials suitable for use in the invention include actives, biologics, amino acids, proteins, peptides, nucleotides, nucleic acids, and analogues, homologs and first order derivatives thereof. The biologically active material can be selected from a variety of known classes of drugs, including, however not limited to: anti-obesity drugs, central nervous system stimulants, carotenoids, corticosteroids, elastase inhibitors, anti-fungals, oncology therapies, anti-emetics, analgesics, cardiovascular agents, anti-inflammatory agents, such as NSAIDs and COX-2 inhibitors, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives (hypnotics and neuroleptics), astringents, alpha-adrenergic receptor blocking agents, beta-adrenoceptor blocking agents, blood products and substitutes, cardiac inotropic agents, contrast media, cough suppressants (expectorants and mucolytics), diagnostic agents, diagnostic imaging agents, diuretics, dopaminergics (anti-Parkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, and xanthines.

A description of these classes of biologically active materials and a listing of species within each class can be found in Martindale's 'The Extra Pharmacopoeia', 31st Edition (The Pharmaceutical Press, London, 1996), and the 'Physician's Desk Reference' ($60^{th}$ Ed., 2005), both specifically incorporated by reference and familiar to those of skill in the art. The active agents are commercially available and/or can be prepared by techniques known in the art.

Additionally, examples of suitable biologically active materials include, however are not limited to, those listed below:

Analgesics and anti-inflammatory agents: aloxiprin, auranofm, azapropazone, benorylate, diflunisal, etodolac, fenbufen, fenoprofen calcim, flurbiprofen, ibuprofen, indomethacin, ketoprofen, meclofenamic acid, mefenamic acid, nabumetone, naproxen, oxaprozin, oxyphenbutazone, phenylbutazone, piroxicam, sulindac.

Anthelmintics: albendazole, bephenium hydroxynaphthoate, cambendazole, dichlorophen, ivermectin, mebendazole, oxanniquine, oxfendazole, oxantel embonate, praziquantel, pyrantel embonate, thiabendazole.

Anti-arrhythmic agents: amiodarone HCl, disopyramide, flecainide acetate, quinidine sulphate.

Anti-bacterial agents: benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim.

Anti-coagulants: dicoumarol, dipyridamole, nicoumalone, phenindione.

Anti-depressants: amoxapine, ciclazindol, maprotiline HCl, mianserin HCl, nortriptyline HCl, trazodone HCl, trimipramine maleate.

Anti-diabetics: acetohexamide, chlorpropamide, glibenclamide, gliclazide, glipizide, tolazamide, tolbutamide.

Anti-epileptics: beclamide, carbamazepine, clonazepam, ethotoin, methoin, methsuximide, methylphenobarbitone, oxcarbazepine, paramethadione, phenacemide, phenobarbitone, phenytoin, phensuximide, primidone, sulthiame, valproic acid.

Anti-fungal agents: amphotericin, butoconazole nitrate, clotrimazole, econazole nitrate, fluconazole, flucytosine, griseofulvin, itraconazole, ketoconazole, miconazole, natamycin, nystatin, sulconazole nitrate, terbinafine HCl, terconazole, tioconazole, undecenoic acid.

Anti-gout agents: allopurinol, probenecid, sulphinpyrazone.

Anti-hypertensive agents: amlodipine, benidipine, darodipine, dilitazem HCl, diazoxide, felodipine, guanabenz acetate, indoramin, isradipine, minoxidil, nicardipine HCl, nifedipine, nimodipine, phenoxybenzamine HCl, prazosin HCl, reserpine, terazosin HCl.

Anti-malarials: amodiaquine, chloroquine, chlorproguanil HCl, halofantrine HCl, mefloquine HCl, proguanil HCl, pyrimethamine, quinine sulphate.

Anti-migraine agents: dihydroergotamine mesylate, ergotamine tartrate, methysergide maleate, pizotifen maleate, sumatriptan succinate.

Anti-muscarinic agents: atropine, benzhexol HCl, biperiden, ethopropazine HCl, hyoscine butyl bromide, hyoscyamine, mepenzolate bromide, orphenadrine, oxyphencylcimine HCl, tropicamide.

Anti-neoplastic agents and immunosuppressants: aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone.

Anti-protazoal agents: benznidazole, clioquinol, decoquinate, diiodohydroxyquinoline, diloxanide furoate, dinitolmide, furzolidone, metronidazole, nimorazole, nitrofurazone, ornidazole, tinidazole.

Anti-thyroid agents: carbimazole, propylthiouracil.

Anxiolvtic, sedatives, hypnotics and neuroleptics: alprazolam, amylobarbitone, barbitone, bentazepam, bromazepam, bromnperidol, brotizolam, butobarbitone, carbromal, chlordiazepoxide, chlormethiazole, chlorpromazine, clobazam, clotiazepam, clozapine, diazepam, droperidol, ethinamate, flunanisone, flunitrazepam, fluopromazine, flupenthixol decanoate, fluphenazine decanoate, flurazepam, haloperidol, lorazepam, lormetazepam, medazepam, meprobamate, methaqualone, midazolam, nitrazepam, oxazepam, pentobarbitone, perphenazine pimozide, prochlorperazine, sulpiride, temazepam, thioridazine, triazolam, zopiclone.

Beta-Blockers: acebutolol, alprenolol, atenolol, labetalol, metoprolol, nadolol, oxprenolol, pindolol, propranolol.

Cardiac Inotropic agents: amrinone, digitoxin, digoxin, enoximone, lanatoside C, medigoxin.

Corticosteroids: beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone.

Diuretics: acetazolamide, amiloride, bendrofluazide, bumetanide, chlorothiazide, chlorthalidone, ethacrynic acid, frusemide, metolazone, spironolactone, triamterene.

Anti-Parkinson agents: bromocriptine mesylate, lysuride maleate.

Gastro-intestinal agents: bisacodyl, cimetidine, cisapride, diphenoxylate HCl, domperidone, famotidine, loperamide, mesalazine, nizatidine, omeprazole, ondansetron HCl, ranitidine HCl, sulphasalazine.

Histamine H1-receptor antagonists: acrivastine, astemizole, cinnarizine, cyclizine, cyproheptadine HCl, dimenhydrinate, flunarizine HCl, loratadine, meclozine HCl, oxatomide, terfenadine, triprolidine.

Lipid regulating agents: bezafibrate, clofibrate, fenofibrate, gemfibrozil, probucol.

Local anaesthetics: Neuro-muscular agents: pyridostigmine.

Nitrates and other anti-anginal agents: amyl nitrate, glyceryl trinitrate, isosorbide dinitrate, isosorbide mononitrate, pentaerythritol tetranitrate.

Nutritional agents: betacarotene, vitamin A, vitamin B2, vitamin D, vitamin E, vitamin K.

Opioid analgesics: codeine, dextropropyoxyphene, diamorphine, dihydrocodeine, meptazinol, methadone, morphine, nalbuphine, pentazocine, medazocine, fentanyl.

Oral vaccines: Vaccines designed to prevent or reduce the symptoms of diseases of which the following is a representative however not exclusive list: Influenza, Tuberculosis, Meningitis, Hepatitis, Whooping Cough, Polio, Tetanus, Diphtheria, Malaria, Cholera, Herpes, Typhoid, HIV, AIDS, Measles, Lyme disease, Travellers' Diarrhea, Hepatitis A, B and C, Otitis Media, Dengue Fever, Rabies, Parainfluenza, Rubella, Yellow Fever, Dysentery, Legionnaires Disease, *Toxoplasmosis*, Q-Fever, Haemorrhegic Fever, Argentina Haemorrhagic Fever, Caries, Chagas Disease, Urinary Tract Infection caused by *E. coli*, Pneumoccocal Disease, Mumps, and Chikungunya.

Vaccines to prevent or reduce the symptoms of other disease syndromes of which the following is a representative, however not exclusive list of causative organisms: *Vibrio* species, *Salmonella* species, *Bordetella* species, *Haemophilus* species, *Toxoplasmosis gondii*, Cytomegalovirus, *Chlamydia* species, Streptococcal species, Norwalk Virus, *Escherischia coli, Helicobacter pylori*, Rotavirus, *Neisseria gonorrhae, Neisseria meningiditis*, Adenovirus, Epstein Barr Virus, Japanese Encephalitis Virus, *Pneumocystis carini*, Herpes simplex, Clostridia species, Respiratory Syncytial Virus, *Klebsielia* species, *Shigella* species, *Pseudomonas aeruginosa*, Parvovirus, *Campylobacter* species, *Rickettsia* species, Varicella zoster, *Yersinia* species, Ross River Virus, J. C. Virus, *Rhodococcus equi*,

*Moraxella catarrhalis, Borrelia burgdorferi* and *Pasteurella haemolytica*. Further specific examples include opioids such as fentanyl or midazolam.

Vaccines directed to non-infections immuno-modulated disease conditions: such as topical and systematic allergic conditions such as Hayfever, Asthma, Rheumatoid Arthritis and Carcinomas.

Vaccines for veterinary use: including those directed to Coccidiosis, Newcastle Disease, Enzootic pneumonia, Feline leukaemia, Atrophic rhinitis, Erysipelas, Foot and Mouth disease, Swine, pneumonia, and other disease conditions and other infections and auto-immune disease conditions affecting companion and farm animals.

Proteins, peptides and recombinant drugs: insulin (hexameric/dimeric/monomeric forms), glucagon, growth hormone (somatotropin), polypeptides or their derivatives, (preferably with a molecular weight from 1000 to 300,000), calcitonins and synthetic modifications thereof, enkephalins, interferons (especially Alpha-2 interferon for treatment of common colds), IHRH and analogues (nafarelin, buserelin, zolidex), GHRH (growth hormone releasing hormone), secretin, bradykin antagonists, GRF (growth releasing factor), THF, TRH (thyrotropin releasing hormone), ACTH analogues, IGF (insulin like growth factors), CGRP (calcitonin gene related peptide), atrial natriurectic peptide, vasopressin and analogues (DDAVP, lypressin), factor-VIII, G-CSF (granulocyte-colony stimulating factor), EPO (erythropoitin).

Sex hormones: clomiphene citrate, danazol, ethinyloestradiol, medroxyprogesterone acetate, mestranol, methyltestosterone, norethisterone, norgestrel, oestradiol, conjugated oestrogens, progesterone, stanozolol, stiboestrol, testosterone, tibolone.

Spermicides: nonoxynol 9.

Stimulants: amphetamine, dexamphetamine, dexfenfluramine, fenfluramine, mazindol, pemoline.

Notwithstanding the general applicability of the method of the invention, more specific examples of biologically active materials include, but are not limited to: haloperidol (dopamine antagonist), DL isoproterenol hydrochloride (β-adrenergic agonist), terfenadine (H1-antagonist), propranolol hydrochloride (β-adrenergic antagonist), desipramine hydrochloride (antidepressant), sildenafil citrate, tadalafil and vardenafil. Minor analgesics (cyclooxygenase inhibitors), fenamic acids, piroxicam, Cox-2 inhibitors, naproxen, and others, may all benefit from being formulated into an oral dosage form of the present invention.

Further examples of biologically active materials include, but are not limited to: alfaxalone, acetyl digoxin, acyclovir analogs, alprostadil, aminofostin, anipamil, antithrombin III, atenolol, azidothymidine, beclobrate, beclomethasone, belomycin, benzocaine and derivatives, beta carotene, beta endorphin, beta interferon, bezafibrate, binovum, biperiden, bromazepam, bromocryptine, bucindolol, buflomedil, bupivacaine, busulfan, cadralazine, camptothesin, canthaxanthin, captopril, carbamazepine, carboprost, cefalexin, cefalotin, cefamandole, cefazedone, cefluoroxime, cefinenoxime, cefoperazone, cefotaxime, cefoxitin, cefsulodin, ceftizoxime, chlorambucil, chromoglycinic acid, ciclonicate, ciglitazone, clonidine, cortexolone, corticosterone, cortisol, cortisone, cyclophosphamide, cyclosporin A and other cyclosporins, cytarabine, desocryptin, desogestrel, dexamethasone esters such as the acetate, dezocine, diazepam, diclofenac, dideoxyadenosine, dideoxyinosine, digitoxin, digoxin, dihydroergotamine, dihydroergotoxin, diltiazem, dopamine antagonists, doxorubicin, econazole, endralazine, enkephalin, enalapril, epoprostenol, estradiol, estramustine, etofibrate, etoposide, factor ix, factor viii, felbamate, fenbendazole, fenofibrate, fexofenedine, flunarizin, flurbiprofen, 5-fluorouracil, flurazepam, fosfomycin, fosmidomycin, furosemide, gallopamil, gamma interferon, gentanicin, gepefrine, gliclazide, glipizide, griseofulvin, haptoglobulin, hepatitis B vaccine, hydralazine, hydrochlorothiazide, hydrocortisone, ibuprofen, ibuproxam, indinavir, indomethacin, iodinated aromatic x-ray contrast agents such as iodamide, ipratropium bromide, ketoconazole, ketoprofen, ketotifen, ketotifen fumarate, K-strophanthin, labetalol, *lactobacillus* vaccine, lidocaine, lidoflazin, lisuride, lisuride hydrogen maleate, lorazepam, lovastatin, mefenamic acid, melphalan, memantin, mesulergin, metergoline, methotrexate, methyl digoxin, methylprednisolone, metronidazole, metisoprenol, metipranolol, metkephamide, metolazone, metoprolol, metoprolol tartrate, miconazole, miconazole nitrate, minoxidil, misonidazol, molsidomin, nadolol, nafiverine, nafazatrom, naproxen, natural insulins, nesapidil, nicardipine, nicorandil, nifedipine, niludipin, nimodipine, nitrazepam, nitrendipine, nitrocamptothesin, 9-nitrocamptothesin, olanzapine, oxazepam, oxprenolol, oxytetracycline, penicillins such as penicillin G benethamine, penecillin O, phenylbutazone, picotamide, pindolol, piposulfan, piretanide, piribedil, piroxicam, pirprofen, plasminogenici activator, prednisolone, prednisone, pregnenolone, procarbacin, procaterol, progesterone, proinsulin, propafenone, propanolol, propentofyllin, propofol, propranolol, raloxifene, rifapentin, simvastatin, semi-synthetic insulins, sobrerol, somastotine and its derivatives, somatropin, stilamine, sulfinalol hydrochloride, sulfinpyrazone, suloctidil, suprofen, sulproston, synthetic insulins, talinolol, taxol, taxotere, testosterone, testosterone propionate, testosterone undecanoate, tetracane HI, tiaramide HCl, tolmetin, tranilast, triquilar, tromantadine HCl, urokinase, valium, verapamil, vidarabine, vidarabine phosphate sodium salt, vinblastine, vinburin, vincamine, vincristine, vindesine, vinpocetine, vitamin A, vitamin E succinate, and X-ray contrast agents.

In addition, it is also expected that new chemical entities (NCE) and other actives for which the solid dosage forms of the present invention are suitable for delivery of will be created or become commercially available in the future and can be used as the biologically active material.

The biological active material may be an active material that binds to one or more adrenergic receptors. Preferably, the active material that binds to one or more adrenergic receptors is adrenaline (epinephrine), or an adrenaline salt, such as adrenaline bitartrate or adrenaline hydrochloride. Alternatively, the active material that binds to one or more adrenergic receptors may be provided in the form of analogues and compounds related to adrenaline, such as norepinephrine, isoprenaline; or sympathomimetic agents such as tyramine, ephedrine, pseudoephedrine, the amphetamines, salbutamol, and terbutaline.

The biologically active material may be an N-methyl-D-aspartate receptor antagonist. Preferably, the N-methyl-D-aspartate receptor antagonist is chosen from the list comprising: dextromethorphan, dextrorphan or ketamine.

The biologically active material may be a cyclic guanosine monophosphate (cGMP) phosphodiesterase type 5 (PDE5) inhibitor. Preferably, the cyclic guanosine monophosphate (cGMP) phosphodiesterase type 5 (PDE5) inhibitor is sildenafil or a pharmaceutically acceptable salt thereof. Preferably, the sildenafil salt is sildenafil citrate.

Preferably, the solid dosage form is a form selected from the group consisting of: a wafer; tablet; capsule; pill; powder; pellet; granule; and film. The solid dosage form should be adapted to not leave a residue of said dosage form in the oral cavity that is detectable by the patient. Whichever form the solid dosage form is provided in; it should quickly disintegrate in the oral cavity, and allow the rapidly dissolving biologically active material to be absorbed by diffusion through the oral mucosa and directly into the systemic blood circulation system. Preferably, the solid dosage form is a fast dissolving solid dosage form.

Constituents

Preferably, the solid dosage form is substantially free of starch. In a further embodiment of the invention a pharmaceutical composition comprising the solid dosage form is also substantially free of starch. Preferably, the solid dosage form is a fast dissolving solid dosage form.

The precise quantity of biologically active material in the solid dosage form will depend on the type of biologically active material selected. However, the active material is generally present in an amount from 0.02 to 95%, preferably 0.02 to 20% or preferably 0.1 to 75%, 1 to 45% by dry weight of the dosage form.

The biologically active material may be generally present in the solid dosage form in an amount selected from the group consisting of: 5 mg; 10 mg; 15 mg; 20 mg; 25 mg; 30 mg; 35 mg, 40 mg, 45 mg, 50 mg, 60 mg and 100 mg.

Preferably, the solid dosage form of the present invention also comprises at least one matrix forming agent.

In the freeze-dried systems of the prior art, gelatine is the most commonly used carrier or structure forming agent due to its wall-forming ability. Gelatine is a water soluble polymer, and as such, when mixed with active pharmaceutical ingredients in water, the increasing viscosity of the solution over time may cause a decreasing solubility of poorly soluble drugs in the mixture, and lead to a suspension of the drug in gelatine matrix. This can cause phase separation to occur; and the drug in amorphous or crystalline forms may not be homogenously dispersed in the matrix, which will eventually affect the dissolution and absorption of the final product. Therefore, preferably gelatine is not present in the solid dosage form of the present invention.

The effectiveness of the solid dosage form of the present invention relies on the biologically active material dissolving in a small volume of fluid, such as in the oral cavity, prior to absorption into the systemic circulation. Therefore, the rate of dissolution of the dosage form is important. In a preferred embodiment of the present invention, the solid dosage form comprises a super-disintegrant as at least one matrix forming material.

Other polymer materials suitable for forming a matrix may be selected for specific application in the solid dosage form, especially for site-specific drug delivery system such as in the oral cavity. Matrix forming agents of the present invention may be selected from the group consisting of: non-mammalian gelatine, dextrin, soy protein, wheat protein, psyllium seed protein, acacia gum, guar gum, agar gum, xanthin gum, polysaccharides; alginates; sodium carboxymethylcellulose; carrageenans; dextrans; pectins; sugars; amino acids; starch; modified starches; carboxymethylcellulose; hydroxypropylmethylcellulose; hydroxypropyl cellulose and methyl cellulose inorganic salts; synthetic polymers; amylopectin, polypeptide/protein or poly-saccharide complexes.

The matrix forming material in the solid dosage form may be a carbohydrate. Preferably, the carbohydrate is selected from the group consisting of: mannitol; dextrose; lactose; galactose; trehalose; and cyclodextrin.

In a highly preferred embodiment, at least one matrix forming agent in the solid dosage form is glycine. Glycine is an amino acid with excellent wetting properties and is suitable for the fast dissolving formulation. Low amounts of glycine may be used in the formulation of the present invention to control the dissolution rate of the dosage form. Furthermore, glycine may also be used as an anti-collapsing agent, which maintains the dosage form from shrinking either during the manufacture process or after packing. In one embodiment, the glycine is present in the dosage form of the present invention in an amount from 0.2 to 7.5%, more preferably from about 0.5% to about 5% dry weight of the dosage form. Preferably, the glycine is present in an amount from 0.5 to 5 weight % by dry weight of the composition of the dosage form.

In a highly preferred embodiment, at least one matrix forming agent in the solid dosage form is sodium carboxymethylcellulose. When at least one matrix forming agent is sodium carboxymethylcellulose, the polymer is present in a concentration of from about 0.1% to about 19% by dry weight of the solid dosage form. In a preferred embodiment the sodium carboxymethylcellulose is present in an amount of about 0.1% to about 15% by dry weight of the dosage form. In a highly preferred embodiment of the present invention, the sodium carboxymethylcellulose is present in an amount of about 0.1% to about 1.0% by dry weight of the solid dosage form. Preferably, the sodium carboxymethylcellulose is present in an amount by dry weight of the composition of the dosage form selected from the group consisting of: 0.05% to 19%; 0.1% to 15%; and 0.1% to 10%.

In another embodiment of the present invention, the dosage form comprises amylopectin as at least one matrix forming agent. Amylopectin is capable of increasing the release of the biologically active agent by promoting formulation disintegration. Amylopectin may be present in the dosage form at a concentration about 2% up to no great than 20% by dry weight of the solid dosage form. Amylopectin may be present in an amount of about 2% to about 17% dry weight of the dosage form. Preferably, amylopectin is present in an amount by dry weight of the composition of the dosage form selected from the group consisting of: 2% to 17%; and 2% to 15%.

According to another embodiment of the invention, the solid dosage form may include a matrix forming agent such as mannitol. Mannitol is a component that may aid in the crystalline structure and impart hardness of the dosage form. When mannitol is present in the dosage form, it occurs in a concentration of from about 5% to about 80%, preferably from about 10% to about 60%, and most preferably from about 10% to about 50% by dry weight of the dosage form.

The solid dosage form may contain an inorganic salt. Preferably, the inorganic salt is selected from the group consisting of: sodium phosphate; sodium chloride; and aluminium silicates.

The solid dosage form of the invention may contain an amino acid. Preferably, the amino acid is selected from the group consisting of: glycine; L-alanine; L-aspartic acid; L-glutamic acid; L-hydroxyproline; L-isoleucine; L-leucine; and L-phenylalanine.

The solid dosage form of the invention may also preferably be substantially free of starch.

To achieve a rapid dissolution of biologically active materials from the solid dosage form of the invention, diluents may be added as at least one matrix forming material. Diluents include microcrystalline cellulose (e.g., Avicel PH 101® and Avicel PH 102®), lactose, starch and sorbitol. These diluents may be present in the dosage form either alone or as a mixture in different ratios, and may be about 1% to about 80%, preferably about 2% to about 50%, either individually or cumulatively.

In one embodiment of the present invention, the solid dosage form comprises microcrystalline cellulose as the at least one matrix forming agent. Microcrystalline cellulose may act as a filler and binder in the dosage form of the present invention. Microcrystalline cellulose has the ability to compact with minimum compression pressures, and results in a hard, stable dosage form, preferably one that is fast dissolving. Due to its large surface area and high internal porosity, microcrystalline cellulose is able to absorb and retain large amounts of water, which is desirable in the dosage form of the invention. When the solid dosage form of the present invention comprises microcrystalline cellulose, it is present in an amount of about 1% to about 10%, and preferably from about 1% to about 8% by dry weight of the dosage form.

The solid dosage form or the pharmaceutical composition of the invention may preferably be substantially free of Avicel.

In another preferred embodiment, the solid dosage form comprises at least one lubricant. The dosage form of the present invention may include lubricants such as polyethylene glycol (PEG) 1000, 2000, 4000 and 6000, sodium lauryl sulphate, fats or oils. One advantage of the use of these lubricants is to aid in the removal of the dosage form from the mould. These lubricants may be present in the dosage form either alone or as a mixture in different ratios, and may be between 0.05% to 5%, preferable between 0.1% and 2%, preferable about 1.5%, either individually or cumulatively. In one embodiment, the composition includes between 0.05% to 5% polyethylene glycol 2000, preferably between 0.1% and 2% polyethylene glycol 2000, preferably about 1.5% polyethylene glycol 2000 by dry weight of the dosage form, or as mixtures of the various glycols. Alternatively, the PEG 2000 can be replaced by PEG 1000.

In another preferred embodiment, the solid dosage form comprises at least one buffer reagent. Preferably, the buffer reagent in the solid dosage form provides a saliva pH1 of 7.0 to 7.8 when dissolved in the oral cavity. Such buffer reagents may improve the sublingual absorption of weak base compounds. The solid buffer reagent may be selected from the group comprising: sodium dihydrogen phosphate dehydrate, sodium hydrogen phosphate, sodium hydrogen carbonate and sodium carbonate, which may be present in the dosage form either alone or as a mixture in different ratios in a concentration of about 0.01% to about 10% by weight of the composition.

Alternatively, the solid buffer reagent may be chosen from the list comprising: alginic acid, ascorbic acid, citric acid, malic acid, succinic acid and tartaric acid, which may be present in the dosage form either alone or as a mixture in different ratios in a concentration of about 0.01% to about 10% by weight of the composition. Preferably, the buffer reagent is citric acid, which may be present in a concentration of about 0.01% to about 10% by weight of the solid dosage form, more preferably between 0.1% and 5%, most preferably about 2.0%.

For example, if the biologically active material in the solid dosage form is sildenafil, the molecular structure of sildenafil has both weakly acid centre and weakly basic centre. It means sildenafil solubility in water is affected by the solution pH value and the two optimum pH (pHmax) values are 4.5 and 10.24. Therefore, to improve transmucosal absorption of sildenafil, the solid dosage form may comprise a solid buffer reagent that produces a saliva pH of 5.0 to 6.0 when dissolved in oral cavity. Increasing the pH of the solution of sildenafil can decrease the ratio of unionized to ionized particles, which will lead to enhanced transmucosal absorption.

Preferably, the buffer reagent is sodium carbonate, which may be present in a concentration of about 0.01% to about 10% by weight of the solid dosage form, more preferably between 0.1% to 1%, most preferably about 0.3% or 0.5% of the solid dosage form.

The solid dosage form may, in certain embodiments, include at least one absorption enhancer. The absorption enhancer may be a polysaccharide and may be positively charged. Preferably, the absorption enhancer is β-cyclodextrin or its derivatives. The β-cyclodextrin or derivative may be present in a concentration of from about 0.01% to about 10% by dry weight of the dosage form, preferably between 0.2% to 2%, and most preferably about 1%. Alternatively, the at least one absorption enhancer may comprise glyceryl trinitrate (also known as GTN or nitroglycerin) or a derivative thereof. The glyceryl trinitrate or derivative may be present in a concentration of from about 0.01% to about 20% by dry weight of the dosage form, more preferably between 0.2% to 4%, and most preferably about 2%.

The solid dosage form of the present invention may comprise flocculating agents to maintain even disbursement of the biologically active material in the matrix during the manufacture process. The flocculating agent may be gums. Preferable, the gum is xanthan gum. The xanthan gum may be present in a concentration of about 0.01% to about 10% by dry weight of the solid dosage form, preferably from about 0.2% to 2%, and most preferably about 1%.

In another preferred embodiment, the solid dosage form comprises at least one surfactant. To aid dissolution of the biologically active material into an aqueous environment such as the oral cavity, a surfactant may be added to the solution as a wetting agent. Suitable surfactants include anionic detergents such as sodium lauryl sulfate, dioctyl sodium sulfosuccinate and dioctyl sodium sulfonate. Cationic detergents may be used and include benzalkonium chloride or benzethomium chloride. The list of possible non-ionic detergents includes lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants may be present in the dosage form either alone or as a mixture in different ratios. Preferably, the surfactant aids in creating a fast dissolving solid dosage form.

Additives which potentially enhance uptake of the biologically active materials may also be present in the solid dosage form. Such additives may be selected from the list comprising: fatty acids such as oleic acid, linoleic acid and linolenic acid.

In order to enhance the aesthetic and taste appeal of the solid dosage form to the subject, the dosage form may also contain at least one additive, such as a colouring agent or flavouring agent. The colouring agent may preferably be FD&C dyes Blue No. 2 and Red No. 40; the flavouring agent may be chosen from the list comprising: orange, mint, raspberry and caramel, and/or sweeteners such as aspartame and saccharin, or a mixture of two or more flavouring agents.

Thus, in a highly preferred embodiment, the present invention provides a solid dosage form adapted for the release of a biologically active material in the oral cavity wherein the dosage form comprises:
(a) at least one biologically active material and
(b) at least one matrix forming agent,
wherein the dosage form substantially dissolves in the oral cavity; wherein the dosage form comprises 0.29% sodium carbonate, 0.59% sodium carboxymethylcellulose, 1.48% PEG 2000, 2.97% glycine, 5.93% microcrystalline cellulose; 14.84% amylopectin, 29.67% lactose and 44.23% mannitol as a dry weight of the solid dosage form; and which does not result in substantial detectable levels of residue left over in the oral cavity of the patient. Preferably, the solid dosage form is a fast dissolving solid dosage form. PEG 2000 could be replaced with PEG 1000 with the same advantages as the oral dosage form described above.

Preferably, the biologically active material in the solid dosage form of the present invention is chosen from the list comprising: at least one cyclic guanosine monophosphate (cGMP) phosphodiesterase type 5 (PDE5) inhibitor, an active material that binds to one or more adrenergic receptors, and an N-methyl-D-aspartate receptor antagonist. Preferably, the N-methyl-D-aspartate receptor antagonist is chosen from the list comprising: dextromethorphan, dextrorphan or ketamine. Preferably, the active material that binds to one or more adrenergic receptors is adrenaline, or an adrenaline salt. Preferably, the cyclic guanosine monophosphate (cGMP) phosphodiesterase type 5 (PDE5) inhibitor is sildenafil or a pharmaceutically acceptable salt thereof. Preferably, the sildenafil salt is sildenafil citrate.

Carriers and Excipients

As discussed above, the solid dosage forms of the present invention may include one or more pharmaceutically acceptable carriers. The use of such pharmaceutically acceptable carriers for the manufacture of medicaments such as solid dosage forms, including fast dissolving solid dosage forms, is well known in the art. Except insofar as any conventional pharmaceutically acceptable carrier is incompatible with the biologically active material, use thereof in the manufacture of a solid dosage form according to the invention is contemplated.

Pharmaceutical acceptable carriers according to the invention may include one or more of the following examples:
(1) surfactants and polymers, including, however not limited to polyethylene glycol (PEG), polyvinylpyrrolidone, polyvinylalcohol, crospovidone, polyvinylpyrrolidone-polyvinylacrylate copolymer, cellulose derivatives, hydroxypropylmethyl cellulose, hydroxypropyl cellulose, carboxymethylethyl cellulose, hydroxypropylmethyl cellulose phthalate, polyacrylates and polymethacrylates, urea, sugars, polyols, and their polymers, emulsifiers, sugar gum, starch, organic acids and their salts, vinyl pyrrolidone and vinyl acetate; and/or
(2) binding agents such as various celluloses and cross-linked polyvinylpyrrolidone, microcrystalline cellulose; and/or
(3) filling agents such as lactose monohydrate, lactose anhydrous, mannitol, microcrystalline cellulose and various starches; and/or
(4) lubricating agents such as agents that act on the flowability of the powder to be compressed, including colloidal silicon dioxide, talc, stearic acid, magnesium stearate, calcium stearate, silica gel; and/or
(5) sweeteners such as any natural or artificial sweetener including sucrose, xylitol, sodium saccharin, cyclamate, aspartame, and acesulfame K; and/or
(6) flavouring agents; and/or
(7) preservatives such as potassium sorbate, methylparaben, propylparaben, benzoic acid and its salts, other esters of parahydroxybenzoic acid such as butylparaben, alcohols such as ethyl or benzyl alcohol, phenolic chemicals such as phenol, or quaternary compounds such as benzalkonium chloride; antioxidants such as ascorbic acid, potassium sorbate, sodium bisulfate sodium metabisulfite and sorbic acid; and/or
(8) buffers; and/or
(9) diluents such as pharmaceutically acceptable inert fillers, such as microcrystalline cellulose, lactose, dibasic calcium phosphate, saccharides, and/or mixtures of any of the foregoing; and/or
(10) wetting agents such as corn starch, potato starch, maize starch, and modified starches, croscarmellose sodium, crospovidone, sodium starch glycolate, and mixtures thereof; and/or
(11) disintegrants; and/or
(12) effervescent agents such as effervescent couples such as an organic acid (e.g., citric, tartaric, malic, fumaric, adipic, succinic, and alginic acids and anhydrides and acid salts), or a carbonate (e.g. sodium carbonate, potassium carbonate, magnesium carbonate, sodium glycine carbonate, L-lysine carbonate, and arginine carbonate) or bicarbonate (e.g. sodium bicarbonate or potassium bicarbonate);
(13) absorption enhancer such as glyceryl trinitrate; and/or
(14) other pharmaceutically acceptable excipients.

In another embodiment, more than one biologically active material may be combined into the solid dosage form of the present invention. In one example, if the biologically active material is adrenaline, a fast dissolving solid dosage form may be achieved which provides for different release characteristics—early release from adrenaline, and later release from a larger average size adrenaline.

Solid dosage forms of the invention suitable for use in animals, and in particular in human beings, typically must be sterile and stable under the conditions of manufacture and storage. The solid dosage forms of the invention comprising the biologically active material can be formulated as a solid, a liposome, or other ordered structures suitable to high drug concentration adapted for oral delivery.

Actual dosage strengths of the biologically active material in the solid dosage form of the invention may be varied in accordance with the nature of the biologically active material, as well as the potential increased efficacy due to the advantages of providing and administering the biologically active material. Thus as used herein "therapeutically effective amount" will refer to an amount of biologically active material required to effect a therapeutic response in a subject. Amounts effective for such a use will depend on: the desired therapeutic effect; the potency of the biologically active material; the desired duration of treatment; the stage and severity of the disease being treated; the weight and general state of health of the patient; and the judgment of the prescribing physician.

For example, if adrenaline is the biologically active material in the solid dosage form of the invention, the actual dosage strengths of the adrenaline may be varied in accordance the nature of the anti-allergic/anti-anaphylaxis, as well as the potential increased efficacy due to the advantages of providing and administering the antiallergic.

The solid dosage forms of the invention are orally administered to a subject. Solid dosage forms for oral administration include wafers, capsules, tablets, pills, powders, pellets, films and granules. Preferably, the solid dosage form is administered sub-lingually. Preferably, the solid dosage form is a fast dissolving solid dosage form.

Incorporating any of the normally employed excipients, such as those previously listed, and generally 0.1% to 95% of the biologically active material, and more preferably 0.1% to 75% of the material, will form a pharmaceutically acceptable non-toxic solid dosage form for oral administration.

Although the solid dosage form of the present invention may be administered as a wafer, tablet, capsule; pill; powder; pellet; granule; or film, the oral dosage form of the present invention is also suitable for use with a nebulizer, either jet or ultrasonic, and will typically comprise the solid dosage form suspended in water. The dosage form of the present invention may also include a buffer and a simple sugar (e.g., for protein stabilization and regulation of osmotic pressure). The nebulizer formulation may also contain a surfactant, to reduce or prevent surface induced aggregation of the compounds caused by atomization of the solution in forming the aerosol. Preferably, the solid dosage form is a fast dissolving solid dosage form.

The nebulized solid dosage form should preferably not leave a residue of said dosage form in the oral cavity that is detectable by the patient. The rapidly dissolving biologically active material in the nebulized dosage form should quickly be absorbed by diffusion through the oral mucosa and directly into the systemic blood circulation system.

According to another aspect of the present invention, there is provided a solid dosage form adapted for the release of an active material that binds to one or more adrenergic receptors in the oral cavity wherein the dosage form comprises:
  (a) an active material that binds to one or more adrenergic receptors, and
  (b) at least one matrix forming agent,
wherein the dosage form substantially dissolves in the oral cavity. Preferably, the solid dosage form is a fast dissolving solid dosage form. Preferably, the active material that binds to one or more adrenergic receptors is adrenaline, or an adrenaline salt. Alternatively, the adrenaline may be provided in the form of analogs and compounds related to adrenaline, such as norepinephrine, isoprenaline; or sympathomimetic agents such as tyramine, ephedrine, pseudoephedrine, the amphetamines, salbutamol, and terbutaline.

In one embodiment, the active material that binds to one or more adrenergic receptors, such as adrenaline, is present in an amount by dry weight of the solid dosage form selected from the group consisting of: 0.01 to 95%; 0.1 to 75% and 1 to 45%.

In another embodiment, the dosage form comprises:
  (a) 0.01 to 95 (dry) weight % of an active material that binds to one or more adrenergic receptors;
  (b) between 2 to 17% (dry) weight % of amylopectin;
  (c) between 0.01 to 50) (dry) weight % of at least one matrix forming agent;
  (d) between 0.01 to 40 (dry) weight % of a filling agent;
  (e) between 0.01 to 10 (dry) weight % of an amino acid; and
  (f) between 0.01 to 20 (dry) weight % of a glycol/surfactant
  (g) between 0.01 to 60 (dry) weight % carbohydrate;
  (h) between 0.1 to 1 (dry) weight % of a solid buffer reagent;
  (i) between 0.01 to 20 (dry) weight % of a absorption enhancer In a highly preferred embodiment, the present invention provides a solid dosage form adapted for the release of an active material that binds to one or more adrenergic receptors, such as adrenaline, in the oral cavity wherein the dosage form comprises:
  (a) an active material that binds to one or more adrenergic receptors; and
  (b) at least one matrix forming agent,
wherein the dosage form substantially dissolves in the oral cavity, wherein the dosage form comprises 0.25% sodium carbonate, 0.50% sodium carboxymethylcellulose, 1.25% PEG 2000, 2.49% glycine, 2.49% microcrystalline cellulose; 12.49% amylopectin, 24.98% lactose, 2.00% glyceryl trinitrate and 37.46% mannitol as a dry weight of the solid dosage form, and which does not result in substantial detectable levels of residue left over in the oral cavity of the patient. Preferably, the solid dosage form is a fast dissolving solid dosage form.

In another embodiment, the dosage form comprises a quantity of an active material that binds to one or more adrenergic receptors, such as adrenaline, selected from the group consisting of: 5 mg; 10 mg; 15 mg; 20 mg; 25 mg; 30 mg; 35 mg, 40 mg, 45 mg, 50 mg, 60 mg and 100 mg.

According to another aspect of the present invention, there is provided a solid dosage form adapted for the release of at least one cyclic guanosine monophosphate (cGMP) phosphodiesterase type 5 (PDE5) inhibitor in the oral cavity wherein the dosage form comprises:
  (a) at least one cyclic guanosine monophosphate (cGMP) phosphodiesterase type 5 (PDE5) inhibitor, and
  (b) at least one matrix forming agent,
wherein the dosage form substantially dissolves in the oral cavity. Preferably, the solid dosage form is a fast dissolving solid dosage form. Preferably, the cyclic guanosine monophosphate (cGMP) phosphodiesterase type 5 (PDE5) inhibitor is sildenafil or a pharmaceutically acceptable salt thereof. Preferably, the sildenafil salt is sildenafil citrate.

In one embodiment, the at least one cyclic guanosine monophosphate (cGMP) phosphodiesterase type 5 (PDE5) inhibitor is present in an amount by dry weight of the solid dosage form selected from the group consisting of: 0.01 to 95%; 0.1 to 75% and 1 to 45%.

In another embodiment, the dosage form comprises:
  (a) 0.01 to 95 (dry) weight % of at least one cyclic guanosine monophosphate (cGMP) phosphodiesterase type 5 (PDE5) inhibitor;
  (b) between 2 to 17% (dry) weight % of amylopectin;
  (c) between 0.01 to 50) (dry) weight % of at least one matrix forming agent;
  (d) between 0.01 to 40 (dry) weight % of a filling agent;
  (e) between 0.01 to 10 (dry) weight % of an amino acid; and
  (f) between 0.01 to 20 (dry) weight % of a glycol/surfactant
  (g) between 0.01 to 60 (dry) weight % carbohydrate;
  (h) between 0.1 to 1 (dry) weight % of a solid buffer reagent;
  (i) between 0.01 to 20 (dry) weight % of a absorption enhancer In a highly preferred embodiment, the present invention provides a solid dosage form adapted for the release of at least one cyclic guanosine monophosphate (cGMP) phosphodiesterase type 5 (PDE5) inhibitor in the oral cavity wherein the dosage form comprises:
  (a) at least one cyclic guanosine monophosphate (cGMP) phosphodiesterase type 5 (PDE5) inhibitor, and
  (b) at least one matrix forming agent, wherein the dosage form substantially dissolves in the oral cavity, wherein the dosage form comprises 0.29% sodium carbonate, 0.59% sodium carboxymethylcellulose, 1.48% PEG 2000, 2.97% glycine, 5.93% microcrystalline cellulose; 14.84% amylopectin, 29.67% lactose, and 44.23% mannitol as a dry weight of the solid dosage form, and which does not result in substantial detectable levels of residue left over in the oral cavity of the patient. Preferably, the solid dosage form is a fast dissolving solid dosage form.

In another embodiment, the dosage form comprises a quantity of at least one cyclic guanosine monophosphate (cGMP) phosphodiesterase type 5 (PDE5) inhibitor selected from the group consisting of: 5 mg; 10 mg; 15 mg; 20 mg; 25 mg; 30 mg; 35 mg, 40 mg, 45 mg, 50 mg, 60 mg and 100 mg.

According to another aspect of the present invention, there is provided a solid dosage form adapted for the release of an N-methyl-D-aspartate receptor antagonist in the oral cavity wherein the dosage form comprises:
  (a) an N-methyl-D-aspartate receptor antagonist, and
  (b) at least one matrix forming agent,
wherein the dosage form substantially dissolves in the oral cavity. Preferably, the solid dosage form is a fast dissolving solid dosage form. Preferably, the N-methyl-D-aspartate receptor antagonist is chosen from the list comprising: dextromethorphan, dextrorphan or ketamine.

In one embodiment, the N-methyl-D-aspartate receptor antagonist is present in an amount by dry weight of the solid dosage form selected from the group consisting of: 0.01 to 95%; 0.1 to 75% and 1 to 45%.

In another embodiment, the dosage form comprises:
  (a) 0.01 to 95 (dry) weight % of an N-methyl-D-aspartate receptor antagonist;
  (b) between 2 to 17% (dry) weight % of amylopectin;
  (c) between 0.01 to 50) (dry) weight % of at least one matrix forming agent;
  (d) between 0.01 to 40 (dry) weight % of a filling agent;
  (e) between 0.01 to 10 (dry) weight % of an amino acid; and
  (f) between 0.01 to 20 (dry) weight % of a glycol/surfactant
  (g) between 0.01 to 60 (dry) weight % carbohydrate;
  (h) between 0.1 to 1 (dry) weight % of a solid buffer reagent;
  (i) between 0.01 to 20 (dry) weight % of a absorption enhancer In a highly preferred embodiment, the present invention provides a solid dosage form adapted for the release of an N-methyl-D-aspartate receptor antagonist in the oral cavity wherein the dosage form comprises:
  (a) an N-methyl-D-aspartate receptor antagonist; and
  (b) at least one matrix forming agent,
wherein the dosage form substantially dissolves in the oral cavity, wherein the dosage form comprises 0.25% sodium carbonate, 0.50% sodium carboxymethylcellulose, 1.25% PEG 2000, 2.49% glycine, 2.49% microcrystalline cellulose; 12.49% amylopectin, 24.98% lactose, and 37.46% mannitol as a dry weight of the solid dosage form, and which does not result in substantial detectable levels of residue left over in the oral cavity of the patient. Preferably, the solid dosage form is a fast dissolving solid dosage form.

In another embodiment, the dosage form comprises an N-methyl-D-aspartate receptor antagonist selected from the group consisting of: 5 mg; 10 mg; 15 mg; 20 mg; 25 mg; 30 mg; 35 mg, 40 mg, 45 mg, 50 mg, 60 mg and 100 mg.

In another embodiment, the solid dosage form provides reduced burning, irritation and/or discomfort on administration and/or swallowing compared to convention dosage forms.

In another embodiment, the dosage form is adapted for delivery via the oral cavity mucosa and into the systemic blood circulation system.

According to another aspect of the present invention there is provided a wafer comprising a solid dosage form adapted for the release of a biologically active material in an oral cavity. Preferably, the solid dosage form wafer is a fast dissolving solid dosage form wafer. Preferably, the biologically active material is chosen from the list comprising: at least one cyclic guanosine monophosphate (cGMP) phosphodiesterase type 5 (PDE5) inhibitor, an active material that binds to one or more adrenergic receptors and an N-methyl-D-aspartate receptor antagonist. Preferably, the N-methyl-D-aspartate receptor antagonist is chosen from the list comprising: dextromethorphan, dextrorphan or ketamine. Preferably, the cyclic guanosine monophosphate (cGMP) phosphodiesterase type 5 (PDE5) inhibitor is sildenafil or a pharmaceutically acceptable salt thereof. Preferably, the sildenafil salt is sildenafil citrate. Preferably, the active material that binds to one or more adrenergic receptors is adrenaline, or an adrenaline salt. The wafer may be accompanied by instructions for its use.

Preferably, the solid dosage form wafer substantially dissolves once placed in the oral cavity in a time period selected from the group consisting of: less than 2 minutes, less than 1 minute, less than 50 seconds, less than 40 seconds, less than 30 seconds, less than 20 seconds, less than 15 seconds, less than 10 seconds, less than 7.5 seconds, less than 5 seconds, less than 4 seconds, less than 3 seconds, less than 2 seconds after administration of the dosage form. Preferably, the solid dosage form wafer is a fast dissolving solid dosage form wafer.

More preferably, the solid dosage form wafer completely dissolves once placed in the oral cavity in a time period selected from the group consisting of: less than 2 minutes; less than 1 minute; less than 50 seconds; less than 40 seconds; less than 30 seconds; less than 20 seconds; less than 15 seconds; less than 10 seconds; less than 7.5 seconds; less than 5 seconds; less than 4 seconds; less than 3 seconds; and less than 2 seconds after administration of the dosage form. Preferably, the solid dosage form wafer is a fast dissolving solid dosage form wafer.

Further features of the invention provide for a solid dosage form wafer according to the invention, wherein said dosage form substantially dissolves in the oral cavity without leaving a residue of said dosage form in the oral cavity that is detectable by a subject. Preferably, the solid dosage form wafer completely dissolves after oral, preferably sublingual, administration to the patient. As such, the subject has no urge to swallow the wafer dosage form and thus the biologically active material bypasses the gastrointestinal tract and the hepatic first-pass effect and is absorbed directly into the systemically circulating blood. Preferably, the solid dosage form wafer is a fast dissolving solid dosage form wafer.

Pharmaceutical Composition

The present invention also provides a pharmaceutical composition comprising the solid dosage form of the invention. Preferably, the solid dosage form is a fast dissolving solid dosage form.

The pharmaceutical composition of the present invention can be formulated to additionally contain conventional additives or supplementary ingredients in the usual amounts of such materials. The composition can be in the form of a solid, a liposome, or other ordered structures suitable to high drug concentration adapted for oral delivery. Preferably the pharmaceutical composition is formulated to dissolve rapidly in the oral environment.

The composition may, in one embodiment, be formulated to be substantially free of preservatives, physiological or mucosal absorption enhancers, or propellants. The composition may, in an alternative embodiment, be formulated to contain preservatives, physiological or mucosal absorption enhancers, or propellants.

Method

According to a further aspect of the present invention, there is provided a method to produce the solid dosage form of the present invention comprising the steps of:
a) combining at least one matrix forming agent with a biologically active material to form a mixture; and
b) freeze drying the mixture to form the solid dosage form.

Preferably, the solid dosage form is a fast dissolving solid dosage form.

There is also provided a method of producing the solid dosage form of the invention, comprising the steps of:
a) combining at least one matrix forming agent with an active material that binds to one or more adrenergic receptors to form a homogeneous mixture; and
b) freeze drying the mixture to form the solid dosage form.

Preferably, the solid dosage form is a fast dissolving solid dosage form.

There is also provided a method of producing the solid dosage form of the invention, comprising the steps of:
a) combining at least one matrix forming agent with at least one cyclic guanosine monophosphate (cGMP) phosphodiesterase type 5 (PDE5) inhibitor to form a homogeneous mixture; and
b) freeze drying the mixture to form the solid dosage form.
c) Preferably, the solid dosage form is a fast dissolving solid dosage form.

There is also provided a method of producing the solid dosage form of the invention, comprising the steps of:
a) combining at least one matrix forming agent with an N-methyl-D-aspartate receptor antagonist to form a homogeneous mixture; and
b) freeze drying the mixture to form the solid dosage form.

Preferably, the solid dosage form is a fast dissolving solid dosage form.

Preferably, the method provides an oral solid dosage form wherein said dosage form substantially dissolves in the oral cavity without leaving a residue of said dosage form in the oral cavity that is detectable by a subject. Preferably, the solid dosage form is a fast dissolving solid dosage form.

Preferably, the method according to the invention produces a solid dosage form which substantially dissolves once placed in the oral cavity in a time period selected from the group consisting of: less than 2 minutes, less than 1 minute, less than 50 seconds, less than 40 seconds, less than 30 seconds, less than 20 seconds, less than 15 seconds, less than 10 seconds, less than 7.5 seconds, less than 5 seconds, less than 4 seconds, less than 3 seconds, less than 2 seconds after administration.

More preferably, the solid dosage form completely dissolves once placed in the oral cavity in a time period selected from the group consisting of: less than 2 minutes; less than 1 minute; less than 50 seconds; less than 40 seconds; less than 30 seconds; less than 20 seconds; less than 15 seconds; less than 10 seconds; less than 7.5 seconds; less than 5 seconds; less than 4 seconds; less than 3 seconds; and less than 2 seconds after administration of the dosage form.

In a preferred embodiment of the present invention, the mixture comprising the matrix forming agent and the biologically active material is measured (by weight or volume) into a preformed plastic or aluminium blister mould (individual dose). The blister mould is placed into a freeze dryer for 24 hours and the resultant fast dissolving solid dosage form is then sealed with aluminium or plastics foil to prevent moisture absorption. Preferably, the freeze drying technique is used to remove the solvent from the blister mould. Sealing the solid dosage form into the plastic or aluminium foil prevents or reduces moisture absorption.

Preferably, the method of the present invention forms a solid dosage form that is a wafer. Preferably, the solid dosage form wafer is a fast dissolving solid dosage form wafer.

In one embodiment of the present invention, the method may require that the pH of the mixture is adjusted to a pH within the range of between 3.0 and 8.0, preferably between 6.4 and 7.8. If required, the pH may be adjusted by using an acid, such as hydrochloric acid, phosphoric acid or citric acid; or a basic compound such as sodium hydroxide, sodium dihydrogen phosphate dehydrate, sodium hydrogen phosphate, sodium hydrogen carbonate and sodium carbonate.

In another embodiment, the method may include the step of using a solvent, such as water. If water is used as a solvent, it is preferable to be removed by freeze drying.

Kits

The present invention also provides a kit comprising a solid dosage form of the invention and instructions for its use.

In a further aspect of the present invention, there is provided a kit comprising:
a) the solid dosage form, wherein the dosage form comprises:
(i) at least one biologically active material, and
(ii) at least one matrix forming agent, and
b) instructions for its use
wherein the dosage form substantially dissolves in the oral cavity. Preferably, the solid dosage form is a fast dissolving solid dosage form.

Preferably, the biologically active material is chosen from the list comprising: at least one cyclic guanosine monophosphate (cGMP) phosphodiesterase type 5 (PDE5) inhibitor, an active material that binds to one or more adrenergic receptors, and an N-methyl-D-aspartate receptor antagonist. Preferably, the N-methyl-D-aspartate receptor antagonist is chosen from the list comprising: dextromethorphan, dextrorphan or ketamine. Preferably, the active material that binds to one or more adrenergic receptors is adrenaline, or an adrenaline salt. Preferably, the cyclic guanosine monophosphate (cGMP) phosphodiesterase type 5 (PDE5) inhibitor is sildenafil or a pharmaceutically acceptable salt thereof. Preferably, the sildenafil salt is sildenafil citrate.

Method of Treatment

Therapeutic uses of the solid dosage forms of the invention include pain relief, anti-inflammatory activity, migraine treatment, asthma treatment, and treatment of other disorders that require the biologically active material to be administered with a high bioavailability and rapid activity.

The present invention therefore provides a method of treating a disease or disorder in a patient comprising the step of: administering to the patient a pharmaceutical composition comprising the solid dosage form of the invention. Preferably, the solid dosage form is a fast dissolving solid dosage form.

One of the main areas when rapid bioavailability of a biologically active material is required is in the relief of pain. The minor analgesics, such as cyclo-oxygenase inhibitors (aspirin related drugs) or opioids may be prepared as medicaments according to the present invention. Alternatively, N-methyl-D-aspartate receptor antagonists may be used for pain relief and anaesthetics. Preferably, the N-methyl-D-aspartate receptor antagonist is chosen from the list comprising: dextromethorphan, dextrorphan or ketamine. The N-methyl-D-aspartate receptor antagonist may also be administered for the purpose of depression treatment, addiction treatment.

The invention therefore provides a method for providing pain relief, comprising the step of: administering to the patient a pharmaceutical composition comprising the solid dosage form of the invention comprising an N-methyl-D-aspartate receptor antagonist.

The invention also provides a method for providing anaesthesia, comprising the step of: administering to the patient a pharmaceutical composition comprising the solid dosage form of the invention comprising an N-methyl-D-aspartate receptor antagonist. Preferably, the N-methyl-D-aspartate receptor antagonist is chosen from the list comprising: dextromethorphan, dextrorphan or ketamine.

The invention also provides a method of treating depression, comprising the step of: administering to the patient a pharmaceutical composition comprising the solid dosage form of the invention comprising an N-methyl-D-aspartate receptor antagonist. Preferably, the N-methyl-D-aspartate receptor antagonist is chosen from the list comprising: dextromethorphan, dextrorphan or ketamine.

The invention also provides a method of treating addiction, comprising the step of: administering to the patient a pharmaceutical composition comprising the solid dosage form of the invention comprising an N-methyl-D-aspartate receptor antagonist. Preferably, the N-methyl-D-aspartate receptor antagonist is chosen from the list comprising: dextromethorphan, dextrorphan or ketamine.

The N-methyl-D-aspartate receptor antagonist may also be administered for the purpose of treating an epileptic seizure. In one embodiment the epileptic seizure is caused by epilepsy. In a further embodiment, the epilepsy is selected from the group consisting of: benign Rolandic epilepsy, frontal lobe epilepsy, infantile spasms, juvenile myoclonic epilepsy, juvenile absence epilepsy, childhood absence epilepsy (pyknolepsy), hot water epilepsy, Lennox-Gastaut syndrome, Landau-Kleffner syndrome, Dravet syndrome, progressive myoclonus epilepsies, reflex epilepsy, Rasmussen's syndrome, temporal lobe epilepsy, limbic epilepsy, status epilepticus, abdominal epilepsy, massive bilateral myoclonus, catamenial epilepsy, Jacksonian seizure disorder, Lafora disease, and photosensitive epilepsy. In a further embodiment, the epileptic seizure is selected from the group consisting of: nonconvulsive status epilepticus and convulsive status epilepticus.

The invention therefore provides a method of treating an epileptic seizure, comprising the step of: administering to the patient a pharmaceutical composition comprising the solid dosage form of the invention comprising an N-methyl-D-aspartate receptor antagonist. Preferably, the N-methyl-D-aspartate receptor antagonist is chosen from the list comprising: dextromethorphan, dextrorphan or ketamine.

Treatment of cardiovascular disease may also benefit from biologically active materials in a solid dosage form according to the invention, such as treatment of angina pectoris and, in particular, molsidomine may benefit from improved bioavailability. In another example, adrenaline may be administered as a solid dosage form for therapy of acute cardiovascular events such as cardiac arrest or cardiac dysrhythmia. Alternatively, other active materials that bind to one or more adrenergic receptors, such as noradrenaline, may be used in the solid dosage form for the treatment of cardiovascular events.

Other therapeutic uses for biologically active materials in a solid dosage form according to the present invention include treatment of hair loss, sexual dysfunction, or psoriasis. If the solid dosage form of the present invention is being used to treat sexual dysfunction, the dosage form would preferably contain a cyclic guanosine monophosphate (cGMP) phosphodiesterase type 5 (PDE5) inhibitor. Preferably, the cyclic guanosine monophosphate (cGMP) phosphodiesterase type 5 (PDE5) inhibitor is sildenafil or a pharmaceutically acceptable salt thereof. Preferably, the sildenafil salt is sildenafil citrate.

The invention therefore provides a method for treating sexual dysfunction, comprising the step of: administering to the patient a pharmaceutical composition comprising the solid dosage form of the invention comprising at least one cyclic guanosine monophosphate (cGMP) phosphodiesterase type 5 (PDE5) inhibitor. Preferably, the cyclic guanosine monophosphate (cGMP) phosphodiesterase type 5 (PDE5) inhibitor is sildenafil or a pharmaceutically acceptable salt thereof. Preferably, the sildenafil salt is sildenafil citrate.

An additional use for the solid dosage form of the present invention containing a cyclic guanosine monophosphate (cGMP) phosphodiesterase type 5 (PDE5) inhibitor is the treatment of pulmonary hypertension. Preferably, the cyclic guanosine monophosphate (cGMP) phosphodiesterase type 5 (PDE5) inhibitor is sildenafil or a pharmaceutically acceptable salt thereof. Preferably, the sildenafil salt is sildenafil citrate.

The invention therefore provides a method for treating pulmonary hypertension, comprising the step of: administering to the patient a pharmaceutical composition comprising the solid dosage form of the invention comprising at least one cyclic guanosine monophosphate (cGMP) phosphodiesterase type 5 (PDE5) inhibitor. Preferably, the cyclic guanosine monophosphate (cGMP) phosphodiesterase type 5 (PDE5) inhibitor is sildenafil or a pharmaceutically acceptable salt thereof. Preferably, the sildenafil salt is sildenafil citrate.

Further therapeutic uses for biologically active materials in a solid dosage form according to the invention include allergy relief and anaphylaxis treatment. Such disorders benefit from the rapid absorption of biologically active materials such as adrenaline and other active materials that bind to one or more adrenergic receptors.

The invention therefore provides a method for treating anaphylaxis, comprising the step of: administering to the patient a pharmaceutical composition comprising the solid dosage form of the invention comprising an active material that binds to one or more adrenergic receptors. The invention further provides a method for treating an allergic reaction, comprising the step of: administering to the patient a pharmaceutical composition comprising the solid dosage form of the invention comprising an active material that binds to one or more adrenergic receptors. Preferably, the active material that binds to one or more adrenergic receptors is adrenaline, or an adrenaline salt.

Preferably, the methods of treating comprise administering to the patient a solid dosage form of the invention, wherein the dosage form is administered sublingually. Preferably, the solid dosage form is a fast dissolving solid dosage form.

Administration

The solid dosage form of the present invention is suitable for oral administration to a subject. As discussed above, the dosage form comprises at least one biologically active material. The biologically active material is therefore delivered to the subject via the oral cavity mucosa and into the systemic blood system within a relatively short period of time. Preferably, the solid dosage form is a fast dissolving solid dosage form.

In a preferred embodiment, an effective plasma concentration of the biologically active material is reached within a period of no more than two hours, preferable within 30 minutes, 20 minutes, 15 minutes or less than 15 minutes. Most preferably, the effective plasma concentration of the biologically active material is reached within a period of 10 minutes, 9 minutes, 8 minutes, 7 minutes, 6 minutes, 5 minutes, 4 minutes, 3 minutes or 2 minutes. For example, a solid dosage form of the present invention in the form of a sublingual fentanyl wafer may result in detectable plasma fentanyl within 2 to 10 minutes, occurring in most cases within 5 minutes after administration. In other examples, an adrenaline solid dosage form of the present invention may be therapeutic within 5 minutes; a sildenafil solid dosage form within 20 minutes and a ketamine fast dissolving solid dosage form may be therapeutic within 10 minutes.

In another embodiment, the dosage form provides the patient with a peak plasma concentration ($C_{max}$) of the biologically active material selected from the group consisting of: 25 ng/ml; 30 ng/ml; 40 ng/ml; 50 ng/ml; 60 ng/ml; 70 ng/ml; 80 ng/ml; 90 ng/ml; 100 ng/ml; 110 ng/ml; 120 ng/ml; 130 ng/ml; 140 ng/ml; 150 ng/ml; 160 ng/ml; 170 ng/ml; 180 ng/ml; 190 ng/ml; and 200 ng/ml.

When compare with intravenous injection, a solid dosage form of the present invention in the form of a sublingual wafer may produce a much lower $C_{max}$, which may reduce the toxicity of the biologically active material being administered. For example, in a Phase I sublingual fentanyl wafer clinical trial, the $C_{max}$ of a 100 µg fentanyl intravenous infusion (5 min) was 1451.0 pg/mL, however the $C_{max}$ of a 100 µg fentanyl wafer was only 219.3 pg/mL. Similarly, in a Phase I sublingual ketamine wafer clinical trial, the $C_{max}$ of a 10 mg ketamine intravenous infusion (30 min) is 128.1 ng/mL, whereas the $C_{max}$ of a 25 mg ketamine wafer was 71.1 ng/mL.

In another embodiment, the solid dosage form has a median $t_{max}$ of the biologically active material selected from the group consisting of: between 5 minutes to 90 minutes; between 10 minutes and 75 minutes; between 15 minutes and 60 minutes; between 30 minutes and 50 minutes; between 40 minutes and 50 minutes; and 45 minutes. For example, the $T_{max}$ for a 25 mg ketamine wafer form of the solid dosage form of the present invention may be 45 minutes.

In a highly preferred embodiment, the dosage form provides the first detectable plasma concentration of the biologically active material selected from the group consisting of: within 15 minutes; within 14 minutes; within 13 minutes; within 12 minutes; within 11 minutes; within 10 minutes; within 9 minutes; within 8 minutes; within 7 minutes; within 6 minutes; within 5 minutes; within 4 minutes; within 3 minutes; within 2 minutes; and within 1 minute. For example, the first detectable plasma fentanyl concentration, after sublingual administration with a dosage form of the present invention, may be observed between 2 and 10 minutes after administration.

Preferably, the dosage form provides a median bioavailability of the biologically active material in a patient, selected from the group consisting of: between 10 and 60%; between 20 and 40%; between 25 and 35%; between 28 and 30%; and 28%. For example, the solid dosage form may provide a median bioavailability of an N-methyl-D-aspartate receptor antagonist in a patient of 28% wherein the dose of the antagonist is 25 mg. The solid dosage form may also provide a median bioavailability of sublingual ketamine of 29% wherein the dose of ketamine is 25 mg.

In another embodiment, the solid dosage form provides the patient with an effective therapeutic plasma level of the biologically active material over a period selected from the group consisting of: more than 30 minutes, 30 minutes, 25 to 30 minutes, 20 to 25 minutes, 15 to 20 minutes, 10 to 15 minutes, 10 minutes, 9 minutes, 8 minutes, 7 minutes, 6 minutes, 5 minutes, 4 minutes, 3 minutes, or two minutes.

The subject receiving the solid dosage form of the present invention may be an animal or human being. When the subject is a human being, it may be an adult or a child, including elderly adults and infants. In particular the subject may be a subject that is unable to or has difficulties in swallowing.

The present invention has surprisingly found that the addition of sodium carboxymethylcellulose improves the dissolution rate of the solid dosage form. When the amount of sodium carboxymethylcellulose is between about 0.1% and 15% by dry weight of the dosage form, the dosage form releases the active agent rapidly, without leaving a residue in the oral cavity. In addition, the use of gelatine is avoided, and therefore little or no unwanted residue was left in the oral cavity after administration. The addition of lactose and/or mannitol is also advantageous in the solid dosage form of the present invention.

Use

There is also provided the use of a solid dosage form adapted for the release of a biologically active material in the oral cavity wherein the dosage form comprises:

(a) at least one biologically active material, and
(b) at least one matrix forming agent, wherein the dosage form substantially dissolves in the oral cavity in the manufacture of a medicament to treat a disease or disorder. Preferably, the solid dosage form is a fast dissolving solid dosage form.

Preferably, the biologically active material is chosen from the list comprising: at least one cyclic guanosine monophosphate (cGMP) phosphodiesterase type 5 (PDE5) inhibitor, an active material that binds to one or more adrenergic receptors, and an N-methyl-D-aspartate receptor antagonist. Preferably, the N-methyl-D-aspartate receptor antagonist is chosen from the list comprising: dextromethorphan, dextrorphan or ketamine. Preferably, the active material that binds to one or more adrenergic receptors is adrenaline (epinephrine), or an adrenaline salt. Preferably, the cyclic guanosine monophosphate (cGMP) phosphodiesterase type 5 (PDE5) inhibitor is sildenafil or a pharmaceutically acceptable salt thereof. Preferably, the sildenafil salt is sildenafil citrate.

Preferably the disease or disorder is selected from the list comprising: pain, depression, addiction, inflammation, migraine, asthma, epilepsy, acute cardiovascular events such as cardiac arrest or cardiac dysrhythmia, angina pectoris, hair loss, sexual dysfunction, psoriasis, pulmonary hypertension, allergy or anaphylaxis and the provision of anaesthesia.

There is therefore provided the use of a solid dosage form adapted for the release of a biologically active material in the oral cavity wherein the dosage form comprises:
(a) at least one cyclic guanosine monophosphate (cGMP) phosphodiesterase type 5 (PDE5) inhibitor, and
(b) at least one matrix forming agent, wherein the dosage form substantially dissolves in the oral cavity in the manufacture of a medicament to treat a disease or disorder. Preferably, the solid dosage form is a fast dissolving solid dosage form. Preferably the disease or disorder is chosen from the list comprising: sexual dysfunction, pulmonary hypertension.

the use of a solid dosage form adapted for the release of a biologically active material in the oral cavity wherein the dosage form comprises:
(a) an N-methyl-D-aspartate receptor antagonist, and
(b) at least one matrix forming agent, wherein the dosage form substantially dissolves in the oral cavity in the manufacture of a medicament to treat a disease or disorder. Preferably, the solid dosage form is a fast dissolving solid dosage form. Preferably the disease or disorder is chosen from the list comprising: pain, depression, addiction, migraine, epilepsy, and the provision of anaesthesia.

the use of a solid dosage form adapted for the release of a biologically active material in the oral cavity wherein the dosage form comprises:
(a) an active material that binds to one or more adrenergic receptors, and
(b) at least one matrix forming agent, wherein the dosage form substantially dissolves in the oral cavity in the manufacture of a medicament to treat a disease or disorder. Preferably, the solid dosage form is a fast dissolving solid dosage form. Preferably the disease or disorder is chosen from the list comprising: acute cardiovascular events such as cardiac arrest or cardiac dysrhythmia, angina pectoris, allergy or anaphylaxis.

General

Those skilled in the art will appreciate that the invention described herein is susceptible to variations and modifications other than those specifically described. It is to be understood that the invention includes all such variations and modifications. The invention also includes all of the steps, features, compositions and materials referred to or indicated in the specification, individually or collectively and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

The invention described herein may include one or more ranges of values (e.g. size, concentration etc.). A range of values will be understood to include all values within the range, including the values defining the range, and values adjacent to the range that lead to the same or substantially the same outcome as the values immediately adjacent to that value which defines the boundary to the range.

The entire disclosures of all publications (including patents, patent applications, journal articles, laboratory manuals, books, or other documents) cited herein are hereby incorporated by reference. Inclusion does not constitute an admission is made that any of the references constitute prior art or are part of the common general knowledge of those working in the field to which this invention relates.

Throughout this specification, unless the context requires otherwise, the word "comprise" or variations, such as "comprises" or "comprising" will be understood to imply the inclusion of a stated integer, or group of integers, however not the exclusion of any other integers or group of integers. It is also noted that in this disclosure, and particularly in the claims and/or paragraphs, terms such as "comprises", "comprised", "comprising" and the like can have the meaning attributed to it in US Patent law; e.g., they can mean "includes", "included", "including", and the like.

"Therapeutically effective amount" as used herein with respect to methods of treatment and in particular drug dosage, shall mean that dosage that provides the specific pharmacological response for which the drug is administered in a significant number of subjects in need of such treatment. It is emphasized that "therapeutically effective amount," administered to a particular subject in a particular instance will not always be effective in treating the diseases described herein, even though such dosage is deemed a "therapeutically effective amount" by those skilled in the art. It is to be further understood that drug dosages are, in particular instances, measured as oral dosages, or with reference to drug levels as measured in blood.

The term "inhibit" is defined to include its generally accepted meaning which includes prohibiting, preventing, restraining, and lowering, stopping, or reversing progression or severity, and such action on a resultant symptom. As such the present invention includes both medical therapeutic and prophylactic administration, as appropriate.

The term "biologically active material" is defined to mean a biologically active compound or a substance which comprises a biologically active compound. In this definition, a compound is generally taken to mean a distinct chemical entity where a chemical formula or formulas can be used to describe the substance. Such compounds would generally, however not necessarily be identified in the literature by a unique classification system such as a CAS number. Some compounds may have a more complex and have a mixed chemical structure. For such compounds they may only have an empirical formula or be qualitatively identified. A compound would generally be a pure material, although it would be expected that up to 10%, 20%, 30%, 40%, 50%, 60%, 70%, 80%, 90% of the substance could be other impurities and the like. Examples of biologically active compounds are, however not limited to, fungicides, pesticides, herbicides, seed treatments, cosmeceuticals, cosmetics, complementary medicines, natural products, vitamins, nutrients, neutraceuticals, pharmaceutical actives, biologics, amino acids, proteins, peptides, nucleotides, nucleic acids, additives, foods and food ingredients and analogues, homologs and first order derivatives thereof. A substance that contains a biological active compound is any substance which has as one of its components a biological active compound. Examples of substances containing biologically active compounds are, however not limited to, pharmaceutical formulations and products, cosmetic formulations and products, industrial formulations and products, agricultural formulations and products, foods, seeds, cocoa and cocoa solids, coffee, herbs, spices, other plant materials, minerals, animal products, shells and other skeletal material.

Any of the terms, "biological(ly) active", "active", "active material" shall have the same meaning as biologically active material.

As used herein "pharmaceutically acceptable carrier" includes any and all solvents, dispersion media, coatings, antibacterial and antifungal agents, isotonic and absorption delaying agents, and the like that are physiologically compatible. Preferably, the carrier is suitable for oral administration.

EXAMPLES

The present invention will now be described with reference to the following non-limiting Examples. The description of the Examples is in no way limiting on the preceding paragraphs of this specification, however is provided for exemplification of the methods and compositions of the invention.

Example 1

A formulation of the present invention, in the form of a solid dosage form (wafer), was prepared in accordance with the method and ingredients as set out below in Table 1:

TABLE 1

Fast Dissolving Solid Dosage Form (Wafer) Formulation

| Ingredient | Amount (g) | % by weight |
|---|---|---|
| Sodium carbonate BP/USP | 10 | 0.075 |
| Sodium carboxymethylcellulose BP/USP | 20 | 0.149 |
| Polyethylene glycol 2000 BP/USP | 50 | 0.374 |
| Glycine BP/USP | 100 | 0.747 |
| Microcrystalline cellulose BP/USP | 200 | 1.495 |
| Amylopectin BP/USP | 500 | 3.737 |
| Lactose BP/USP | 1000 | 7.474 |
| Mannitol BP/USP | 1500 | 11.211 |
| Purified water BP/USP | 10000 | 74.738 |

Sodium carboxymethylcellulose and amylopectin were added in a portion of purified water by mixing thoroughly with a stirrer. The mixture was then heated to 50° C. for ten minutes to allow dissolving of the polymers. Once the solution cooled down to room temperature, polyethylene glycol 2000, glycine, sodium carbonate, microcrystalline cellulose, lactose and mannitol were added individually, under stirring to obtain a homogenously solution. The viscosity of the solution was measured at 25° C. using a Brookfield Digital Viscometer (Brookfield Engineering Laboratories Inc., MA, USA).

The resulting mixture was transferred by pipette and accurately weighed into preformed blister packs, and then transferred into a freezer (−30° C.) for approximately 24 hours. After freezing, the sample was freeze-dried (DYNA-VAC, Australia) for 24 hours. The prepare sample was stored in desiccator over silica gel at a room temperature.

The following additional wafer formulations were prepared by the method as set out above. Essentially Samples 1 to 6 are based on the formulation described above, with the addition of flavour and/or colour agents.

Sample 1. Additionally Contained a Flavour.

| Ingredient | Amount (g) | % by weight |
|---|---|---|
| Sodium carbonate | 1 | 0.08 |
| Sodium carboxymethylcellulose | 2 | 0.15 |
| Polyethylene glycol 2000 | 5 | 0.37 |
| Orange flavour | 10 | 0.74 |
| Glycine | 10 | 0.74 |
| Microcrystalline cellulose | 20 | 1.48 |
| Amylopectin | 50 | 3.71 |
| Lactose | 100 | 7.42 |
| Mannitol | 150 | 11.13 |
| Purified water | 1000 | 74.18 |

Sample 2. Additionally Contained a Flavour and a pH Adjuster (Citric Acid).

| Ingredient | Amount (g) | % by weight |
|---|---|---|
| Sodium carbonate | 1 | 0.07 |
| Sodium carboxymethylcellulose | 2 | 0.15 |
| Citric acid | 5 | 0.37 |
| Polyethylene glycol 2000 | 5 | 0.37 |
| Mint flavour | 10 | 0.74 |
| Glycine | 10 | 0.74 |
| Microcrystalline cellulose | 20 | 1.48 |
| Amylopectin | 50 | 3.70 |
| Lactose | 100 | 7.39 |
| Mannitol | 150 | 11.09 |
| Purified water | 1000 | 73.91 |

Sample 3. Additionally Contained Flavour and a Colouring Agent

| Ingredient | Amount (g) | % by weight |
|---|---|---|
| FD & C red | 0.1 | 0.01 |
| Sodium carbonate | 1 | 0.07 |
| Sodium carboxymethylcellulose | 2 | 0.15 |
| Polyethylene glycol 2000 | 5 | 0.37 |
| Grape flavour | 9.9 | 0.74 |
| Glycine | 10 | 0.74 |
| Microcrystalline cellulose | 20 | 1.48 |
| Amylopectin | 50 | 3.71 |
| Lactose | 100 | 7.42 |
| Mannitol | 150 | 11.13 |
| Purified water | 1000 | 74.18 |

Sample 4. Additionally Contained Flavour, a Colouring Agent and an Absorption Enhancer.

| Ingredient | Amount (g) | % by weight |
|---|---|---|
| FD & C blue | 0.1 | 0.01 |
| Sodium carbonate | 1 | 0.07 |
| Sodium carboxymethylcellulose | 2 | 0.15 |
| β-Cyclodextrin | 5 | 0.37 |
| Polyethylene glycol 2000 | 5 | 0.37 |
| Grape flavour | 9.9 | 0.73 |
| Glycine | 10 | 0.74 |
| Microcrystalline cellulose | 20 | 1.48 |
| Amylopectin | 50 | 3.71 |
| Lactose | 100 | 7.42 |
| Mannitol | 145 | 10.76 |
| Purified water | 1000 | 74.19 |

Sample 5. Additionally Contained a Colouring Agent and a Sweetener

| Ingredient | Amount (g) | % by weight |
|---|---|---|
| FD & C red | 0.1 | 0.01 |
| Sodium carbonate | 1 | 0.07 |
| Sodium carboxymethylcellulose | 2 | 0.15 |
| Aspartame | 5 | 0.37 |
| Polyethylene glycol 2000 | 5 | 0.37 |
| Cherry flavour | 9.9 | 0.73 |
| Glycine | 10 | 0.74 |
| Microcrystalline cellulose | 20 | 1.48 |
| Amylopectin | 50 | 3.71 |
| Lactose | 100 | 7.42 |
| Mannitol | 145 | 10.76 |
| Purified water | 1000 | 74.19 |

Sample 6. Additionally Contained a Colouring Agent and a pH Adjuster

| Ingredient | Amount (g) | % by weight |
|---|---|---|
| FD & C red | 0.1 | 0.01 |
| Sodium carbonate | 1 | 0.07 |
| Sodium carboxymethylcellulose | 2 | 0.15 |
| Sodium hydrogen carbonate | 5 | 0.37 |
| Polyethylene glycol 2000 | 5 | 0.37 |
| Raspberry flavour | 9.9 | 0.73 |
| Glycine | 10 | 0.74 |
| Microcrystalline cellulose | 20 | 1.48 |
| Amylopectin | 50 | 3.71 |
| Lactose | 100 | 7.42 |
| Mannitol | 145 | 10.76 |
| Purified water | 1000 | 74.19 |

Various batches of the solid dosage wafer form were then prepared based on the formulation shown in Table 1 and prepared as set out above, also containing midazolam (base) or fentanyl citrate (2.5 µg fentanyl base for 50 wafers. Strength equivalent of 50 µg fentanyl base) as the biologically active material. The batch number and the ingredients are listed in Table 2.

TABLE 2

Midazolam or Fentanyl Compositions Used for Investigations

| Ingredient | Batch 071501B Amount (g) | Batch 07150213 Amount (g) | Batch 0820A Amount (g) | Batch 0820B Amount (g) | Batch 0905MD Amount (g) | Batch 1003 FEN Amount (g) |
|---|---|---|---|---|---|---|
| Amylopectin | 1.0 | 1.0 | 1.0 | 0.00 | 1.0 | 0.5 |
| Mannitol | 3.0 | 3.0 | 3.0 | 3.0 | 3.0 | 1.5 |
| Lactose | 2.0 | 2.0 | 2.0 | 2.0 | 2.0 | 1.0 |
| Glycine | 0.2 | 0.2 | 0.5 | 0.3 | 0.2 | 0.1 |
| PEG 2000 | 0.1 | 0.1 | 0.1 | 0.1 | 0.1 | 0.05 |
| Sodium Carboxymethylcellulose | 0.04 | 0.04 | 0.04 | 0.04 | 0.04 | 0.02 |
| Sodium carbonate | 0 | 0.02 | 0 | 0 | 0.02 | 0.01 |
| Starch | 1.0 | 0 | 0 | 0 | 0 | 0 |
| Avicel | 0.2 | 0 | 0.00 | 0.2 | 0.2 | 0.1 |
| Active pharmaceutical ingredient | 0 | 0 | 0 | 0 | 0.255 midazolam (base) | 0.001 fentanyl citrate (2.5 mg fentanyl base) |
| Purified water | 40 | 40 | 40 | 40 | 40 | 20 |

General Observations

It was found that there was no significant difference between the use of polyethylene glycol 1000 or polyethylene glycol 2000 in the wafer formulation (results not shown).

The addition of starch resulted in a hard wafer, and was less suitable for the fast dissolving solid dosage form of the present invention.

Uniformity of Weight

The uniformity of the weight of the fast dissolving dosage wafer form was tested in accordance with the British Pharmacopoeia (BP) 2009 test. Twenty wafers from each of the formulations listed in Table 2 were individually weighed, and the average weight and relative standard was calculated. All the prepared wafers from different formulations were within the accepted weight variation from between 0.25 to 2%.

Hardness

The hardness of the dosage formulations listed in Table 2 was also tested. The mechanical strength of a tablet is referred to as "hardness". The hardness of the wafer was determined using an Erweka Hardness Tester (Germany). The values of hardness from different formulations ranged from 0.5 to 4.0 kg. It was observed that the hardness of the formulation increased when Avicel was added to the formulation (results not shown).

Friability

The strength of the fast dissolving solid dosage wafer forms, i.e. their ability to be reduced from a solid substance into smaller pieces was measured. The test was conducted according to BP 2009 method (i.e. friability of uncoated tablets), using the Erweka friability tester (Germany). A sample of 20 wafers was weighed accurately and placed in the apparatus. A rotation time of four minutes at 25 rpm was used. Wafers were removed and reweighed and the percentage weight loss was calculated. It was found that the weight loss of the 20 wafers ranged from 8 to 20%. Although this weight loss does not comply with the BP 2009 standard of about 1% weight loss for compressed tablets, there is no such standard for wafers in either the BP or USP monograph.

Moisture Analysis

The moisture content of the wafers was analysed after lyophilisation using the 870 Karl Fisher Titrino Plus (Metrohm Ag, Germany). The results show that the residual moisture content varied between 1% to 5% for different formulations.

Scanning Electron Microscopic Analysis

Surface morphology and cross-sections of selected wafer formulations were observed using scanning electron microscope (SE M) (Zeiss, EVO 40 XVP, the Oxford Instrument, UK). Cross-section sample were prepared by cutting a thin slice of the wafer using a scalpel. Samples were coated with carbon prior to examination. The accelerating voltage was 10 kV.

The SEM images shown in FIGS. 1 to 6 illustrate the highly porous nature of the wafers on both surface and the inner structure. Clearly, there were morphological differences between different formulations. These differences indicated that the excipients used influence the microstructure of the wafer. In addition, the microstructure might give an explanation about the different hardness, friability, disintegration time, and even the dissolution profiles of wafer prepared from different formulations.

Powder X-Ray Diffraction (XRD)

X-ray diffraction experiments were performed using Bruker D8 Advance (Germany) with detector LynEye. The radiation used was nickel filtered CuKα, which was generated using an acceleration voltage of 40 kV and a cathode current of 40 mA. The samples were scanned over a 2 theta range of 7.5 to 70 degree, and counting time at 1 second per 0.02 degree.

Figure 7:
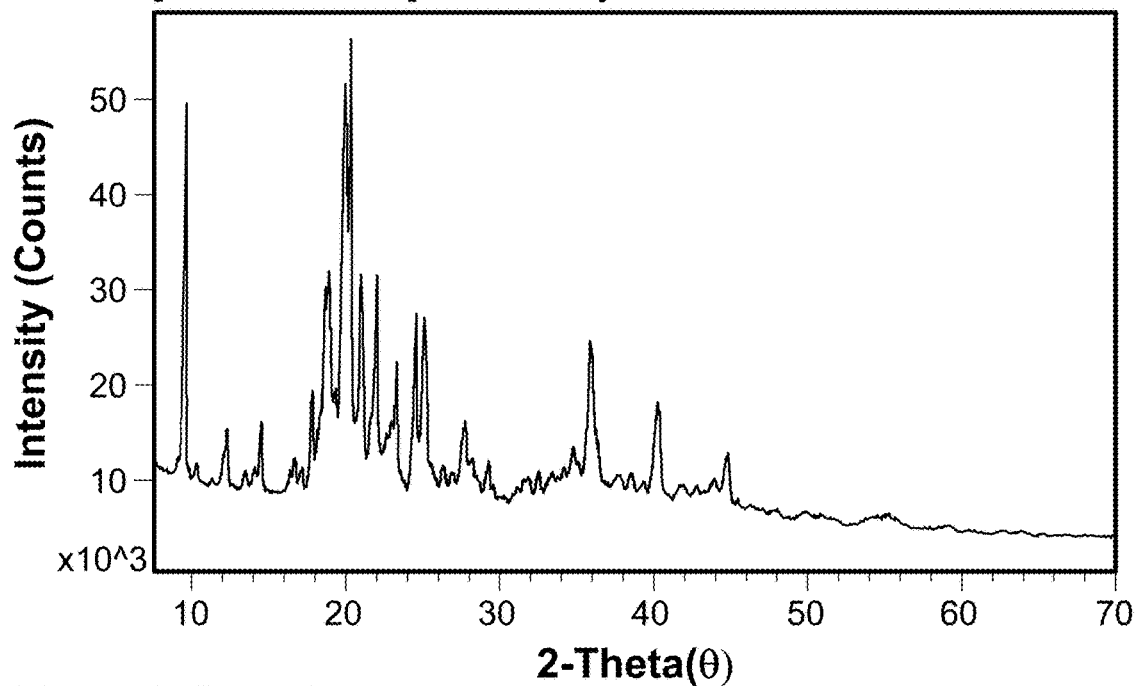
FIG. 7 shows powder X-ray diffraction spectra of wafers from batch number 071501A and 071502B.
Figure 7:
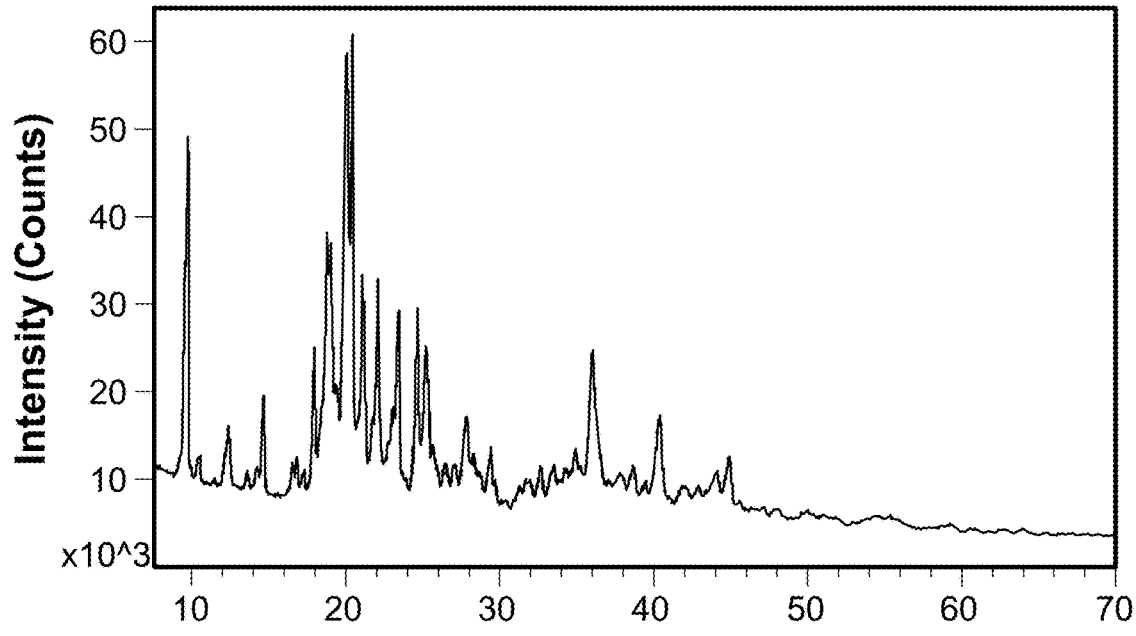
Figure 8:
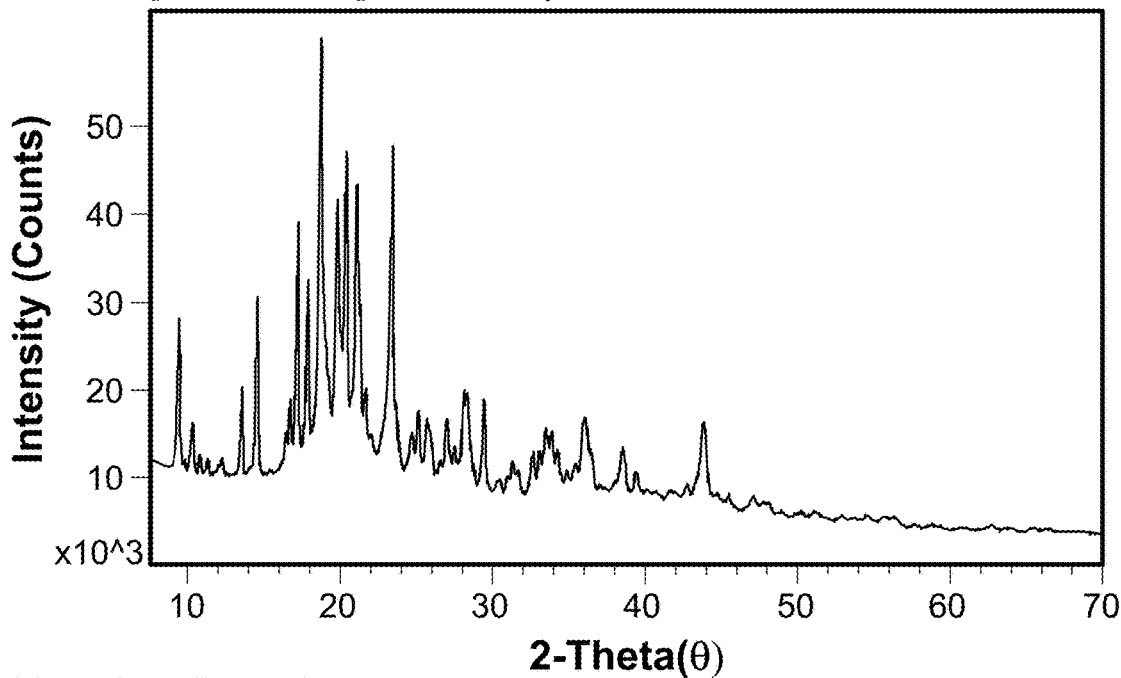
FIG. 8 shows powder X-ray diffraction spectra of wafers from batch numbers 0820A and 0820B.
Figure 8:
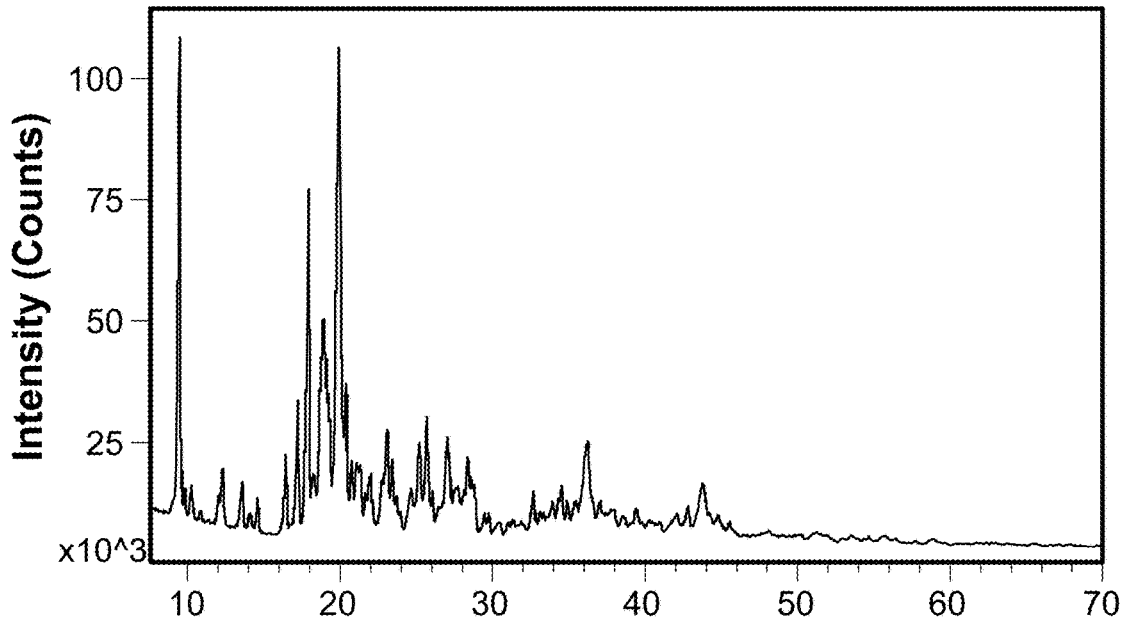
Figure 9:
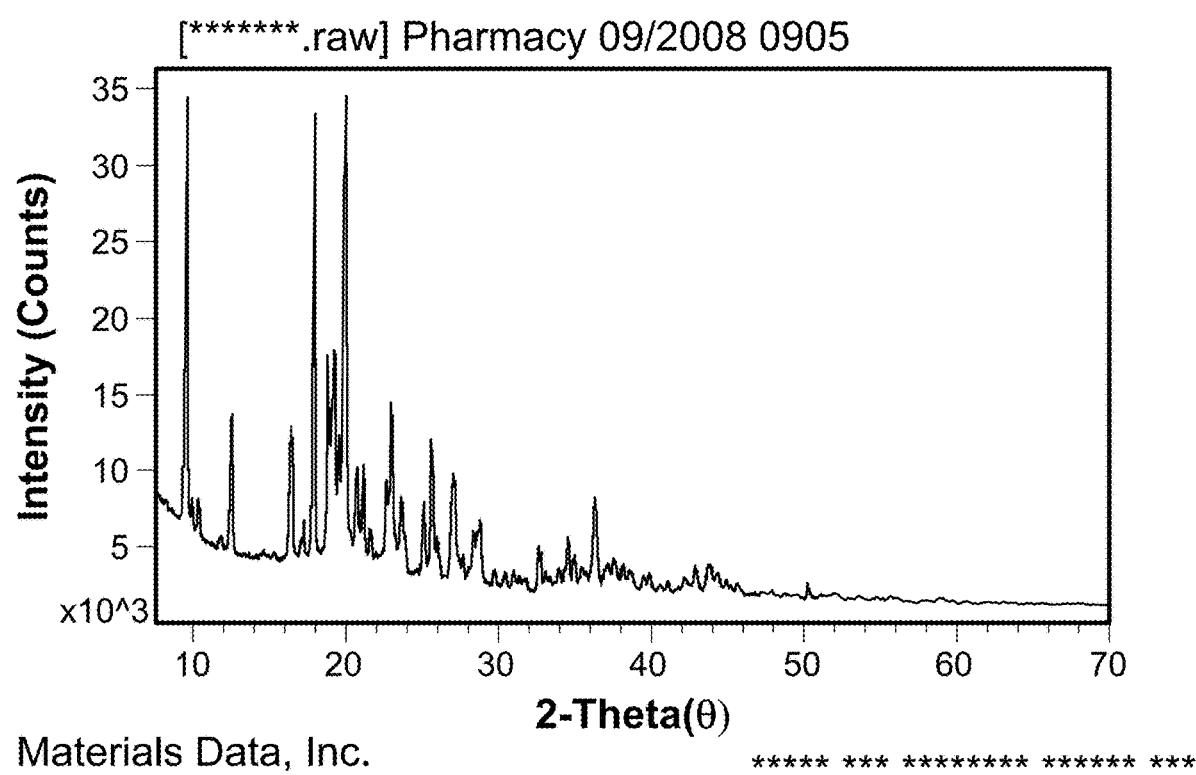
FIG. 9 shows a powder X-ray diffraction spectrum of wafer from batch number 0905MD.
Figure 10A:
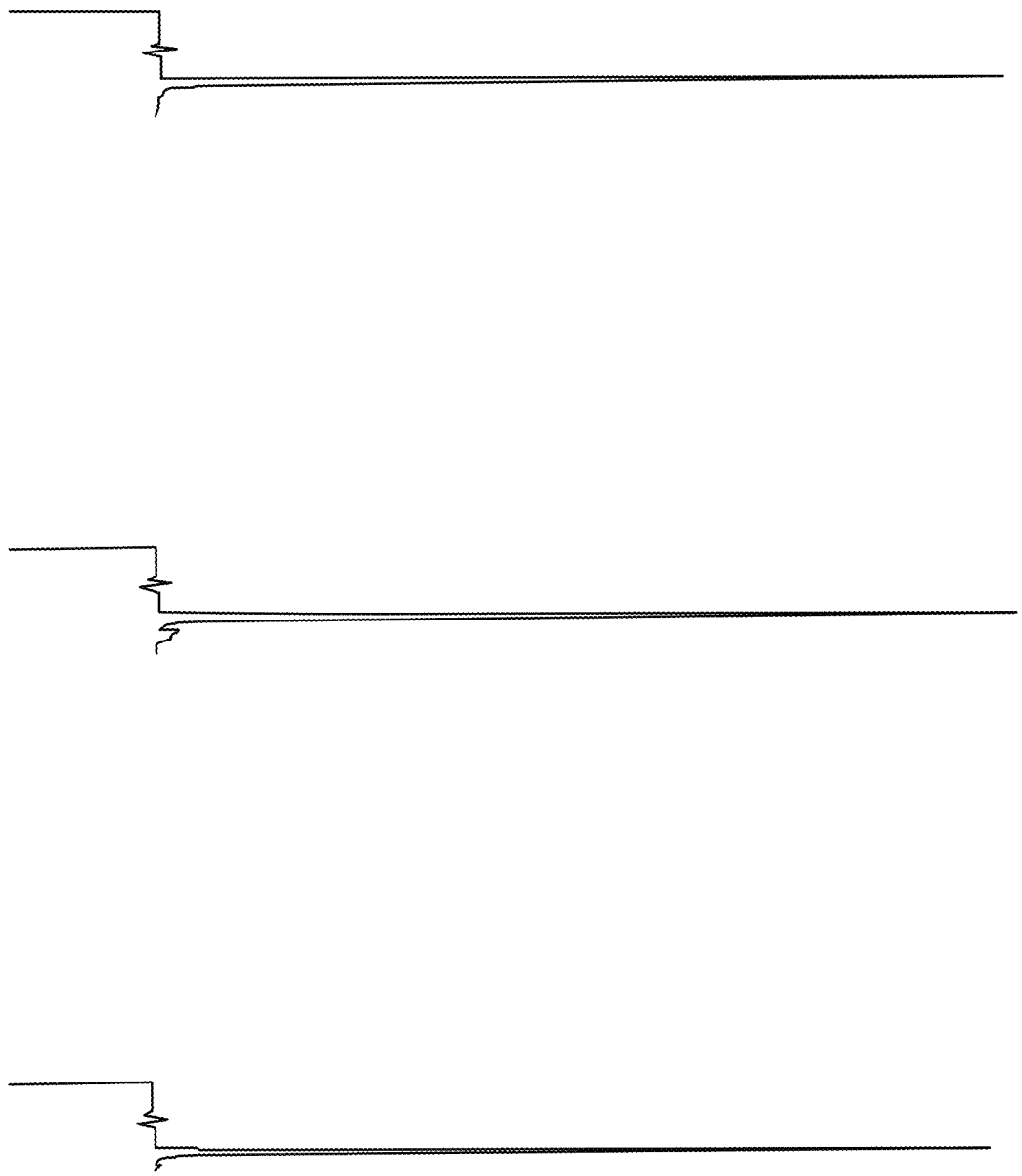
FIG. 10 shows [A] Typical HPLC chromatograms of standard midazolam sample at 4.05 µg/mL (n=3); [B] Midazolam powder dissolution samples at 1 minute and 5 minutes; [C] Midazolam powder dissolution sample at 10 minutes; [D] Midazolam powder dissolution sample 15 minutes; and [E] standard midazolam sample at 8.1 µg/ml.
Figure 10B:
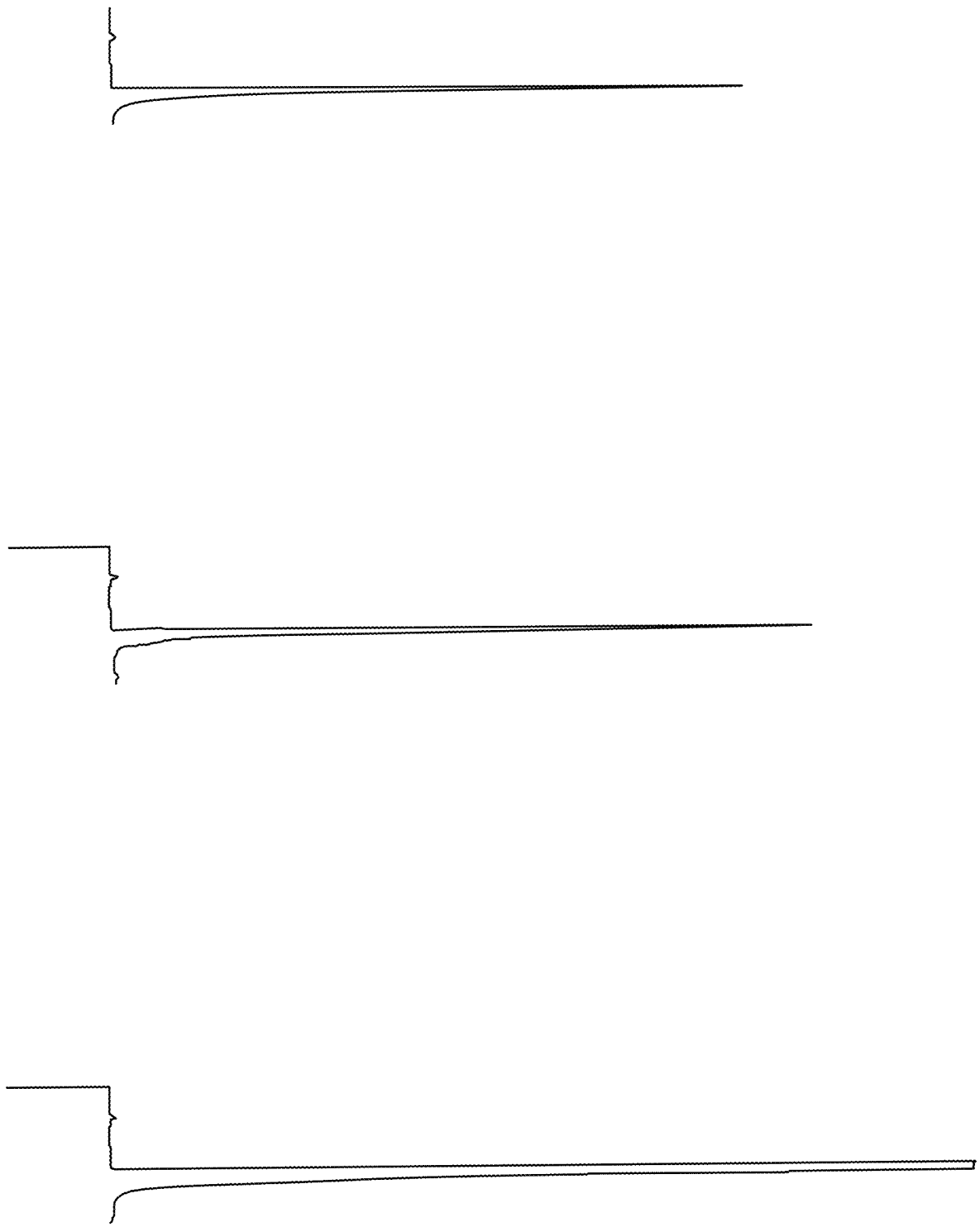
Figure 10C:
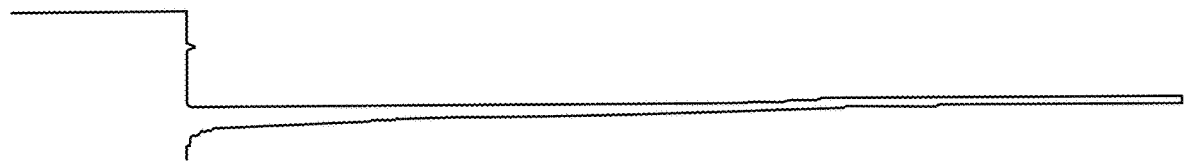
Figure 10C:
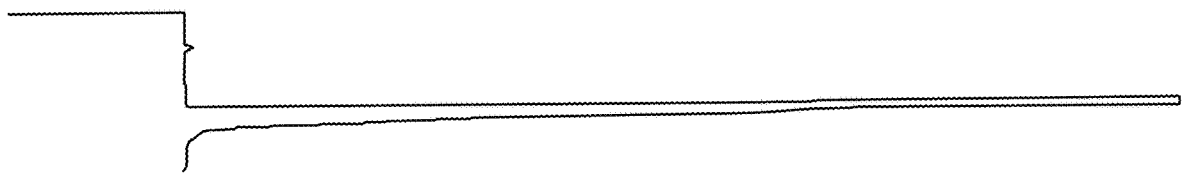
Figure 10D:
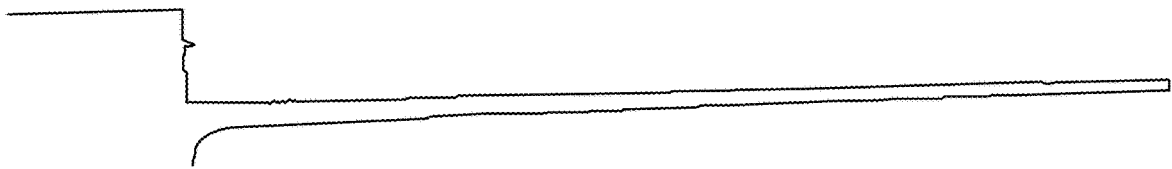
Figure 10D:
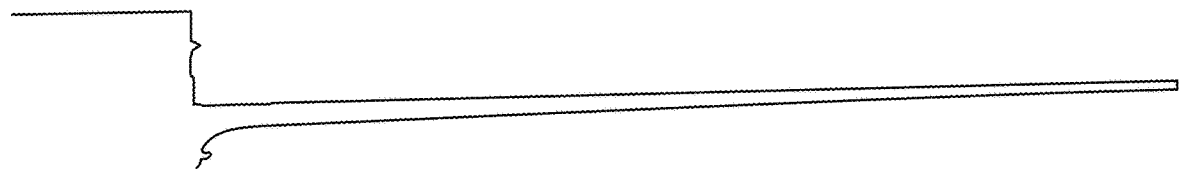
Figure 10E:
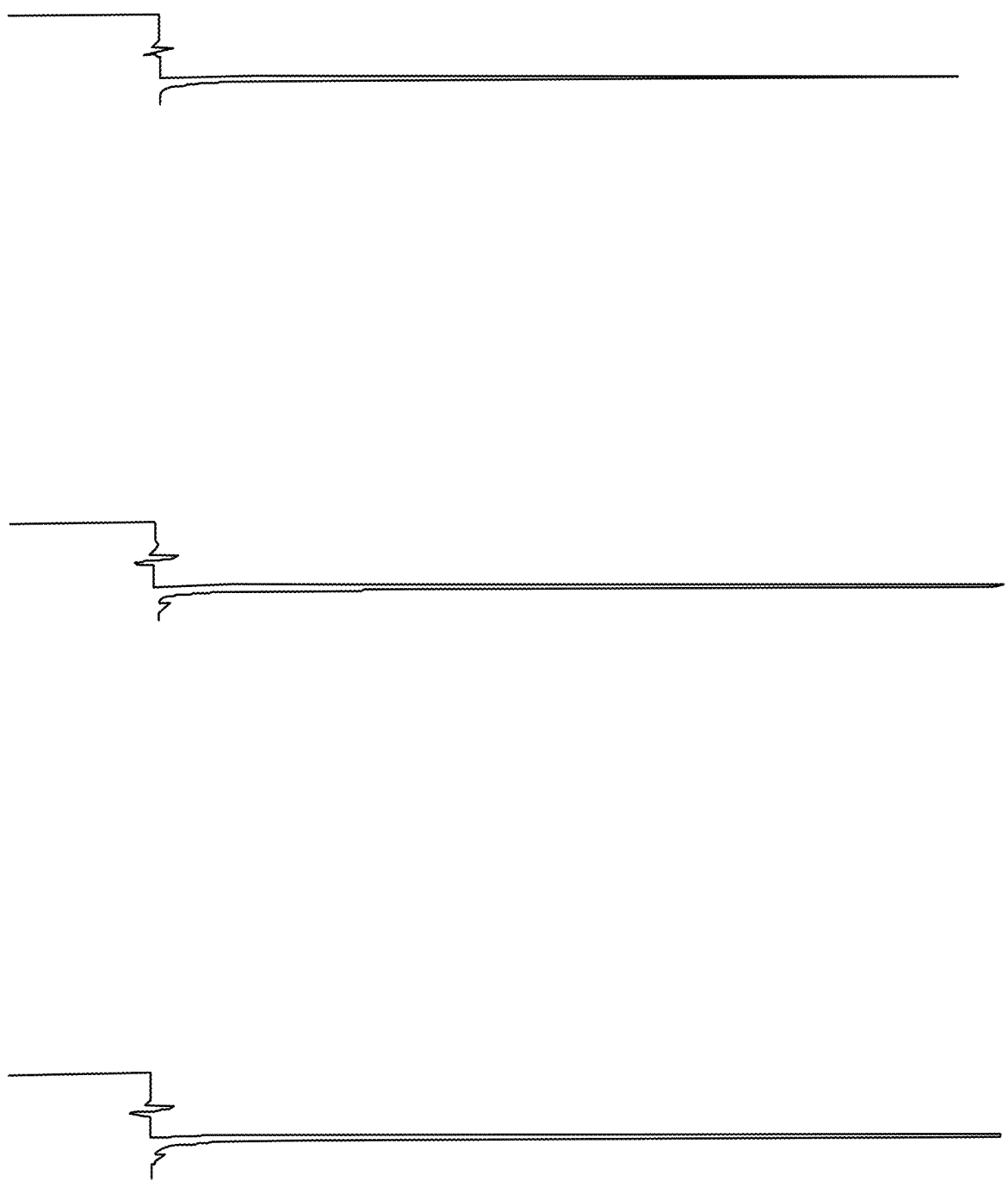
Figure 11:
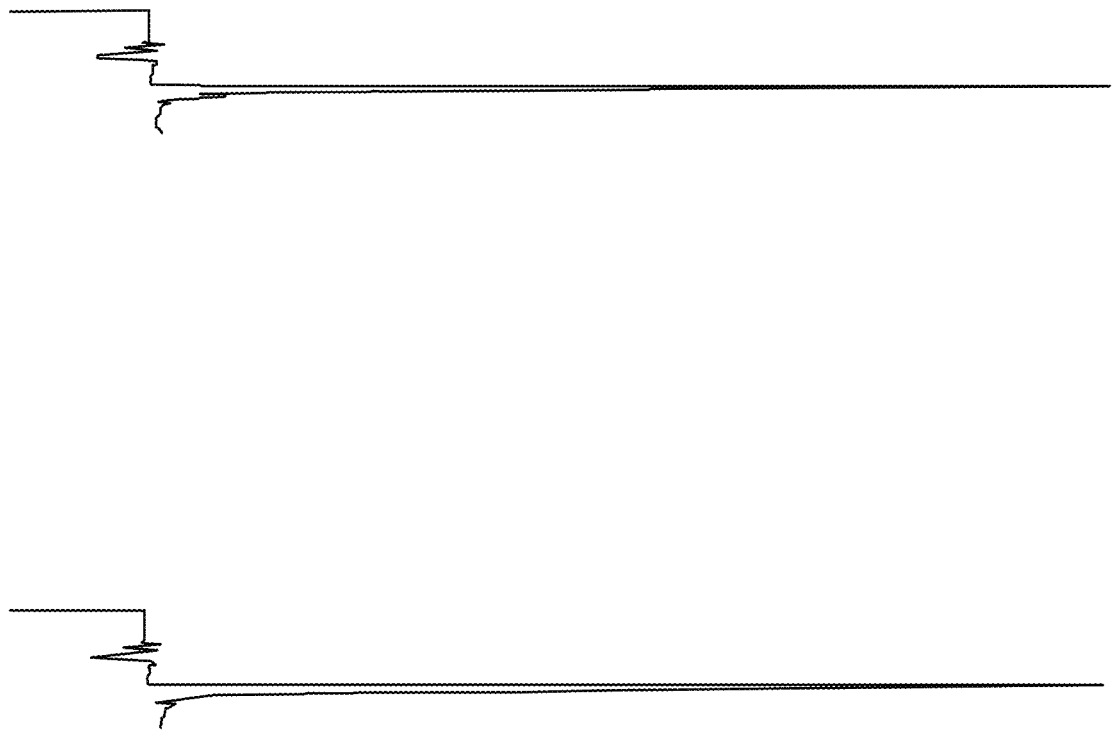
FIG. 11 shows typical HPLC chromatograms of dissolution wafer Sample S1 at 45 seconds and 1 minute.
Figure 12:
FIG. 12 shows a typical HPLC chromatogram of dissolution wafer Sample S1 at 10 minutes.
Figure 13:
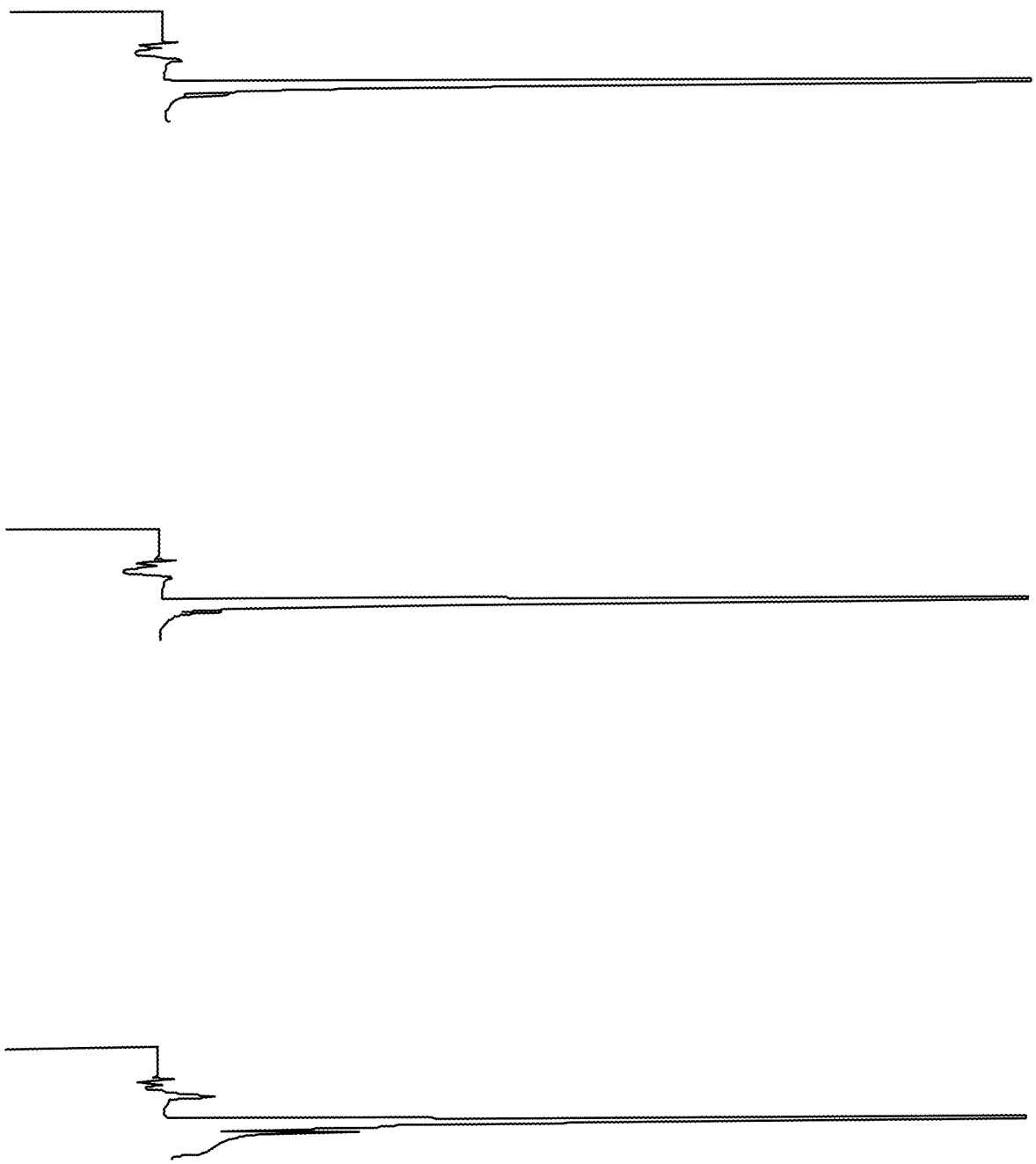
FIG. 13 shows typical HPLC chromatograms of dissolution wafer Sample S2 at 5 and 10 minutes.
Figure 14:
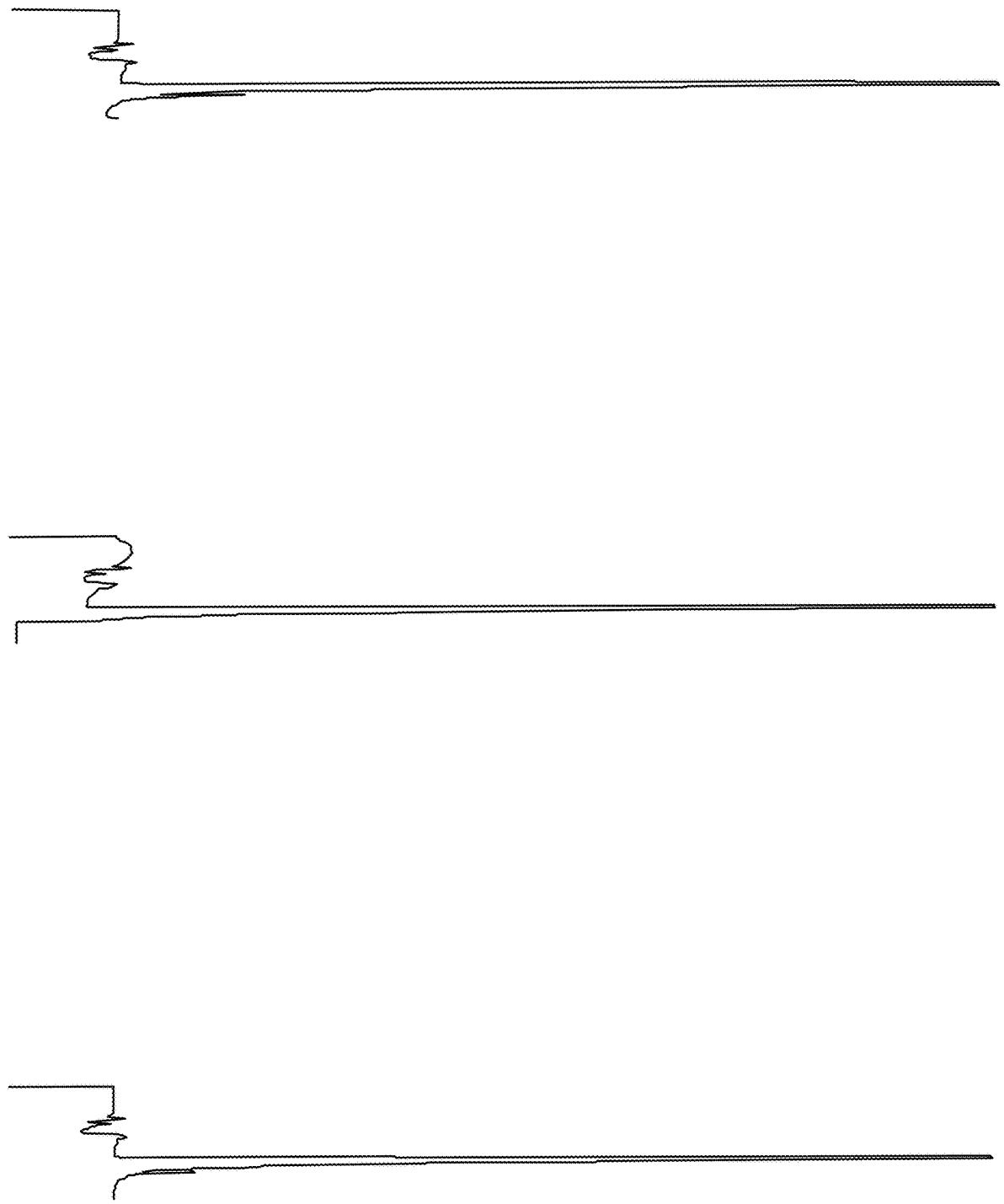
FIG. 14 shows typical HPLC chromatograms of dissolution wafer Sample S2 at 30 seconds and 2 minutes.
Figure 15:
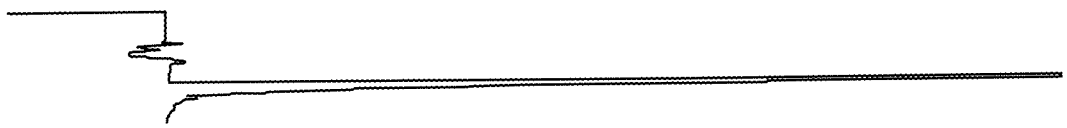
FIG. 15 shows typical HPLC chromatograms of dissolution wafer Sample S3 at 20 seconds and at 1 minute.
Figure 15:
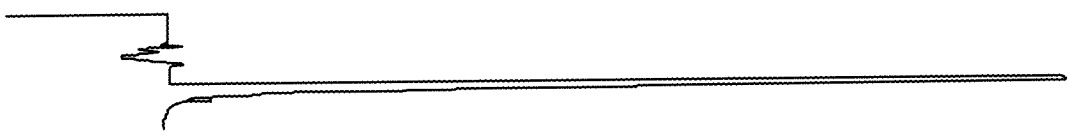
Figure 15:
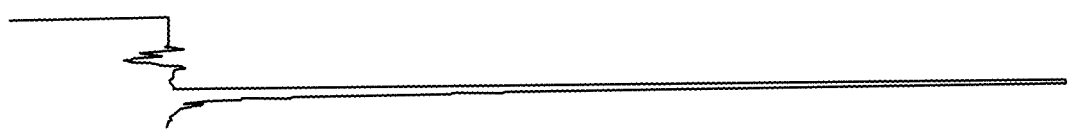
Figure 16:
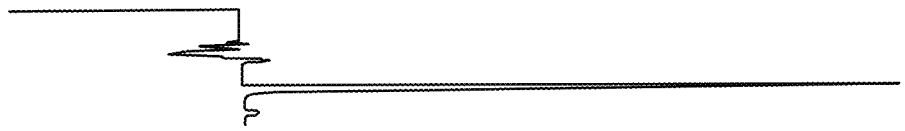
FIG. 16 shows typical HPLC chromatograms of standard midazolam sample at 1.01 µg/mL.
Figure 16:
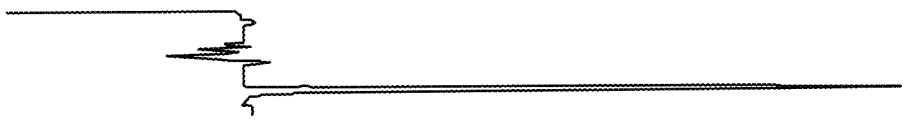
Figure 16:
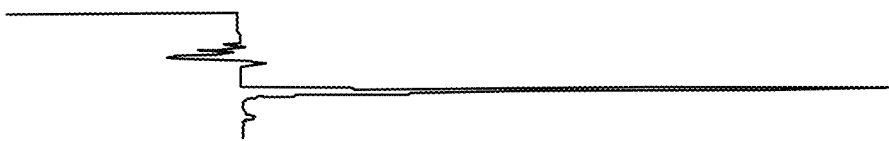

The physical state of the materials in the wafer was evident in the X-ray diffraction spectra. Spectra for three different formulations as prepared in accordance with Table 2 are shown in FIGS. 7 to 9. It was observed that all the powder patterns of wafer prepared are dominated by intense scattering peaks approximately located at 2-theta of 9.58°, 19, 68° and 20.05°, which indicating a crystalline nature. This finding was also supported by the data generated from the SEM (see FIGS. 1-6). Indeed, the excipients used in the formulations, such as glycine, lactose, mannitol and microcrystalline cellulose are crystalline in nature. It was observed that there was minimal physical state change in the solid dispersion.

Disintegration and Dissolution Analysis

Disintegration and dissolution tests were carried out using Apparatus I (BP 2009, Basket apparatus). The Erweka dissolution apparatus (Hesenstamm, Germany) was used for both tests. The temperature of the medium was kept at 37±0.5° C.

For the disintegration test, a wafer was placed in the cylindrical basket and wetted on the underside by contact with distilled water in the cylindrical vessel. The time of total dissolution of each wafer was noted, and a mean value was calculated.

Figure 17:
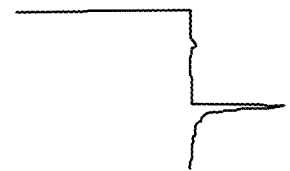
FIG. 17 shows typical HPLC chromatograms of Midazolam powder dissolution sample at 30 seconds.
Figure 17:
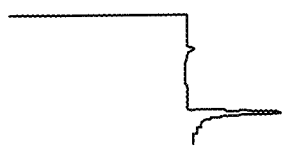
Figure 17:
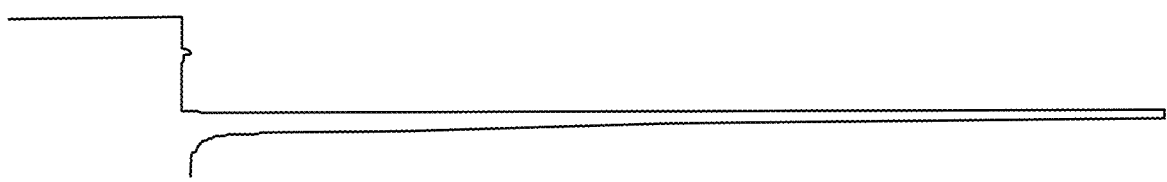
Figure 18:
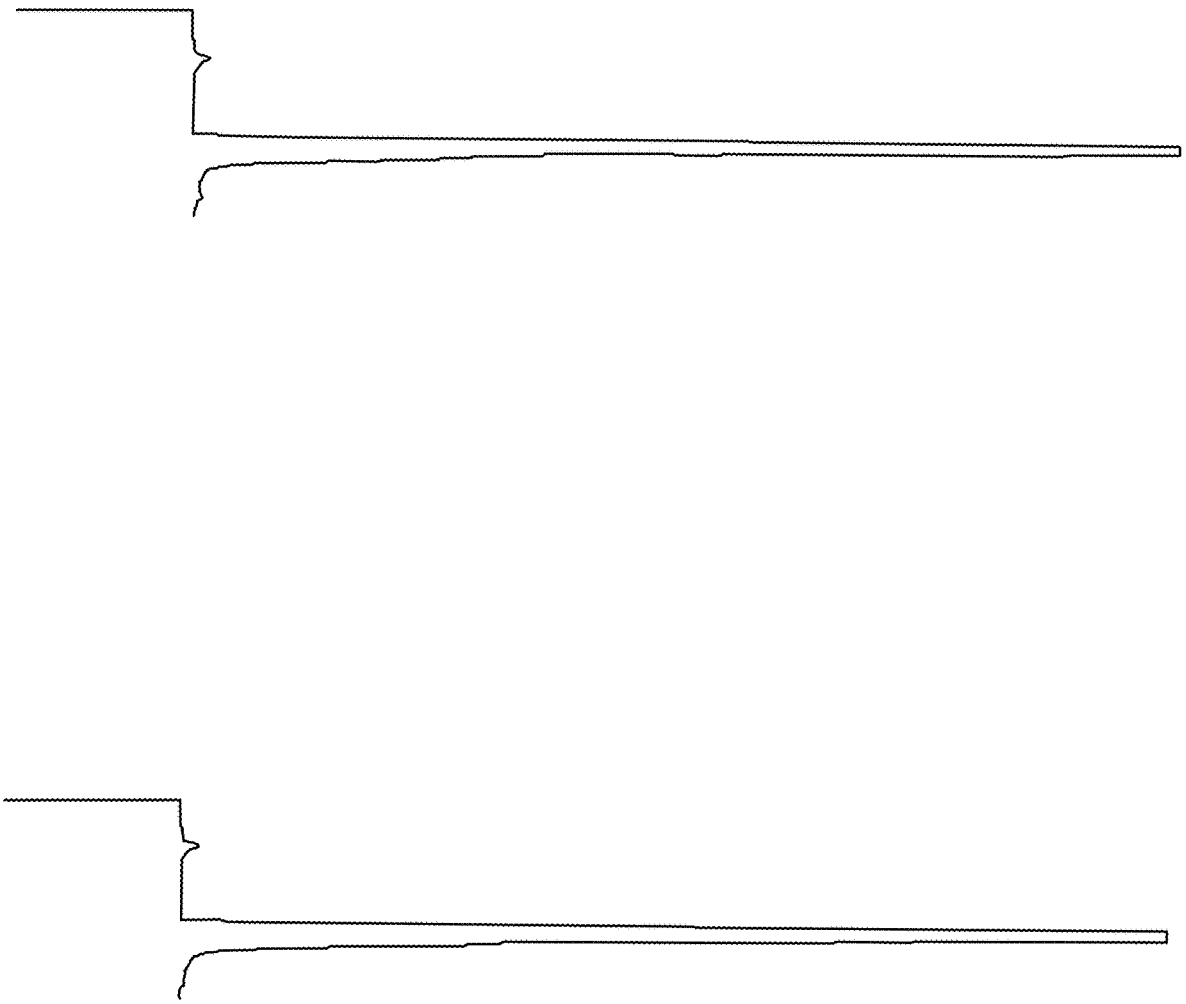
FIG. 18 shows typical HPLC chromatograms of dissolution wafer 1 at 1 minute and 5 minutes.
Figure 19:
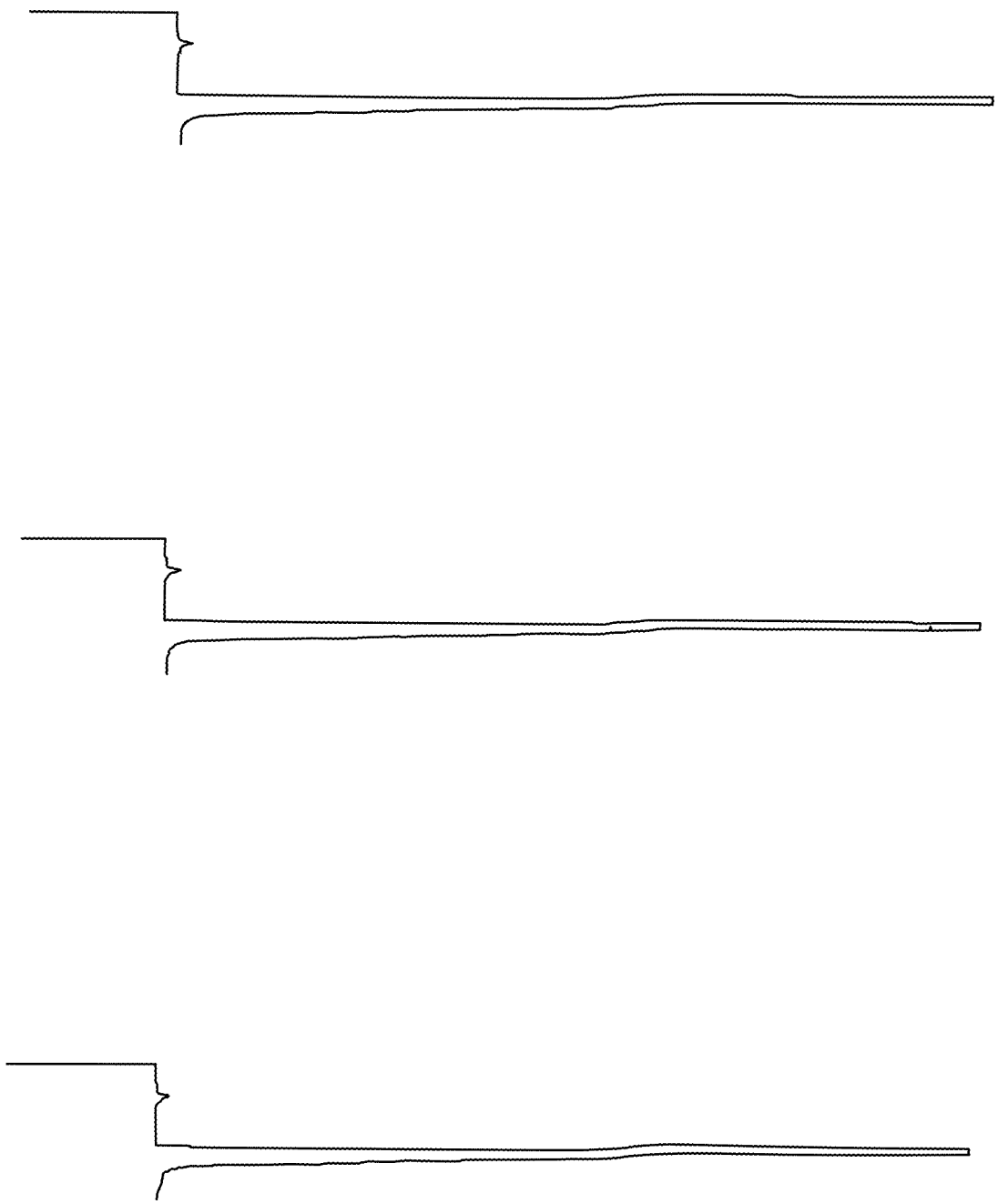
FIG. 19 shows typical HPLC chromatograms of dissolution wafer 1 at 5, 10 and 15 minutes.
Figure 20:
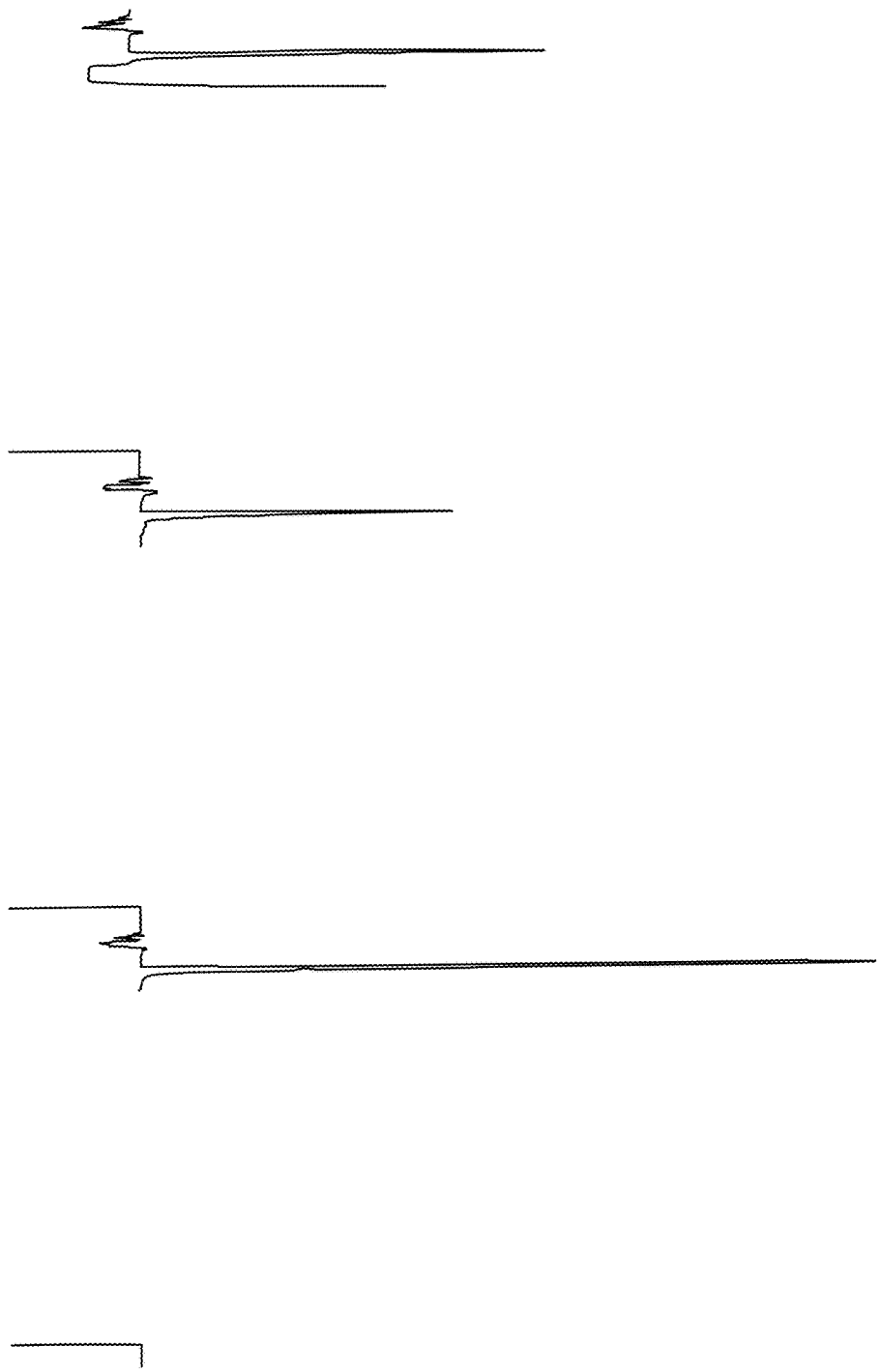
FIG. 20 shows a typical HPLC chromatogram of drug loading test wafer sample No. 1.
Figure 21:
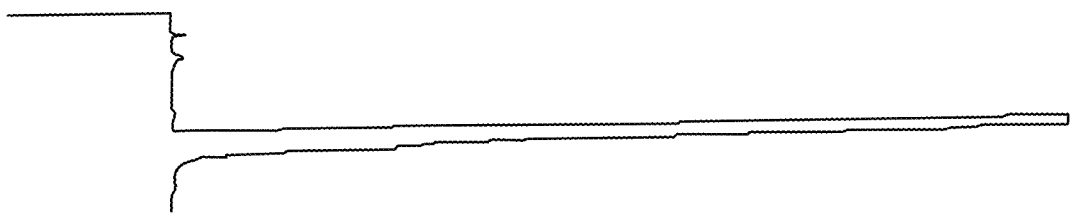
FIG. 21 shows typical HPLC chromatograms of dissolution wafer 2 at 30 seconds.
Figure 21:
Figure 22:
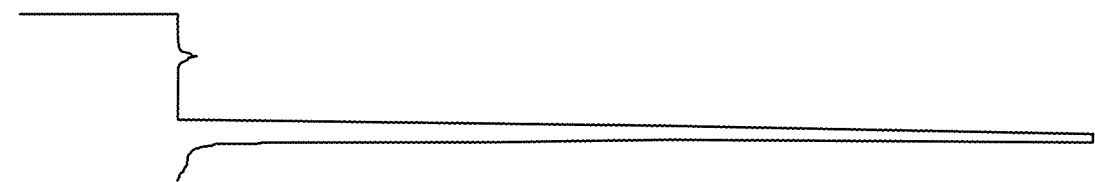
FIG. 22 shows typical HPLC chromatograms of dissolution wafer 2 at 1 minute and 5 minutes.
Figure 22:
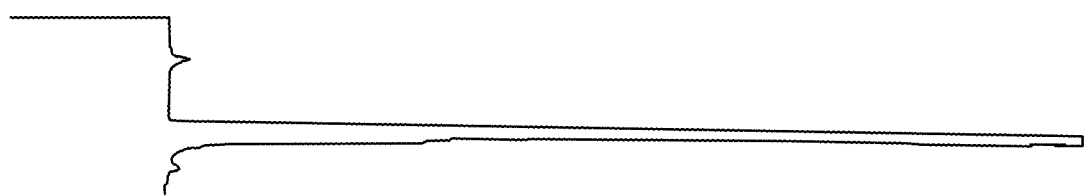
Figure 23:
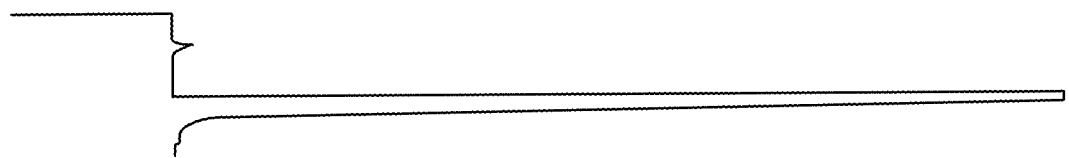
FIG. 23 shows typical HPLC chromatograms of dissolution wafer 2 at 10, 15 and 30 minutes.
Figure 23:
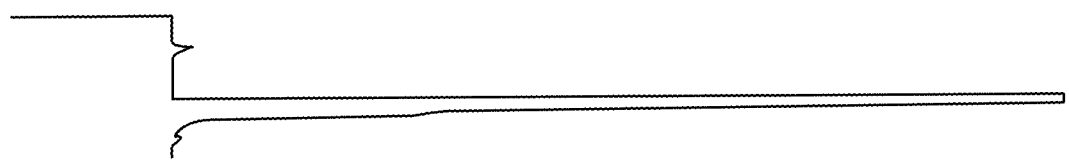
Figure 23:
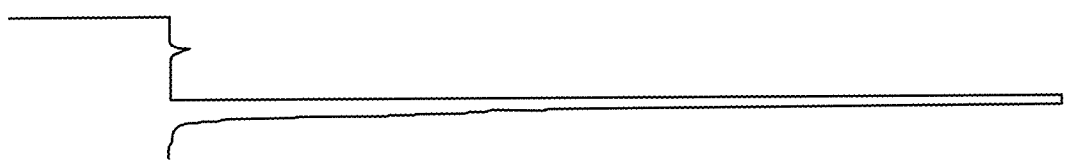
Figure 24:
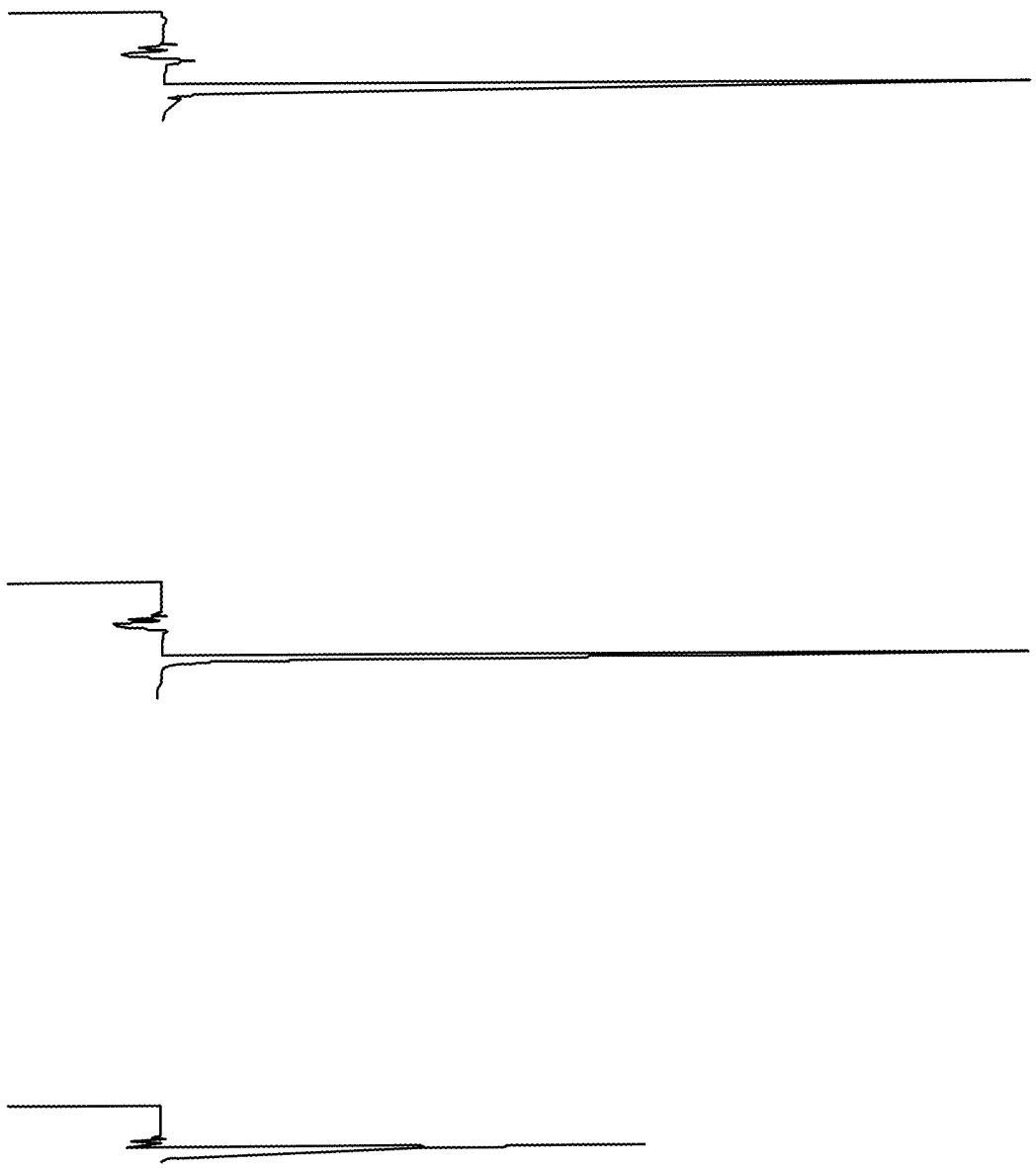
FIG. 24 shows typical HPLC chromatograms of drug loading test wafer sample No. 2.
Figure 25:
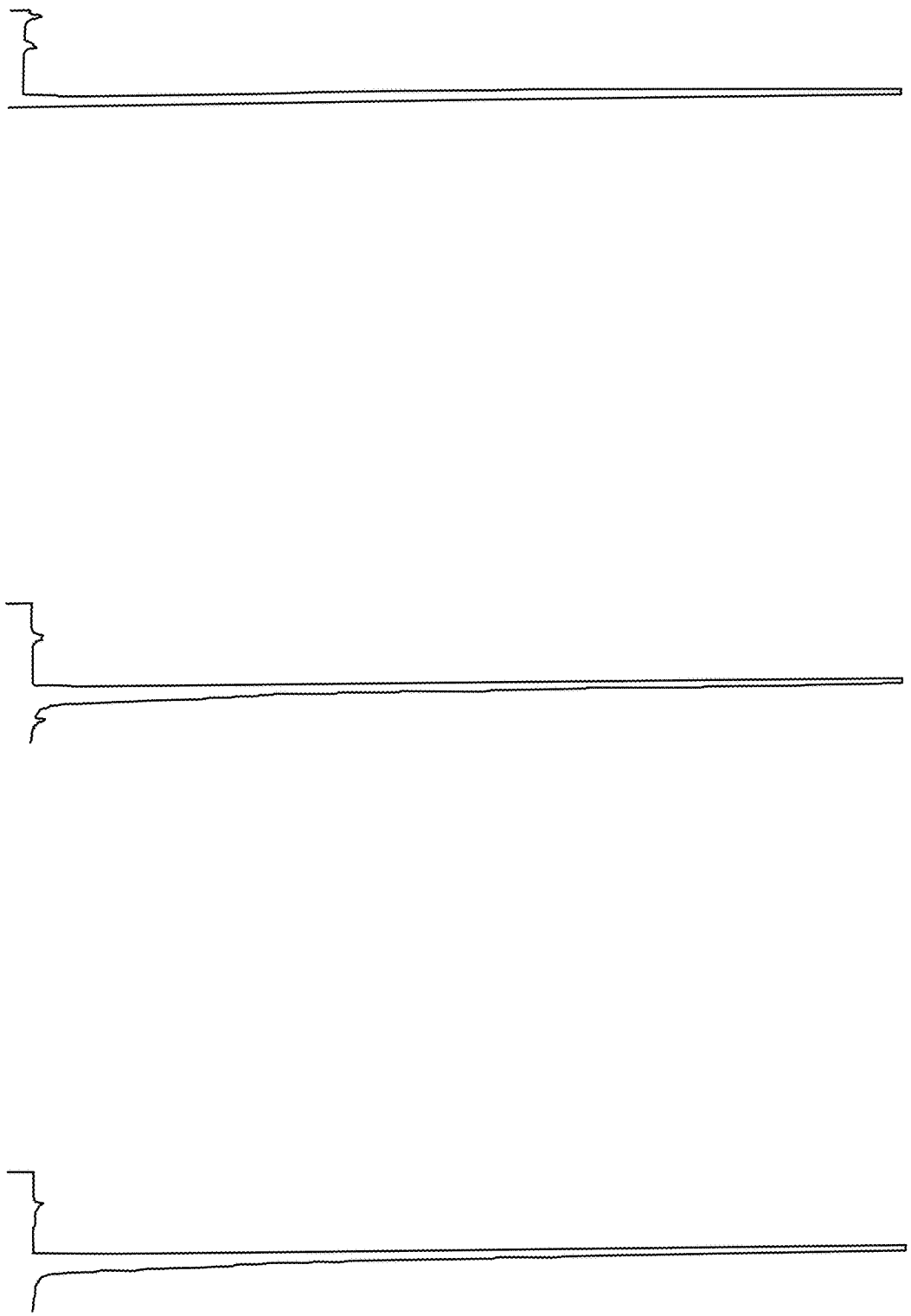
FIG. 25 shows typical HPLC chromatograms of dissolution wafer 3 at 30 seconds.
Figure 26:
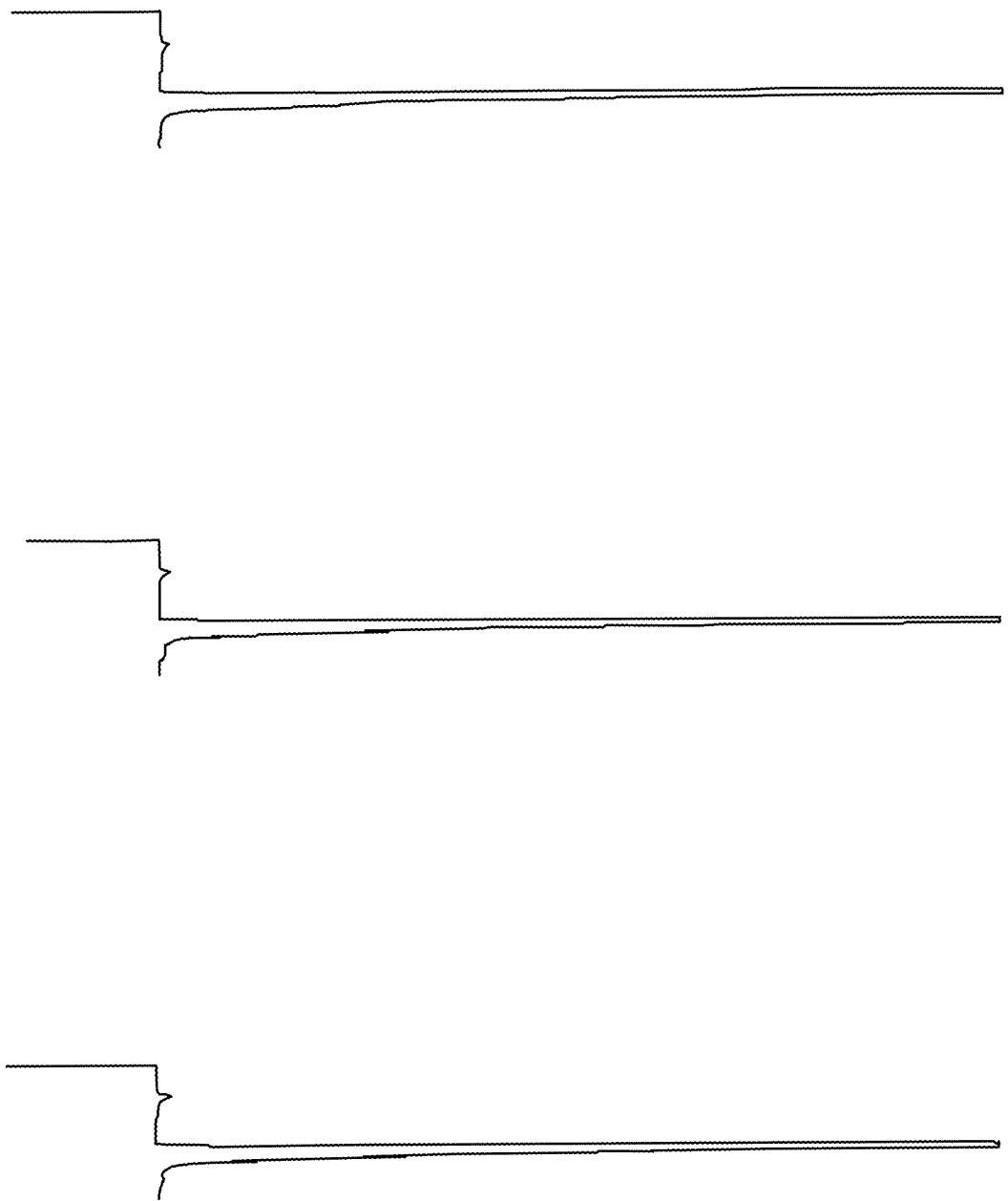
FIG. 26 shows typical HPLC chromatograms of dissolution wafer 3 at 1 minute and 5 minutes.
Figure 27:
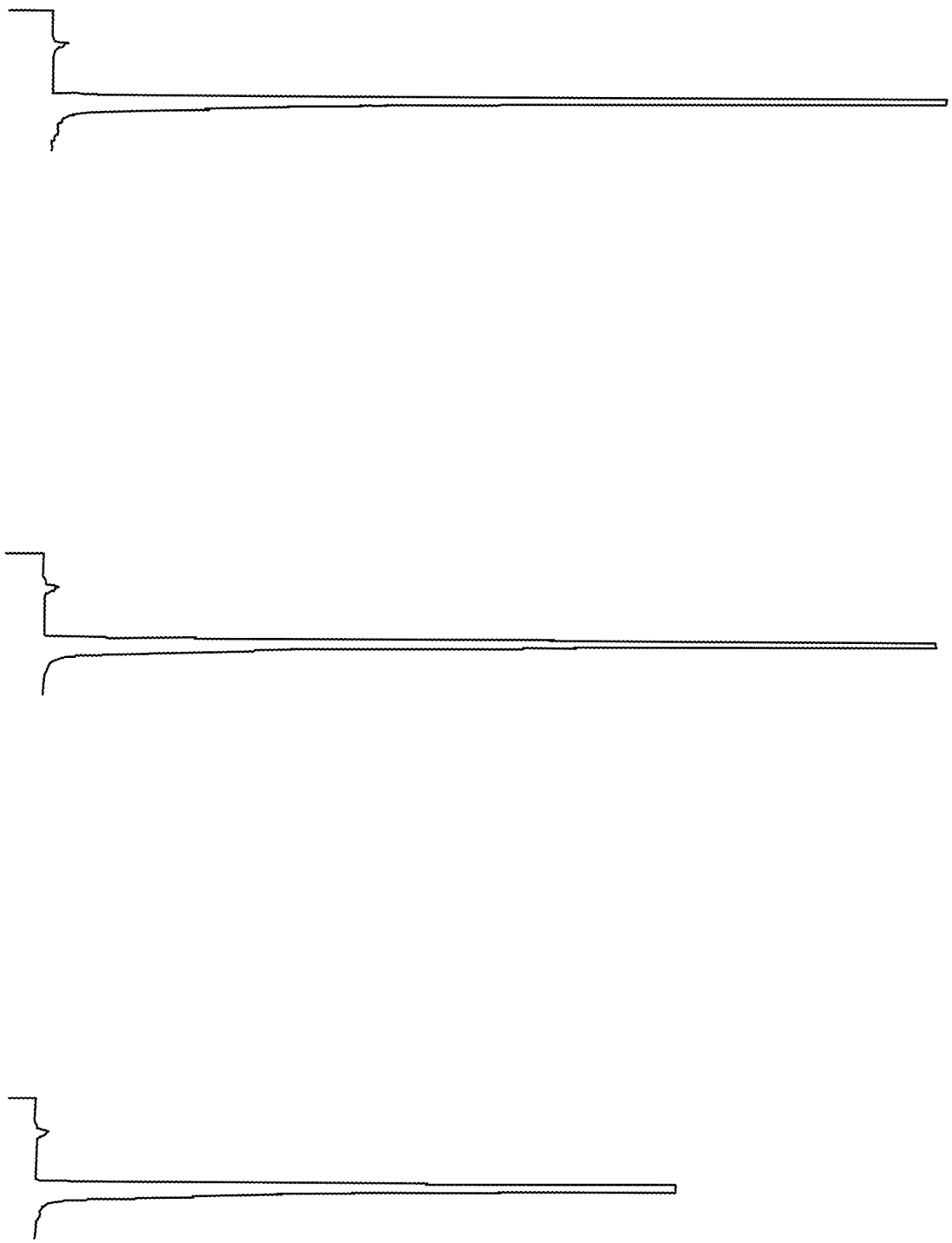
FIG. 27 shows typical HPLC chromatograms of dissolution wafer 3 at 10 and 15 minutes.
Figure 28:
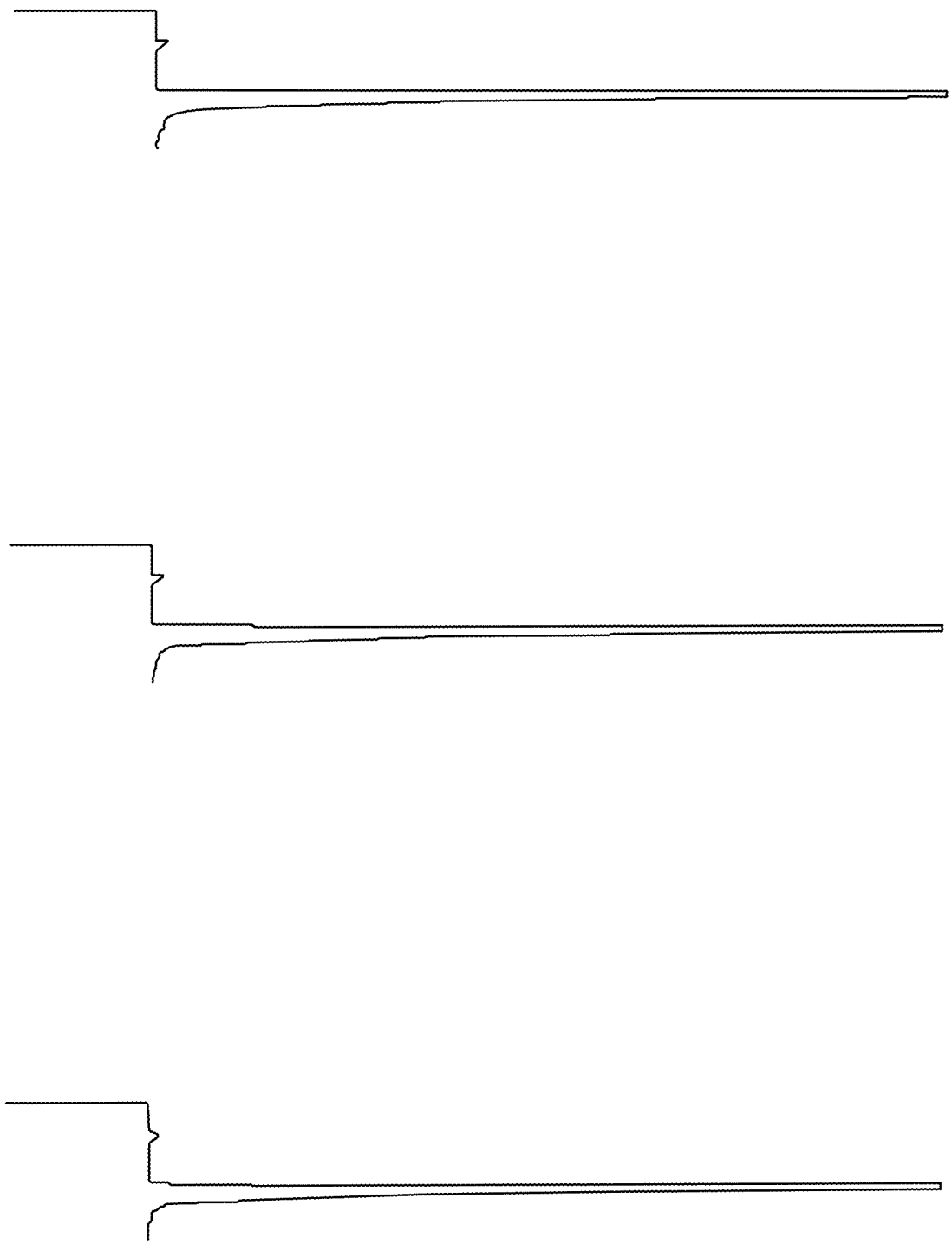
FIG. 28 shows typical HPLC chromatograms of dissolution wafer 3 at 30, 45 and 60 minutes.
Figure 29:
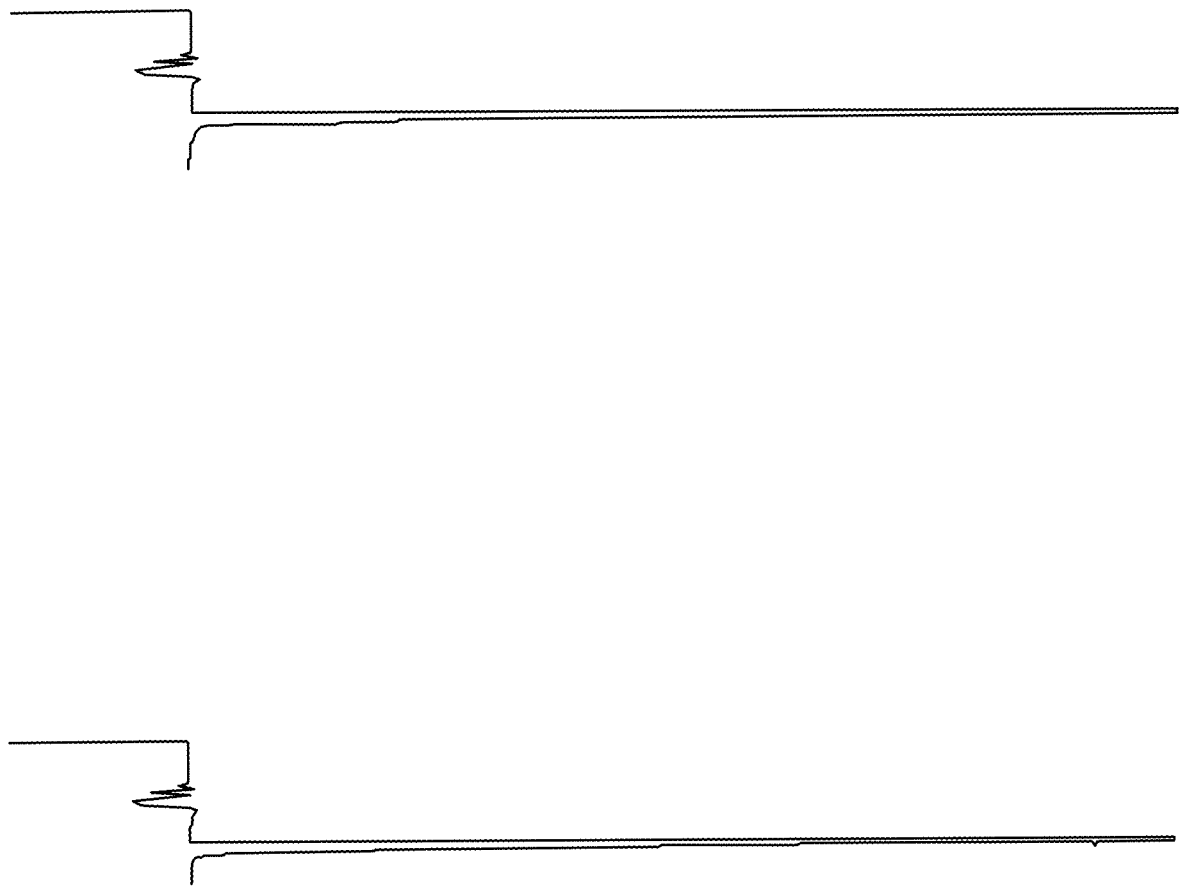
FIG. 29 shows typical HPLC chromatograms of drug loading test wafer sample No. 3.

For the dissolution testing a wafer (Batch 0905MD) containing midazolam as a model drug was used to determine the mechanism of drug release from the system following the both BP basket and USP paddle methods (see FIG. 17). Dissolution medium was 500 mL phosphate buffer solution (pH value is closed to saliva fluid at 6.8), with a paddle rotation speed at 75 rpm. At given interval (e.g., 0.5, 1, 2, 3, 5 10 15, 20 and 30 min), 2 mL of solution was sampled and replaced with an equal volume of fresh medium to maintain a constant total volume. Samples were filtered through a 0.2 μm Millipore filter. The drug released was measured by HPLC.

The HPLC system consisted of a Waters 1525 pump, a Waters Symmetry $C_{18}$ column (5 μm, 150×4.6 mm), and Waters UV 484 detector. The mobile phase was acetonitrile: 10 mM ammonium acetate buffer (40:60, v/v, pH 4.10) and the flow rate was 1.2 mil/min at ambient temperature. The peaks were recorded at 220 nm, and the limit of quantitation was approximately 1 ng/ml. The calibration curve for the concentrations 1-32.4 μg/mL (six-point calibration) was linear [y=870714x+52057 (r=0.9998), y representing the peak area of midazolam and x the concentration of the samples].

Figure 30:
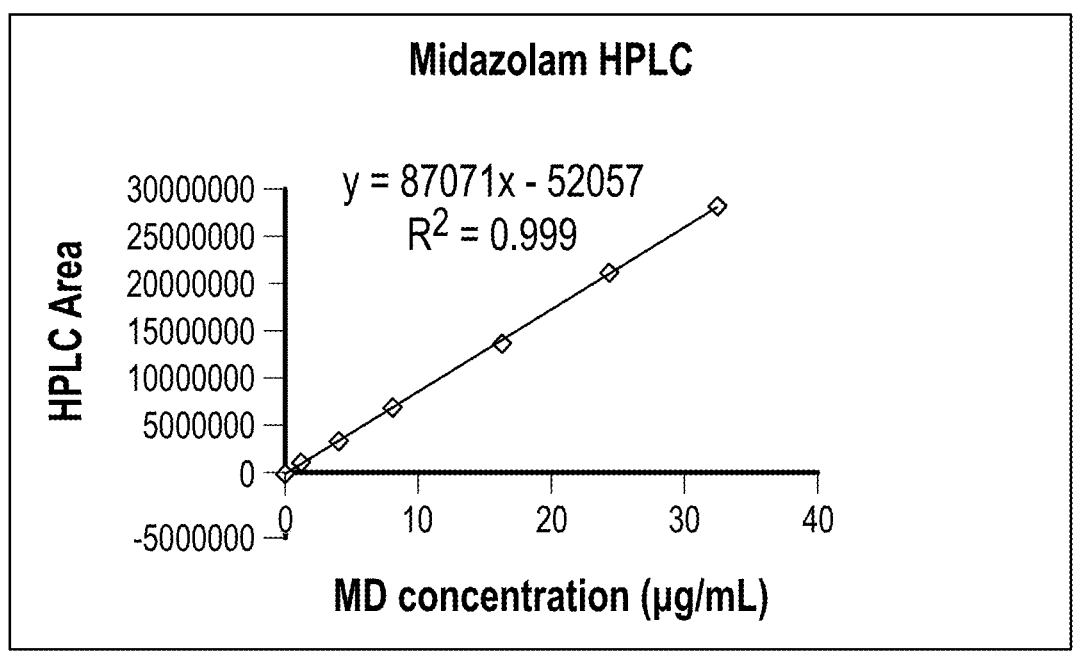
FIG. 30 shows a standard HPLC calibration curve of midazolam (1 to 32.4 µg/mL).
Figure 31:
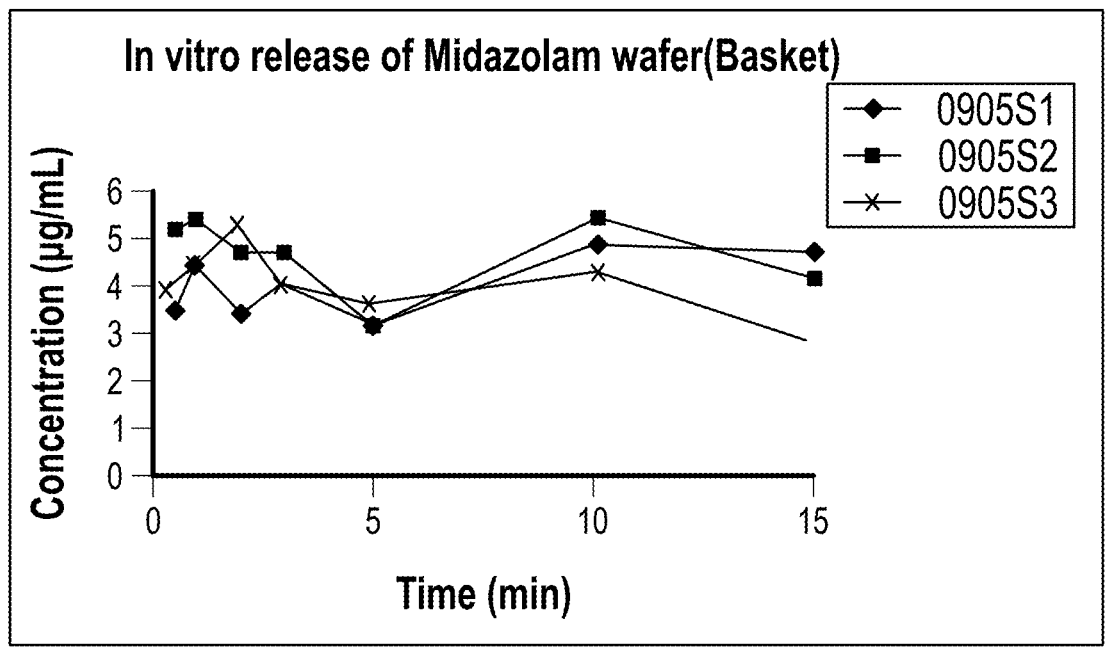
FIG. 31 shows cumulative concentration of midazolam released from wafer and midazolam powder in phosphate buffer solution (pH 6.8) at 37° C.
Figure 31:
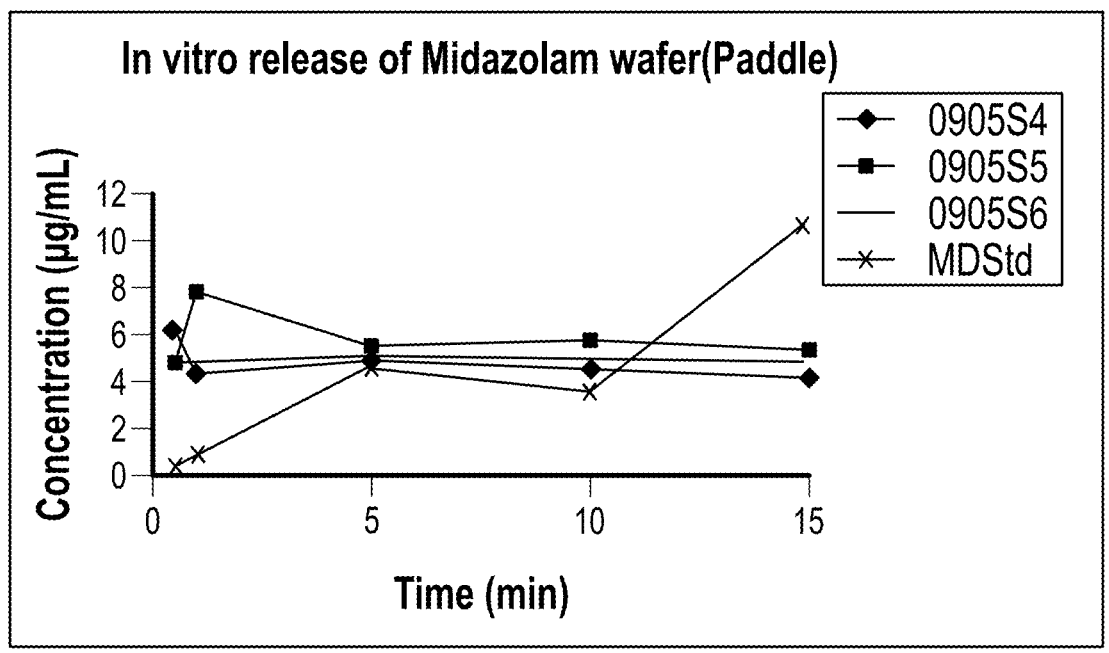

A standard HPLC calibration curve for midazolam is shown in FIG. 30. The results as shown in FIG. 31 demonstrate that the average disintegration times were less than 15 seconds; and the dissolution studies also indicated a fast release rate of midazolam, Almost 75% of midazolam had dissolved in one minute. The raw midazolam powder was considerably slower. This may indicate the changing of midazolam crystal form in the wafer, which was also evident in the X-ray. The X-ray spectrum pointed to an amorphization of midazolam during the freeze-drying process.

The results of the HPLC analysis on various samples of the formulation as prepared in accordance with Table 1 are shown in FIGS. 11 to 29. FIGS. 10A to 10E illustrate the HPLC of standard midazolam sample, and midazolam powder dissolution samples. FIGS. 11 to 16 are HPLC chromatograms of dissolution wafer samples 1 to 3 (S1, S2 and S3, BP basket method). Briefly, the samples 1, 2 and 3 were prepared according to Table 1 and are triplicate samples of the same formulation. FIG. 17 illustrates the HPLC chromatogram of Batch 0905MD, which contains midazolam as a model drug.

FIGS. 18 to 29 reflect the HPLC chromatograms of another three dissolution wafer samples (USP paddle methods). As discussed above, the dissolution rate of the wafer containing test drug midazolam was measured. Samples were taken at 0.5 minute, 1 minute, 5, minutes, 10 minutes and 15 minutes.

The results of wafers 1 to 3 (Batch 0905MD) are shown over these time limits in FIGS. 18 to 29. A drug loading test was also conducted for another three wafers (Batch 0905MD).

It was shown that the wafers of the present invention were able to completely dissolve in about 15 seconds and did not leave behind any residue.

A wafer (Batch 1003FEN) containing fentanyl as a model drug was used to determine the mechanism of drug release from the system following the BP basket method. The dissolution rates of the wafer were determined in a small volume (10 mL phosphate buffer solution, pH 6.8) with a basket rotation speed at 50 rpm. At given interval (e.g., 0.5, 1, 2, 3, 4, 5, 7, 10 and 15 min), 0.5 mL of solution was sampled and replaced with an equal volume of fresh medium. The drug released was measured by HPLC.

Figure 32:
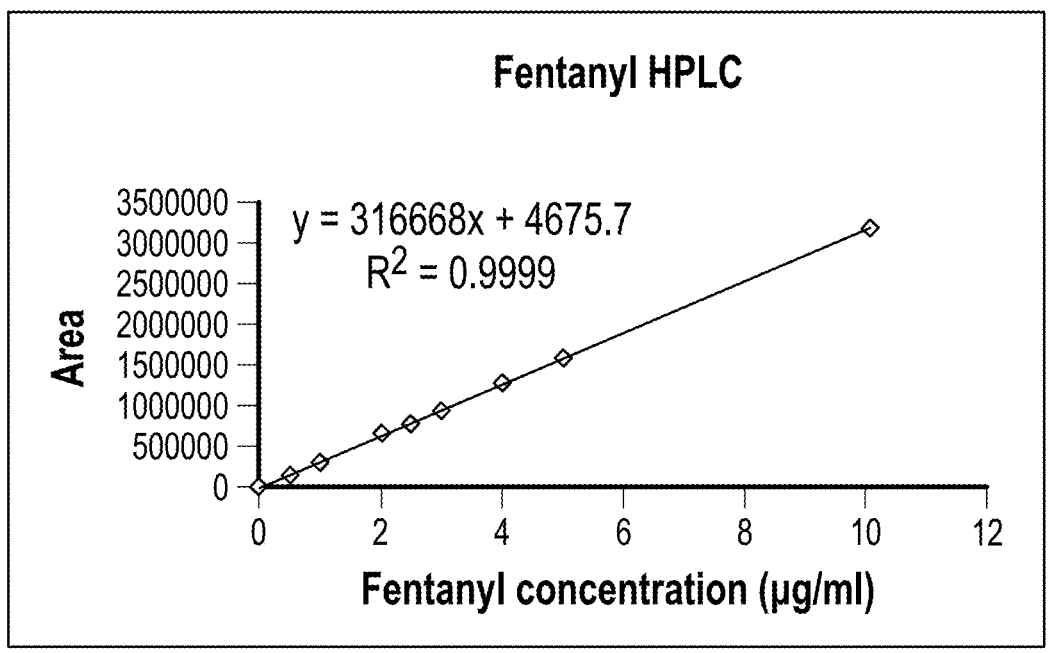
FIG. 32 shows a standard HPLC calibration curve of fentanyl (0.5 to 10 µg/mL).

The mobile phase was methanol: 0.4% phosphoric acid (50:50, v/v, pH 2.3) and the flow rate was 1.2 ml/min at ambient temperature. The monitoring wavelength was at 210 nm. The calibration curve for the concentrations 0.5-10 μg/mL (eight-point calibration) was linear [y=316668x+ 4675.7, (r=0.9999), y representing the peak area of fentanyl and x the concentration of the samples]. The assay standard curve is shown in FIG. 32.

Figure 33:
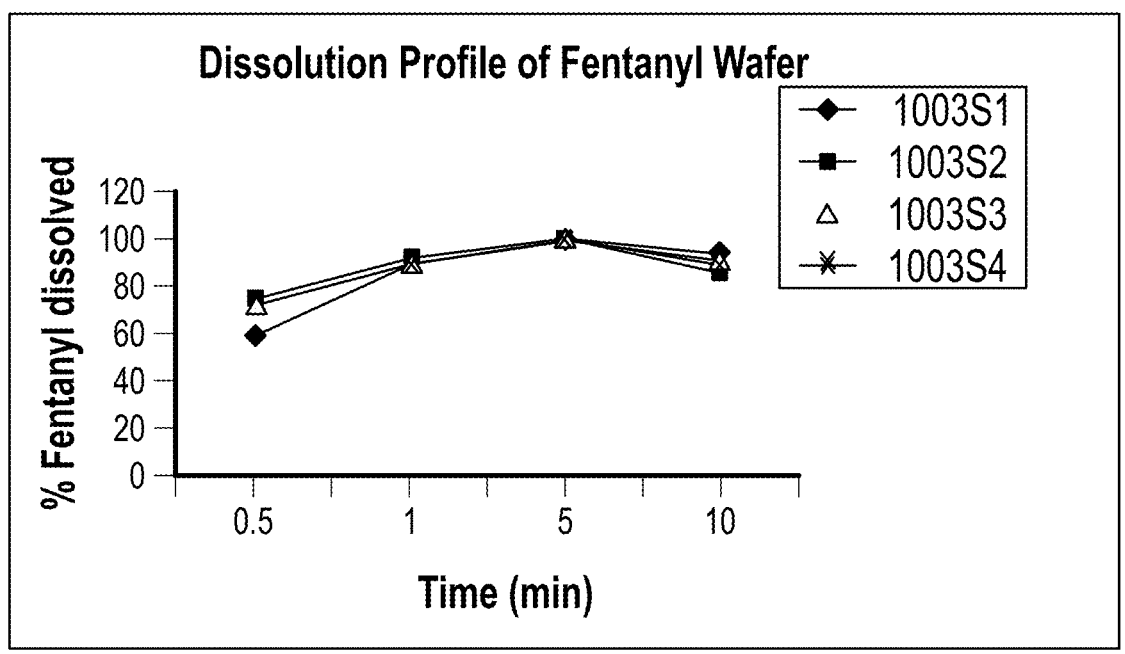
FIG. 33 shows dissolution profiles of fentanyl wafer in phosphate buffer solution (pH 6.8) at 37° C., (n=4).
Figure 34A:
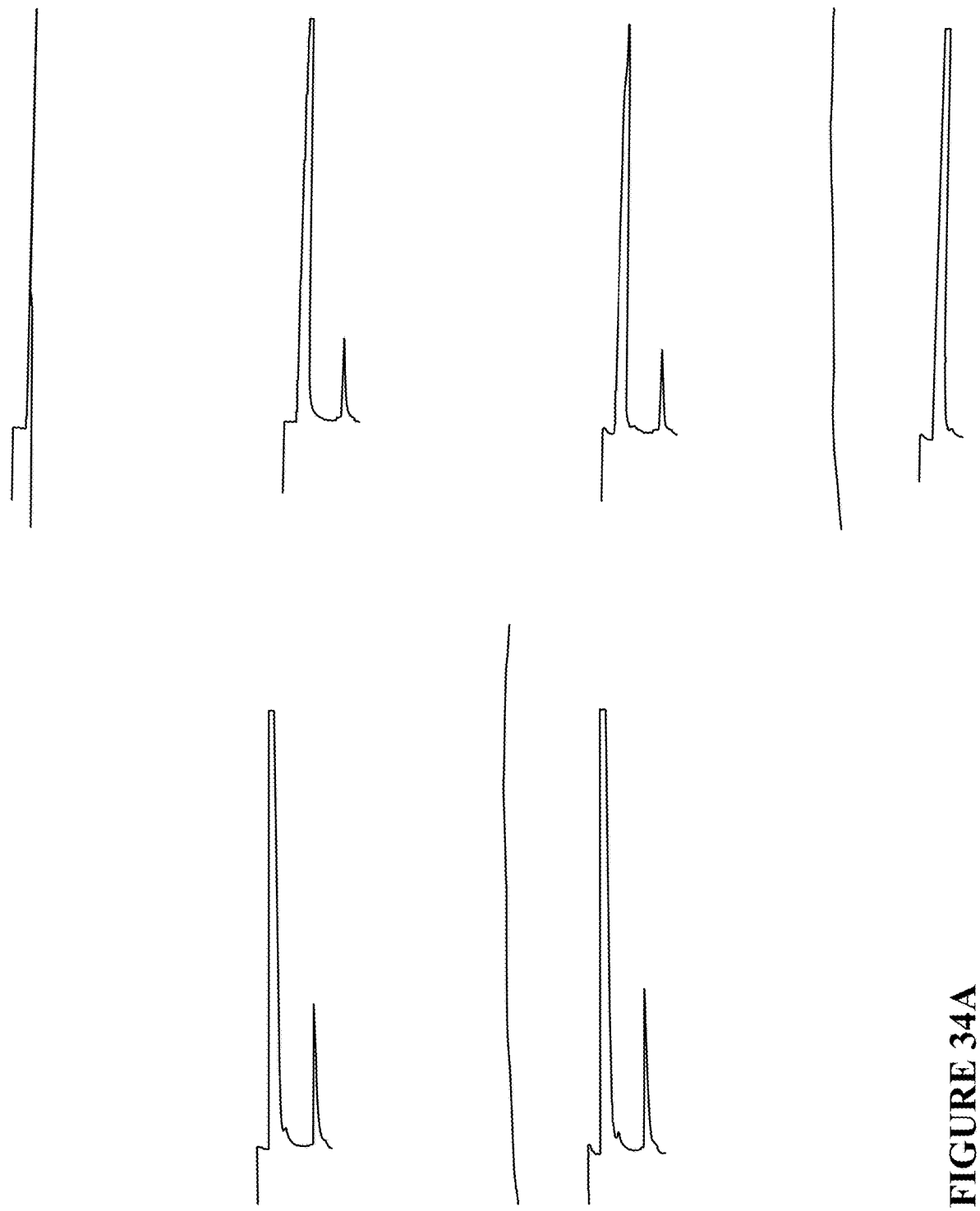
FIG. 34 A to E shows typical HPLC chromatograms of dissolution samples 1 to 3 of fentanyl wafers at sampling times of 0.5, 1, 5, 10, 15 and 20 minutes.
Figure 34B:
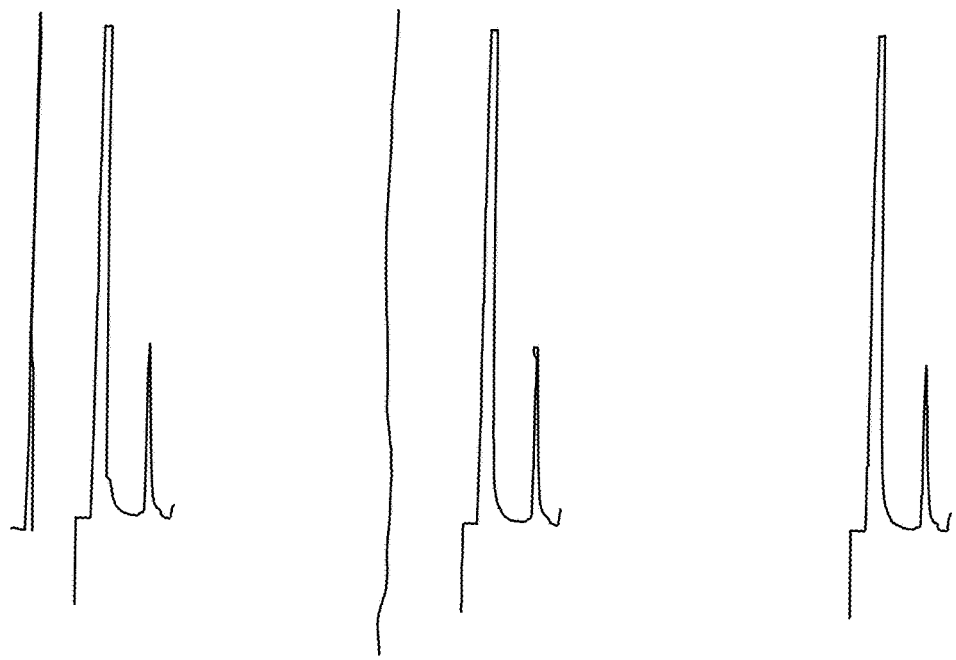
Figure 34B:
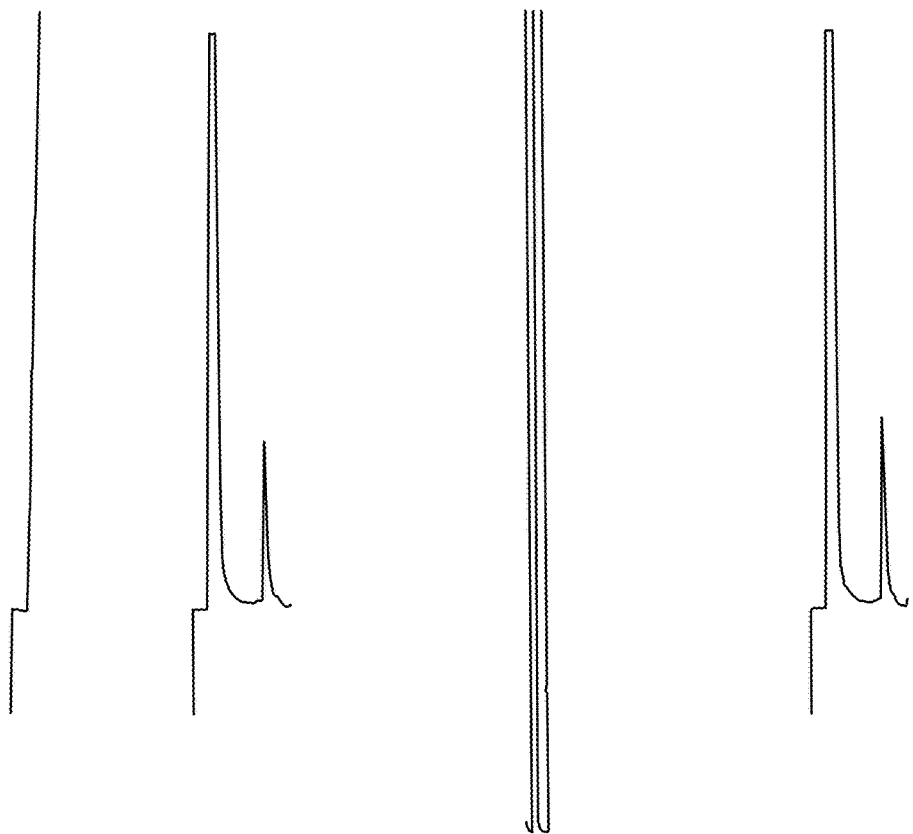
Figure 34C:
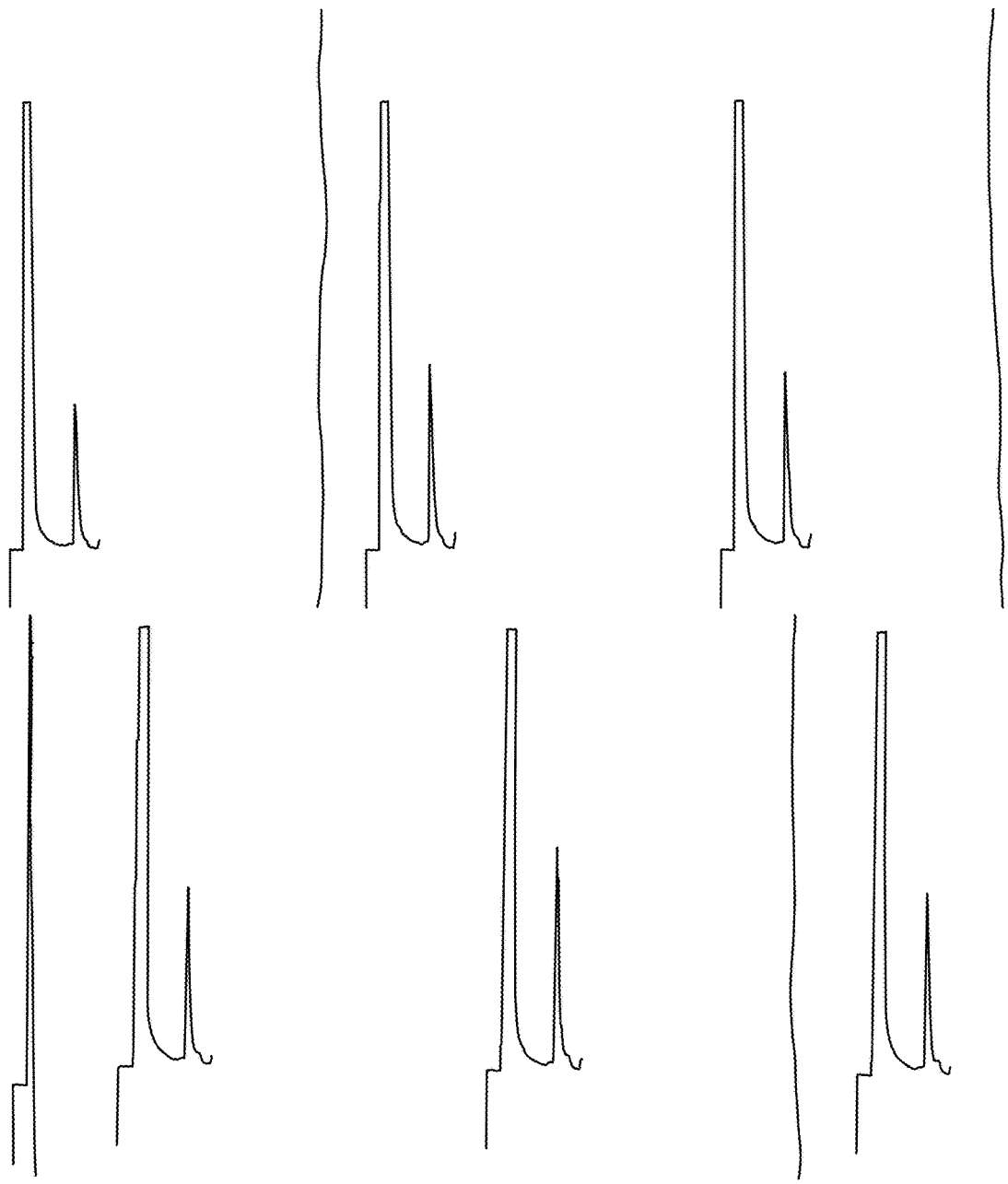
Figure 34D:
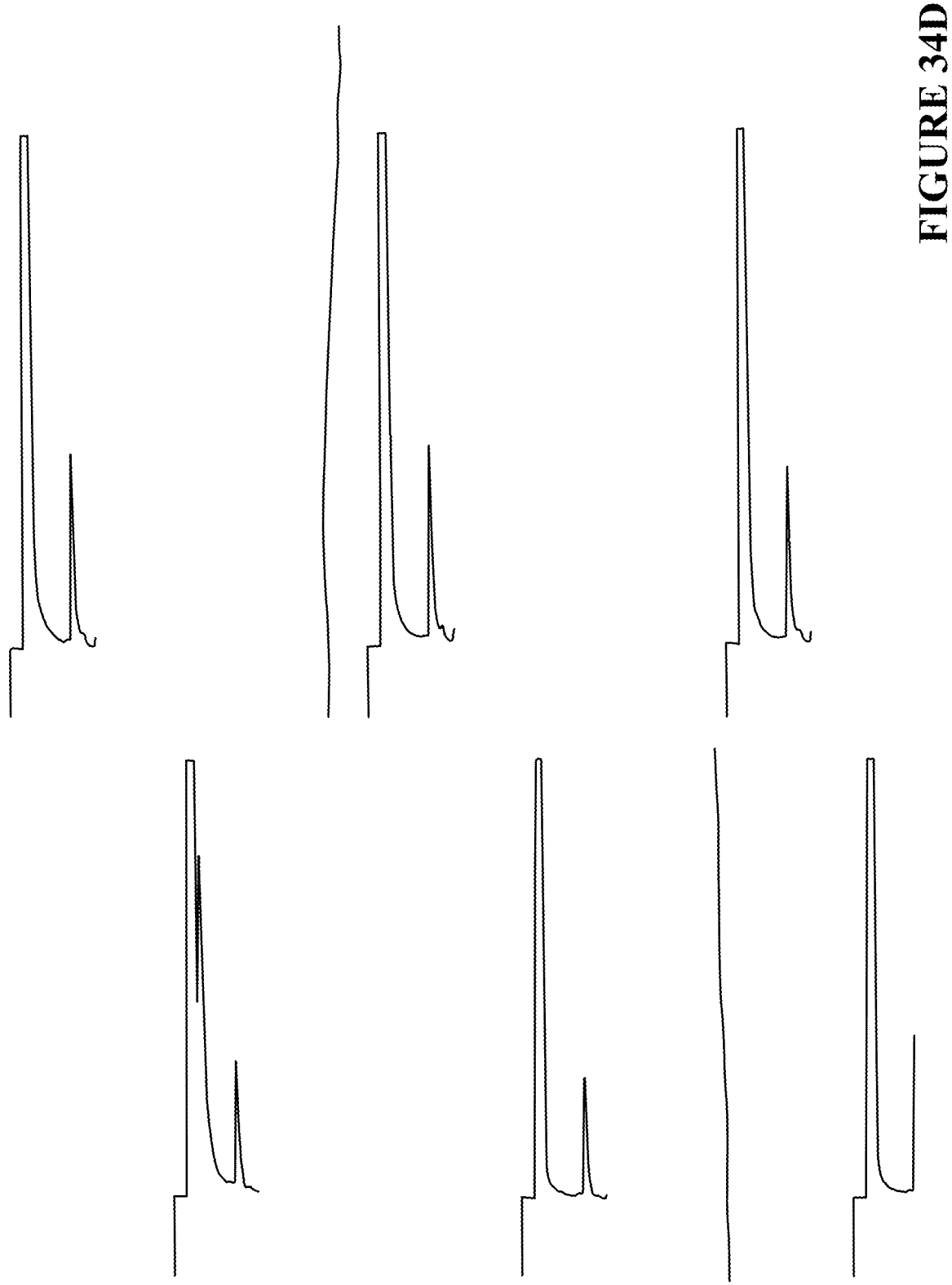
Figure 34E:
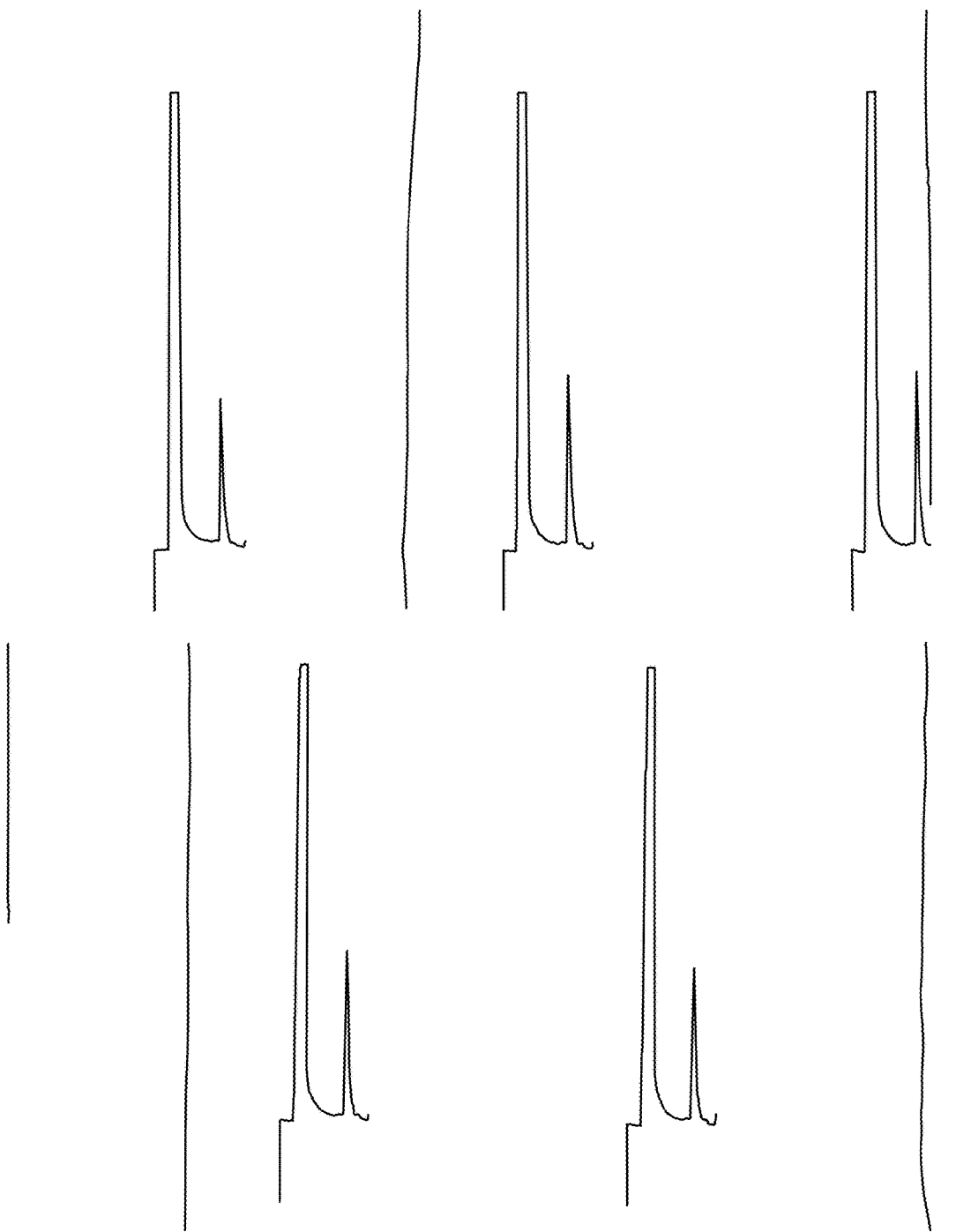
Figure 35A:
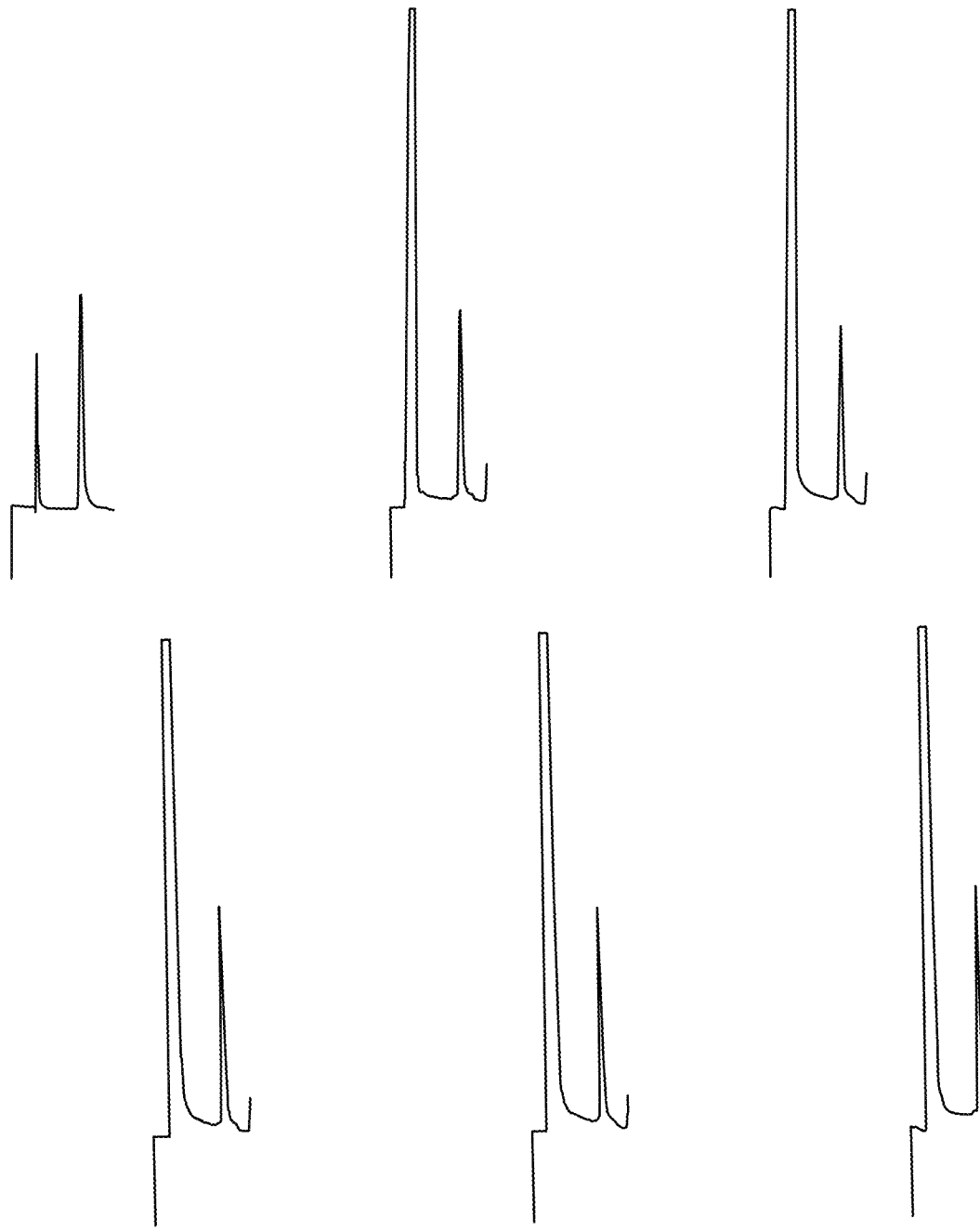
FIG. 35 A to J shows typical HPLC chromatograms of dissolution samples 4 to 6 of fentanyl wafers at sampling times of 1, 2, 3, 4, 5, 7 and 10 minutes.
Figure 35B:
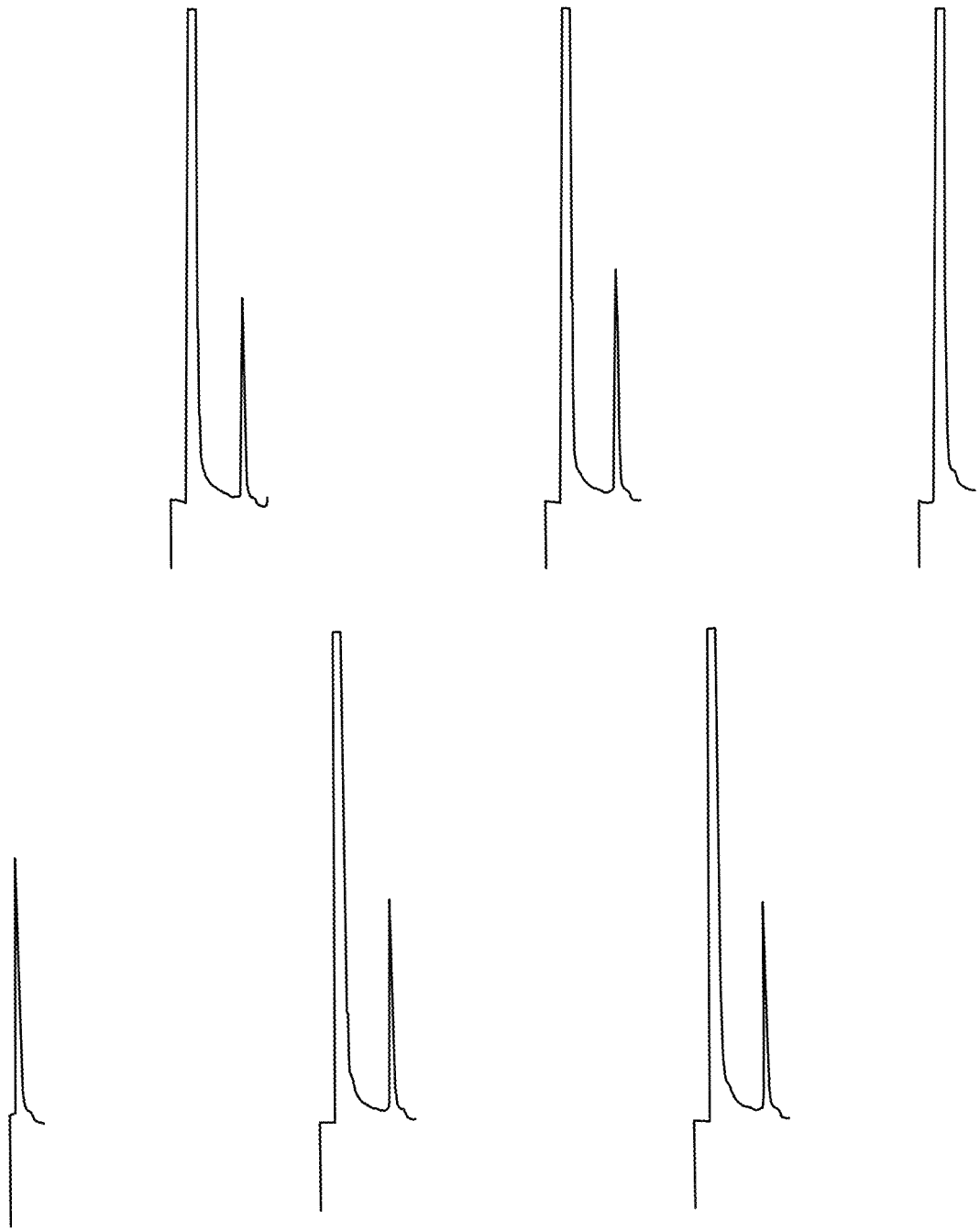
Figure 35C:
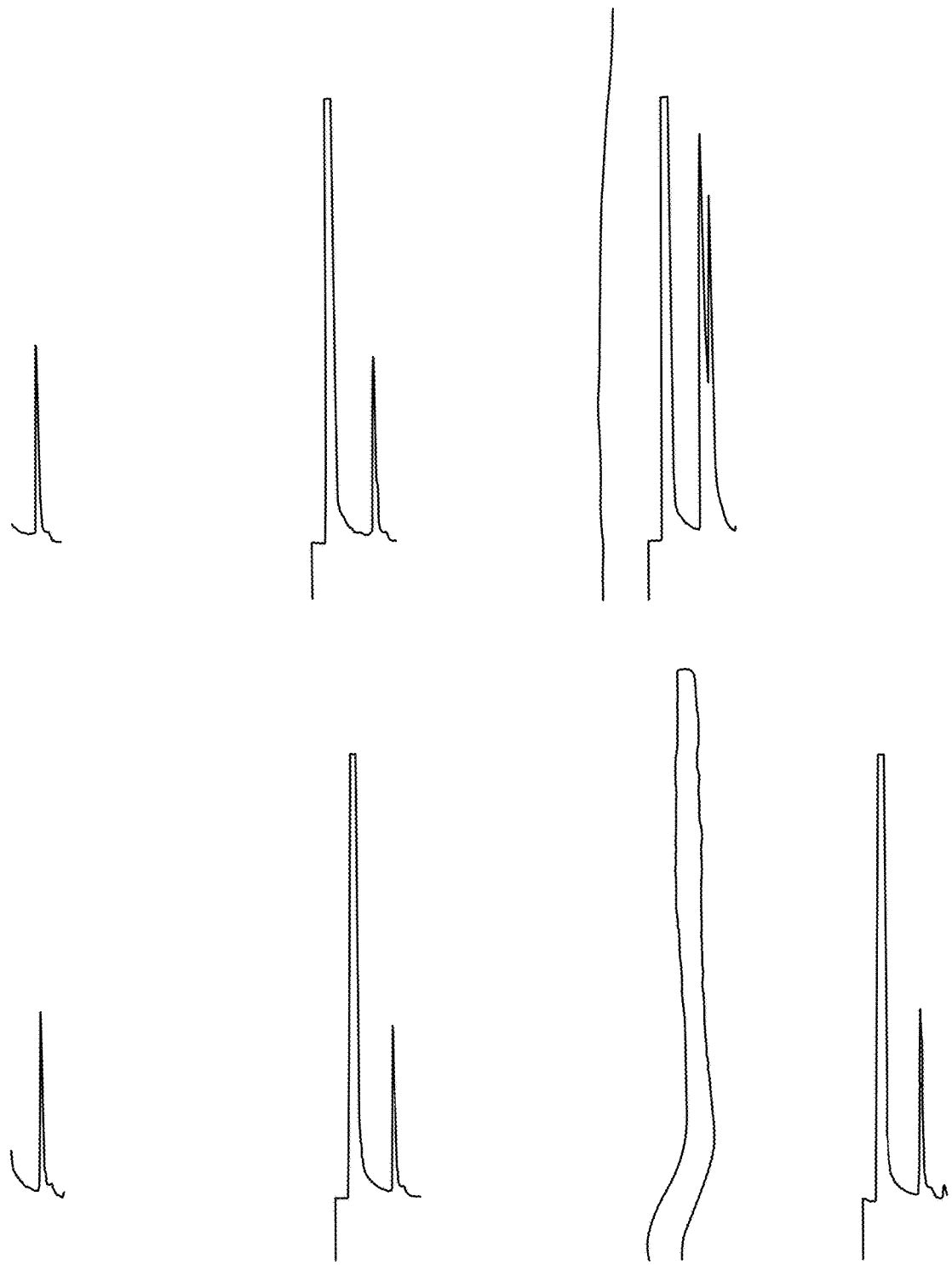
Figure 35D:
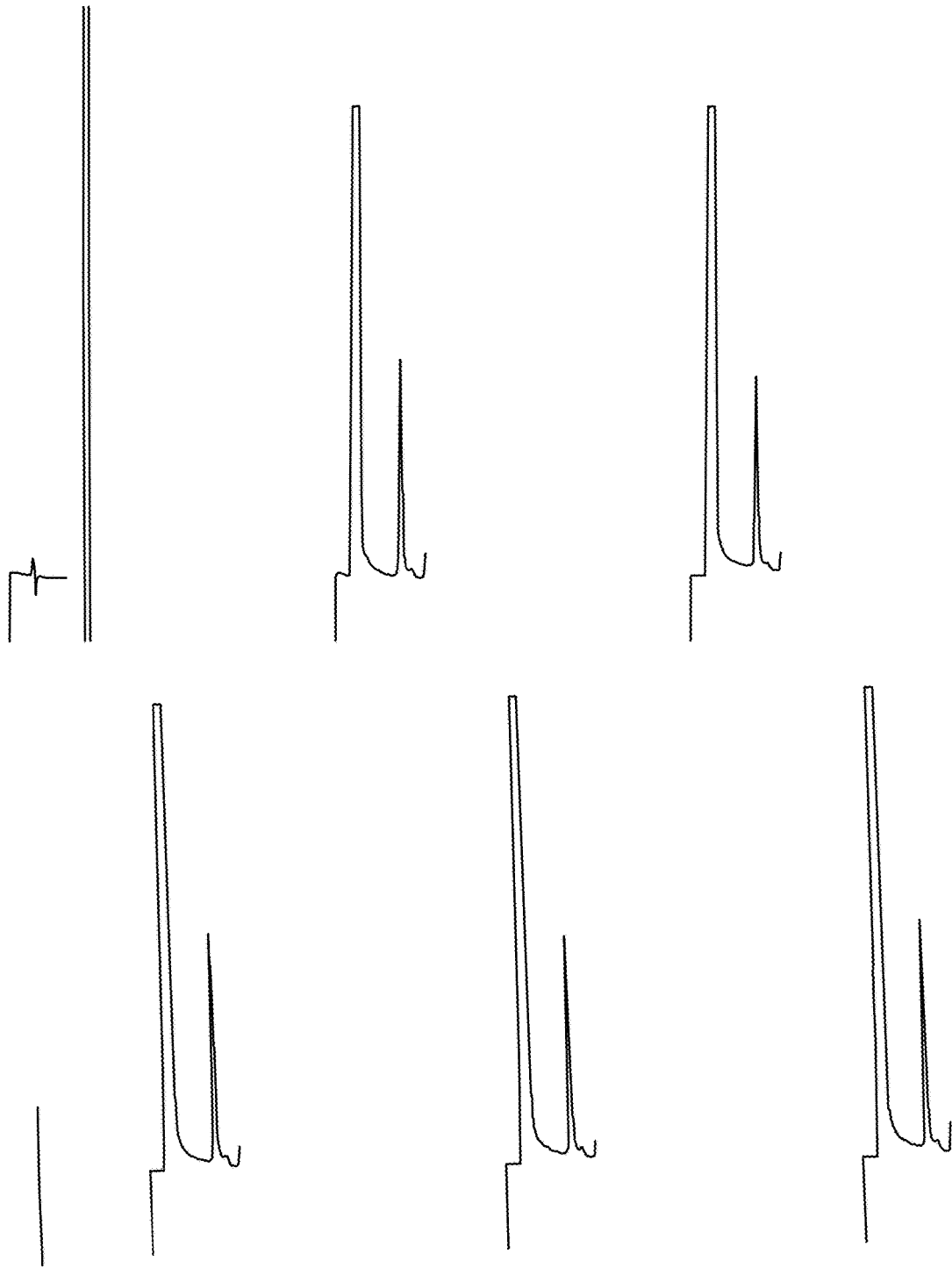
Figure 35E:
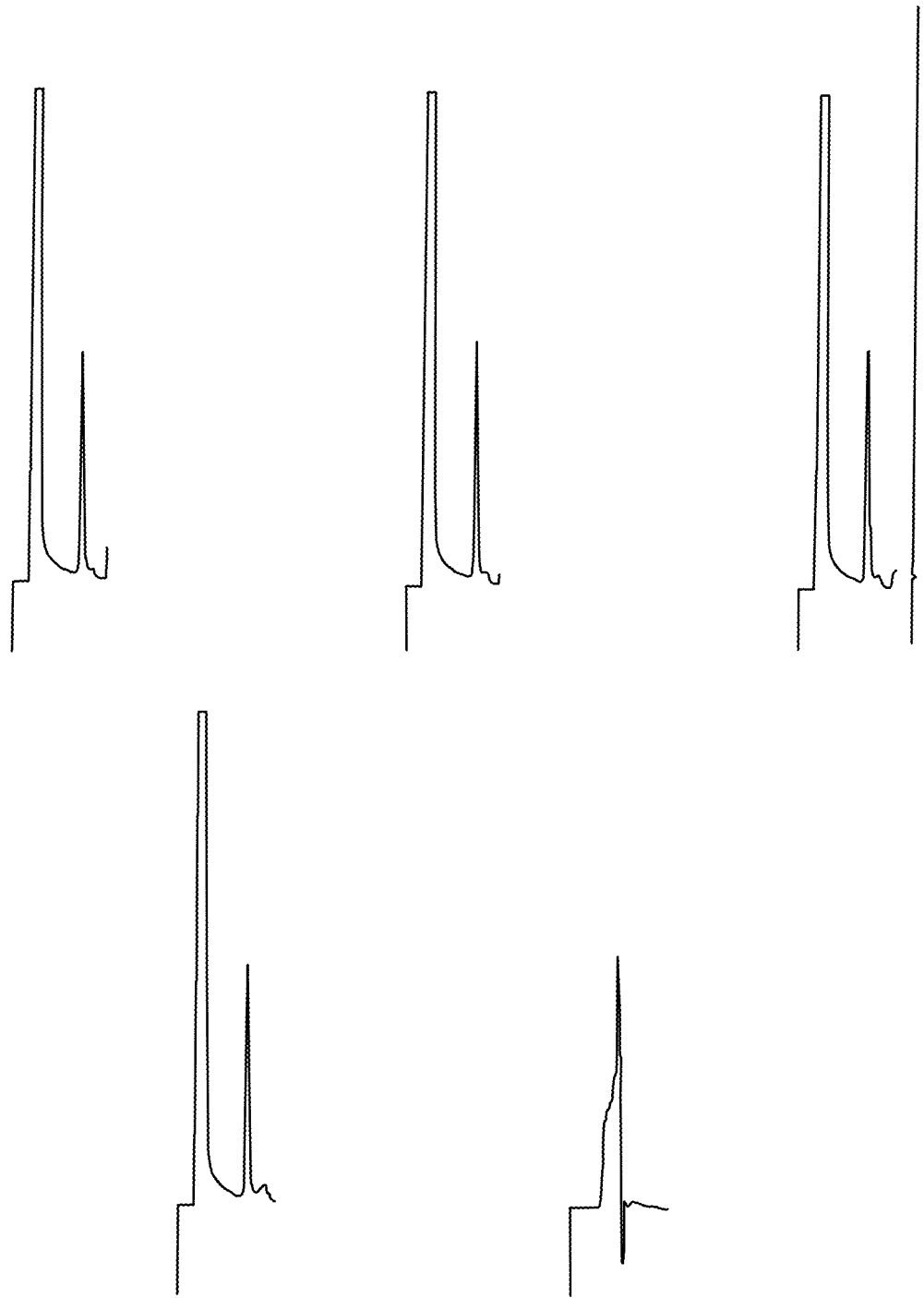
Figure 35F:
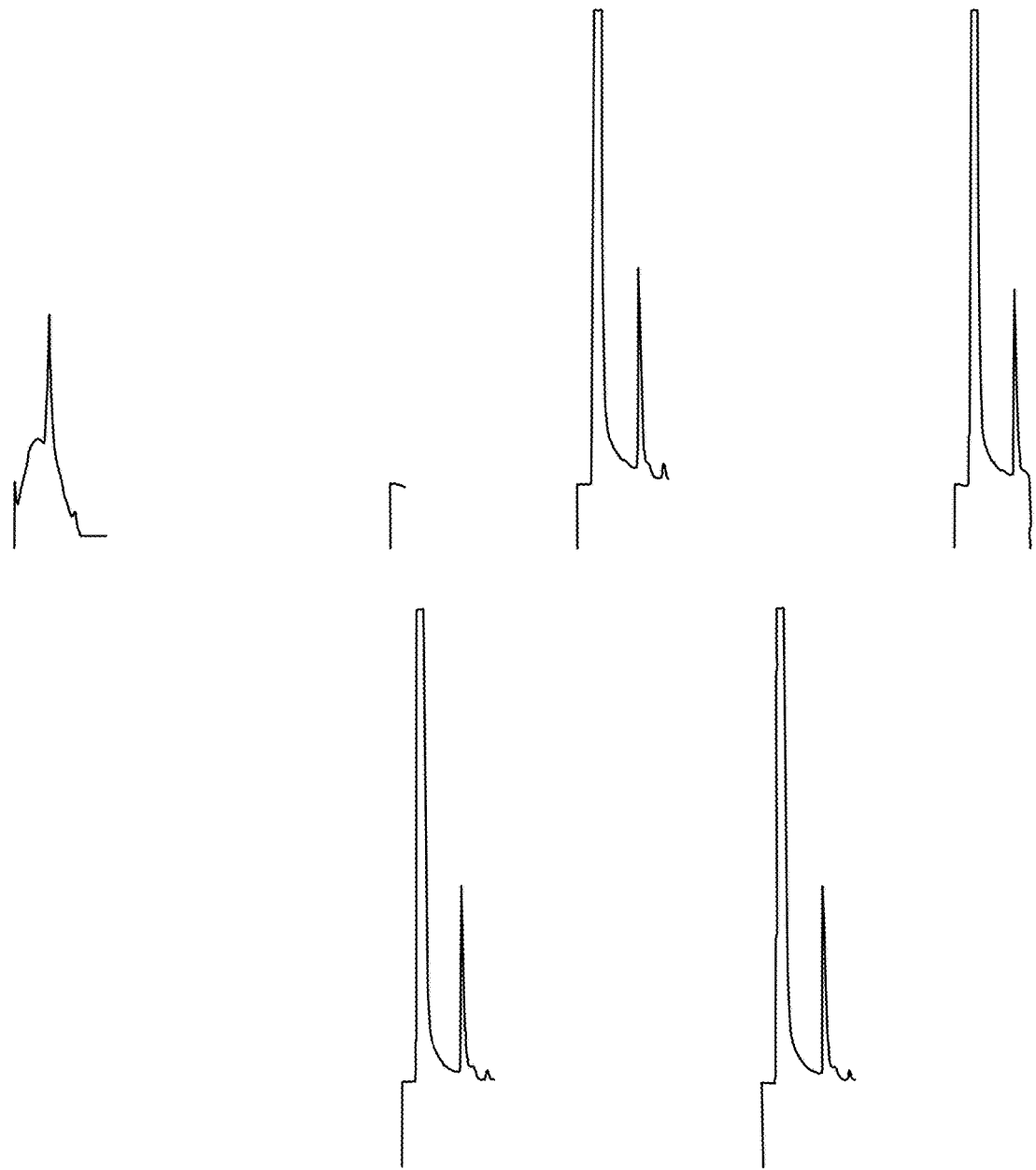
Figure 35G:
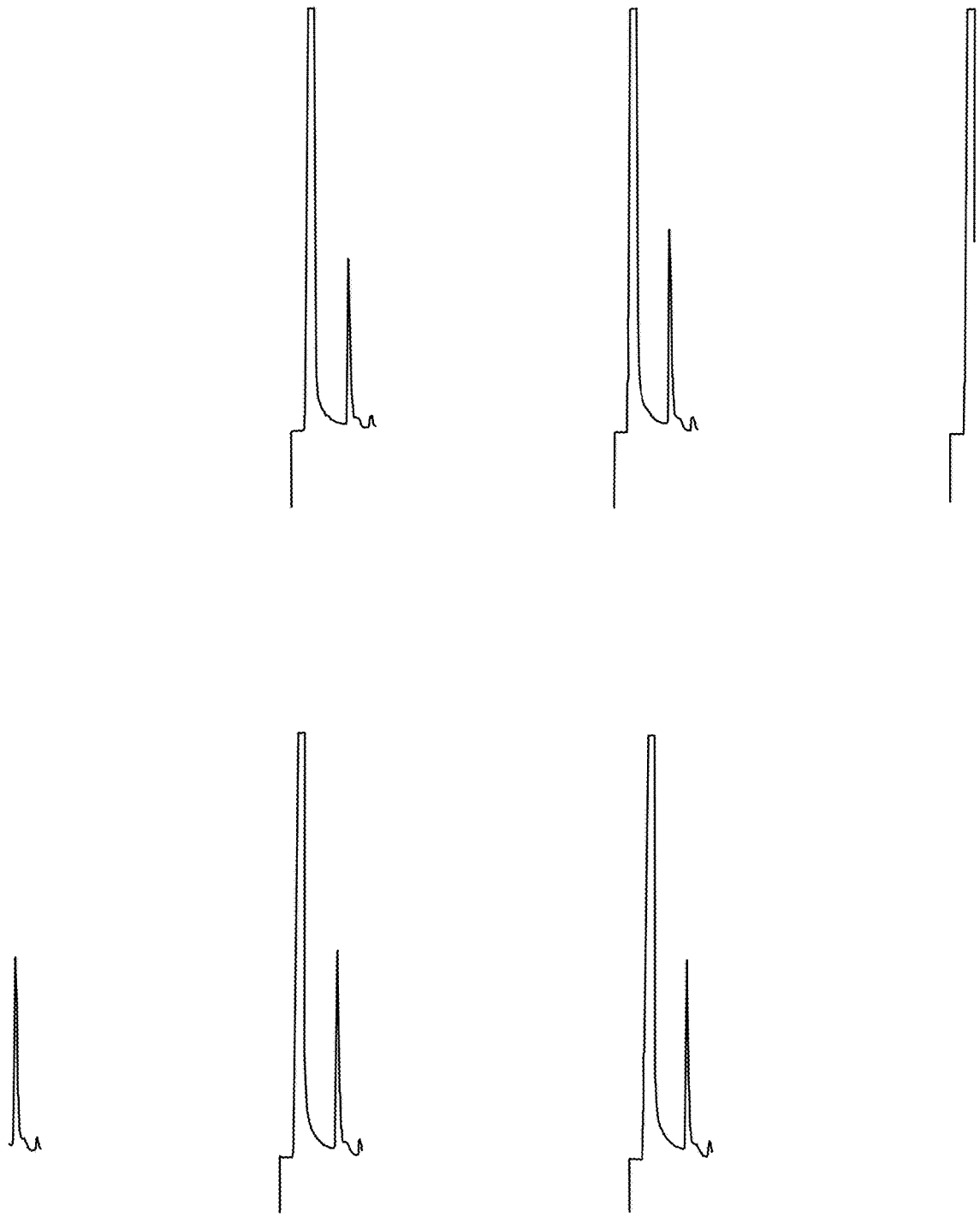
Figure 35I:
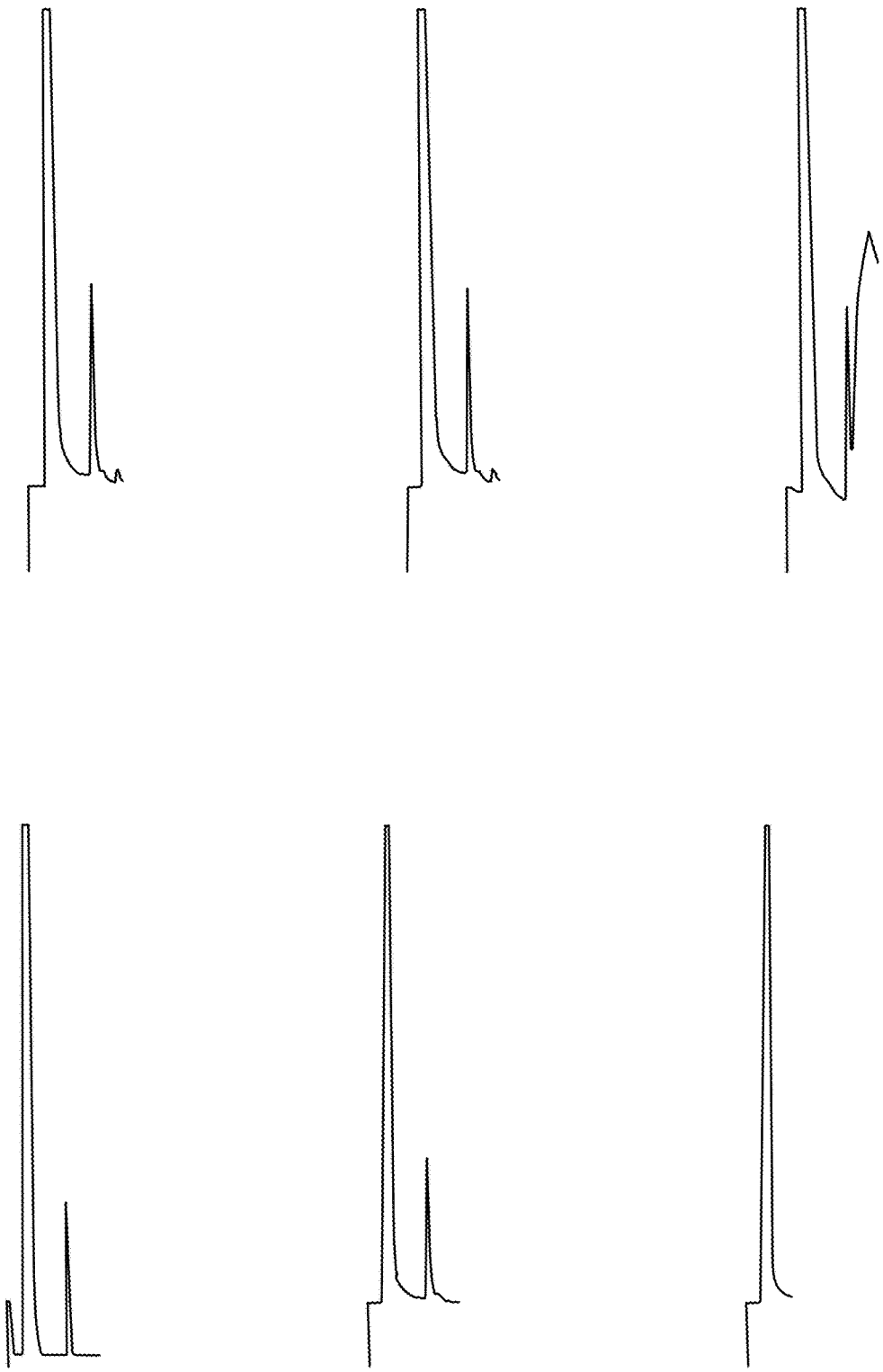
Figure 35J:
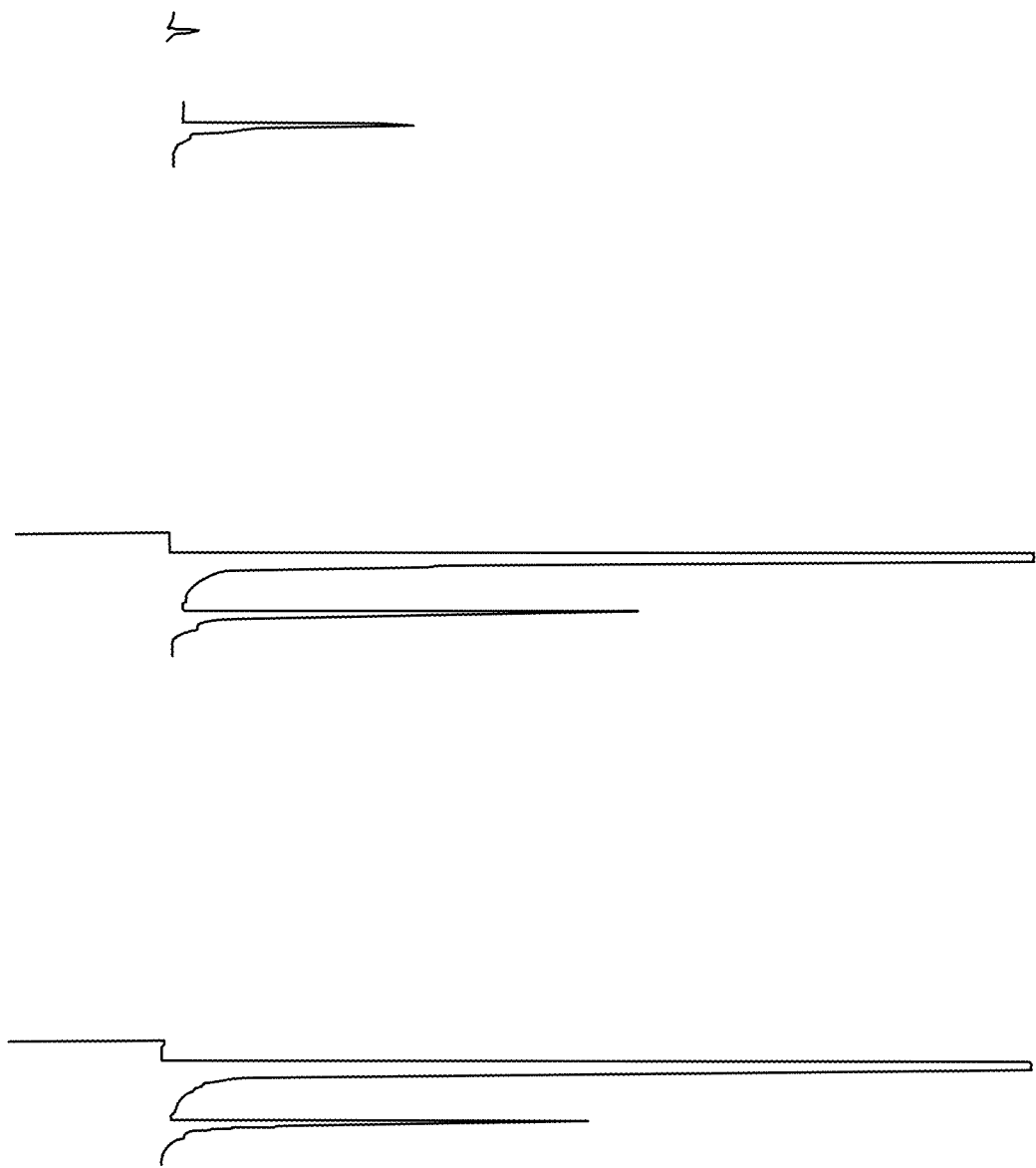

The prepared fentanyl wafer (batch 1003FEN) showed a weight variation of ±2.55%, and the mean percentage fentanyl content of the wafer was 91.32% (BP standard for uniformity content limits 85 to 115%). The average disintegration times were less than 15 seconds; and the dissolution studies also indicated a fast release rate of fentanyl. Almost 90% of fentanyl had dissolved in one minute. The dissolution profiles are presented in FIG. 33.

The HPLC chromatograms of six dissolution samples of fentanyl wafers were collected and is shown in FIGS. 34 A to E (samples 1 to 3) and FIGS. 35 A to J. (samples 4 to 6). The sampling of each test wafer was conducted at time of 0.5, 1, 5, 10, 15 and 20 minutes for dissolution samples 1 to 3, and at 1, 2, 3, 4, 5, 7 and 10 minutes for dissolution samples 4 to 6.

The fast dissolving dosage form is a solid dispersion of drug into a porous matrix. After administration, this dosage form quickly disintegrates in the oral cavity, and allows rapidly dissolving drug to be absorbed by diffusion directly into the systemic circulation, and the first-pass effect is avoided. This invention has the potential to provide an alternate route of drug administration and results in lower rates of side effect.

Example 2

A formulation of the present invention, in the form of a solid dosage form (wafer) containing ketamine, was prepared in accordance with the method and ingredients as set out below in Table 3:

TABLE 3

Compositions of Ketamine Fast Dissolving Solid Dosage Form (Strength equivalent of 25 mg of ketamine base)

| Ingredient (BP/USP) | Amount (g) | % by weight |
| --- | --- | --- |
| Sodium carbonate | 1 | 0.07 |
| Sodium carboxymethylcellulose | 2 | 0.15 |
| Polyethylene glycol 2000 | 5 | 0.36 |
| Glycine | 1 | 0.07 |
| Microcrystalline cellulose | 2 | 0.15 |
| Amylopectin | 50 | 3.64 |
| Ketamine | 62.5 | 4.55 |
| Lactose | 100 | 7.28 |
| Mannitol | 150 | 10.92 |
| Purified water | 1000 | 72.81 |

The dosage form wafers containing ketamine were produced using the method of Example 1 above.

The following additional formulations were prepared by the method of Example 1. Samples 1 to 6 are based on the formulation described above (strength equivalent of 25 mg ketamine base), with the addition of flavour and/or colour agents.

Sample 1. Additionally Contained a Flavour.

| Ingredient | Amount (g) | % by weight |
| --- | --- | --- |
| Sodium carbonate | 1 | 0.07 |
| Sodium carboxymethylcellulose | 2 | 0.14 |
| Polyethylene glycol 2000 | 5 | 0.35 |
| Orange flavour | 10 | 0.71 |
| Glycine | 10 | 0.71 |
| Microcrystalline cellulose | 20 | 1.42 |
| Amylopectin | 50 | 3.54 |
| Ketamine | 62.5 | 4.43 |
| Lactose | 100 | 7.09 |
| Mannitol | 150 | 10.63 |
| Purified water | 1000 | 70.90 |

Sample 2. Additionally Contained a Flavour and a pH Adjuster (Citric Acid).

| Ingredient | Amount (g) | % by weight |
| --- | --- | --- |
| Sodium carbonate | 1 | 0.07 |
| Sodium carboxymethylcellulose | 2 | 0.14 |
| Citric acid | 5 | 0.35 |
| Polyethylene glycol 2000 | 5 | 0.35 |
| Mint flavour | 10 | 0.71 |
| Glycine | 10 | 0.71 |
| Microcrystalline cellulose | 20 | 1.41 |
| Amylopectin | 50 | 3.53 |
| Ketamine | 62.50 | 4.42 |
| Lactose | 100 | 7.06 |
| Mannitol | 150 | 11.09 |
| Purified water | 1000 | 70.65 |

Sample 3. Additionally Contained a Flavour and a Colouring Agent

| Ingredient | Amount (g) | % by weight |
| --- | --- | --- |
| FD & C red | 0.1 | 0.01 |
| Sodium carbonate | 1 | 0.07 |
| Sodium carboxymethylcellulose | 2 | 0.14 |
| Polyethylene glycol 2000 | 5 | 0.35 |
| Grape flavour | 9.9 | 0.70 |
| Glycine | 10 | 0.71 |
| Microcrystalline cellulose | 20 | 1.42 |
| Amylopectin | 50 | 3.54 |
| Ketamine | 62.5 | 4.43 |
| Lactose | 100 | 7.09 |
| Mannitol | 150 | 10.43 |
| Purified water | 1000 | 70.90 |

Sample 4. Additionally Contained a Flavour, a Colouring Agent and an Absorption Enhancer

| Ingredient | Amount (g) | % by weight |
| --- | --- | --- |
| FD & C blue | 0.1 | 0.01 |
| Sodium carbonate | 1 | 0.07 |
| Sodium carboxymethylcellulose | 2 | 0.14 |
| β-Cyclodextrin | 5 | 0.35 |
| Polyethylene glycol 2000 | 5 | 0.35 |
| Grape flavour | 9.9 | 0.70 |
| Glycine | 10 | 0.71 |
| Microcrystalline cellulose | 20 | 1.41 |
| Amylopectin | 50 | 3.53 |
| Ketamine | 62.5 | 4.42 |
| Lactose | 100 | 7.06 |
| Mannitol | 145 | 10.24 |
| Purified water | 1000 | 70.65 |

Sample 5. Additionally Contained a Colouring Agent and a Sweetener

| Ingredient | Amount (g) | % by weight |
| --- | --- | --- |
| FD & C red | 0.1 | 0.01 |
| Sodium carbonate | 1 | 0.07 |
| Sodium carboxymethylcellulose | 2 | 0.14 |
| Aspartame | 5 | 0.35 |
| Polyethylene glycol 2000 | 5 | 0.35 |
| Cherry flavour | 9.9 | 0.70 |
| Glycine | 10 | 0.71 |
| Microcrystalline cellulose | 20 | 1.41 |
| Amylopectin | 50 | 3.53 |
| Ketamine | 62.5 | 4.42 |
| Lactose | 100 | 7.06 |
| Mannitol | 145 | 10.24 |
| Purified water | 1000 | 70.65 |

Sample 6. Additionally Contained a Colouring Agent and a pH Adjuster

| Ingredient | Amount (g) | % by weight |
|---|---|---|
| FD & C red | 0.1 | 0.01 |
| Sodium carbonate | 1 | 0.07 |
| Sodium carboxymethylcellulose | 2 | 0.14 |
| Sodium hydrogen carbonate | 5 | 0.35 |
| Polyethylene glycol 2000 | 5 | 0.35 |
| Raspberry flavour | 9.9 | 0.70 |
| Glycine | 10 | 0.71 |
| Microcrystalline cellulose | 20 | 1.41 |
| Amylopectin | 50 | 3.53 |
| Ketamine | 62.5 | 4.42 |
| Lactose | 100 | 7.06 |
| Mannitol | 145 | 10.24 |
| Purified water | 1000 | 70.65 |

Various strength of ketamine fast dissolving solid dosage form (wafers) were then prepared based on the formulation shown in Table 3 and prepared as set out in Example 1 above. The batch number and the ingredients are listed in Table 4.

TABLE 4

Ketamine Compositions Used for Investigations

| Ingredient | Batch 20110323K (strength equivalent of 25 mg ketamine base) Amount (g) | Batch 20110528 (strength equivalent of 25 mg ketamine base) Amount (g) | Batch 20110820 (strength equivalent of 50 mg ketamine base) Amount (g) |
|---|---|---|---|
| Amylopectin | 1.0 | 1.0 | 1.2 |
| Mannitol | 3.0 | 3.0 | 2.9 |
| Lactose | 2.0 | 2.0 | 1.9 |
| Glycine | 0.2 | 0.2 | 0.3 |
| Polyethylene glycol 2000 | 0.1 | 0.1 | 0.1 |
| Sodium Carboxymethylcellulose | 0.04 | 0.04 | 0.04 |
| Sodium carbonate | 0.02 | 0.02 | 0.05 |
| Avicel | 0.2 | 0.2 | 0.2 |
| Active pharmaceutical ingredient | 1.250 ketamine (base) | 1.250 ketamine (base) | 2.50 ketamine (base) |
| Purified water | 40 | 40 | 40 |

In Vitro Studies

The in vitro studies were to describe the physicochemical properties of freeze-dried ketamine (equivalent to 25 mg of ketamine base) fast dissolving solid dosage form.

Uniformity of Weight

The uniformity of the weight of the ketamine wafers was tested as provided in Example 1. Twenty wafers from the formulations listed in Table 4 were individually weighed, and the average weight and relative standard deviation was calculated. All the prepared wafers from different formulations were within the accepted weight variation of 0.25 to 2%.

Hardness

The hardness of the wafer was also tested in accordance with the method given in Example 1. The hardness values from different formulations ranged from 0.5 to 4.0 kg. Batch 20110528 gave a hardness of 0.5 to 1.0 kg and this formulation was then used in subsequent clinical trial. This formulation enables a fast dissolution rate and allows for easy handling.

Friability

The strength of ketamine wafers was tested according the method of Example 1. A sample of 20 ketamine wafers had a percentage weight loss of between 8 to 20%.

Moisture Analysis

The moisture content of the ketamine wafers was analysed as provided in Example 1. The results showed that the residual moisture content was around 4%.

Scanning Electron Microscopic Analysis

Figure 36:
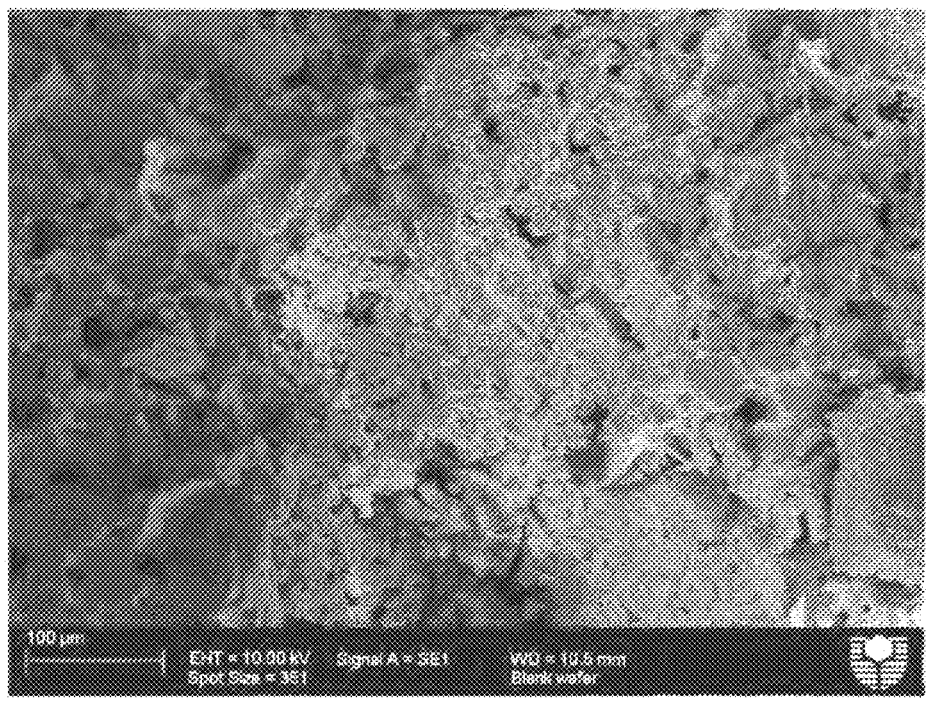
FIG. 36 shows scanning electron micrographs of the surface of a blank fast dissolving dosage form.
Figure 37:
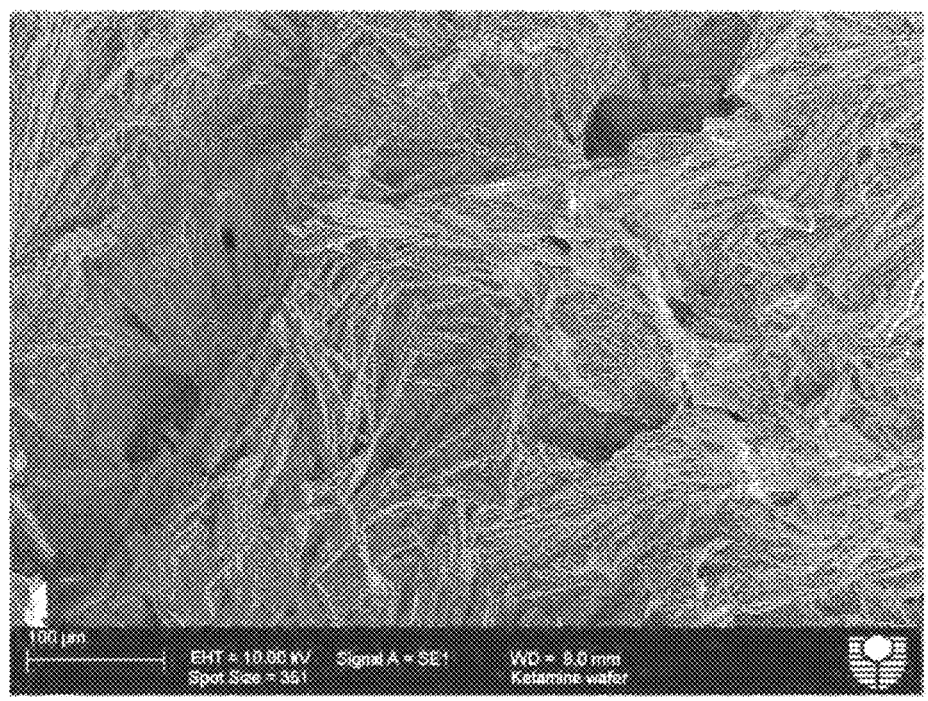
FIG. 37 shows scanning electron micrographs of the surface of ketamine fast dissolving dosage form.

Surface morphology and cross-section of selected wafer formulation samples were observed using the method provided in Example 1. The SEM images shown in FIGS. 36 and 37 illustrate the highly porous nature of the ketamine containing wafers for both surface and the inner structures.

Powder X-Ray Diffraction (XRD)

Powder X-ray diffraction experiments were performed using the method of Example 1.

Figure 38:
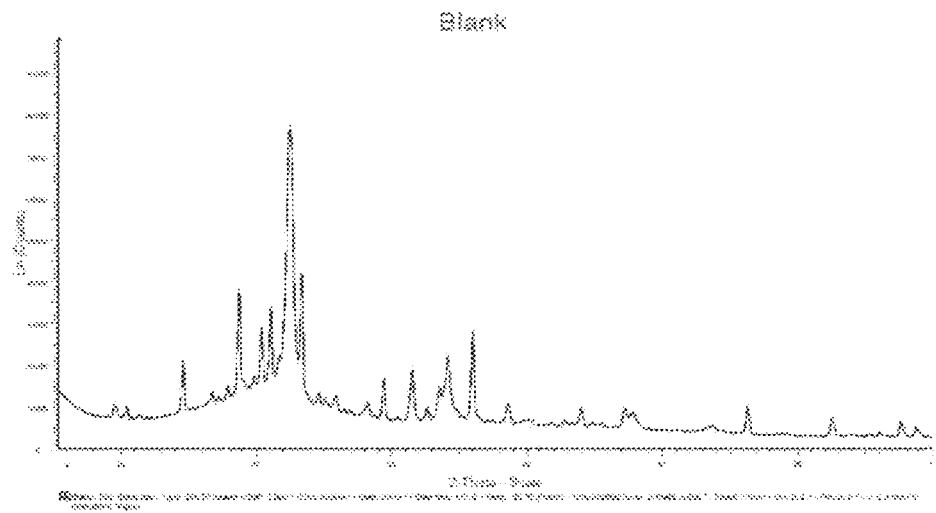
FIG. 38 shows powder X-ray diffraction spectra of a blank fast dissolving dosage form.
Figure 39:
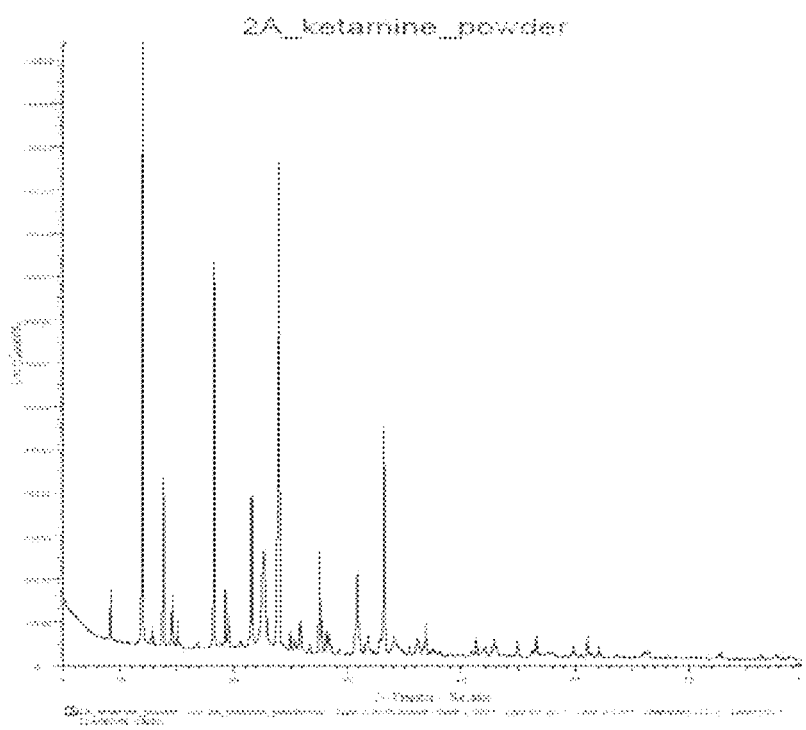
FIG. 39 shows powder X-ray diffraction spectra of ketamine powder.
Figures 40, 41:
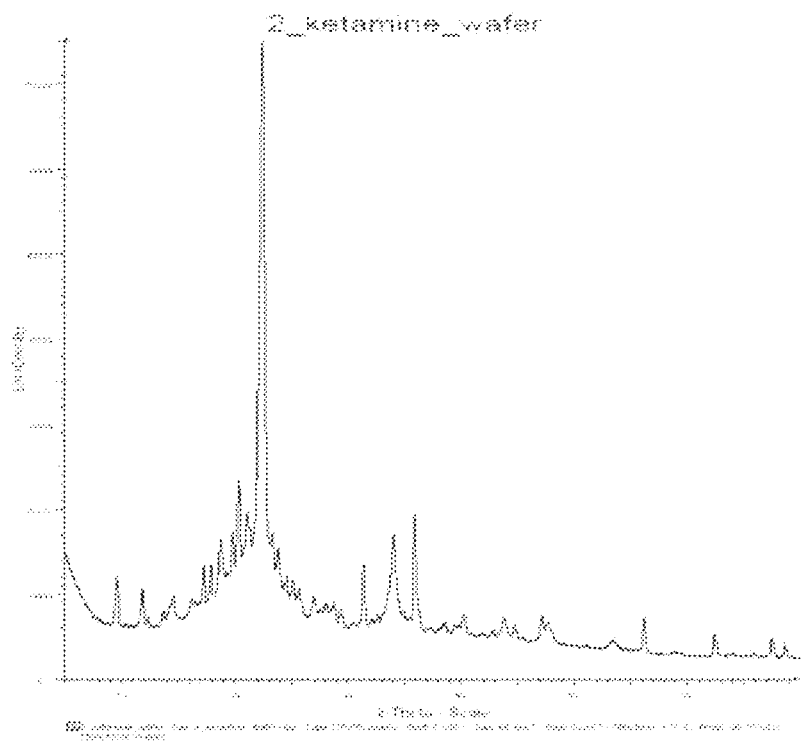
FIG. 40 shows a powder X-ray diffraction spectrum of ketamine fast dissolving dosage form.
FIG. 41 shows typical HPLC chromatograms of dissolution ketamine wafer Sample S2 at 1 minute.
Figure 42:
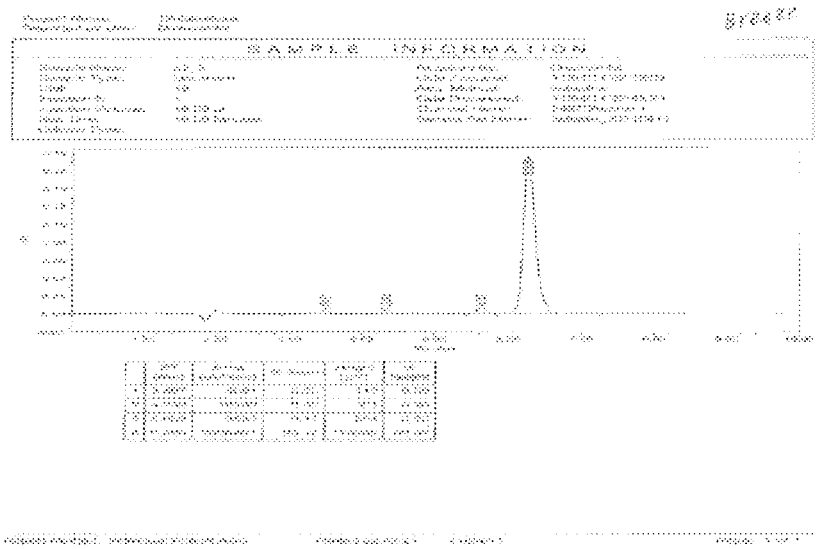
FIG. 42 shows a typical HPLC chromatogram of dissolution ketamine wafer Sample S2 at 3 minutes.
Figure 43:
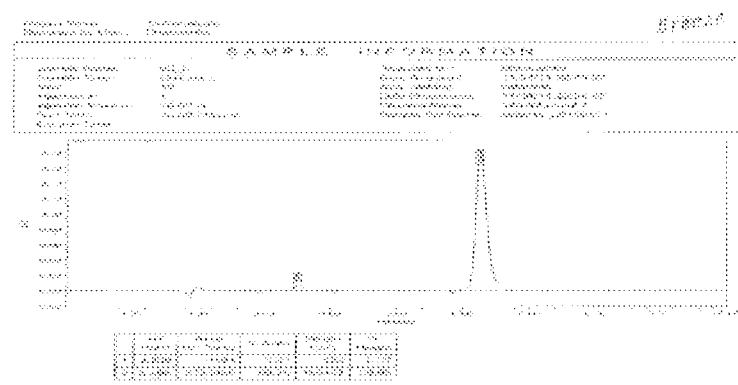
FIG. 43 shows typical HPLC chromatograms of dissolution ketamine wafer Sample S2 at 5 minutes.
Figure 44:
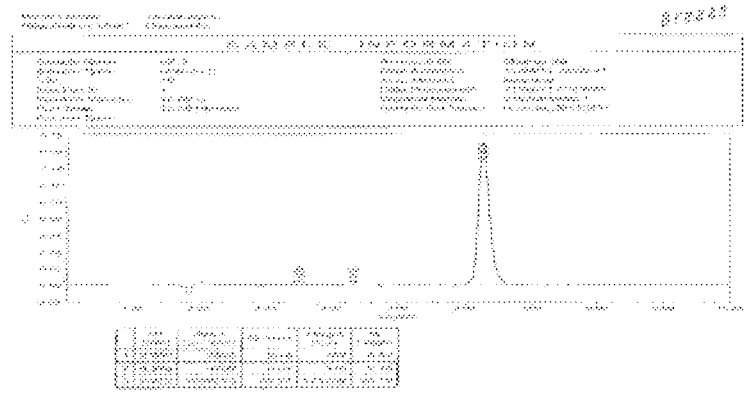
FIG. 44 shows typical HPLC chromatograms of dissolution ketamine wafer Sample S2 at 7 minutes.
Figure 45:
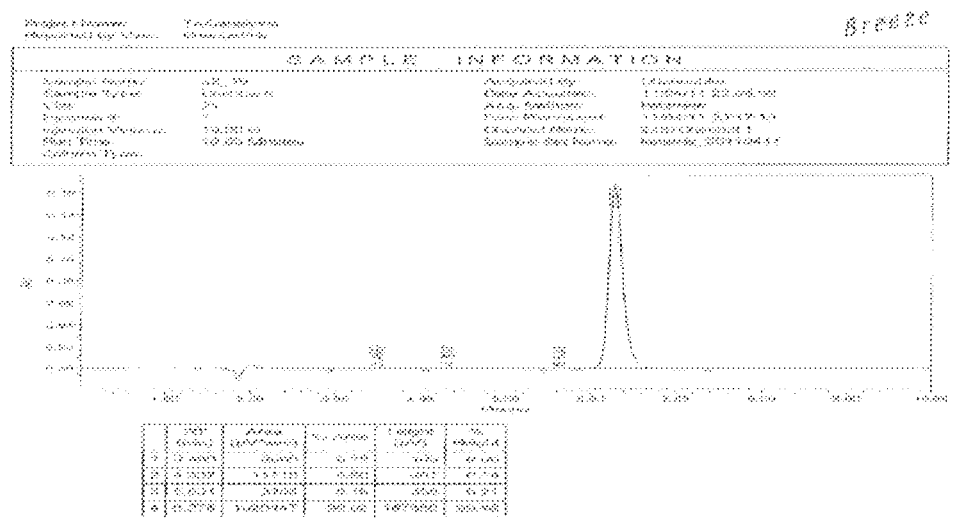
FIG. 45 shows typical HPLC chromatograms of dissolution ketamine wafer Sample S2 at 10 minutes.
Figure 46:
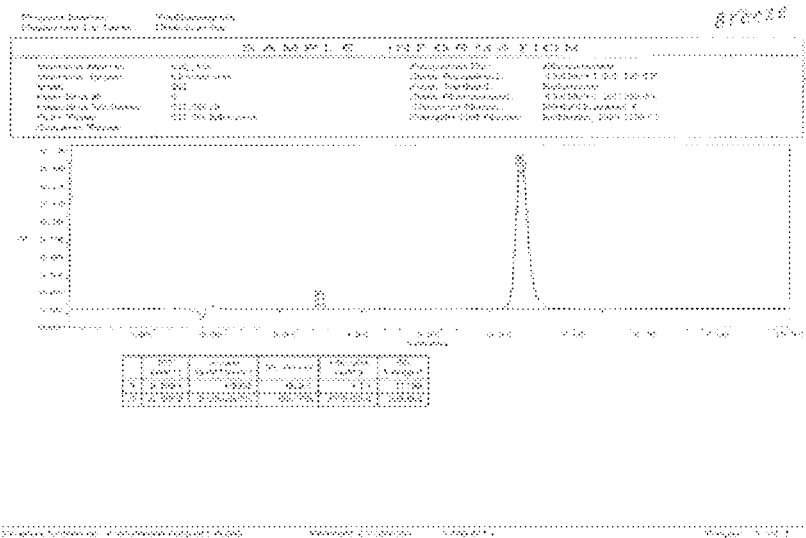
FIG. 46 shows typical HPLC chromatograms of dissolution ketamine wafer Sample S2 at 15 minutes.
Figure 47:
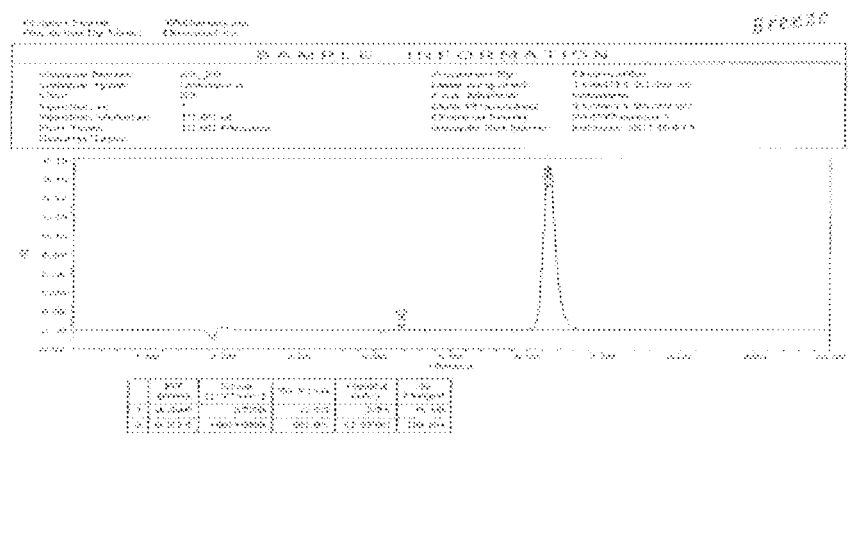
FIG. 47 shows typical HPLC chromatograms of dissolution ketamine wafer Sample S2 at 20 minutes.
Figure 48:
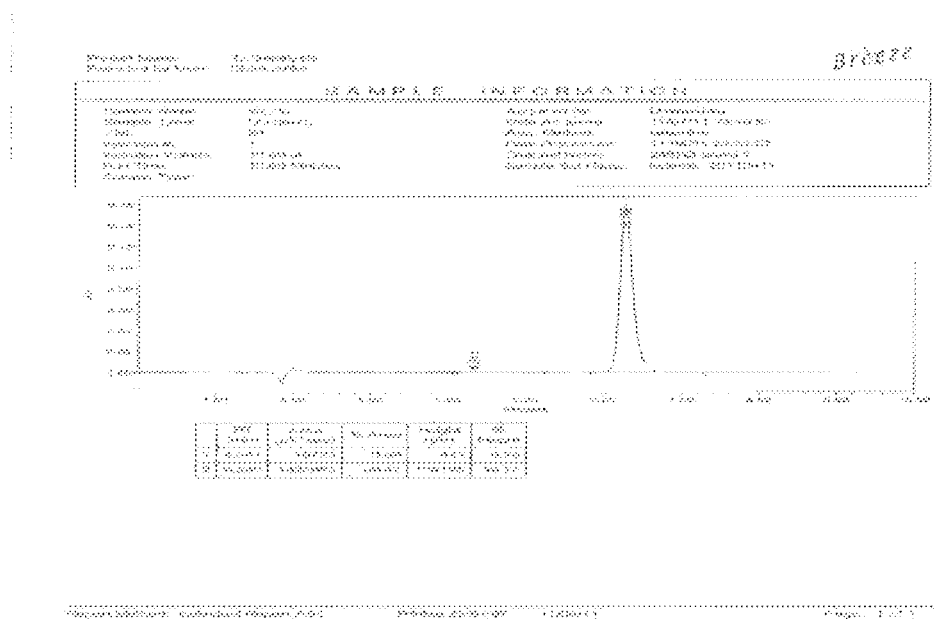
FIG. 48 shows typical HPLC chromatograms of dissolution ketamine wafer Samples S2 at 30 minutes.

The physical state of the materials in the ketamine containing wafers was evident in the X-ray diffraction spectra. Spectra for three different formulations prepared in accordance with Table 4 are shown in FIGS. 38, 39 and 40. It was observed that all the powder patterns of wafers prepared were dominated by intense scattering peaks approximately located at 2-theta of 9.58°, 19, 68° and 20.05°, which indicating a crystalline nature of the excipient Avicel. This finding was also supported by the data generated from the SEM. Indeed, the excipients used in the formulations, such as glycine, lactose, mannitol and microcrystalline cellulose are crystalline in nature. However, all became amorphous after freeze-drying.

Disintegration and Dissolution Analysis

Disintegration and dissolution tests were carried out according to Example 1.

For the disintegration test, it was shown that the ketamine containing wafers of the present invention were able to completely dissolve in about 15 seconds and did not leave behind any residue.

For the dissolution testing, a wafer from Batch 20110528 containing ketamine was used to determine the level of drug release from the formulation. The dissolution rates of the ketamine wafer were determined in a large volume (200 mL phosphate buffer solution, 25 mM, pH 6.8) with a basket rotation speed at 75 rpm. At given intervals (e.g., 1, 3, 5, 7, 10, 15, 20 and 30 min), 1.0 mL of solution was sampled and replaced with an equal volume of fresh medium. The drug released was measured by HPLC with a C18 column (150× 4.6 mm, 5 µm), a mobile phase of 15% v/v acetonitrile in 85% of 50 mM $H_3PO_4$, 20 mM triethylamine HCl (pH 3.00) and the flow rate was 1.5 ml/min at ambient temperature. The monitoring wavelength was at 210 nm. The HPLC chromatograms of dissolution ketamine wafer were shown In FIGS. 41 to 48.

Figure 49:
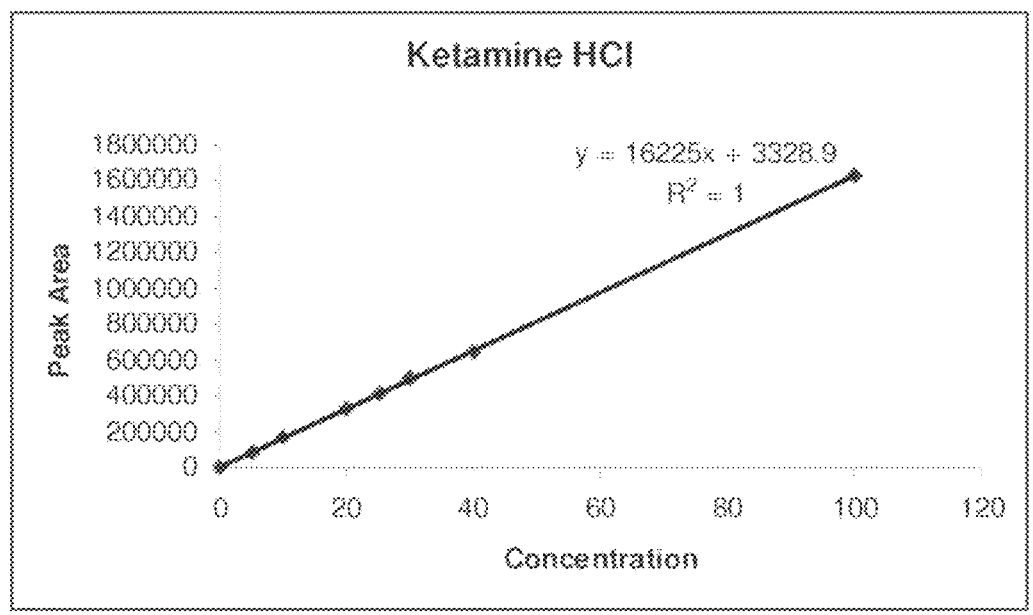
FIG. 49 shows a standard HPLC calibration curve of ketamine hydrochloride (5 to 100 µg/mL).

The calibration curve for the concentrations 5 to 100 µg/mL (seven-point calibration) was linear [Y=16225X+ 3328.9, ($R^2$=1), Y representing the peak area of ketamine and X the concentration of the samples]. The assay standard curve is shown in FIG. 49.

Figure 50:
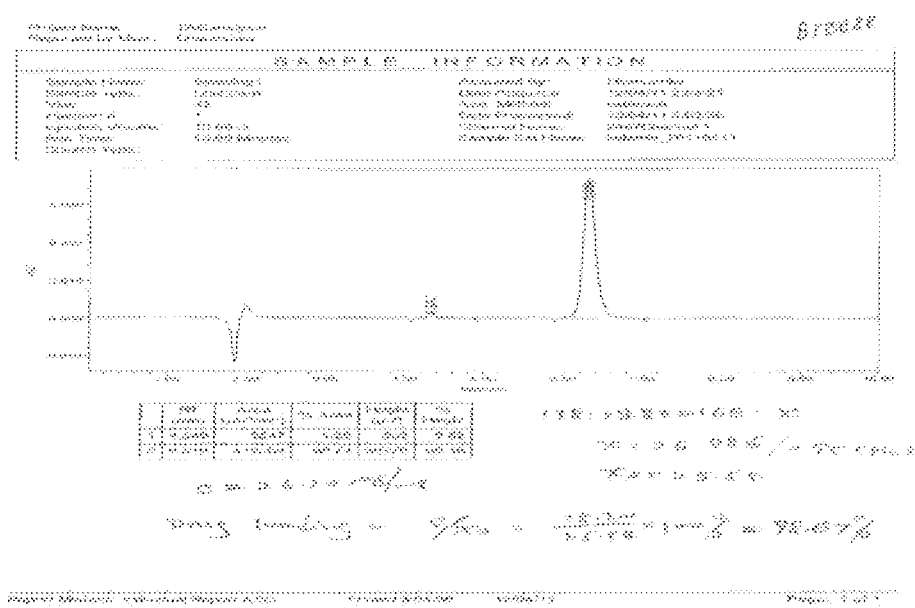
FIG. 50 shows a typical HPLC chromatogram of drug loading test ketamine wafer sample No. 1.

The prepared ketamine wafer (Batch 20110528) showed a weight variation of ±2.55%, and the mean percentage ketamine content of the wafer was 98.67% (BP standard for uniformity content limits 85 to 115%). The HPLC chromatogram is shown in FIG. 50.

The average disintegration times (BP disintegration apparatus) were less than 5 seconds; and the dissolution studies also indicated a fast release rate of ketamine. Almost 95% of ketamine had dissolved within one minute. This may indicate the changing of ketamine crystal form in the wafer, which was also evident in the X-ray. The X-ray spectrum pointed to an amorphization of ketamine during the freeze-drying process.

Figure 51:
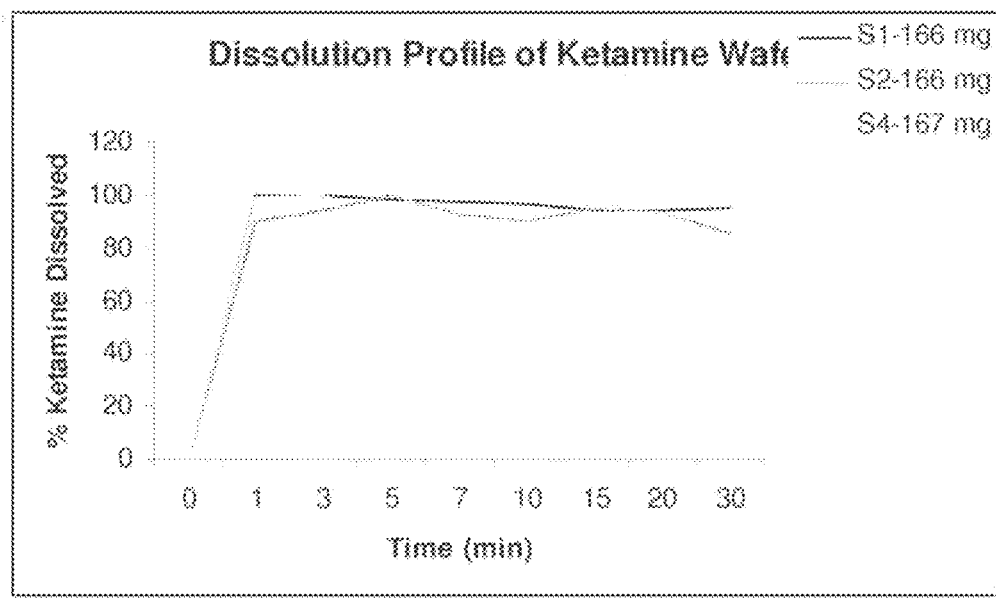
FIG. 51 shows dissolution profiles of ketamine wafer in phosphate buffer solution (pH 6.8) at 37° C., (n=3).

The dissolution profiles are presented in FIG. 51.

The ketamine wafer is a solid dispersion of ketamine hydrochloride into a porous matrix. After administration, this dosage form is quickly disintegrates in the oral cavity, and allows rapidly dissolving ketamine to be absorbed by diffusion directly into the systemic circulation, and the first-pass effect is avoided. This invention has the potential to provide an alternate route of drug administration and results in lower rates of side effect.

In Vivo Studies

The aims of the in vivo study were to: 1) investigate the pharmacokinetic profile of ketamine wafer (equivalent to 25 mg of ketamine base, Batch Number: 20110528 in Table 4); 2) determine the absolute bioavailability of a single 25 mg sublingual dose of ketamine wafer; and 3) evaluate the clinical characteristics and acceptability of the present invention using modified Likert, and Bond and Lader scales.

Ethical Approval

The protocol was approved by the Royal Adelaide Human Research Ethics Committee. This trial was registered with the Australian Therapeutic Goods Administration under the Clinical Trial Notification Scheme (CTN: 2011/0292).

Study Subjects

All volunteers gave their written informed consent on an approved subject consent form, prior to undergoing trial procedures. Subjects included in the study were between 19 to 41 years of age, had a body mass index between 22 and 30 kg/m$^2$, had no history of or showed no presence of drug or alcohol dependence or abuse, had normal findings on the clinical history and laboratory testing, were free of sublingual or buccal ulceration or disease, and had negative findings on HIV, hepatitis B and C viral testing.

A total of eight healthy males who met the study inclusion and exclusion criteria were enrolled in this study.

Study Plan and Design

This was a single-centre (Pain and Anaesthesia Research Clinic, Royal Adelaide Hospital, Adelaide, SA 5005, Australia), randomized, open-label, single-dose, two-treatment, two-period, two-way crossover study. According to the randomization plan, subjects were divided into two groups, in a 1:1 ratio using a computer-generated table of random numbers.

The volunteers received both a single 10 mg intravenous (IV) dose of ketamine (diluted to 30 mL in saline and administered as an IV infusion over 30 min) and a 25 mg sublingual (SL) wafer dose of ketamine. The sequence of treatment periods was balanced and randomised. The wafer was administered by placing it under the tongue. The volunteer was requested to avoid swallowing for at least ten minutes, to minimize loss of ketamine via the oral route and hence through gut and liver metabolism (the first pass effect). The total study duration was four weeks, including a 14-day screening period and a seven-day wash-out period.

Measurements of pharmacokinetics, tolerability and safety were carried out for 24 hours following both dosing occasions. The total residency period at the Pain and Anaesthesia Research Clinic was 28 hours in Period 1 and 29 hours in Period 2.

Blood samples (5 mL) for quantification of ketamine concentration were taken following both IV and SL administration at pre dose (within 5 minutes of scheduled dosing time), 5, 10, 15, 30, 35 and 45 minutes, and at 1, 1.5, 2, 2.5, 3, 4, 6, 8, 12, and 24 hours post dose. Samples up to and including the 8 hour post-dose sample were to be collected within two minutes of nominal time, thereafter all post-dose samples were to be collected within ten minutes of nominal time. The actual blood collection time was recorded in the source documents. All deviations outside of the windows specified above were to be documented as protocol deviations. The total amount of blood to be taken throughout the study duration was approximately 275 mL.

After collection, the blood samples were immediately centrifuged at 4° C., 2000-2500 g for 15 minutes and the plasma extracted and placed into polypropylene storage tubes. The plasma was stored at −80° C.±10° C. until transfer to the bioanalytical laboratory.

Pharmacokinetic Analysis

The analysis of the plasma concentrations of racemic ketamine was performed using a validated HPLC method with UV detection, with a lower limit of quantification of 2 ng/mL and <20% bias and imprecision.

Standard non-compartmental analysis was used to derive Pharmacokinetic variables, except for $C_{max}$, $t_{max}$ and $t_{first}$, which were taken as observations from the plasma concentration time profile of each subject. Actual times were used when reporting $t_{max}$. The terminal rate constant ($\lambda_z$) was estimated by log-linear regression, i.e. the slope of the natural log concentration vs. time curve where $\lambda=-1*$slope. The linear regression in the terminal phase used the last three to six data points, at a minimum three points. The terminal $t_{1/2}$ was calculated as $t_{1/2}=\ln(2)/\lambda_z$.

The area under the plasma concentration time curve to the last quantifiable plasma concentration ($AUC_{last}$) was obtained using the linear up and log down method and extrapolated to infinity with $C_{last}/\lambda_z$ (last quantifiable plasma concentration divided by $\lambda_z$) to obtain the total AUC, $AUC_{INF}$. The extrapolated portion of the AUC, $AUC_{extr}$, was obtained by $(1-AUC_{tlast}/AUC_{INF})*100$. The total area under the first moment curve, $AUMC_{INF}$, was calculated in a similar manner to $AUC_{INF}$ and MRT was obtained as $AUMC_{INF}/AUC_{INF}$ correcting mean residence time ($MRT_{i.v.}$) for the duration of the 30 minute IV infusion. Clearance (CL) was calculated as dose/$AUC_{INF}$ for IV administration and in the same way for the sublingual dose. The clearance for a non-IV route is expressed as CL/F i.e. a ratio of clearance and bioavailability as the latter is unknown. The volume of distribution, $V_z$, was calculated as $CL/\lambda_z$. The MAT for the sublingual administration was obtained as the difference between the MRT for the two routes of administration as, $MRT_{SL}-MRT_{IV}$. The bioavailability (F) of ketamine was calculated as the ratio of the dose adjusted $AUC_{INF}$ following IV and sublingual dosing according to $AUC_{SL}/AUC_{IV}*dose_{IV}/dose_{SL}$.

Safety and Tolerability

Safety assessments included scheduled adverse event (AE) probes, spontaneous AE reporting, routine laboratory investigations, 12-lead electrocardiograms (ECGs) and vital sign evaluation during a 24 hour period from start of dosing. A full physical examination was performed before the first dosing occasion and 24 hours after the second dosing occasion.

Local tolerability was assessed, by using Likert scales, at pre dose, 5, 10, 15, 30 and 45 minutes and one hour post dose administration. Modified Bond and Lader scales to assess sedation and altered perception, by using the three factors "alertness", "contentedness" and "calmness", were performed at pre dose, 30 minutes post dose and at hours 1, 1.5, 2, 2.5, 3, 4, 6, 8, 12, and 24 hours post dose administration.

Statistical Analysis

Standard summary statistics were computed by treatment for each pharmacokinetic variable. The 90% confidence interval (CI) was calculated for the bioavailability.

Results

The individual values and summary statistics for volunteer characteristics are reported in Table 5.

TABLE 5

Subject Demographics

| Subject Randomization No. | Age (years) | Body weight (kg) | Height (cm) | BMI (m$^2$) |
|---|---|---|---|---|
| 1 | 19 | 74.6 | 184.0 | 22.0 |
| 2 | 31 | 100.0 | 183.2 | 29.9 |
| 3 | 23 | 77.0 | 173.0 | 25.7 |
| 4 | 19 | 74.7 | 168.0 | 26.4 |
| 5 | 41 | 87.8 | 183.5 | 26.1 |
| 6 | 20 | 85.0 | 183.0 | 25.4 |
| 7 | 21 | 79.1 | 185.0 | 23.1 |
| 8 | 25 | 108.5 | 191.0 | 30.0 |
| n | 8 | 8 | 8 | 8 |
| Mean (SD) | 25 (7.6) | 85.8 (12.49) | 181.3 (7.29) | 26.1 (2.83) |
| Min-Max | 19-41 | 74.6-108.5 | 168.0-191.0 | 22.0-30.0 |

Plasma Concentrations of Racemic (RS) Ketamine

Figure 52:
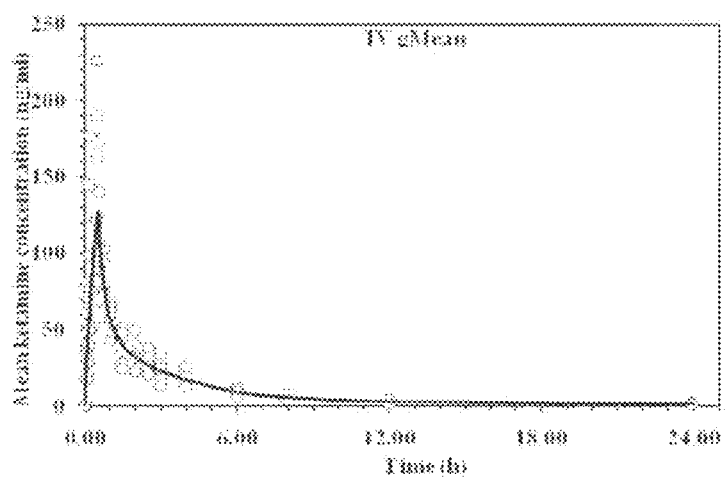
FIG. 52 shows a geometric mean with overlay of individual RS ketamine plasma concentrations for the entire sampling period, following a 10 mg dose given during a 30 minute intravenous infusion to eight healthy volunteers.
Figure 53:
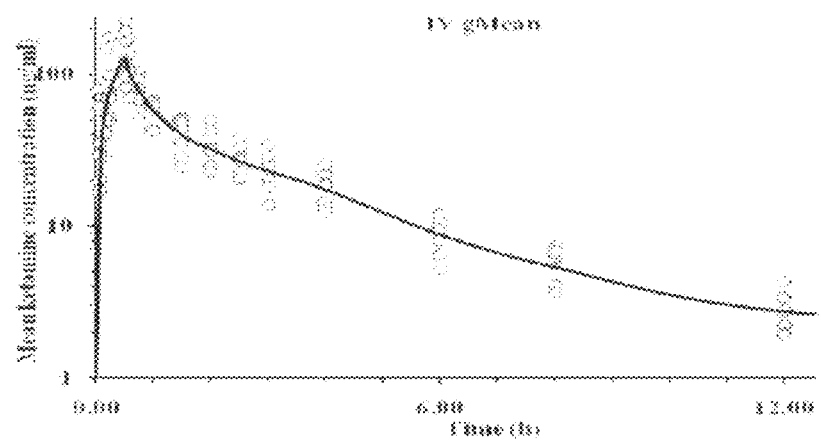
FIG. 53 shows a geometric mean with overlay of individual RS ketamine plasma concentrations during the first 12 hours following a 10 mg dose given during a 30 minute intravenous infusion to eight healthy volunteers.
Figure 54:
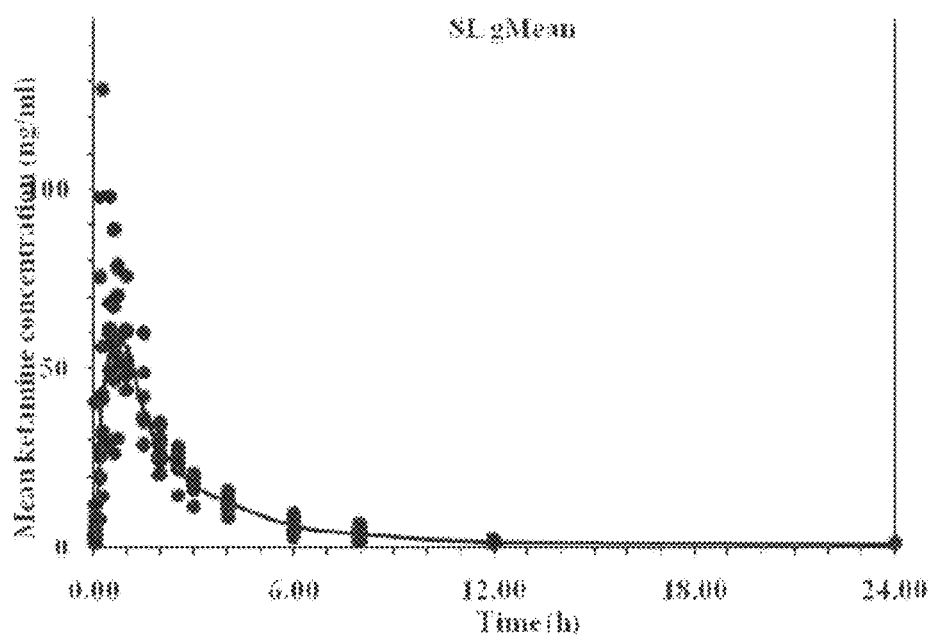
FIG. 54 shows a geometric mean with an overlay of individual RS ketamine plasma concentrations for the entire sampling period, following a 25 mg sublingual dose to eight healthy volunteers.
Figure 55:
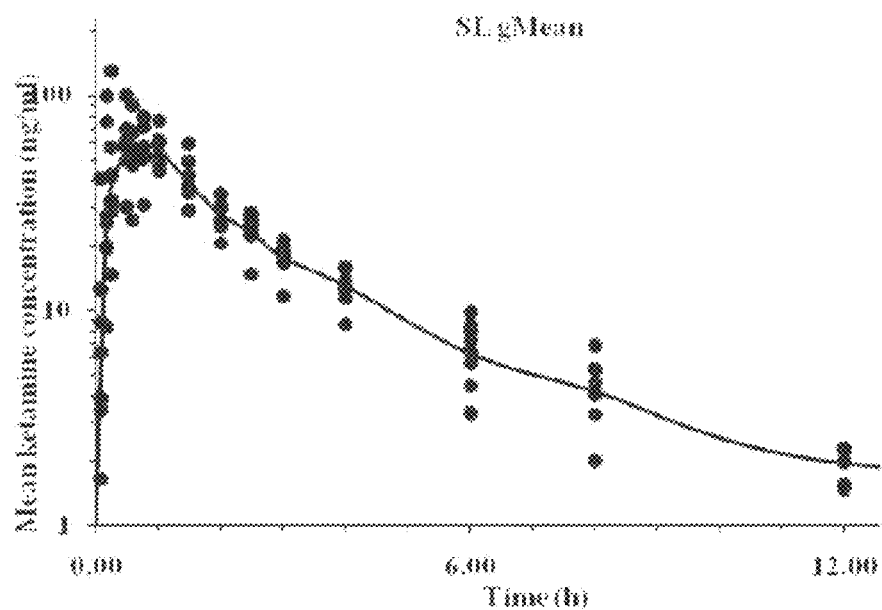
FIG. 55 shows a geometric mean with overlay of individual RS ketamine plasma concentrations during the first 12 hours following a 25 mg sublingual dose to eight healthy volunteers.

The geometric mean ($g_{mean}$) with an overlay of individual RS ketamine plasma concentrations for all subjects following IV administration for the entire sampling period is depicted in FIG. 52. For clarity, the first 12 hours following dosing are shown separately in FIG. 53. The geometric mean with an overlay of individual RS ketamine plasma concentrations for all subjects for the entire sampling period following SL administration are shown in FIG. 54 and the first 12 hours are shown in FIG. 55.

Following IV dosing, $C_{max}$ occurred at the end of the infusion in all but one subject (No. 6), where the $C_{max}$ was observed in the sample taken five minutes after the end of the 30 minutes infusion.

Figure 56:
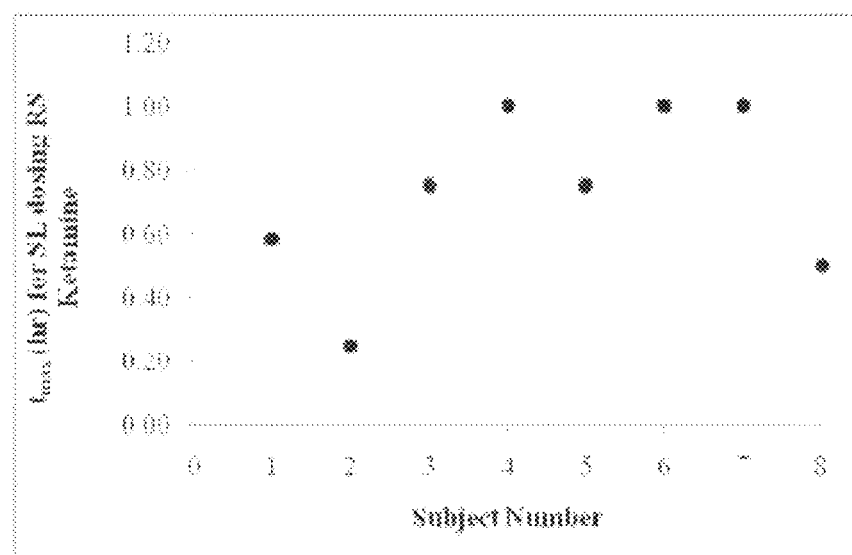
FIG. 56 shows individual (S=Subject randomization number) $t_{max}$ for RS ketamine following 25 mg sublingual dose to eight healthy volunteers.

For the SL dose, the median time of the main peak i.e. $t_{max}$, was 0.75 hour with the earliest peak detected at 0.25 hour and the latest at 1 hour following dosing. Subjects 4, 5, 6 and 7 had multiple minor peaks in their plasma concentration time profile observed during the first three hours following dose administration. Individual $t_{max}$ values are shown in FIG. 56.

Figure 57:
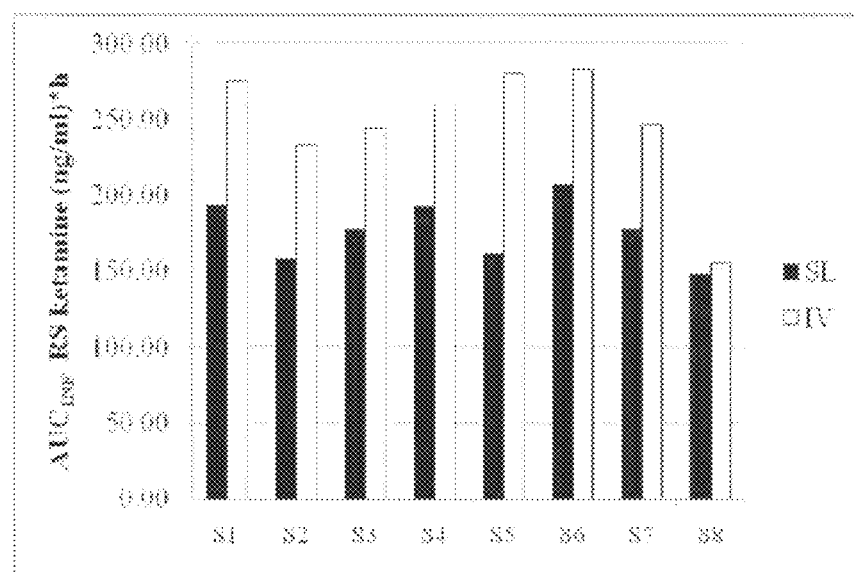
FIG. 57 shows individual (S=Subject randomization number) $AUC_{INF}$ for RS ketamine following a 10 mg dose given during a 30 minute intravenous infusion (IV, open bars) or 25 mg sublingually (SL, filled bars) to eight healthy volunteers.

Table 6 presents individual estimates and summary statistics for the main pharmacokinetic variables. Individual $AUC_{INF}$ values for both routes of administration are shown in FIG. 57. The extrapolated portion of the AUC, $AUC_{extr}$, was very small for both routes of administration, which is indicative of a high quality in the estimation of the AUC values. For IV, the $AUC_{extr}$ was 3-7% and for SL it was 2-9%.

Figure 58:
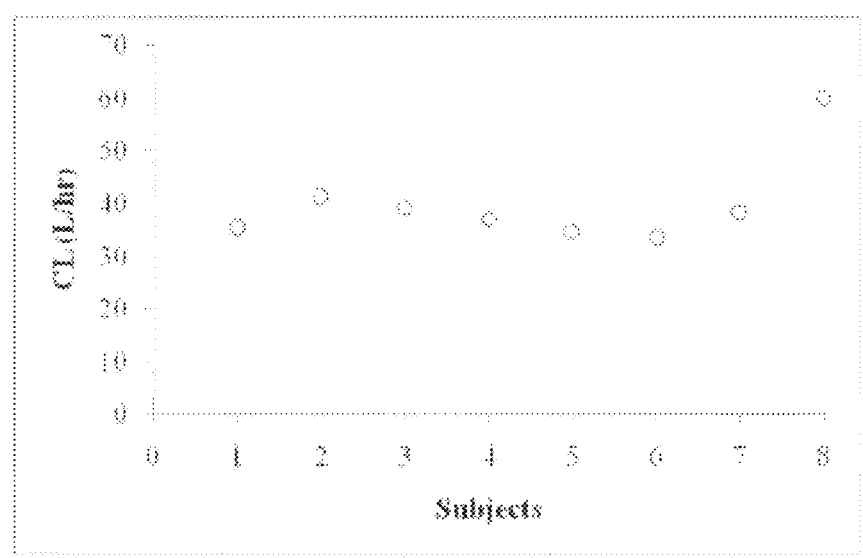
FIG. 58 shows individual (Subject randomization number) clearance (CL) for RS ketamine following a 10 mg dose given during a 30 minute intravenous infusion to eight healthy volunteers.

Individual estimates of CL for the IV route are presented in FIG. 58. Following SL dosing the CL is confounded by F, and hence cannot be compared to the values obtained following IV dosing. Median CL for IV dosing was 37.7 L/hr.

Figure 59:
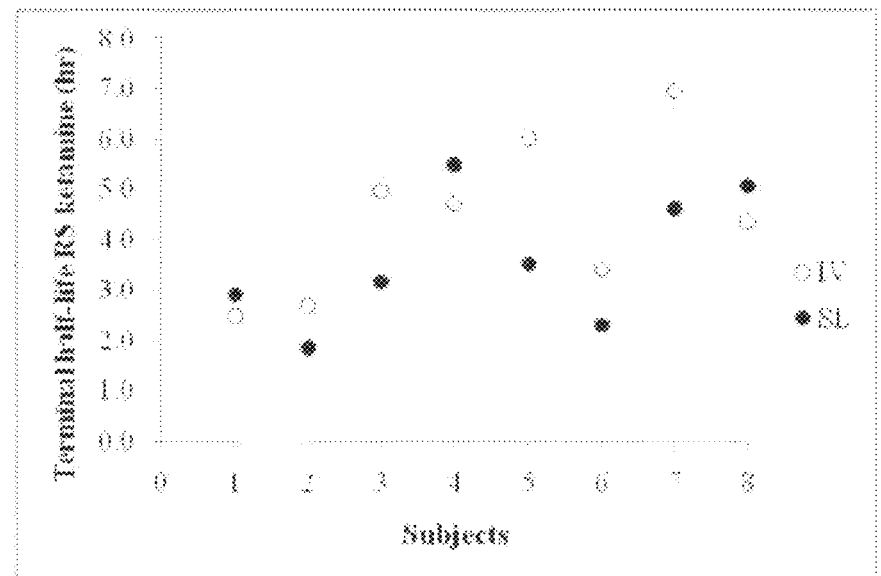
FIG. 59 shows individual (S=Subject randomization number) terminal half-life $t_{1/2}$ for RS ketamine following a 10 mg dose given during a 30 minutes intravenous infusion (IV, open circles) or 25 mg sublingually (SL, filled circles) to eight healthy volunteers.

The terminal half-lives following IV and SL dosing were comparable, with medians of 4.5 and 3.4 hours, respectively. Similar half-lives for the IV and SL routes indicates that the absorption is fast, or else the slower absorption half-life would be governing the terminal phase of the plasma concentration time curve and hence show a considerably longer half-life than IV administration. Individual values for both routes of administration are provided in FIG. 59.

TABLE 6

Individual pharmacokinetic variables and summary statistics of RS ketamine following administration of 10 mg as a 30 minute IV infusion and 25 mg SL to eight healthy volunteers.

| Subject | $C_{max,I}$ (ng/mL) | $t_{max,IV}$ (hr) | $C_{max,S}$ (ng/mL) | $t_{max,SL}$ (hr) | $AUC_{INF}$ (hr*ng/mL) | $AUC_{INF}$ (hr*ng/mL) | CL (L/hr) | $V_Z$ (L) | $t_{1/2,I}$ (hr) | $t_{1/2,}$ (hr) |
|---|---|---|---|---|---|---|---|---|---|---|
| 1 | 226.6 | 0.5 | 88.76 | 0.58 | 282.73 | 202.89 | 35.37 | 126 | 2.5 | 2.9 |
| 2 | 163.2 | 0.5 | 128.2 | 0.25 | 243.24 | 162.52 | 41.11 | 158 | 2.7 | 1.8 |
| 3 | 190.2 | 0.5 | 78.77 | 0.75 | 254.59 | 184.28 | 39.28 | 283 | 5.0 | 3.2 |
| 4 | 124.2 | 0.5 | 60.24 | 1 | 270.02 | 203.47 | 37.03 | 253 | 4.7 | 5.5 |
| 5 | 120.3 | 0.5 | 50.02 | 0.75 | 289.22 | 171.90 | 34.58 | 300 | 6.0 | 3.5 |
| 6 | 101.8 | 0.6 | 76.12 | 1 | 299.44 | 211.33 | 33.40 | 164 | 3.4 | 2.3 |
| 7 | 83.18 | 0.5 | 51.79 | 1 | 261.00 | 186.14 | 38.31 | 385 | 7.0 | 4.6 |
| 8 | 81.12 | 0.52 | 61.17 | 0.5 | 167.21 | 161.64 | 59.81 | 375 | 4.3 | 5.1 |
| Gmean | 128.0 | 0.50 | 71.08 | 0.75 | 254.98 | 184.65 | 39.22 | 237 | 4.5 | 3.4 |
| Min- | 81.12- | 0.50- | 50.02- | 0.25- | 167.21- | 161.64- | 40- | 126 | 2.5- | 1.8 |
| CV | 16 | NA | 14 | 21 | 8 | 4 | 8 | 18 | 16 | 17 | a gmean is provided for all variables except for $t_{max}$ and $t_{1/2}$ where medians are shown
NA Not applicable The IV and SL plasma concentration time curves were similar in shape, except for four subjects having 2-3 peaks for the SL route. Following $C_{max}$, concentrations declined biphasically for both IV and SL although the trend was more prominent for IV.

The first quantifiable concentration following both IV and SL dosing was at five minutes for all subjects, which indicates a fast absorption for the SL dose. Plasma concentrations were below limit of quantification in six subjects at 24 hours and in one subject at 12 hours for SL dosing. Following IV dosing, all subjects had quantifiable levels at 12 hours and four subjects at 24 hours.

Bioavailability and Absorption

In a majority of subjects, the SL wafer dissolved within 30 seconds to one minute.

Figure 60:
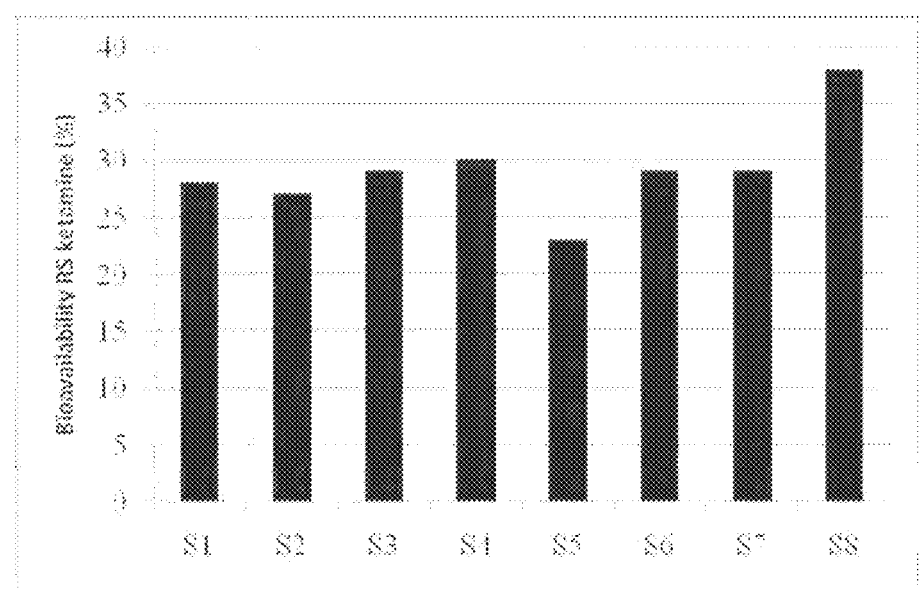
FIG. 60 shows individual estimates for all subjects (S=subject number) of bioavailability (F) % following administration of 25 mg RS ketamine to eight healthy volunteers.

Individual estimates of bioavailability are shown in FIG. 60 and individual bioavailability and MAT (mean absorption time) values together with summary statistics are provided in Table 7. Subject No. 8 had a noticeably higher bioavailability, 38%, than others. This subject was not markedly different in comparison to other subjects, apart from having the highest extrapolated areas, 9% for SL and 7% for IV, and a double peak for the SL dose. The median and 90% CI

[lower, upper] for bioavailability was 29 [27, 31]%, showing the very low inter subject variability.

TABLE 7

Individual (Subject = randomization number), median, minimum and maximum of RS ketamine bioavailability (F) and mean absorption time (MAT) following SL administration of 25 mg to eight healthy volunteers.

| Subject | F (%) | MAT (hr) |
|---|---|---|
| 1 | 28 | 1.1 |
| 2 | 27 | −0.83 |
| 3 | 29 | −1.1 |
| 4 | 30 | 0.86 |
| 5 | 23 | −1.1 |
| 6 | 29 | −0.56 |
| 7 | 29 | 0.20 |
| 8 | 38 | 0.64 |
| Median | 29 | −0.18 |
| Min-Max | 23-38 | −1.1-1.1 |
| 90% CI [lower, upper] | [27, 31] | NA* |

*Not applicable

The MAT represents the average time molecules of ketamine take to pass from the administration site, SL space, to the systemic circulation. The individual MRT values were comparable for the two routes of administration, median of 3.9 for IV and 3.8 hours for SL, indicating a fast absorption. A small difference, i.e. a small MAT, between the MRT for IV and SL indicates fast absorption. Taking the difference between two similar values might produce negative values, as is seen in some of the MAT values, due to naturally occurring variability.

In summary, the PK of the SL wafer is characterised by fast absorption and low variability in bioavailability. This taken together with low variability in clearance translates into low variability in exposure. Low variability allows for increased accuracy in predicting total exposure and hence pharmacological effect of the SL wafer, which might be expected to increase its utility in the clinical setting.

Pharmacodynamic Results
Bond and Lader Mood Rating Scales

The Bond and Lader scales comprise a total of 16 100-mm lines anchored at either end by antonyms. Participants marked their current subjective state between the antonyms on the line. Each line was scored as millimetres to the mark from the negative antonym. From the resultant scores, three measures derived by factor analysis were isolated. These have been described by Bond and Lader as representing the following:

Factor1: "alertness" (represented by lines anchored by alert-drowsy, attentive-dreamy, lethargic-energetic, muzzy-clearheaded, well-coordinated-clumsy, mentally slow-quick witted, strong-feeble, interested-bored, incompetent-proficient);
Factor 2: "contentedness" (contented-discontented, troubled-tranquil, happy-sad, antagonistic-friendly, withdrawn-sociable) and
Factor 3: "calmness" (calm-excited, tense-relaxed);
Scores for each factor represent the unweighted average number of millimetres (maximum 100 mm) from the negative antonym for the individual scales contributing to the factor.

Hence the maximum score for Factor 1 is 900; for Factor 2, 500 and for Factor 3, 200.

Figure 61:
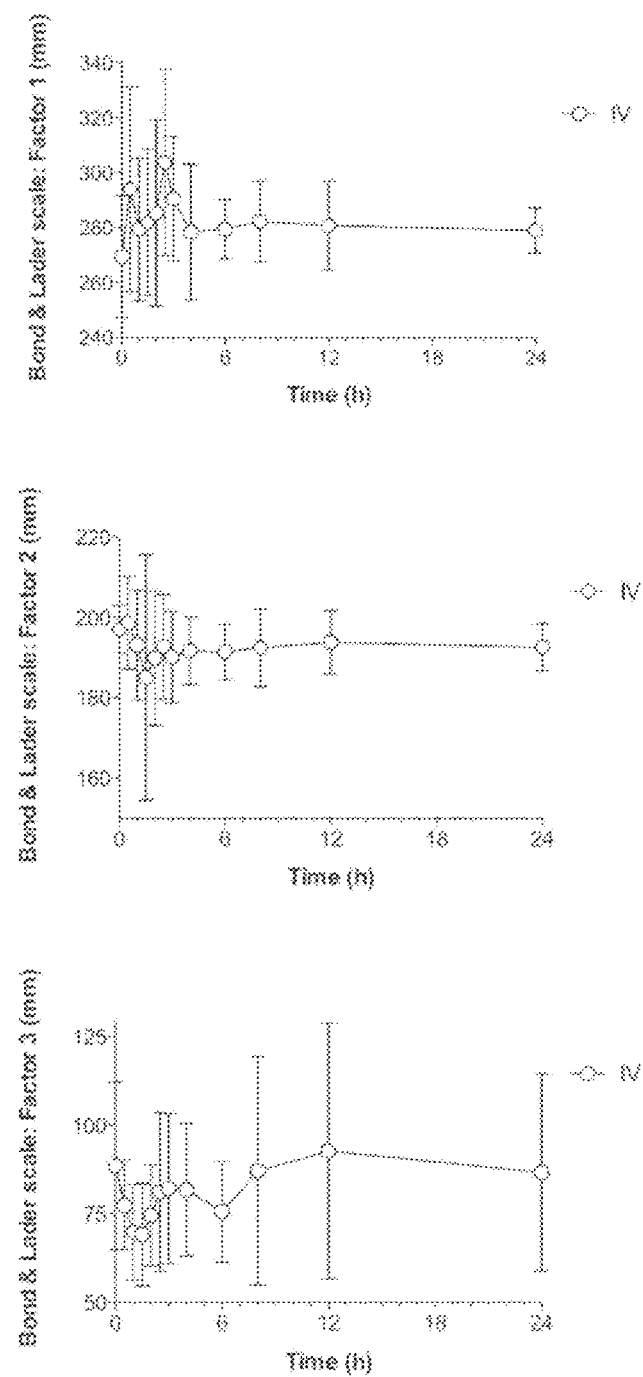
FIG. 61 shows mood rating scale profile for IV administration. The mean (SD) scores for Factors "alertness" (Factor 1), "contentedness" (Factor 2) and "calmness" (Factor 3) observed following a 30 minute intravenous infusion of 10 mg ketamine to healthy volunteers.
Figure 62:
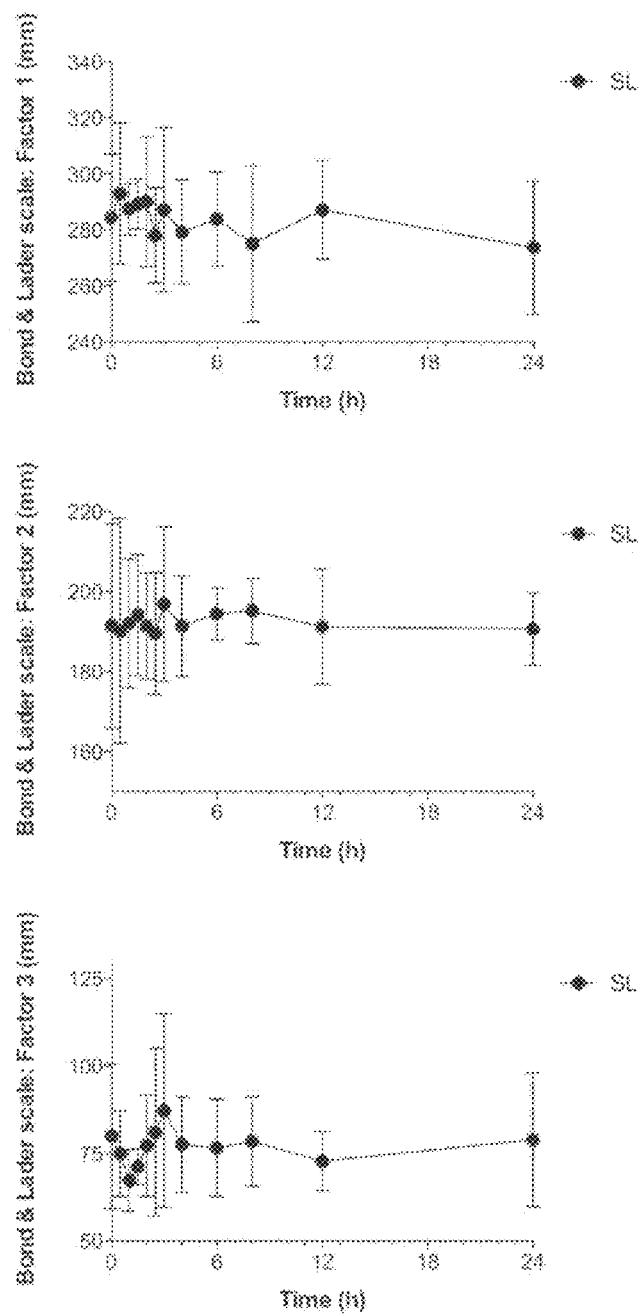
FIG. 62 shows mood rating scale profile for sublingual administration. The mean (SD) scores for Factors "alertness" (Factor 1), "contentedness" (Factor 2) and "calmness" (Factor 3) observed following sublingual administration of a 25 mg ketamine wafer to healthy volunteers.

The mood rating scales showed no clear trends for effects. Following SL dosing the Factors "alertness" and "contentedness" were fluctuating around the pre-dose level throughout the 24 hr observation period while "calmness" showed an initial decrease during the first hour after dosing, likely due to excitement caused by dosing and the local tolerability observations during the first 30-60 minutes, followed by a steady increase and full recovery by 2.5 hr post dose. The shapes of the profiles following IV dosing were comparable to that of SL dosing. Profiles of mean (SD) values for each Factor of the mood rating scales following IV and SL dosing are depicted in FIG. 61 and FIG. 62, respectively.

Modified Likert Scales of Local Tolerability

Figure 63:
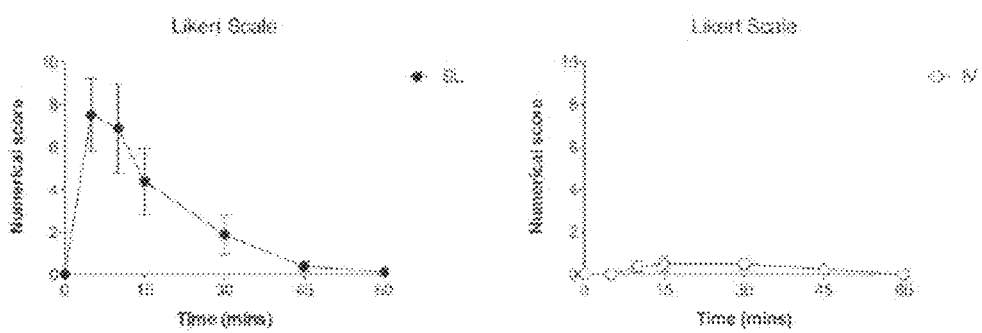
FIG. 63 shows total modified Likert Scales of local tolerability

Modified Likert scales were used to assess the following symptoms: cheek irritation; burning sensation; bitterness and nausea. As expected, values were generally zero for all values following IV administration although there were sporadic values of one or two. Following SL administration, values were generally zero or sporadically one or two for "cheek irritation" and were similar for "burning sensation" although there was a single value of three reported at 10 minutes by subject 3. For "nausea", values showed the same trend as for IV with mainly zero values but sporadic values of one or two. However values for "bitterness" were different from IV: all subjects reported non-zero post dose values although the peak ranged from 1-9 with one subject each reporting a peak of one and three, with the remainder being five or greater. The highest value was at five minutes in four subjects; at 10 minutes in two subjects; 15 minutes in one subject and one subject reported values of nine at both five and 10 minutes. All values had returned to zero by one hour (FIG. 63).

There were no clinically relevant changes or trends for abnormalities in ECG, vital signs, haematology, clinical chemistry or urinalysis.

In summary, the sublingual wafer formulation of ketamine has been developed as a potential adjunct in acute and chronic pain management, and other disorders. The median bioavailability from this example is 29% with very low inter subject variability, which is favourable for a relatively narrow therapeutic index drug such as ketamine. Low variability also increases the utility of the wafer in terms of reproducible exposure and hence analgesic effect. Ketamine administered as a 25 mg sublingual wafer to healthy volunteers, was safe and well tolerated with the exception of mild and transient CNS-type symptoms, as expected based on the existing clinical experience of ketamine. The local tolerability was excellent, and any local irritant effects are expected to be mild and resolve within 30-60 minutes following dosing.

Example 3

A formulation of the present invention, in the form of a solid dosage form (wafer) containing sildenafil, was prepared in accordance with the method and ingredients as set out below in Table 8:

TABLE 8

Compositions of Sildenafil Fast Dissolving Solid Dosage Form (Strength equivalent of 25 mg of sildenafil base).

| Ingredient | Amount (g) | % by weight |
|---|---|---|
| Sodium carbonate BP/USP | 1 | 0.07 |
| Sodium carboxymethylcellulose BP/USP | 2 | 0.14 |

TABLE 8-continued

Compositions of Sildenafil Fast Dissolving Solid Dosage Form (Strength equivalent of 25 mg of sildenafil base).

| Ingredient | Amount (g) | % by weight |
|---|---|---|
| Polyethylene glycol 2000 BP/USP | 5 | 0.34 |
| Glycine BP/USP | 10 | 0.68 |
| Microcrystalline cellulose BP/USP | 10 | 0.68 |
| Citric acid BP/USP | 10 | 0.68 |
| Amylopectin BP/USP | 50 | 3.42 |
| Lactose BP/USP | 100 | 6.84 |
| Mannitol BP/USP | 150 | 10.25 |
| Sildenafil BP/USP | 125 | 8.54 |
| Purified water BP/USP | 1000 | 68.35 |

The dosage form wafers containing sildenafil (25 mg) were produced using the method of Example 1 above.

The following additional formulations were prepared by the method as set out above. Essentially Samples 1 to 6 are based on the formulation described above, with the addition of flavour and/or colour agents.

Sample 1. Additionally Contained a Flavour.

| Ingredient | Amount (g) | % by weight |
|---|---|---|
| Sodium carbonate | 1 | 0.07 |
| Sodium carboxymethylcellulose | 2 | 0.15 |
| Polyethylene glycol 2000 | 5 | 0.37 |
| Orange flavour | 10 | 0.74 |
| Glycine | 10 | 0.74 |
| Citric acid | 10 | 0.74 |
| Microcrystalline cellulose | 20 | 1.47 |
| Amylopectin | 50 | 3.68 |
| Lactose | 100 | 6.84 |
| Mannitol | 150 | 10.25 |
| Sildenafil BP/USP | 125 | 8.54 |
| Purified water | 1000 | 66.41 |

Sample 2. Additionally Contained a Flavour and a pH Adjuster (Citric Acid)

| Ingredient | Amount (g) | % by weight |
|---|---|---|
| Sodium carbonate | 1 | 0.07 |
| Sodium carboxymethylcellulose | 2 | 0.15 |
| Polyethylene glycol 2000 | 5 | 0.37 |
| Citric acid | 10 | 0.74 |
| Mint flavour | 10 | 0.74 |
| Glycine | 10 | 0.74 |
| Microcrystalline cellulose | 20 | 1.47 |
| Amylopectin | 50 | 3.68 |
| Lactose | 100 | 6.84 |
| Mannitol | 150 | 10.25 |
| Sildenafil BP/USP | 125 | 8.54 |
| Purified water | 1000 | 67.15 |

Sample 3. Additionally Contained Flavour and a Colouring Agent

| Ingredient | Amount (g) | % by weight |
|---|---|---|
| FD & C red | 0.1 | 0.01 |
| Sodium carbonate | 1 | 0.07 |
| Sodium carboxymethylcellulose | 2 | 0.15 |
| Polyethylene glycol 2000 | 5 | 0.37 |
| Grape flavour | 9.9 | 0.73 |
| Glycine | 10 | 0.74 |
| Microcrystalline cellulose | 20 | 1.48 |
| Amylopectin | 50 | 3.71 |
| Lactose | 100 | 6.84 |
| Mannitol | 150 | 10.25 |
| Sildenafil BP/USP | 125 | 8.54 |
| Purified water | 1000 | 67.11 |

Sample 4. Additionally Contained a Flavour, a Colouring Agent and an Absorption Enhancer

| Ingredient | Amount (g) | % by weight |
|---|---|---|
| FD & C blue | 0.1 | 0.01 |
| Sodium carbonate | 1 | 0.07 |
| Sodium carboxymethylcellulose | 2 | 0.15 |
| β-Cyclodextrin | 5 | 0.37 |
| Polyethylene glycol 2000 | 5 | 0.37 |
| Grape flavour | 9.9 | 0.73 |
| Glycine | 10 | 0.74 |
| Citric acid | 10 | 0.74 |
| Microcrystalline cellulose | 20 | 1.47 |
| Amylopectin | 50 | 3.71 |
| Lactose | 100 | 6.84 |
| Mannitol | 150 | 10.25 |
| Sildenafil BP/USP | 125 | 8.54 |
| Purified water | 1000 | 66.01 |

Sample 5. Additionally Contained a Colouring Agent and a Sweetener

| Ingredient | Amount (g) | % by weight |
|---|---|---|
| FD & C red | 0.1 | 0.01 |
| Sodium carbonate | 1 | 0.07 |
| Sodium carboxymethylcellulose | 2 | 0.15 |
| Aspartame | 5 | 0.37 |
| Polyethylene glycol 2000 | 5 | 0.37 |
| Cherry flavour | 9.9 | 0.73 |
| Glycine | 10 | 0.74 |
| Microcrystalline cellulose | 20 | 1.48 |
| Amylopectin | 50 | 3.71 |
| Lactose | 100 | 6.84 |
| Mannitol | 150 | 10.25 |
| Sildenafil BP/USP | 125 | 8.54 |
| Purified water | 1000 | 66.74 |

Sample 6. Additionally Contained a Colouring Agent and a pH Adjuster

| Ingredient | Amount (g) | % by weight |
|---|---|---|
| FD & C red | 0.1 | 0.01 |
| Sodium carbonate | 1 | 0.07 |
| Sodium carboxymethylcellulose | 2 | 0.15 |
| Sodium hydrogen carbonate | 5 | 0.37 |
| Polyethylene glycol 2000 | 5 | 0.37 |
| Raspberry flavour | 9.9 | 0.73 |
| Glycine | 10 | 0.74 |
| Microcrystalline cellulose | 20 | 1.48 |
| Amylopectin | 50 | 3.71 |
| Lactose | 100 | 6.84 |
| Mannitol | 150 | 10.25 |
| Sildenafil BP/USP | 125 | 8.54 |
| Purified water | 1000 | 66.74 |

Various batches of sildenafil fast dissolving solid dosage form wafers were then prepared based on the formulation shown in Table 8 and prepared as set out in Example 1 above. The batch number and the ingredients are listed in Table 9.

TABLE 9

Compositions of Sildenafil Formulations Used for Investigations
(Strength equivalent of 25 mg of sildenafil base)

| Ingredient | Batch 071501B Amount (g) | Batch 071502B Amount (g) | Batch 0820A Amount (g) | Batch 0820B Amount (g) | Batch 20120628 Amount (g) |
| --- | --- | --- | --- | --- | --- |
| Amylopectin | 1.0 | 1.0 | 1.0 | 0.00 | 1.0 |
| Mannitol | 3.0 | 3.0 | 3.0 | 3.0 | 3.0 |
| Lactose | 2.0 | 2.0 | 2.0 | 2.0 | 2.0 |
| Glycine | 0.2 | 0.2 | 0.5 | 0.3 | 0.2 |
| PEG 2000 | 0.1 | 0.1 | 0.1 | 0.1 | 0.1 |
| Sodium Carboxymethylcellulose | 0.04 | 0.04 | 0.04 | 0.04 | 0.04 |
| Sodium carbonate | 0 | 0.02 | 0 | 0 | 0.02 |
| Starch | 1.0 | 0 | 0 | 0 | 0 |
| Citric acid | 0 | 0 | 0 | 0 | 0.2 |
| Avicel | 0.2 | 0.2 | 0.00 | 0.2 | 0.2 |
| Active pharmaceutical ingredient | 0 | 0 | 0 | 0 | 2.5 sildenafil (base) |
| Purified water | 40 | 40 | 40 | 40 | 40 |

In Vitro Studies

Uniformity of Weight

The uniformity of the weight of the sildenafil wafer was tested as provided in Example 1. Twenty wafers from the formulations listed in Table 9 were individually weighed, and the average weight and relative standard deviation was calculated. All the prepared wafers from different formulations were within the accepted weight variation of 0.25 to 2%.

Hardness

The hardness of the wafer was also tested in accordance with the method given in Example 1. The hardness values from different formulations ranged from 0.5 to 4.0 kg. Batch 20120628 gave a hardness of the wafer at 0.5 to 1.0 kg and this formulation was used in the subsequent clinical trial. This formulation enables a fast dissolution rate and allows for easy handling.

Friability

The strength of sildenafil wafers (including their ability to be reduced from a solid substance into smaller pieces) was measured in accordance with the method given in Example 1. A sample of 20 sildenafil wafers had a percentage weight loss of between 8 to 20%.

Moisture Analysis

The moisture content of the sildenafil wafers was analysed as provided in Example 1. The results showed that the residual moisture content was around 4%.

Scanning Electron Microscopic Analysis

Figure 64:
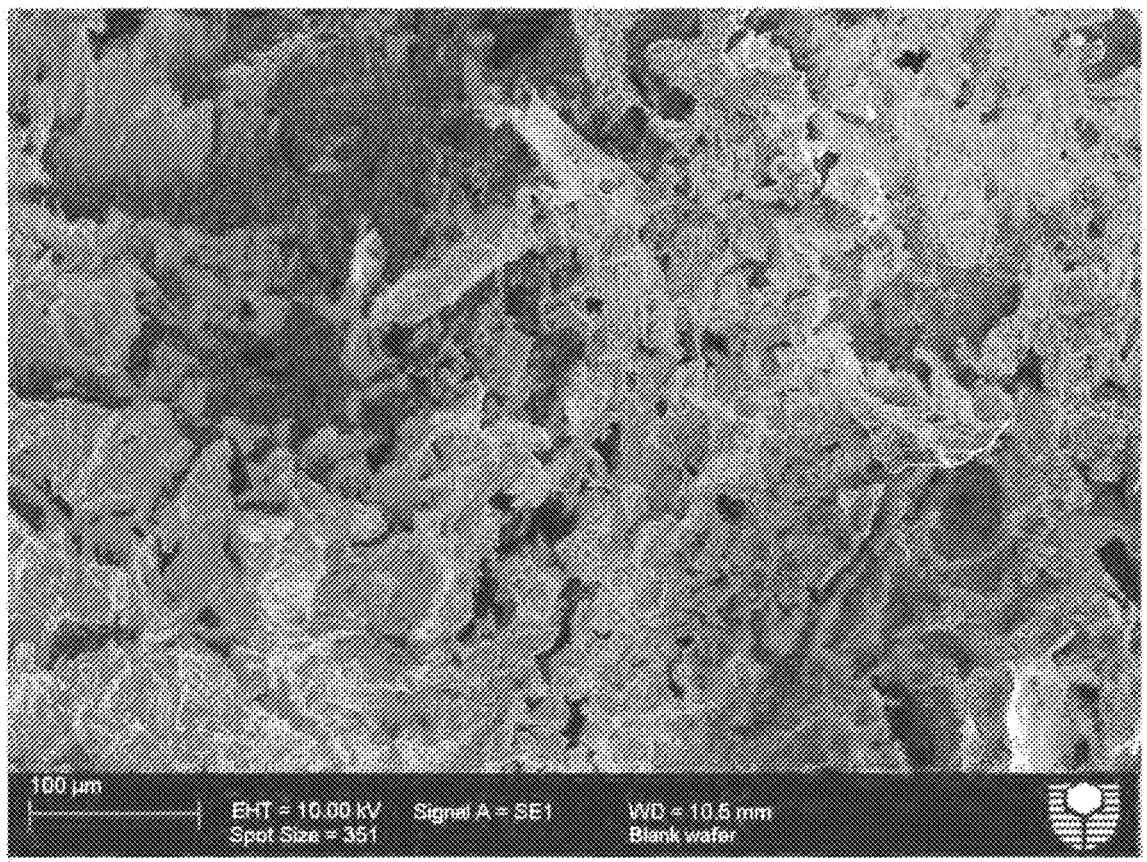
FIG. 64 shows scanning electron micrographs of the surface of a blank fast dissolving dosage form.
Figure 65:
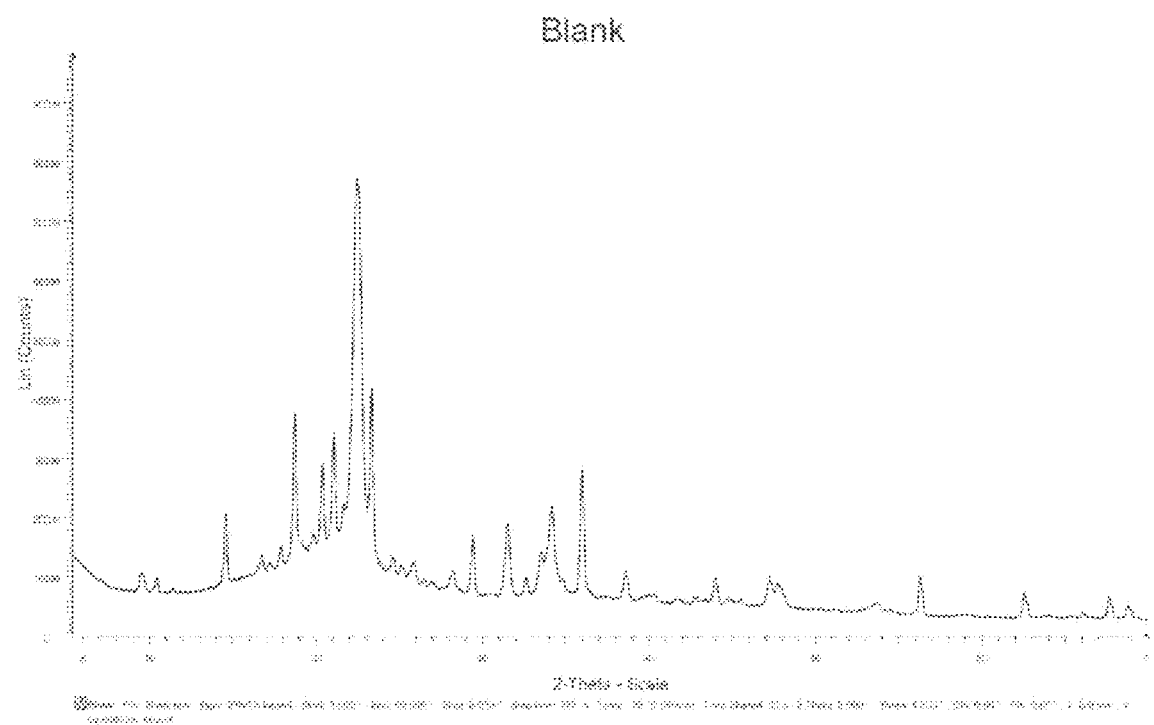
FIG. 65 shows a powder X-ray diffraction spectra of a blank fast dissolving dosage form.

Surface morphology and cross-section of selected wafer formulation samples were observed using the method provided in Example 1. The SEM images shown in FIGS. 64 and 65 show clear morphological differences between blank and sildenafil wafers.

Powder X-Ray Diffraction (XRD)

Powder X-ray diffraction experiments were performed using the method of Example 1.

Figure 66:
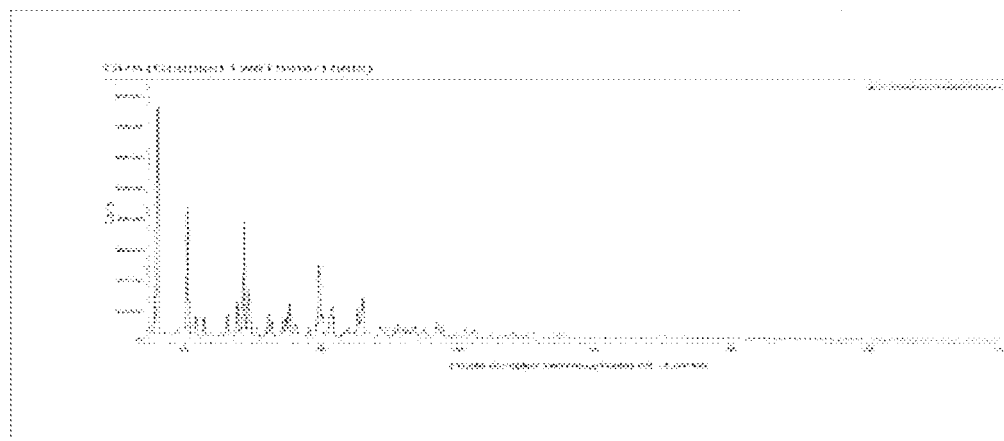
FIG. 66 shows powder X-ray diffraction spectra of sildenafil powder.
Figure 67:
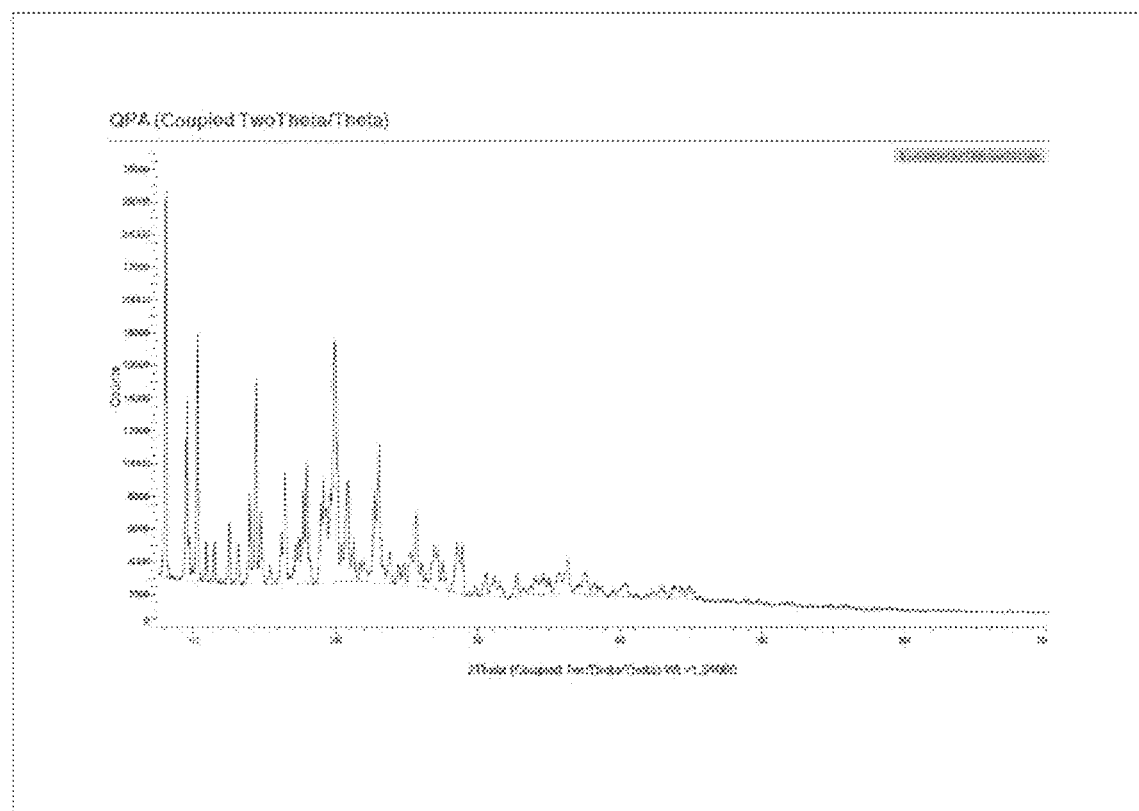
FIG. 67 shows a powder X-ray diffraction spectrum of sildenafil fast dissolving dosage form.
Figure 68:
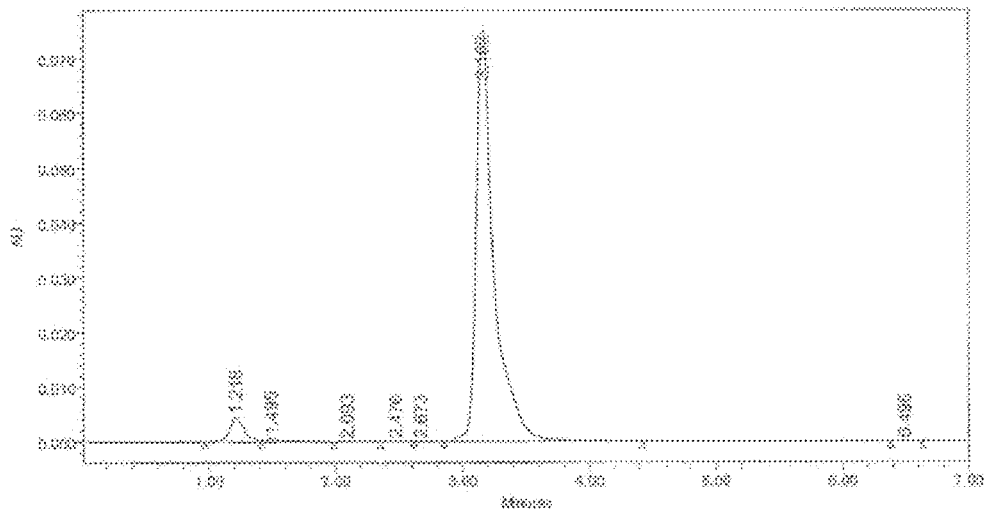
FIG. 68 shows typical HPLC chromatograms of dissolution sildenafil wafer Sample S1 at 1 minute.
Figure 69:
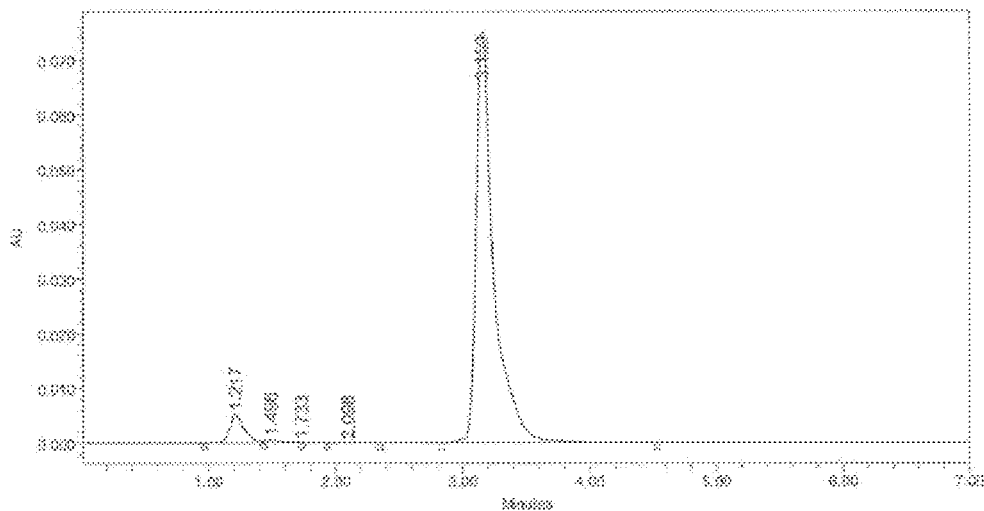
FIG. 69 shows a typical HPLC chromatogram of dissolution sildenafil wafer Sample S1 at 3 minutes.
Figure 70:
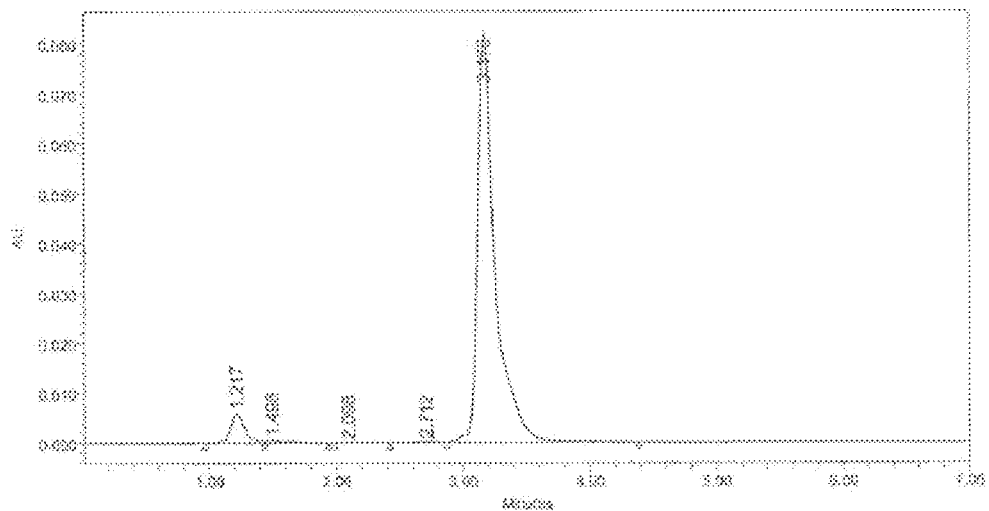
FIG. 70 shows typical HPLC chromatograms of dissolution sildenafil wafer Sample S1 at 5 minutes.
Figure 71:
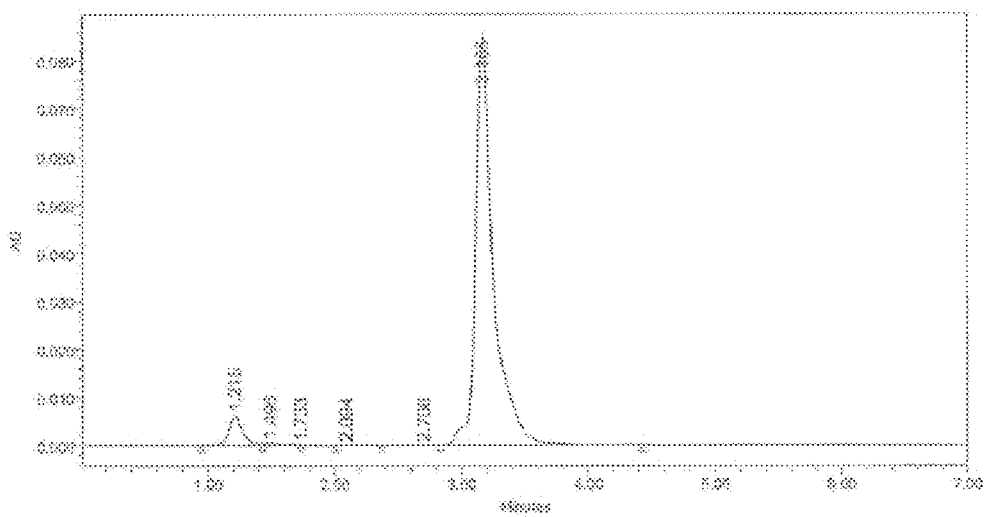
FIG. 71 shows typical HPLC chromatograms of dissolution sildenafil wafer Sample S1 at 7 minutes.
Figure 72:
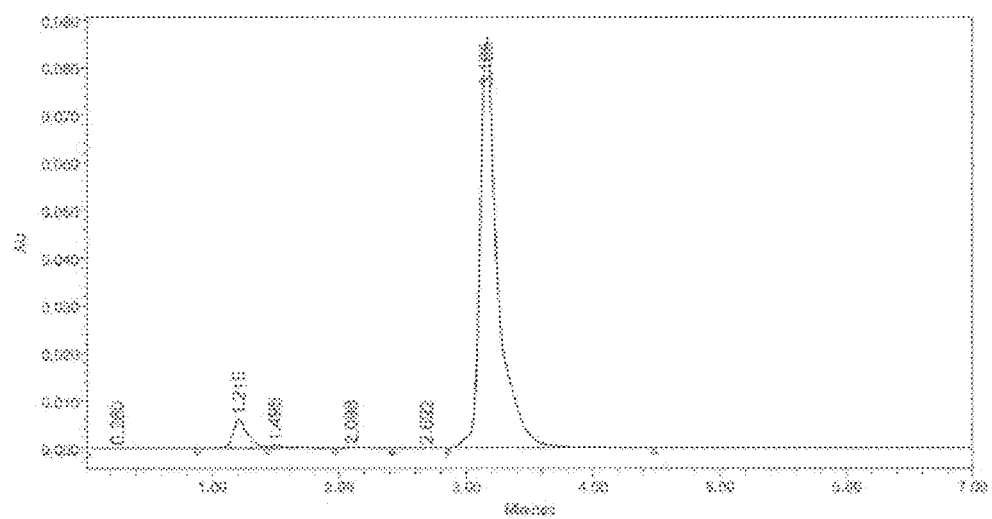
FIG. 72 shows typical HPLC chromatograms of dissolution sildenafil wafer Sample S1 at 10 minutes.
Figure 73:
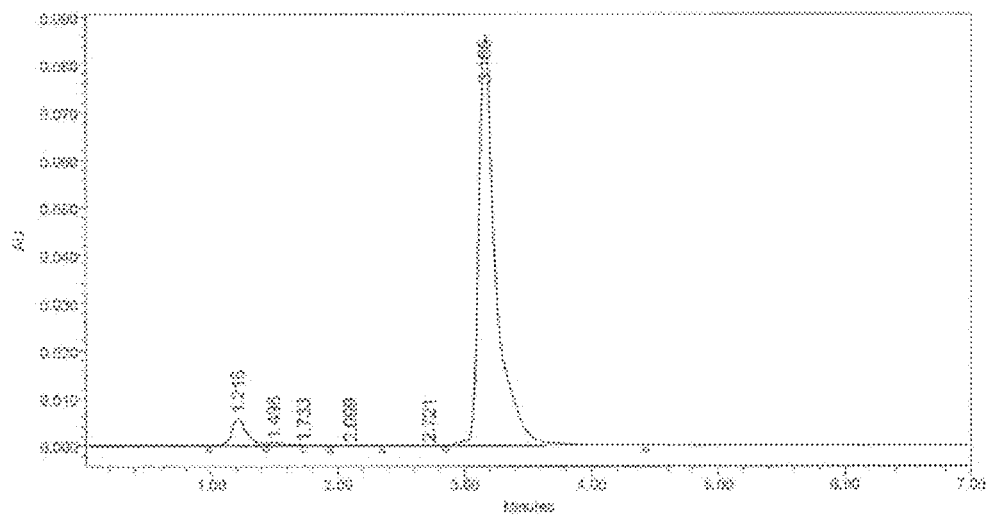
FIG. 73 shows typical HPLC chromatograms of dissolution sildenafil wafer Sample S1 at 15 minutes.
Figure 74:
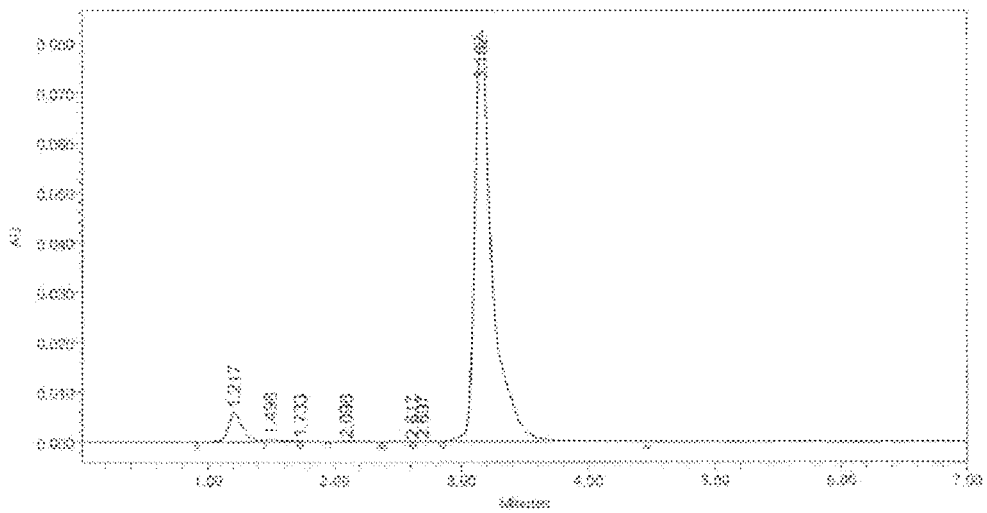
FIG. 74 shows typical HPLC chromatograms of dissolution sildenafil wafer Sample S1 at 20 minutes.
Figure 75:
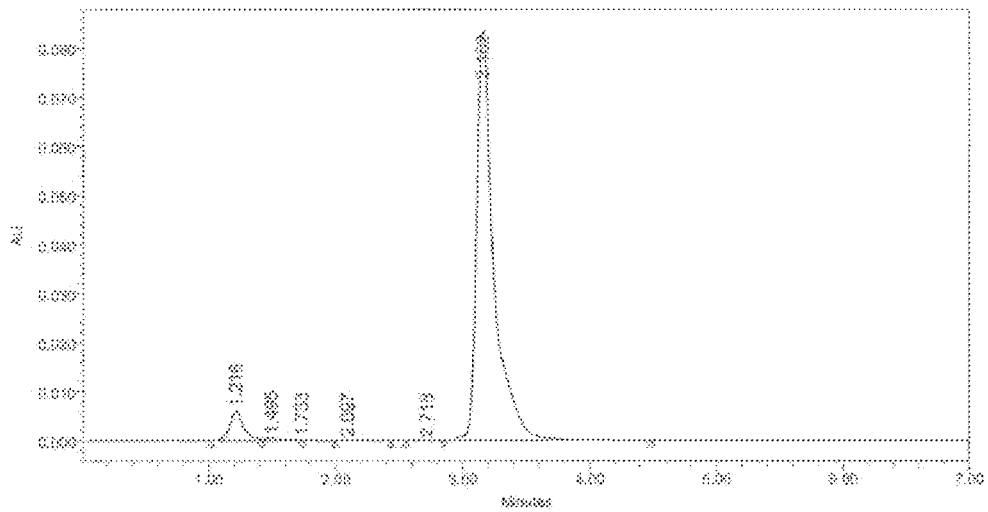
FIG. 75 shows typical HPLC chromatograms of dissolution sildenafil wafer Sample S1 at 30 minutes.
Figure 76:
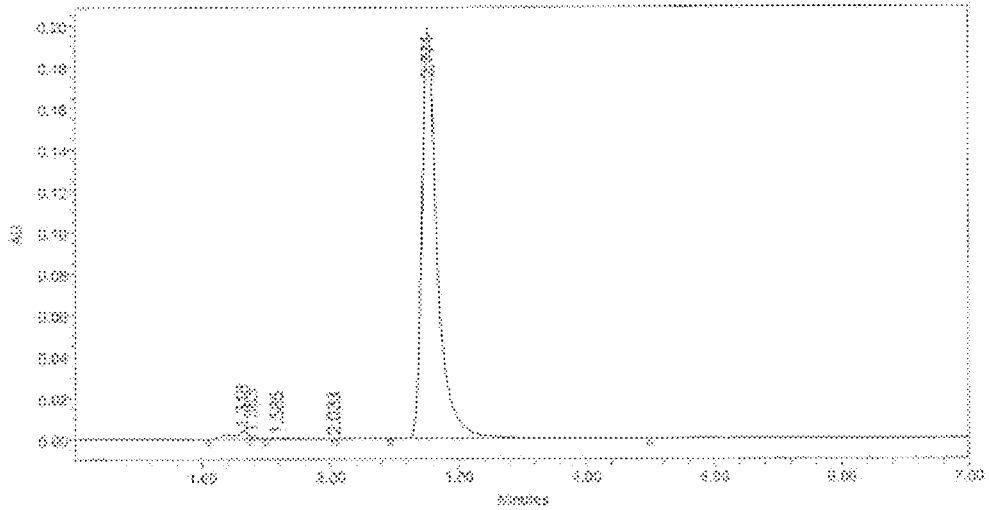
FIG. 76 shows a typical HPLC chromatogram of drug loading test sildenafil wafer sample No. 1.

The physical state of the materials in the sildenafil wafers was evident in the X-ray diffraction spectra. Spectra for three different formulations as prepared in accordance with Table 9 are shown in FIGS. 66, 67 and 68. It was observed that all the powder patterns of wafers prepared were dominated by intense scattering peaks approximately located at 2-theta of 9.58°, 19, 68° and 20.05°, which indicating a crystalline nature of the excipient Avicel. This finding was also supported by the data generated from the SEM. Indeed, the excipients used in the formulations, such as glycine, lactose, mannitol and microcrystalline cellulose are crystalline in nature. However, it seemed all became amorphous after freeze-drying.

Disintegration and Dissolution Analysis

Disintegration and dissolution tests were carried out according to Example 1.

For the disintegration test, it was shown that the sildenafil containing wafers of the present invention were able to completely dissolve in about 15 seconds and did not leave behind any residue.

For the Dissolution Testing:

Dissolution tests were carried out using Apparatus I (BP 2009, Basket apparatus). The Erweka dissolution apparatus (Hesenstamm, Germany) was used for both tests. The temperature of the medium was kept at 37±0.5° C. A wafer (Batch 20120628) containing sildenafil was used to determine the level of drug release from the formulation. The dissolution rates of the sildenafil wafer were determined using the method given in Example 2

Figure 77:
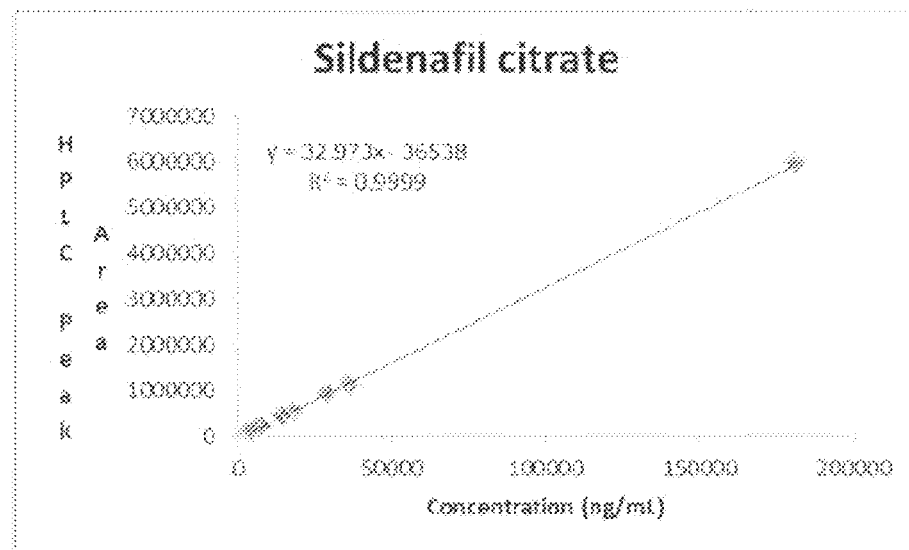
FIG. 77 shows standard HPLC calibration curve of sildenafil 5 to 100 µg/mL).

The calibration curve for the concentrations 5 to 100 µg/mL of sildenafil (seven-point calibration) was linear [Y=32.973X−36538, (r=0.9999), Y representing the peak area of sildenafil and X the concentration of the samples]. The assay standard curve is shown in FIG. 77.

The prepared sildenafil wafer (Batch 20120628) showed a weight variation of ±2.55%, and the mean percentage sildenafil content of the wafer was 98.67% (BP standard for uniformity content limits 85 to 115%). The average disintegration times (BP disintegration apparatus) were less than 5 seconds; and the dissolution studies also indicated a fast release rate of sildenafil. Almost 95% of sildenafil had dissolved within one minute. This may indicate the changing of sildenafil crystal form in the wafer, which was also evident in the X-ray. The X-ray spectrum pointed to an amorphization of sildenafil during the freeze-drying process.

Figure 78:
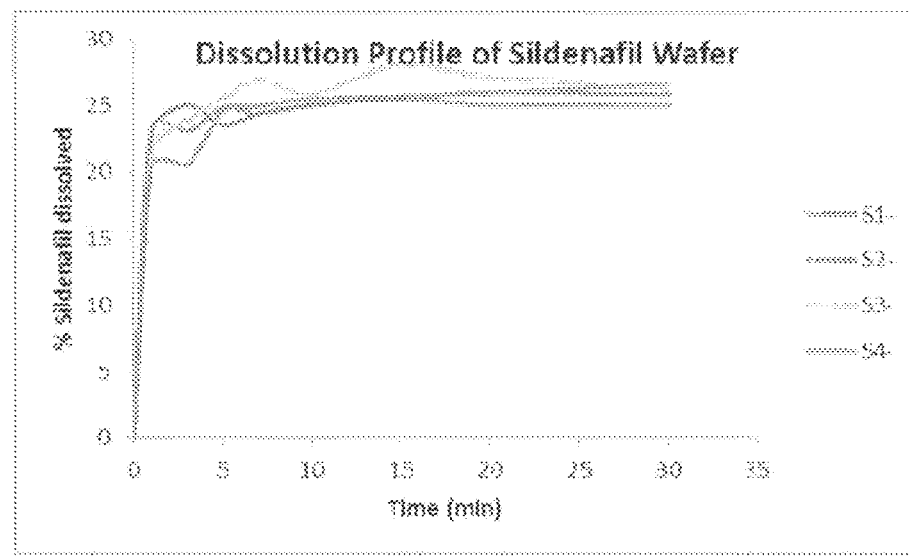
FIG. 78 Dissolution profiles of sildenafil wafer in phosphate buffer solution (pH 6.8) at 37° C., (n=4).

The dissolution profiles are presented in FIG. 78.

The sildenafil wafer is a solid dispersion of sildenafil hydrochloride into a porous matrix. After administration, this dosage form quickly disintegrates in oral cavity, and allows the rapidly dissolving sildenafil to be absorbed by diffusion directly into the systemic circulation, and the first-pass effect is avoided. This invention has the potential to provide an alternate route of drug administration and results in lower rates of side effect.

Example 4

A formulation of the present invention, in the form of a solid dosage form (wafer) containing adrenaline, was prepared in accordance with the method and ingredients as set out below in Table 10:

TABLE 10

Composition of Adrenaline Fast Dissolving Solid Dosage Form (Strength equivalent of 40 mg of adrenaline base)

| Ingredient (BP/USP) | Amount (g) | % by weight |
|---|---|---|
| Sodium carbonate | 1 | 0.07 |
| Sodium carboxymethylcellulose | 2 | 0.15 |
| Polyethylene glycol 2000 | 5 | 0.36 |
| Glycine | 1 | 0.07 |
| Microcrystalline cellulose | 2 | 0.15 |
| Amylopectin | 50 | 3.64 |
| Adrenaline (Base) | 100 | 7.28 |
| Lactose | 100 | 7.28 |
| Mannitol | 150 | 10.92 |
| Purified water | 1000 | 70.08 |

The fast dissolving dosage form (wafer) containing adrenaline was produced using the method of Example 1 above.

The following additional formulations were prepared by the method as set out above. Samples 1 to 6 are based on the formulation described above (strength equivalent of 40 mg adrenaline base), with the addition of flavour and/or colour agents.

Sample 1. Additionally Contained a Flavour

| Ingredient | Amount (g) | % by weight |
|---|---|---|
| Sodium carbonate | 1 | 0.07 |
| Sodium carboxymethylcellulose | 2 | 0.14 |
| Polyethylene glycol 2000 | 5 | 0.35 |
| Orange flavour | 10 | 0.71 |
| Glycine | 10 | 0.71 |
| Microcrystalline cellulose | 20 | 1.42 |
| Amylopectin | 50 | 3.54 |
| Adrenaline (Base) | 100 | 7.09 |
| Lactose | 100 | 7.09 |
| Mannitol | 150 | 10.63 |
| Purified water | 1000 | 68.25 |

Sample 2. Additional Contained a Flavour and a pH Adjuster (Citric Acid).

| Ingredient | Amount (g) | % by weight |
|---|---|---|
| Sodium carbonate | 1 | 0.07 |
| Sodium carboxymethylcellulose | 2 | 0.14 |
| Citric acid | 5 | 0.35 |
| Polyethylene glycol 2000 | 5 | 0.35 |
| Mint flavour | 10 | 0.71 |
| Glycine | 10 | 0.71 |
| Microcrystalline cellulose | 20 | 1.41 |
| Amylopectin | 50 | 3.53 |
| Adrenaline (Base) | 100 | 7.06 |
| Lactose | 100 | 7.06 |
| Mannitol | 150 | 11.09 |
| Purified water | 1000 | 67.52 |

Sample 3. Additionally Contained Flavour and a Colouring Agent

| Ingredient | Amount (g) | % by weight |
|---|---|---|
| FD & C red | 0.1 | 0.01 |
| Sodium carbonate | 1 | 0.07 |
| Sodium carboxymethylcellulose | 2 | 0.14 |
| Polyethylene glycol 2000 | 5 | 0.35 |
| Grape flavour | 9.9 | 0.70 |
| Glycine | 10 | 0.71 |
| Microcrystalline cellulose | 20 | 1.42 |
| Amylopectin | 50 | 3.54 |
| Adrenaline (Base) | 100 | 7.09 |
| Lactose | 100 | 7.09 |
| Mannitol | 150 | 10.43 |
| Purified water | 1000 | 68.45 |

Sample 4. Additionally Contained a Flavour, a Colouring Agent and an Absorption Enhancer

| Ingredient | Amount (g) | % by weight |
|---|---|---|
| FD & C blue | 0.1 | 0.01 |
| Sodium carbonate | 1 | 0.07 |
| Sodium carboxymethylcellulose | 2 | 0.14 |
| Glyceryl Trinitrate | 28.57 | 2.00 |
| Polyethylene glycol 2000 | 5 | 0.35 |
| Grape flavour | 9.9 | 0.70 |
| Glycine | 10 | 0.71 |
| Microcrystalline cellulose | 20 | 1.41 |
| Amylopectin | 50 | 3.53 |
| Adrenaline (Base) | 100 | 7.06 |
| Lactose | 100 | 7.06 |
| Mannitol | 145 | 10.24 |
| Purified water | 1000 | 66.72 |

Sample 5. Additionally Contained a Colouring Agent and a Sweetener

| Ingredient | Amount (g) | % by weight |
|---|---|---|
| FD & C red | 0.1 | 0.01 |
| Sodium carbonate | 1 | 0.07 |
| Sodium carboxymethylcellulose | 2 | 0.14 |
| Aspartame | 5 | 0.35 |
| Polyethylene glycol 2000 | 5 | 0.35 |
| Cherry flavour | 9.9 | 0.70 |
| Glycine | 10 | 0.71 |
| Microcrystalline cellulose | 20 | 1.41 |
| Amylopectin | 50 | 3.53 |
| Adrenaline (Base) | 100 | 7.06 |
| Lactose | 100 | 7.06 |

-continued

| Ingredient | Amount (g) | % by weight |
|---|---|---|
| Mannitol | 145 | 10.24 |
| Purified water | 1000 | 68.42 |

Sample 6. Additionally Contained a Colouring Agent and a pH Adjuster

| Ingredient | Amount (g) | % by weight |
|---|---|---|
| FD & C red | 0.1 | 0.01 |
| Sodium carbonate | 1 | 0.07 |
| Sodium carboxymethylcellulose | 2 | 0.14 |
| Sodium hydrogen carbonate | 5 | 0.35 |
| Polyethylene glycol 2000 | 5 | 0.35 |
| Raspberry flavour | 9.9 | 0.70 |
| Glycine | 10 | 0.71 |
| Microcrystalline cellulose | 20 | 1.41 |
| Amylopectin | 50 | 3.53 |
| Adrenaline (Base) | 100 | 7.06 |
| Lactose | 100 | 7.06 |
| Mannitol | 145 | 10.24 |
| Purified water | 1000 | 68.37 |

Various strength of adrenaline bitartrate fast dissolving solid dosage form (wafer) were then prepared based on the formulation shown in Table 10 and prepared as set out in Example 1 above. The batch number and the ingredients are listed in Table 11.

TABLE 11

Adrenaline Compositions Used for Investigations

| Ingredient | Batch (strength equivalent of 40 mg adrenaline base) Amount (g) | Batch (strength equivalent of 40 mg adrenaline base) Amount (g) | Batch (strength equivalent of 60 mg adrenaline base) Amount (g) |
|---|---|---|---|
| Amylopectin | 1.0 | 1.0 | 1.2 |
| Mannitol | 3.0 | 3.0 | 2.9 |
| Lactose | 2.0 | 2.0 | 1.9 |
| Glycine | 0.2 | 0.2 | 0.3 |
| Polyethylene glycol 2000 | 0.1 | 0.1 | 0.1 |
| Sodium Carboxymethylcellulose | 0.04 | 0.04 | 0.04 |
| Sodium carbonate | 0.02 | 0.02 | 0.05 |
| Avicel | 0.2 | 0.2 | 0.2 |
| Glyceryl Trinitrate | 2.0 | 2.0 | 2.0 |
| Adrenaline bitartrate | 3.638 | 3.638 | 5.458 |
| Purified water | 38 | 38 | 37 |

Example 5

A Phase I Pharmacokinetic and Bioavailability Study of a Sublingual Fentanyl Wafer in Healthy Volunteers
Methods
Study Subjects Healthy volunteers gave written informed consent on an approved subject consent form, before undergoing trial procedures. Subjects were included in the study were between 19 and 32 years of age, had a body mass index between 18 and 30 kg/m$^2$, had no history or evidence of drug or alcohol dependence or abuse, had normal findings after a clinical history and laboratory testing, were free of SL (sublingual) or buccal ulceration or disease, and had negative findings for human immunodeficiency virus, hepatitis B, and hepatitis C viral testing.

Twenty-four volunteers who met the study inclusion and exclusion criteria were enrolled in this study. On the basis of an SD of the area under the curve (AUC), values of 35% and a 20% difference being significant gives a power of 84% ($\alpha$=0.05).

Study Design

This was a single-centre (Linear Clinical Research Ltd., Perth, Australia), randomized, open-label, single-dose, 2-treatment, 2-period, 2-way crossover study. According to the randomization plan, subjects were divided into 2 groups, in a 1:1 ratio using a computer-generated table of random numbers. The volunteers were given either IV fentanyl citrate or a sublingual fentanyl citrate wafer (based on Batch: 1003FEN formulation of Example 1; equivalent to 100 μg of fentanyl). Each volunteer subsequently received the alternative route after a 7-day washout period.

The wafer was administered by placing it under the tongue. The volunteer was requested to avoid swallowing for as long as possible, at least for 10 minutes. A naltrexone tablet (50 mg) was administered orally every 12 hours from before day 1 to the evening of day 2 (12 hours after the last fentanyl dose), so as to block any systemic effects of fentanyl.

Before commencement of the study, a dedicated IV cannula was placed in the forearm for subsequent venous blood sampling. Blood samples (7 mL) were taken pre-dose before the commencement of wafer administration and then at 2, 5, 10, 15, 20, 30, 45, 60, 120, 180, 360, 460, 600, 720, 960, and 1440 minutes after administration commencement. For IV infusion, blood samples were taken at pre-dose, at 2 and 3 minutes after commencement, and at 5 minutes (end infusion), then at 7, 10, 15, 20, 25, 30, 45, 60, 120, 180, 360, 460, 600, 720, 840, 960, and 1440 minutes from infusion commencement.

After collection, the blood samples were immediately centrifuged at 4° C., 2000 to 2500 g for 15 minutes and the plasma extracted and placed into polypropylene storage tubes. The plasma was stored at −80° C.±10° C. until transfer to the bioanalytical laboratory. Sample extracts were analysed on an API 4000 LC-MS/MS system (Applied Biosystems, Foster City, CA), preceded by a Shimadzu Prominence high-performance liquid chromatography system with d5-fentanyl as the internal standard. The assay had a limit of detection of 10 pg/mL. Precision was determined by duplicate analyses of plasma containing 10, 40, and 400 pg/mL fentanyl. The results were precise to within ±6.2%, ±3.3%, and ±1.7% of the mean measured concentration values of 10, 40, and 400 pg/mL, respectively, and accurate to within 102%, 99.9%, and 101.4% of the nominal concentrations of 10, 40, and 400 pg/mL, respectively. At each concentration the number of replicates was 6.

Pharmacokinetic Analysis

The pharmacokinetic parameters were determined using Phoenix WinNonlin version 6.1 (Pharsight, A Certara™ Company, St. Louis, MO). The pharmacokinetic data were $C_{max}$, $t_{max}$, $AUC_{0\ to\ 12}$, $AUC_{0\text{-}t}$, $AUC_{0\text{-}\infty}$, $k_{el}$, and $t_{1/2}$. First detectable fentanyl plasma concentration after SL administration ($C_{first}$) and the time to $C_{first}$ ($t_{first}$) were read directly from the plasma fentanyl concentration-time curves. The terminal elimination rate constant ($k_{el}$) was determined as the slope of the regression line of best fit to the approximately log-linear terminal elimination phase. All fitting was performed with unity weighting of the data. The terminal elimination half-life ($t_{1/2}$) was obtained from $k_{el}$ and equaled $\ln 2/k_{el}$. The $AUC_{0\ to\ 12}$ and $AUC_{0\text{-}t}$ values were obtained using the trapezoidal rule. The extrapolation to $AUC_{0\text{-}\infty}$ was calculated from $AUC_{0\text{-}t} + C_t/k_{el}$.

Safety and Tolerability

Safety and tolerability were assessed by monitoring vital signs (arterial blood pressure and heart rate) after fentanyl administration. A full physical examination was performed before and 48 hours after drug administration. Laboratory tests and a 12-lead electrocardiogram were performed at baseline and completion of the study. Adverse events were assessed using direct observation, spontaneous reporting, and nonspecific questioning.

Statistical Analysis

Summary statistics were computed by treatment of each pharmacokinetic parameter. Bioavailability of SL fentanyl was determined separately for each subject as the ratio of Cmax. $AUC_{0\ to\ 12}$, $AUC_{0-t}$, and $AUC_{0-\infty}$ for SL administration in comparison with IV administration. Overall bioavailability was estimated as the back-transform of the difference between treatments for log-transformed $C_{max}$, $AUC_{0\ to\ 12}$, $AUC_{0-t}$, and $AUC_{0-\infty}$ values using a linear model with terms for treatment, period, sequence, and subject within sequence. The 90% confidence interval (CI) was also calculated, and P values <0.05 were considered statistically significant. All analyses were conducted using SAS version 9.2 (SAS Institute Inc., 2008). Differences in formulations were evaluated using Student t tests.

Results

Twenty-four patients were randomized, 12 to the SL:IV sequence and 12 to the IV:SL sequence. Two volunteers did not complete the SL or the IV administration arm of the study and were eliminated from all analyses. The volunteer characteristics are reported in FIG. 79.

Pharmacokinetic Results

Figures 79, 80:
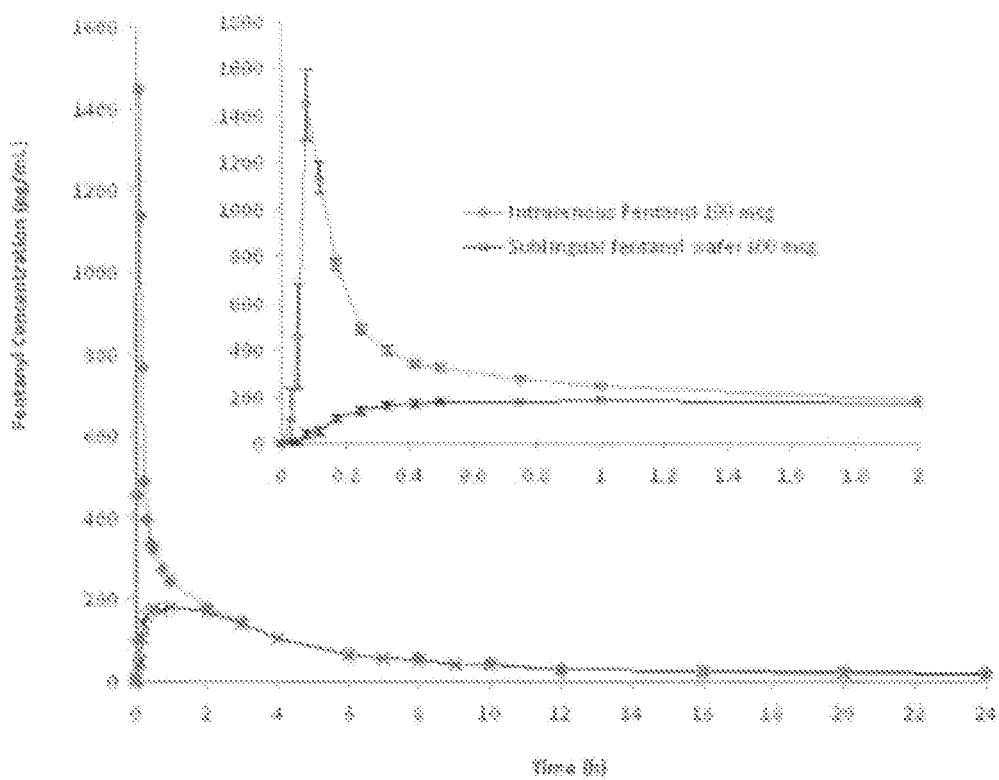
FIG. 79 shows a table showing the demographic characteristics of the study volunteers according to example 4.
FIG. 80 shows a graph showing the mean (±SEM) plasma concentration (pg/mL) over time profiles for sublingual fentanyl water and IV fentanyl. Inset figure is an expanded profile for the initial two-hour period.
Figure 81:
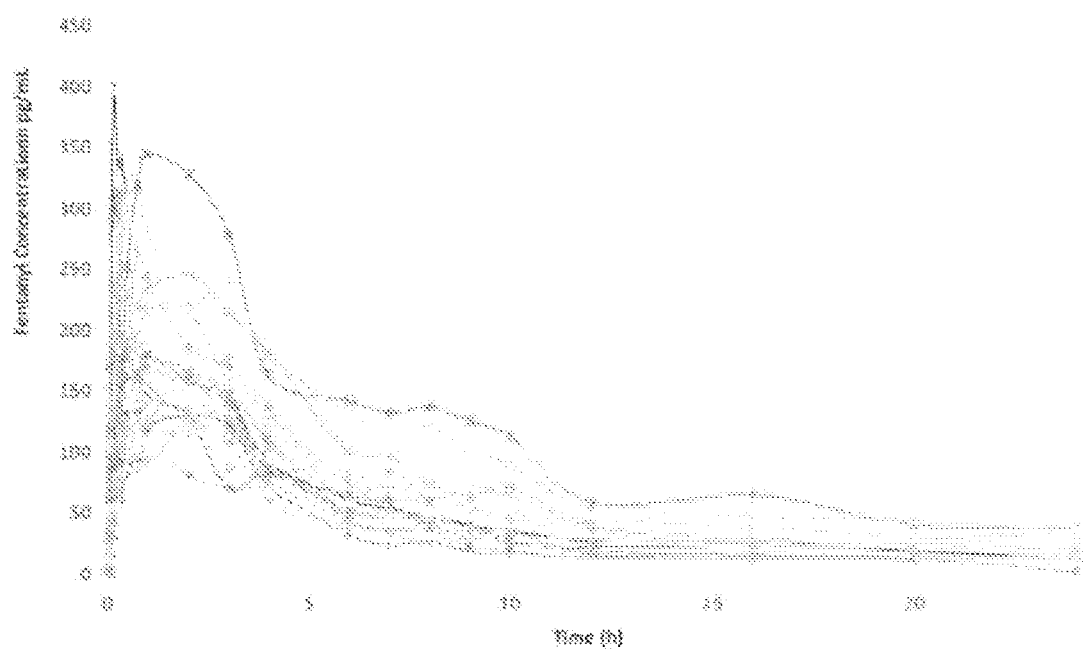
FIG. 81 shows a graph showing the plasma concentration data (pg/mL) over time profiles for sublingual fentanyl wafer for each volunteer (n=22).

Mean plasma (±SEM) fentanyl concentration versus time curves for the IV and SL routes are shown in FIG. 80. Individual subject plasma concentration profiles are shown for the SL route in FIG. 81. The mean values (±1 SD) for the plasma pharmacokinetic parameters $C_{max}$, $t_{max}$, $AUC_{0\ to\ 12}$, $AUC_{0-t}$, and $AUC_{0-\infty}$ for fentanyl are shown in FIG. 82. The first detectable plasma fentanyl concentration ($C_{first}$), after SL administration, was observed between 2 and 10 minutes after administration. The cumulative percentage of the 22 volunteers with $t_{first}$ at 2, 5, and 10 minutes and their mean plasma fentanyl concentration ($C_{first}$) were 12.5% (32.4 pg/mL), 62.5% (30.7 pg/mL), and 100.0% (49.0 pg/mL), respectively.

The mean time to peak plasma concentrations ($t_{max}$) after commencing IV and SL administration was 0.12 hour and 0.92 hour, respectively (P<0.0001) (FIG. 82). The mean (±SD) terminal half-life ($t_{1/2}$) for IV and SL administration was 13.07 t 3.00 hours and 12.49±5.24 hours, respectively (P=0.889). The mean (±SD) terminal elimination rate constant ($k_{el}$) for IV and SL administration was 0.055±0.012 h$^{-1}$ and 0.064±0.025 h$^{-1}$, respectively (P=0.317).

Bioavailability was assessed by the percentage ratios of SL/IV for $AUC_{0\ to\ 12}$, $AUC_{0-t}$, and $AUC_{0-\infty}$ values. The mean bioavailability of SL fentanyl was estimated to be 72.1% (CI, 65.3% to 79.6%) from $AUC_{0\ to\ 12}$, and 73.2% (CI, 66.3% to 80.9%) from $AUC_{0-t}$. Absolute bioavailability was 78.9% (CI, 51.1% to 121.7%) on the basis of the $AUC_{0-\infty}$ values.

The $C_{max}$ of SL fentanyl was 18.8% (CI, 14.4% to 24.6%) of the IV administration value, with the average time to maximum concentration being 0.9 hour. For IV administration, $C_{max}$ generally occurred at the end of the infusion, with a rapid reduction over the half hour immediately post-dose. From approximately 2 hours post-dose, the mean concentration-time profiles were similar for the 2 modes of administration.

Tolerability

All reported adverse events were mild to moderate. The mean (±SD) time for the wafer to dissolve in the SL pouch was 73±76 seconds.

This study was designed as a phase I study to determine the basic pharmacokinetic parameters of a recently developed rapidly dissolving fentanyl wafer. It also collected some data on subject acceptance of the product.

It was found that the $C_{max}$ and $t_{max}$ values for the SL fentanyl (100 µg) wafer were comparable (FIG. 83) to data reported from a previously studied SL fentanyl (100 µg) tablet. The $C_{max}$ and $t_{max}$ values provide an indication of the rate of absorption of drugs. The wafer has similar $C_{max}$, $t_{max}$, and AUC values, in comparison with the SL tablet (P=0.573, 0.331, and 0.103, respectively); no absolute bioavailability data were available for the SL tablet. It was noted that the SL tablet was evaluated in cancer patients over a 10-hour collection period, which causes different $t_{1/2}$ values of 6.1 and 12.5 hours for the tablet and wafer, respectively (P=0.0013).

After SL administration, rapid absorption of fentanyl was evidenced by detectable plasma concentrations within 2 to 10 minutes ($t_{first}$), occurring in most cases within 5 minutes. The wafer formulation had a $C_{first}$ similar to that of the SL tablet. This reflects fentanyl's high permeability into the rich blood-flow (and good venous outflow) of the SL mucosa, which bypasses the hepatic "first-pass" effect. The SL mucosa (100 to 200 µm) is thicker than the nasal mucosa (40 to 80 µm); hence a slower absorption rate was expected in comparison with that reported after IN administration ($t_{max}$ for IN fentanyl 4.2 to 11.4 minutes versus 54.6 minutes for SL fentanyl in this study).

The high bioavailability of fentanyl from the wafer suggests that wafer fentanyl is reliably absorbed sublingually and less likely to be partially swallowed, hence avoiding first-pass metabolism. No attempt was made to apportion bioavailability to these routes of absorption in this study. The analgesic efficacy of the wafer formulation appears satisfactory, on the basis of an earlier pilot study conducted among postoperative surgical patients.

This SL fentanyl wafer resulted in rapidly detectable plasma fentanyl concentrations in healthy volunteers, within 10 minutes of administration, indicating potential for the treatment of breakthrough pain. The bioavailability was 78.9% in relation to IV administration.

The invention claimed is:

1. A fast disintegrating and dissolving solid freeze-dried wafer dosage form with a porous matrix for the release of a biologically active material in an oral cavity wherein said dosage form comprises:
 a) biologically active material at a concentration of 0.02 to 95% by dry weight of the dosage form;
 b) a matrix forming agent comprising amylopectin that is not in the form of starch or modified starch at a concentration from 2% to 17% by dry weight of the dosage form; and
 c) a further matrix forming agent comprising a carbohydrate chosen from the list consisting of: mannitol, dextrose, lactose, galactose, trehalose and cyclodextrin at a concentration from 5% to 80% by dry weight of the dosage form wherein said dosage form disintegrates in the oral cavity, and wherein said biologically active material is absorbed by diffusion directly into the systemic circulation, and wherein the biologically active material is selected from the group consisting of: anti-arrhythmic agents; antihypertensive agents; anti-migraine agents; anxiolytic, sedative, hypnotic and neuroleptic agents; gastro-intestinal agents; histamine H-receptor antagonists; nutritional agents; opioid analgesics; proteins, peptides and recombinant drugs; vasodilators; analgesics and anti-inflammatory agents, and when analysed by powder x-ray diffraction (XRD), the wafer exhibits peaks located at 2-theta values of approximately 9.58 degrees, approximately 19.68 degrees, and approximately 20.05 degrees.

2. The fast disintegrating and dissolving solid dosage form according to claim 1, further comprising microcrystalline cellulose.

3. The fast disintegrating and dissolving solid dosage form according to claim 2, wherein the microcrystalline cellulose is present in an amount from 1 to 10 weight % by dry weight of the dosage form.

4. The fast disintegrating and dissolving solid dosage form according to claim 1, further comprising glycine.

5. The fast disintegrating and dissolving solid dosage form according to claim 4, wherein glycine is present in an amount from 0.5 to 5 weight % by dry weight of the dosage form.

6. The fast disintegrating and dissolving solid dosage form according to claim 1 wherein the biologically active material is selected from group consisting of: flecainide, sumatriptan succinate, midazolam, lorazepam, diazepam, temazepam, famotidine, ondansetron, omeprazole, loratadine, Vitamin D, fentanyl, interferon, tadalafil, vardenafil, diclofenac, fexofenadine, and benzocaine.

7. The fast disintegrating and dissolving solid dosage form according to claim 6 wherein the interferon is selected from the group consisting of: alpha-2 interferon, beta interferon, and gamma interferon.

8. The fast disintegrating and dissolving dosage form of claim 1 comprising: an opioid analgesic, nutritional agent, or protein, peptide and recombinant drug present in an amount from 0.02 to 1 weight % by dry weight of the dosage form.

9. The fast disintegrating and dissolving dosage form of claim 1 comprising: an anxiolytic, a sedative, a hypnotic and neuroleptic agent, a histamine H-receptor antagonist, an anti-hypertensive agent, a vasodilator, analgesic or an anti-inflammatory agent present in an amount from 0.2 to 20 weight % by dry weight of the composition of the dosage form.

10. The fast disintegrating and dissolving dosage form of claim 1 comprising: an anti-arrhythmic agent, an anti-migraine agent, an anxiolytic, a sedative, a hypnotic and neuroleptic agent, a gastro-intestinal agent, a vasodilator, an anti-hypertensive agent, an analgesic or an anti-inflammatory agent present in an amount from 5 to 50 weight % by dry weight of the dosage form.

11. The fast disintegrating and dissolving dosage form of claim 1 comprising: an anti-arrhythmic agent; an anti-hypertensive agent; an anti-migraine agent; an anxiolytic, a sedative, a hypnotic and neuroleptic agent; a gastro-intestinal agent, a histamine H-receptor antagonists, nutritional agent; an opioid analgesic; a protein, a peptide, and recombinant drug; a vasodilator; an analgesic or an anti-inflammatory agent present in an amount from 0.02 to 50 weight % by dry weight of the composition of the dosage form.

* * * * *